(12) United States Patent
Salituro et al.

(10) Patent No.: US 11,732,000 B2
(45) Date of Patent: Aug. 22, 2023

(54) OXYSTEROLS AND METHODS OF USE THEREOF

(71) Applicant: Sage Therapeutics, Inc., Cambridge, MA (US)

(72) Inventors: Francesco G. Salituro, Marlborough, MA (US); Albert Jean Robichaud, Boston, MA (US); Gabriel Martinez Botella, Wayland, MA (US); Boyd L. Harrison, Princeton Junction, NJ (US)

(73) Assignee: Sage Therapeutics, Inc., Cambridge, MA (US)

( * ) Notice: Subject to any disclaimer, the term of this patent is extended or adjusted under 35 U.S.C. 154(b) by 144 days.

(21) Appl. No.: 17/396,034

(22) Filed: Aug. 6, 2021

(65) Prior Publication Data
US 2022/0048943 A1    Feb. 17, 2022

Related U.S. Application Data

(63) Continuation of application No. 15/742,424, filed as application No. PCT/US2016/041175 on Jul. 6, 2016, now Pat. No. 11,117,924.

(60) Provisional application No. 62/332,931, filed on May 6, 2016, provisional application No. 62/189,068, filed on Jul. 6, 2015.

(51) Int. Cl.
| | | |
|---|---|---|
| *C07J 9/00* | (2006.01) | |
| *C07J 7/00* | (2006.01) | |
| *A61P 23/00* | (2006.01) | |
| *A61P 25/20* | (2006.01) | |
| *A61P 3/00* | (2006.01) | |
| *C07J 17/00* | (2006.01) | |
| *C07J 31/00* | (2006.01) | |
| *C07J 13/00* | (2006.01) | |
| *C07J 41/00* | (2006.01) | |

(52) U.S. Cl.
CPC . *C07J 9/00* (2013.01); *A61P 3/00* (2018.01); *A61P 23/00* (2018.01); *A61P 25/20* (2018.01); *C07J 17/00* (2013.01); *C07J 7/002* (2013.01); *C07J 9/005* (2013.01); *C07J 13/005* (2013.01); *C07J 13/007* (2013.01); *C07J 31/006* (2013.01); *C07J 41/0061* (2013.01)

(58) Field of Classification Search
CPC .................................. C07J 7/002; C07J 9/00
See application file for complete search history.

(56) References Cited

U.S. PATENT DOCUMENTS

| | | |
|---|---|---|
| 2,259,698 A | 10/1941 | Johannessohn et al. |
| 2,594,323 A | 4/1952 | Levin et al. |
| 2,673,206 A | 3/1954 | Ryer |
| 3,079,385 A | 2/1963 | Bertin et al. |
| 3,206,459 A | 9/1965 | Cross |
| 4,071,625 A | 1/1978 | Grunwell et al. |
| 4,174,345 A | 11/1979 | Kaiser |
| 4,183,852 A | 1/1980 | Kaiser |
| 4,868,165 A | 9/1989 | Ikekawa |
| 5,232,917 A | 8/1993 | Bolger et al. |
| 5,376,645 A | 12/1994 | Stella et al. |
| 5,512,570 A | 4/1996 | Dorn et al. |
| 5,595,996 A | 1/1997 | Graham et al. |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 6,933,312 B2 | 8/2005 | Price et al. |
| 8,034,798 B2 | 10/2011 | Baulieu et al. |
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |

(Continued)

FOREIGN PATENT DOCUMENTS

| | | |
|---|---|---|
| CN | 1257077 | 6/2000 |
| CN | 1254716 | 5/2008 |

(Continued)

OTHER PUBLICATIONS

Papassotiropoulos et al., "Plasma 24S-hydroxycholesterol a peripheral indicator of neuronal degeneration and potential state marker for Alzheimer's disease," NeuroReport 11(9): 19591-1962 (2000).

(Continued)

*Primary Examiner* — Barbara P Badio
(74) *Attorney, Agent, or Firm* — Haley Guiliano LLP; Karen Mangasarian; Jacob E. Dander

(57) ABSTRACT

Compounds are provided according to Formula (I) and pharmaceutically acceptable salts thereof, and pharmaceutical compositions thereof; wherein $R^1$, $R^2$, and $R^3$ are as defined herein. Compounds of the present invention are contemplated useful for the prevention and treatment of a variety of conditions.

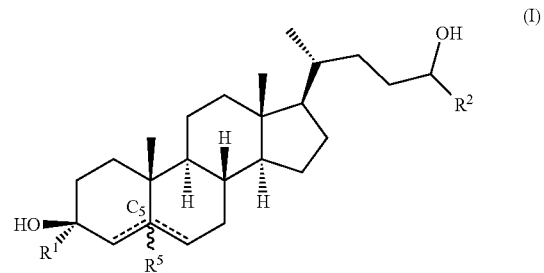

12 Claims, No Drawings

(56) References Cited

U.S. PATENT DOCUMENTS

| | | | |
|---|---|---|---|
| 10,201,550 | B2 | 2/2019 | Salituro et al. |
| 10,227,375 | B2 | 3/2019 | Botella et al. |
| 10,259,840 | B2 | 4/2019 | Harrison et al. |
| 10,696,712 | B2 | 6/2020 | Salituro et al. |
| 10,723,758 | B2 | 7/2020 | Harrison et al. |
| 10,759,828 | B2 | 9/2020 | Upasani et al. |
| 11,104,701 | B2 | 8/2021 | Botella et al. |
| 11,111,266 | B2 | 9/2021 | Salituro et al. |
| 11,149,054 | B2 | 10/2021 | Salituro et al. |
| 2004/0048838 | A1 | 3/2004 | Gronvald et al. |
| 2005/0101573 | A1 | 5/2005 | Faarup et al. |
| 2006/0142241 | A1 | 6/2006 | Yoo |
| 2006/0199790 | A1 | 9/2006 | Baulieu et al. |
| 2007/0032464 | A1 | 2/2007 | Lia et al. |
| 2008/0193423 | A1 | 8/2008 | Brunton et al. |
| 2008/0269183 | A1 | 10/2008 | Mellon et al. |
| 2008/0319026 | A1 | 12/2008 | Gant et al. |
| 2010/0034781 | A1 | 2/2010 | Parhami et al. |
| 2010/0087411 | A1 | 4/2010 | Barraclough et al. |
| 2011/0112077 | A1 | 5/2011 | Kuduk et al. |
| 2011/0160223 | A1 | 6/2011 | Dingledine et al. |
| 2011/0190249 | A1 | 8/2011 | Rees et al. |
| 2012/0035156 | A1 | 2/2012 | Alberati et al. |
| 2012/0040916 | A1 | 2/2012 | Moon et al. |
| 2012/0041016 | A1 | 2/2012 | Frincke |
| 2012/0115169 | A1 | 5/2012 | Mullenix et al. |
| 2013/0210792 | A1 | 8/2013 | Song et al. |
| 2014/0045943 | A1 | 2/2014 | Khan et al. |
| 2014/0148412 | A1 | 5/2014 | Hogenkamp |
| 2014/0235600 | A1 | 8/2014 | Covey et al. |
| 2014/0335050 | A1 | 11/2014 | Haggerty et al. |
| 2015/0158903 | A1 | 6/2015 | Upasani |
| 2015/0291654 | A1 | 10/2015 | Upasani et al. |
| 2015/0376225 | A1 | 12/2015 | Dugar et al. |
| 2016/0022701 | A1 | 1/2016 | Reddy et al. |
| 2016/0031930 | A1 | 2/2016 | Botella et al. |
| 2017/0247405 | A1 | 8/2017 | Harrison et al. |
| 2017/0304321 | A1 | 10/2017 | Quirk et al. |
| 2017/0305960 | A1 | 10/2017 | Botella et al. |
| 2018/0194797 | A1 | 7/2018 | Salituro et al. |
| 2018/0200267 | A1 | 7/2018 | Salituro et al. |
| 2018/0201643 | A1 | 7/2018 | Salituro et al. |
| 2018/0237470 | A1 | 8/2018 | Botella et al. |
| 2018/0362573 | A1 | 12/2018 | Upasani et al. |
| 2018/0371009 | A1 | 12/2018 | Pellicciari et al. |
| 2019/0125764 | A1 | 5/2019 | Salituro et al. |
| 2019/0127414 | A1 | 5/2019 | Botella et al. |
| 2019/0135854 | A1 | 5/2019 | Harrison et al. |
| 2019/0160078 | A1 | 5/2019 | Masuoka et al. |
| 2019/0233465 | A1 | 8/2019 | Robichaud et al. |
| 2019/0248829 | A1 | 8/2019 | Salituro et al. |
| 2019/0359646 | A1 | 11/2019 | Botella et al. |
| 2020/0002371 | A1 | 1/2020 | Salituro et al. |
| 2020/0024300 | A1 | 1/2020 | Salituro et al. |
| 2020/0123195 | A1 | 4/2020 | Salituro et al. |
| 2021/0040138 | A1 | 2/2021 | Harrison et al. |
| 2021/0101925 | A1 | 4/2021 | Salituro et al. |
| 2021/0145848 | A1 | 5/2021 | Salituro et al. |
| 2021/0147468 | A1 | 5/2021 | Salituro et al. |
| 2021/0147470 | A1 | 5/2021 | Upasani et al. |
| 2021/0171567 | A1 | 6/2021 | Botella et al. |
| 2021/0380631 | A1 | 12/2021 | Salituro et al. |
| 2022/0081465 | A1 | 3/2022 | Salituro et al. |
| 2023/0047157 | A1 | 2/2023 | Salituro et al. |
| 2023/0132707 | A1 | 5/2023 | Botella et al. |

FOREIGN PATENT DOCUMENTS

| | | |
|---|---|---|
| FR | 2850023 | 7/2004 |
| GB | 1564806 | 4/1980 |
| JP | 50140435 | 11/1975 |
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 08268917 | 10/1996 |
| JP | 09328498 | 12/1997 |
| JP | H11509844 A | 8/1999 |
| JP | 2005508368 | 3/2005 |
| JP | 2009545535 | 12/2009 |
| RU | 2194712 | 12/2002 |
| RU | 2458065 C2 | 8/2012 |
| WO | WO1980002562 | 11/1980 |
| WO | WO1994027608 | 12/1994 |
| WO | WO1995002409 | 1/1995 |
| WO | WO1995021617 | 8/1995 |
| WO | WO1996012705 | 5/1996 |
| WO | WO1996016076 | 5/1996 |
| WO | WO1996040043 | 12/1996 |
| WO | WO1996040151 | 12/1996 |
| WO | WO1997000884 | 1/1997 |
| WO | WO1997003677 | 2/1997 |
| WO | WO1997042215 | 11/1997 |
| WO | WO1998005337 | 2/1998 |
| WO | WO1999058497 | 11/1999 |
| WO | WO2000068246 | 11/2000 |
| WO | WO2001049703 | 7/2001 |
| WO | WO2002011708 | 2/2002 |
| WO | WO2002053577 | 7/2002 |
| WO | WO2002079221 | 10/2002 |
| WO | WO2002090375 | 11/2002 |
| WO | WO2003039480 | 5/2003 |
| WO | WO2003049685 | 6/2003 |
| WO | WO2003082893 | 10/2003 |
| WO | WO2004055201 | 7/2004 |
| WO | WO2005079810 | 9/2005 |
| WO | WO2008041003 | 4/2008 |
| WO | WO2008063128 | 5/2008 |
| WO | WO2009001097 | 12/2008 |
| WO | WO2009059961 | 5/2009 |
| WO | WO2009073186 | 6/2009 |
| WO | WO2009090063 | 7/2009 |
| WO | WO2010075282 | 7/2010 |
| WO | WO2010088414 | 8/2010 |
| WO | WO2011014661 | 2/2011 |
| WO | WO2011028794 | 3/2011 |
| WO | WO2011067501 | 6/2011 |
| WO | WO2012064501 | 5/2012 |
| WO | WO2012142039 | 10/2012 |
| WO | WO2013019711 | 2/2013 |
| WO | WO2013036835 | 3/2013 |
| WO | WO2013054822 | 4/2013 |
| WO | WO2013056181 | 4/2013 |
| WO | WO2013163455 | 10/2013 |
| WO | WO2014025942 | 2/2014 |
| WO | WO2014115167 | 7/2014 |
| WO | WO2014120786 | 8/2014 |
| WO | WO2014160441 | 10/2014 |
| WO | WO2014160480 | 10/2014 |
| WO | WO2015048316 | 4/2015 |
| WO | WO2015195967 | 12/2015 |
| WO | WO2016007762 | 1/2016 |
| WO | WO2016057713 | 4/2016 |
| WO | WO2017007832 | 1/2017 |
| WO | WO2017007836 | 1/2017 |
| WO | WO2017007840 | 1/2017 |
| WO | WO2017037465 | 3/2017 |
| WO | WO2018064649 | 4/2018 |
| WO | WO2018075698 | 4/2018 |
| WO | WO2018075699 | 4/2018 |
| WO | WO2018170336 | 9/2018 |

OTHER PUBLICATIONS

Solomon et al., "Plasma levels of 24S-hydroxycholesterol reflect brain volumes in patients without objective cognitive impairment but not in those with Alzheimer's disease," Neuroscience Letters 462(1): 89-93 (2009).

U.S. Appl. No. 16/902,730, filed Jun. 16, 2020, Boyd L. Harrison et al., Pending.

U.S. Appl. No. 17/386,364, filed Jul. 27, 2021, Francesco G. Salituro et al., Pending.

(56) References Cited

OTHER PUBLICATIONS

U.S. Appl. No. 17/947,844, filed Sep. 19, 2022, Michael C. Quirk, Pending.
U.S. Appl. No. 18/106,073, filed Feb. 6, 2023, Francesco G. Salituro, Pending.
U.S. Appl. No. 15/517,886, filed Apr. 7, 2017, Michael C. Quirk et al., Pending.
U.S. Appl. No. 16/879,460, filed May 20, 2020, Francesco G. Salituro et al., Pending.
U.S. Appl. No. 16/930,047, filed Jul. 15, 2020, Gabriel Martinez Botella et al., Pending.
U.S. Appl. No. 16/938,348, filed Jul. 24, 2020, James J. Doherty, Pending.
U.S. Appl. No. 16/942,235, filed Jul. 29, 2020, Ravindra B. Upasani et al., Pending.
U.S. Appl. No. 16/943,649, filed Jul. 30, 2020, Francesco G. Salituro et al., Allowed.
U.S. Appl. No. 16/930,047, filed Jul. 15, 2020, Gabriel Martinez Botella et al., Allowed.
U.S. Appl. No. 16/943,649, filed Jul. 30, 2020, Francesco G. Salituro et al., Pending.
Berge et al., "Pharmaceutical salts," Journal of Pharmaceutical Sciences, 66(1):1-19 (1977).
Bjorkhem et al., "Oxysterols in the circulation of patients with the Smith-Lemli-Opitz syndrome: abnormal levels of 24S—and 27-hydroxycholesterol," Journal of Lipid Research, 42(3):366-371 (2001).
Bukelis et al., "Smith-Lemli-Opitz syndrome and autism spectrum disorder," American Journal of Psychiatry, 164(11):1655-1661 (2007).
Cais et al., "Temperature dependence of NRI/NR2B NMDA receptor channels," Neuroscience, 151(2):428-438 (2008).
Cancer [online], [retrieved on Jul. 6, 2007]. Retrieved from the internet, URL http://www.nlm.nih.gov/medlineplus/ cancer.html> (11 pages).
Chen et al., "The chemical biology of clinically tolerated NMDA receptor antagonists," Journal of Neurochemistry, 97(6):1611-1626 (2006).
Citraro et al., "Effects of some neurosteroids injected into some brain areas of WAG/Rij rats, an animal model of generalized absence epilepsy," Neuropharmacology, 50(8):1059-1071 (2006).
Collingridge et al., "The NMDA receptor as a target for cognitive enhancement," Neuropharmacology, 64:13-26 (2013).
Connick et al., "Program No. 613 1/B86," 2009 Neuroscience Meeting Planner, Chicago, IL: Society for Neuroscience (2009) (2 pages).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).
Corman et al., "Structure-activity relationships for side chain oxy sterol agonists of the hedgehog signaling pathway," ACS Medicinal Chemistry Letters, 3(10):828-833 (2012).
Costa et al., "A novel family of negative and positive allosteric modulators of NMDA receptors," Journal of Pharmacology and Experimental Therapeutics, 335(3):614-21 (2010).
Cross et al., "Steroids CCLXXIN[1]. Biologically-active labile ethers IV[2]. The synthesis of 22-oxa-25-azacholesterol and related compounds," Steroids, 5(5):585-598 (1965).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Dayal et al., "Stereospecific synthesis of 3 beta-hydroxylated bile alcohols," Journal of Lipid Research, 25(6):646-650 (1984).
Deng et al., "Fluoro analogs of bioactive oxy-steroids: Synthesis of an EBI2 agonist with enhanced metabolic stability," Bioorganic and Medicinal Chemistry Letters, 26:4888-4891 (2016).

Domasio, "Alzheimer's disease and related dementias," Cecil Textbook of Medicine, 20th edition, 2:1992-1996 (1996).
Elbarbry et al., "Cyclosporine-induced changes in drug metabolizing enzymes in hyperlipemic rabbit kidneys could explain its toxicity," Xenobiotica, 40(11):772-781 (2010).
European Search Partial Supplementary Report for European Application No. 14775126.7, dated Sep. 14, 2016 (7 pages).
Extended European Search Report for Application No. 15809462.3, dated Nov. 29, 2017 (8 pages).
Extended European Search Report for Application No. 16821920.2, dated Jan. 31, 2019 (12 pages).
Extended European Search Report for Application No. 16821924.4, dated Jan. 31, 2019 (12 pages).
Extended European Search Report for Application No. 16821926.9, dated Jan. 31, 2019 (10 pages).
Extended European Search Report for European Application No. 14774060.9, dated Aug. 17, 2016 (11 pages).
Extended European Search Report for European Application No. 14775126.7, Dec. 15, 2016 (6 pages).
Extended European Search Report for European Application No. 15849514.3, dated May 23, 2018 (7 pages).
FDA mulls drug to slow late-stage Alzheimer's [online] (cnn.com/health), [retrieved on Sep. 23, 2003]. Retrieved from the Internet, URL; http://www.cnn.com/2003/HEALTH/conditions/09/24/alzheimers.drug.ap/indexhtml> (2 pages).
Ferriz et al., "Prodrug Design of Phenolic Drugs", Current Pharmaceutical Designs, vol. 16, pp. 2033-2052 (2010).
Festa et al., "Exploitation of cholane scaffold for the discovery of potent and selective farnesoid X receptor (FXR) and G-protein coupled bile acid receptor 1 (GP-BAR$_1$) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Fukuto et al., "Determination of the Mechanism of Demethlenation of (methylenedioxy)phenyl compounds by cytochrome P450 using deuterium isotope effects," Journal of Medicinal Chemistry, 34(9):2871-2876 (1991).
Gee et al., "GABA-dependent modulation of the C1—ionophore by steroids in rat brain," European Journal of Pharmacology, 136(3):419-423 (1987).
Golub et al., "Molecular classification of cancer: class discovery and class prediction by gene expression monitoring," Science, 286(5439):531-537 (1999).
Groden et al., "Determination of Fura-2 dissociation constants following adjustment of the apparent Ca-EGTA association constant for temperature and ionic strength," Cell Calcium, 12:(4)279-287 (1991).
Grynkiewicz et at., "A new generation of Ca2+ indicators with greatly improved fluorescence properties," Journal of Biological Chemistry, 260(6):3440-3345 (1985).
Gunatilaka et al., "Bioactive ergost-5-ene-3 beta, 7 alpha-diol derivatives from *Pseudobersama mossambicensis*," Journal of Natural Products, 55(11):1648-1654 (1992).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistiy, 50(23):4508-4514 (1985).
Hoffmeister et al., "Zur chemie des ecdysons, III: Vergleichende spektrometrische untersuchungen an a.b-ungesättigten steroidketonen," Chemische Berichte, 98(7):2361-2375 (1965).
Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs-from serendipity to rational design," Pharmacological Reviews, 63(3):750-771 (2011).

(56) References Cited

OTHER PUBLICATIONS

Iida et al., "An improved method for the capillary gas chromatographic derivatization of polyhydroxylated steroids having tert-hydroxyl groups," Analytical Sciences, 19(9):1317-1321 (2003).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jurman et al., "Visual identification of individual transfected cells for electrophysiology using antibody-coated beads," Biotechniques, 17(5):876-881 (1994).
Karaki et al., "Structure-activity relationship studies of Niemann-Pick type C1-like 1 (NPC1L1) ligands identified by screening assay monitoring pharmacological chaperone effect," Bioorganic and Medicinal Chemistry, 21(17):5297-5309 (2013).
Khripach et al., "Synthesis of (24S)-hydroxy-and (24S)-24,25-epoxycholesterol analogues, potential agonists of nuclear LXR receptors," Russian Journal of Bioorganic Chemistiy, 32(6):586-594 (2006).
Knoppert et al., "Position paper: Paediatric age categories to be used in differentiating between listing on a model essential medicines list for children," pp. 1-5 (2007).
Kurosawa et al., "Synthesis of 19-hydroxylated bile acids and identification of 3 alpha,7 alpha,12 alpha,19-tetrahydroxy-5 beta-cholan-24oic acid in human neonatal urine," Chemical and Pharmaceutical Bulletin, 43(9):1551-1557 (1995).
Lakhan et al., " NMDA receptor activity in neuropsychiatric disorders," Frontiers in Psychiatry, 4:1-7 (2013).
Lala et al., "Role of nitric oxide in tumor progression: Lessons from experimental tumors," Cancer and Metastasis Reviews, 17(1):91-106 (1998).
Layzer, "Section five-degenerative diseases of the nervous system," Cecil Textbook of Medicine, 20th edition, 2:2050-2057 (1996).
Leoni et al., "Oxysterols as biomarkers in neurodegenerative diseases," Chemistry and Physics of Lipids, 164(6):515-524 (2011).
Leoni et al., "Changes in human plasma levels of the brain specific oxysterol 24S-hydroxycholesterol during progression of multiple sclerosis," Neuroscience Letters, 331(3):163-166 (2002).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7alpha-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).
Lutjohann et al., "Cholesterol homeostasis in human brain: evidence for an age-dependent flux of 24S-hydroxycholesterol from the brain into the circulation," PNAS, 93(18):9799-804 (1996).
Luu et al., "Oxysterols: Old Tale, New Twists," Annual Review of Pharmacology and Toxicology, 56:447-467 (2016).
Madau et al, Program No. 613.2/B87. 2009 Neuroscience Meeting Planner. Chicago, IL: Society for Neuroscience (2009) (3 pages).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Meljon et al., "Analysis by liquid chromatography-mass spectrometry of sterols and oxysterols in brain of the newborn Dhcr7(Δ3-5/ T93M) mouse: a model of Smith-Lemli-Opitz syndrome," Biochemical Pharmacology, 86(1):43-55 (2013).
Monyer et al., "Heteromeric NMDA receptors: molecular and functional distinction of subtypes," Science, 256(5060):1217-1221 (1992).
Mourino et al., "Studies on vitamin D (calciferol) and its analogs. 15. 24-nor-1a,25-dihydroxyvitamin D3 and 24-nor-25¬hydroxy-5,6-trans-vitamin D3," Journal of Medicinal Chemistry, 21(10):1025-1029 (1978).

Nagano et al., "Chemistry and biochemistry of Chinese drugs. Part II. Hydroxylated sterols, cytotoxic towards cancerous cells: synthesis and testing," Journal of Chemical Research, 9:218 (1977).
Niemann-Pick overview [online] retrieved from the internet on Jul. 17, 2021 (URL: https://www.mayoclinic.org/diseases-conditions/niemann-pick/symptoms-causes/syc-20355887).
Niemann-Pick diagnosis-treatment [online] retrieved from the internet on Jul. 17, 2021 (URL: https://www.mayoclinic.org/diseases-conditions/niemann-pick/diagnosis-treatment/drc-20355890).
Olkkonen et al., "Oxysterols and their cellular effectors," Biomolecules, 2(1):76-103 (2012).
Park-Chung et al., "Distinct sites for inverse modulation of N-methyl-D-aspartate receptors by sulfated steroids," Molecular Pharmacology, 52(6): 1113-1123 (1997).
Paul et al., "The major brain cholesterol metabolite 24(S)-hydroxycholesterol is a potent allosteric modulator of N-methyl-D-aspartate receptors," The Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).
PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Jul. 17, 2017 (8 pages).
PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Nov. 12, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).
Pubchem, Cid 132021, Ergostan-3,24-diol, Mar. 5, 2018 (15 pages).
Pubchem, Cid 54083335, Schemb14961477, Nov. 8, 2016 (13 pages).

(56) References Cited

OTHER PUBLICATIONS

Pubchem, Cid 54160779, Schemb14961477, Nov. 8, 2016 (13 pages).
Pubchem, Cid 58455549, Schemb112198161, Nov. 8, 2016 (13 pages).
Pubchem, Cid 65094, 25-Hydroxycholesterol, Nov. 8, 2016 (17 pages).
Pubchem, Cid 66966798, Cholane-3alpha,24,-diol, Nov. 8, 2016 (11 pages).
Pubchem, Cid 70604305, Schemb11 1528874, Nov. 8, 2016 (13 pages).
Pubchem, Cid 71508953, Mar. 5, 2018 (13 pages).
Reddy, "Pharmacology of endogenous neuroactive steroids," Critical Reviews in Neurobiology, 15(3-4):197-234 (2013).
Registry (STN) [online] CAS Registration No. 1392266-35-1; 13392266-34-0; 1271523-00-2; 185138-08-3; 185138-00-5; 1851387-82-0; 66450-87-1 (2012).
Roh et al., "Neuroprotective effects of ginsenoside Rg3 against 24-OH-cholesterol-induced cytotoxicity in cortical neurons," Journal of Ginseng Research, 34(3):246-253 (2010).
Schmidt et al., "Inhibitory effect of oxygenated cholestan-3b-ol derivatives on the growth of *Mycobacterium tuberculosis*," Bioorganic & Medicinal Chemistry Letters, 23(22):6111-6113(2013).
Segal, "Pat hippocampal Neurons in Culture: Responses to Electrical and Chemical Stimuli," Journal of Neurophysiology, 50(6):1249-1264 (1983).
Sepe et al., "Total synthesis and pharmacological characterization of solomonsterol A, a potent marine pregnane-X-receptor agonist endowed with anti-inflammatory activity," Journal of Medicinal Chemistry, 54:4590-4599 (2011).
Stamp et al., "Plasma levels and therapeutic effect of 25-hydroxycholecalciferol in epileptic patients taking anticonvulsant drugs," British Medical Journal, 4(5831):9-12 (1972).
Stastna et al., "Synthesis of C3, C5, and C7 pregnane derivatives and their effect on NMDA receptor responses in cultured rat hippocampal neurons," Steroids, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics Part C: Seminars in Medical Genetics, 160C(4): 285-294 (2012).
Takahashi et al., "Stereochemistry of reduction of the C-24,25 double bond in the conversion of desmosterol into cholesterol," Tetrahedron Letters, 44(2):341-344 (2003).
Takano et al., "Simple synthesis of 3b,24-dihydroxychol-5-en-7-one by oxidative cleavage of the side chain of cholesterol," Chemistry Letters, 14(8):1265-1266 (1985).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron 33:2725-2736 (1977).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694(21):3452-3455 (2004).
Xiangdong et al., "Highly stereoselective synthesis of 24R,25—and 24S, 25-dihydroxysteroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yan et al., "Characterization of a synthetic steroid 24-keto-cholest-5-en-3b,19-diol as a neuroprotectant," CNS Neuroscience & Therapeutics, 21(6):486-495 (2015).
Yang et al., "New cytotoxic oxygenated sterols from marine bryozoan *Bugula neritina*," Natural Product Research, 25(16):1505-1511 (2011).
Zuliani et al., "Plasma 24S-hydroxycholesterol levels in elderly subjects with late onset Alzheimer's disease or vascular dementia: a case-control study," BMC Neurology, 11(121):1-8 (2011).
Zhou et al., "Properties of HERG channels stably expressed in HEK 293 cells studied at physiological temperature," Biophysical Journal, 74(1):230-241 (1998).
U.S. Appl. No. 14/343,603, filed Nov. 25, 2014, Ravindra B. Upasani et al., Abandoned.
U.S. Appl. No. 14/775,401, filed Sep. 11, 2015, Kiran Reddy et al., Abandoned.
U.S. Appl. No. 14/775,678, filed Sep. 12, 2015, Gabriel Martinez Botella et al., Abandoned.
U.S. Appl. No. 15/319,504, filed Dec. 16, 2016, Boyd L. Harrison et al., Issued.
U.S. Appl. No. 15/517,886, filed Apr. 7, 2017, Michael C. Quirk et al., Abandoned.
U.S. Appl. No. 15/588,305, filed May 5, 2017, Gabriel Martinez Botella et al., Abandoned.
U.S. Appl. No. 15/742,422, filed Jan. 5, 2018, Francesco G. Salituro et al., Issued.
U.S. Appl. No. 15/742,424, filed Jan. 5, 2018, Francesco G. Salituro et al., Issued.
U.S. Appl. No. 15/742,425, filed Jan. 5, 2018, Francesco G. Salituro et al., Issued.
U.S. Appl. No. 15/917,263, filed Mar. 9, 2018, Gabriel Martinez Botella et al., Issued.
U.S. Appl. No. 15/917,272, filed Mar. 9, 2018, Gabriel Martinez Botella et al., Abandoned.
U.S. Appl. No. 16/028,790, filed Jul. 6, 2018, Boyd L. Harrison et al., Issued.
U.S. Appl. No. 16/089,896, filed Sep. 28, 2018, Albert Jean Robichaud et al., Abandoned.
U.S. Appl. No. 16/099,122, filed Nov. 5, 2018, Gabriel Martinez Botella et al., Issued.
U.S. Appl. No. 16/114,791, filed Aug. 28, 2018, Ravindra B. Upasani et al., Issued.
U.S. Appl. No. 16/227,013, filed Dec. 20, 2018, Gabriel Martinez Botella et al., Issued.
U.S. Appl. No. 16/227,099, filed Dec. 20, 2018, Francesco G. Salituro et al., Issued.
U.S. Appl. No. 16/315,250, filed Jan. 4, 2019, Francesco G. Salituro et al., Issued.
U.S. Appl. No. 16/338,315, filed Mar. 29, 2019, Francesco G. Salituro et al., Issued.
U.S. Appl. No. 16/343,235, filed Apr. 18, 2019, Francesco G. Salituro et al., Issued.
U.S. Appl. No. 16/343,238, filed Apr. 18, 2019, Francesco G. Salituro et al., Issued.
U.S. Appl. No. 16/879,460, filed May 20, 2020, Francesco G. Salituro et al., Abandoned.
U.S. Appl. No. 16/902,730, filed Jun. 16, 2020, Boyd L. Harrison et al., Abandoned.
U.S. Appl. No. 16/930,047, filed Jul. 15, 2020, Gabriel Martinez Botella et al., Issued.
U.S. Appl. No. 16/938,348, filed Jul. 24, 2020, James J. Doherty, Abandoned.
U.S. Appl. No. 16/942,235, filed Jul. 29, 2020, Ravindra B. Upasani et al., Abandoned.

(56) References Cited

OTHER PUBLICATIONS

U.S. Appl. No. 16/942,245, filed Jul. 29, 2020, Francesco G. Salituro et al., Pending.
U.S. Appl. No. 16/943,649, filed Jul. 30, 2020, Francesco G. Salituro et al., Issued.
U.S. Appl. No. 17/242,860, filed Apr. 28, 2021, Albert Jean Robichaud et al., Pending.
U.S. Appl. No. 17/381,829, filed Jul. 21, 2021, Gabriel Martinez Botella et al., Pending.
U.S. Appl. No. 17/386,364, filed Jul. 27, 2021, Francesco G. Salituro et al., Issued.
U.S. Appl. No. 17/395,155, filed Aug. 5, 2021, Francesco G. Salituro et al., Pending.
U.S. Appl. No. 17/476,153, filed Sep. 15, 2021, Francesco G. Salituro et al., Pending.
U.S. Appl. No. 17/707,303, filed Mar. 29, 2022, Ravindra B. Upasani et al., Pending.
U.S. Appl. No. 17/749,976, filed May 20, 2022, Francesco G. Salituro et al., Pending.
U.S. Appl. No. 17/860,816, filed Jul. 8, 2022, Gabriel Martinez Botella et al., Pending.
U.S. Appl. No. 17/947,844, filed Sep. 19, 2022, Michael C. Quirk et al., Pending.
U.S. Appl. No. 18/077,031, filed Dec. 7, 2022, James J. Doherty, Pending.
U.S. Appl. No. 18/106,073, filed Feb. 6, 2023, Francesco G. Salituro et al., Pending.
U.S. Appl. No. 18/116,557, filed Mar. 2, 2023, Boyd L. Harrison et al., Pending.
Berardelli et al., "EFNS/MDS-ES/ENS [corrected] recommendations for the diagnosis of Parkinson's disease," European Journal of Neurology, 20(1):16-34 (2013).
Dubois et al., "Research criteria for the diagnosis of Alzheimer's disease: revising the NINCDS-ADRDA criteria," Lancet Neurology, 6(8):734-736 (2007).
Dubois et al., "Revising the definition of Alzheimer's disease: a new lexicon," Lancet Neurology, 9(11):1118-27 (2010).
Jack et al., "Hypothetical model of dynamic biomarkers of the Alzheimer's pathological cascade," Lancet Neurology, 9(1):119-128 (2010).
Jack et al., "Introduction to the recommendations from the National Institute on Aging-Alzheimer's Association workgroups on diagnostic guidelines for Alzheimer's disease," Alzheimer's & Dementia, 7(3):257-62 (2011).
Litvan et al., "Diagnostic criteria for mild cognitive impairment in Parkinson's disease: Movement Disorder Society Task Force guidelines," Movement Disorders, 27(3):349-56 (2012).
Litvan et al., "MDS Task Force on mild cognitive impairment in Parkinson's disease: critical review of PD-MCI," Movement Disorders, 26(10):1814-1824 (2011).
Nagasaka et al. "Oxysterol changes along with cholesterol and vitamin D changes in adult phenylketonuric patients diagnosed by newborn mass-screening," Clinica Chimica Acta, 416: 54-59 (2013).
Nasreddine et al., "The Montreal Cognitive Assessment, MoCA: a brief screening tool for mild cognitive impairment," Journal of the American Geriatrics Society, 53(4):695-699 (2005).

OXYSTEROLS AND METHODS OF USE THEREOF

RELATED APPLICATIONS

This application is a continuation of U.S. patent application Ser. No. 15/742,424, filed Jan. 5, 2018, which is a U.S. National Phase Application under 35 U.S.C. § 371 of International Application PCT/US2016/041175, filed Jul. 6, 2016, which claims priority to and the benefit of U.S. Provisional Application No. 62/189,068, filed Jul. 6, 2015, and U.S. Provisional Application No. 62/332,931, filed May 6, 2016. The contents of each of the foregoing applications are incorporated herein by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit Ca2+ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are derived from cholesterol and have been shown to potently and selectively modulate NMDA receptor function. New and improved oxysterols are needed that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols. Further provided are pharmaceutical compositions comprising the compounds of the present invention, and methods of their use and treatment.

In one aspect, provided herein are compounds according to Formula (I):

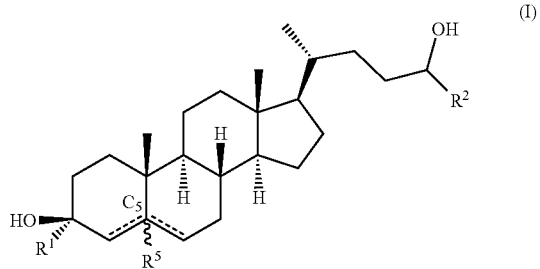

or a pharmaceutically acceptable salt thereof, wherein: $R^1$ is hydrogen or $C_{1-6}$ alkyl; $R^2$ is $C_{1-6}$ alkyl, carbocyclyl, or heterocyclyl; $R^5$ is absent or hydrogen; and ═ represents a single or double bond, wherein when one ═ is a double bond, the other ═ is a single bond and $R^5$ is absent.

In some embodiments, $R^1$ is hydrogen.

In some embodiments, $R^1$ is $C_{1-6}$ alkyl. In some embodiments, $R^1$ is substituted $C_{1-6}$ alkyl. In some embodiments, $R^1$ is unsubstituted $C_{1-6}$ alkyl. In some embodiments, $R^1$ is methyl (e.g., —$CH_3$, —$CF_3$ or —$CH_2OCH_3$), ethyl, or isopropyl. In some embodiments, $R^1$ is methyl (e.g., —$CH_3$) or ethyl (e.g., —$CH_2CH_3$).

In some embodiments, $R^2$ is $C_{1-6}$ alkyl or carbocyclyl. In some embodiments, $R^2$ is substituted $C_{1-6}$ alkyl. In some embodiments, $R^2$ is unsubstituted $C_{1-6}$ alkyl. In some embodiments, $R^2$ is $C_{1-4}$ alkyl. In some embodiments, $R^2$ is substituted $C_{1-4}$ alkyl. In some embodiments, $R^2$ is unsubstituted $C_{1-4}$ alkyl. In some embodiments, $R^2$ is $C_{1-3}$ alkyl. In some embodiments, $R^2$ is substituted $C_{1-3}$ alkyl. In some embodiments, $R^2$ is unsubstituted $C_{1-3}$ alkyl. In some embodiments, $R^2$ is methyl, ethyl (e.g., —$CH_2CH_3$, —$CH_2CF_3$, —$CH(CH_3)(CF_3)$), isopropyl, tertbutyl, or cyclopropyl. In some embodiments, $R^2$ is haloalkyl. In some embodiments, $R^2$ is —$CH_2CF_3$ or —$CH(CH_3)(CF_3)$.

In some embodiments, $R^1$ and $R^2$ are $C_{1-6}$ alkyl. In some embodiments, $R^1$ is $C_{1-6}$ alkyl and $R^2$ is $C_{1-6}$ alkyl, carbocyclyl, or heterocyclyl. In some embodiments, $R^1$ is methyl or ethyl, and $R^2$ is unsubstituted or substituted $C_{1-6}$ alkyl (e.g., haloalkyl). In some embodiments, $R^1$ is methyl or ethyl, and $R^2$ is carbocyclyl or heterocyclyl.

In some embodiments, ═ represents a single bond.

In some embodiments, the compound of Formula (I) is a compound of Formula (I-A) or Formula (I-B):

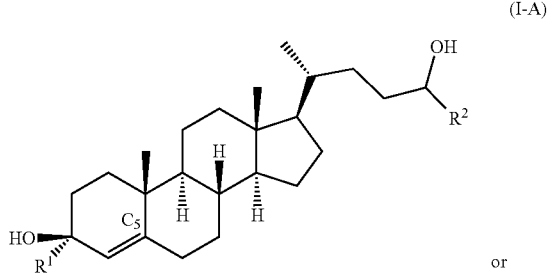

or (I-B)

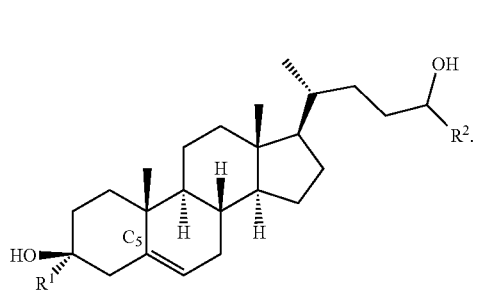

In some embodiments, the compound of Formula (I) is a compound of Formula (I-B-i) or Formula (I-B-ii):

(I-B-i)

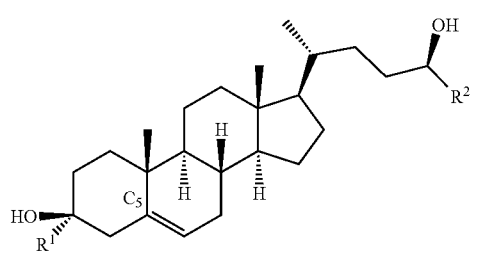

or (I-B-ii)

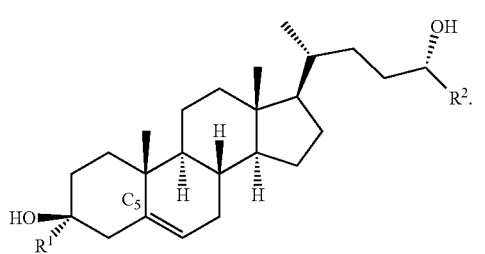

In some embodiments, the compound of Formula (I) is a compound of Formula (I-C):

(I-C)

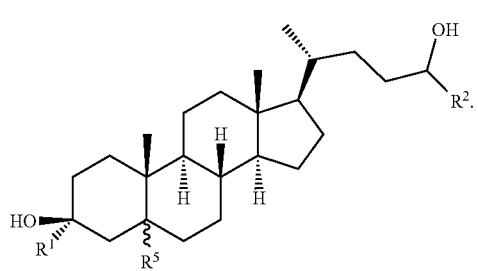

In some embodiments, the compound of Formula (I-C) is a compound of Formula (I-C-i) or (I-C-ii):

(I-C-i)

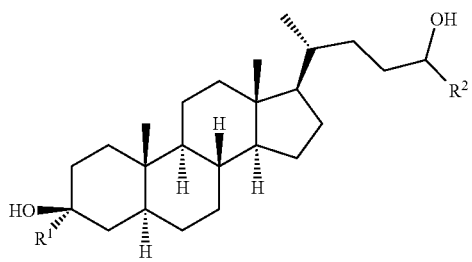

or (I-C-ii)

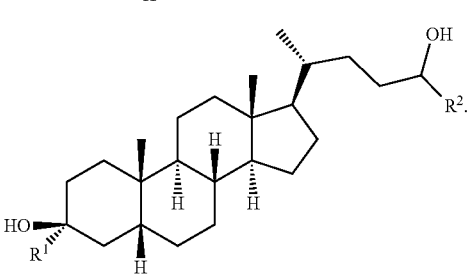

In some embodiments, the compound of Formula (I-C-i) is a compound of Formula (I-C-i-a) or (I-C-i-b):

(I-C-i-a)

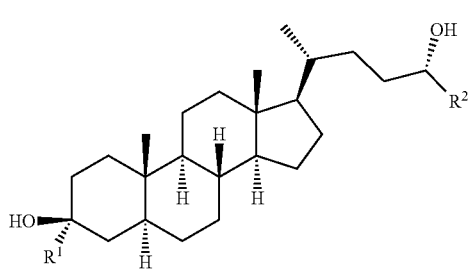

or (I-C-i-b)

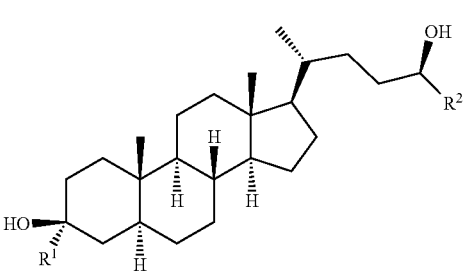

In some embodiments, the compound of Formula (I-C-ii) is a compound of Formula (I-C-ii-a) or (I-C-ii-b):

(I-C-ii-a)

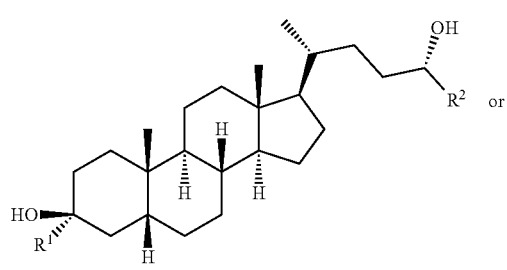

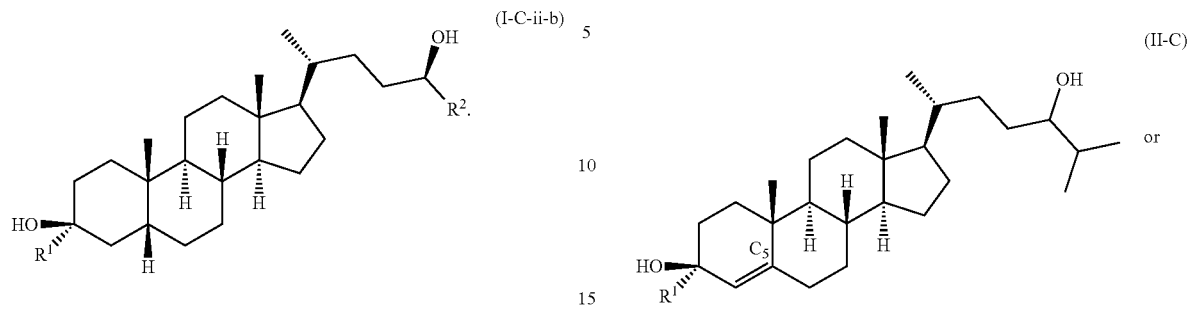
(I-C-ii-b)

In some embodiments, $R^2$ is $C_{1-6}$ alkyl. In some embodiments, $R^2$ is substituted $C_{1-6}$ alkyl. In some embodiments, $R^2$ is $C_{1-6}$ haloalkyl.

In some embodiments, the compound of Formula (I) is a compound of Formula (II):

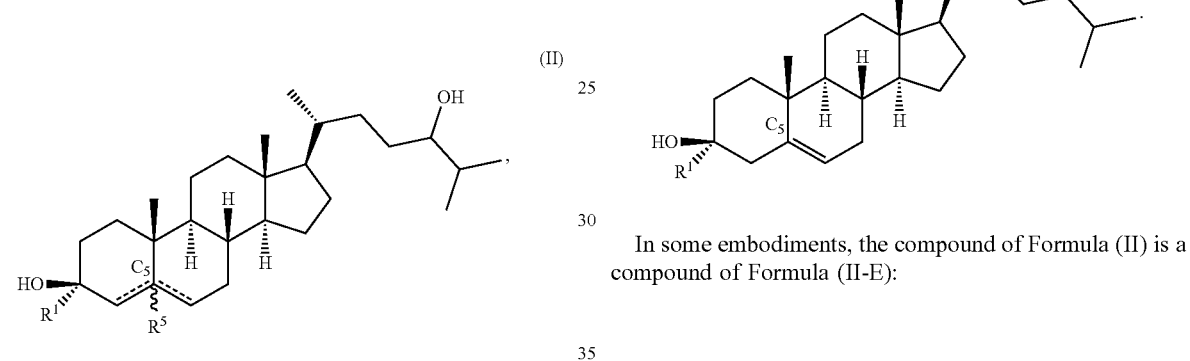
(II)

or a pharmaceutically acceptable salt thereof.

In some embodiments, the compound of Formula (II) is a compound of Formula (II-A) or Formula (II-B):

(II-A)

(II-B)

In some embodiments, the compound of Formula (II) is a compound of Formula (II-C) or Formula (II-D):

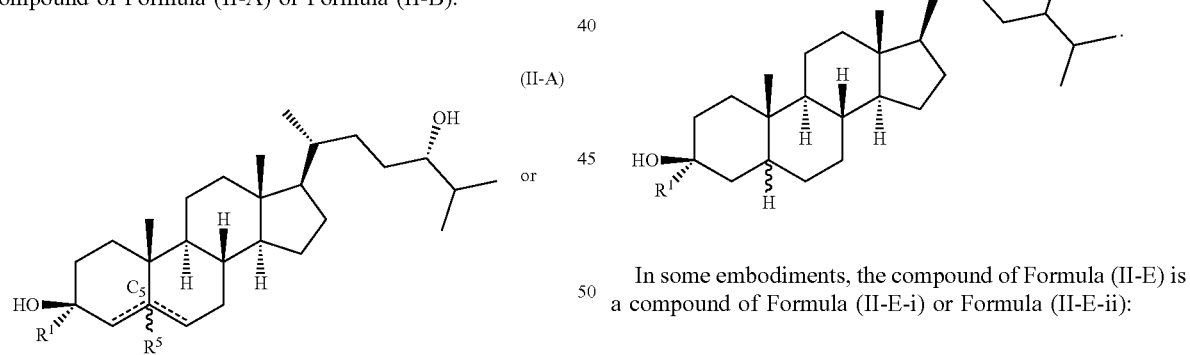
(II-C)

(II-D)

In some embodiments, the compound of Formula (II) is a compound of Formula (II-E):

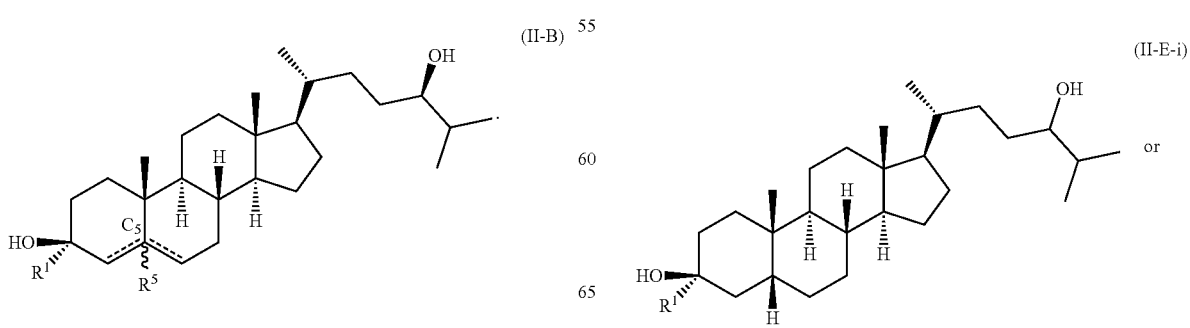
(II-E)

In some embodiments, the compound of Formula (II-E) is a compound of Formula (II-E-i) or Formula (II-E-ii):

(II-E-i)

(II-E-ii)

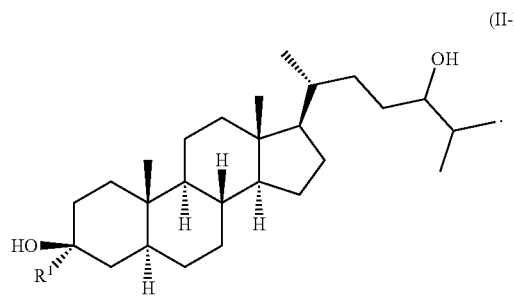

In some embodiments, the compound of Formula (II-E-i) is a compound of Formula (II-E-i-a) or Formula (II-E-i-b):

(II-E-i-a)

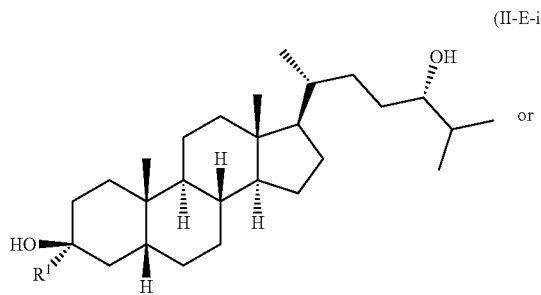

or (II-E-i-b)

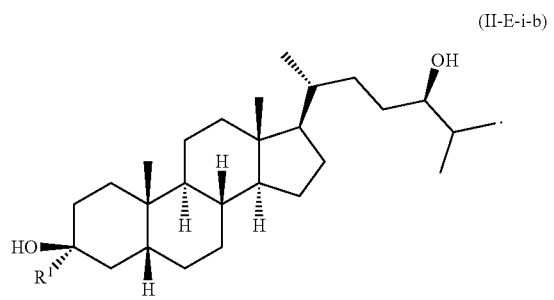

In some embodiments, the compound of Formula (II-E-ii) is a compound of Formula (II-E-ii-a) or Formula (II-E-ii-b):

(II-E-ii-a)

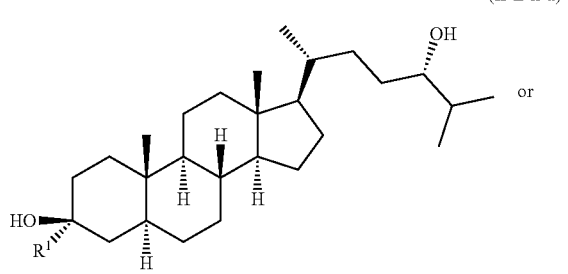

or (II-E-ii-b)

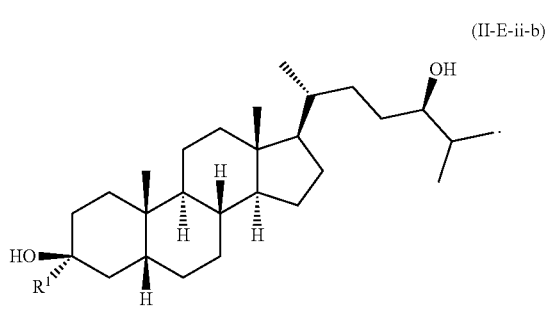

In some embodiments, the compound of Formula (I) is a compound of Formula (VII):

(VII)

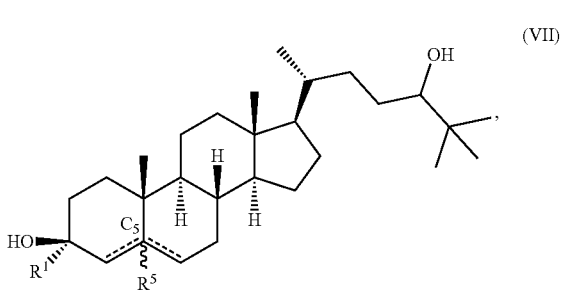

or a pharmaceutically acceptable salt thereof.

In some embodiments, the compound of Formula (VII) is a compound of Formula (VII-A) or Formula (VII-B):

(VII-A)

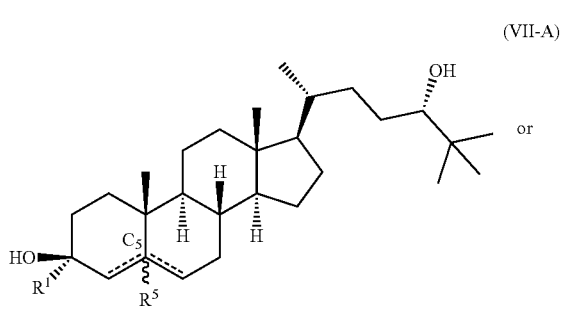

or (VII-B)

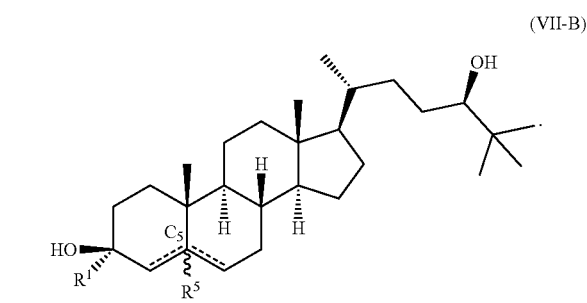

In some embodiments, the compound of Formula (VII) is a compound of Formula (VII-C) or Formula (VII-D):

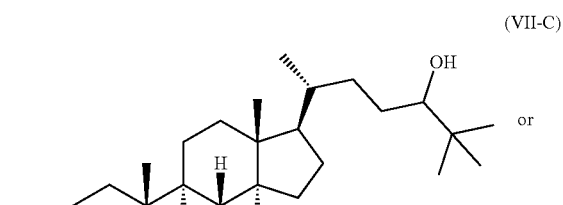
(VII-C)

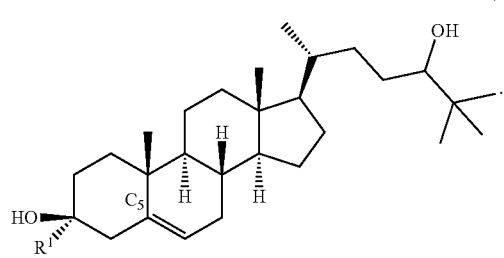
(VII-D)

In some embodiments, the compound of Formula (VII) is a compound of Formula (VII-E):

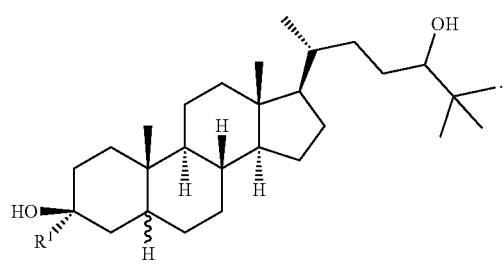
(VII-E)

In some embodiments, the compound of Formula (VII-E) is a compound of Formula (VII-E-i) or Formula (VII-E-ii):

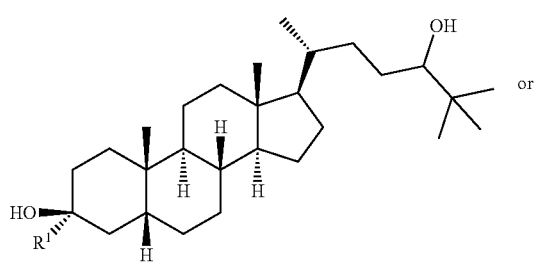
(VII-E-i)

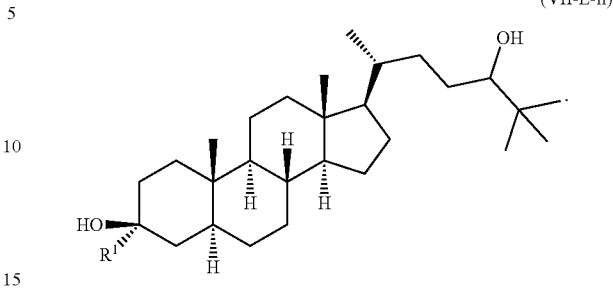
(VII-E-ii)

In some embodiments, the compound of Formula (VII-E-i) is a compound of Formula (VII-E-i-a) or Formula (VII-E-i-b):

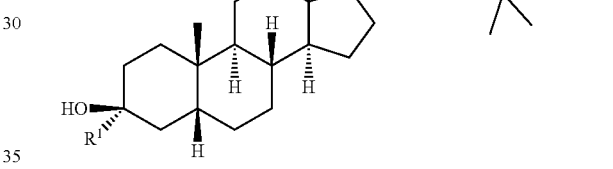
(VII-E-i-a)

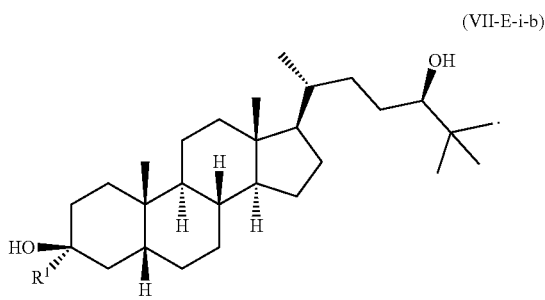
(VII-E-i-b)

In some embodiments, the compound of Formula (VII-E-ii) is a compound of Formula (VII-E-ii-a) or Formula (VII-E-ii-b):

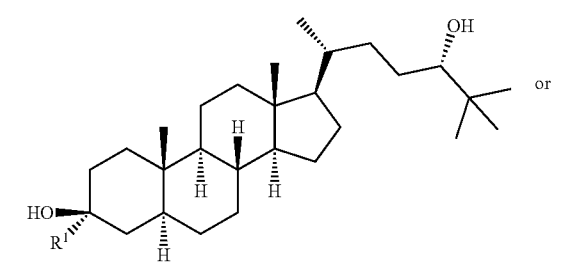
(VII-E-ii-a)

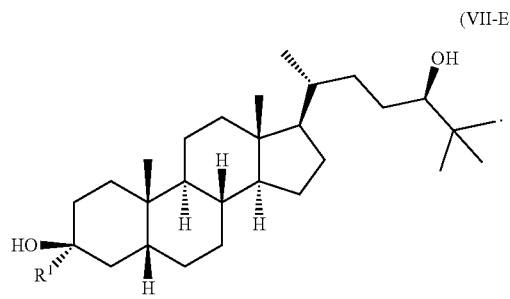
(VII-E-ii-b)

In some embodiments, the compound of Formula (I) is a compound of Formula (III):

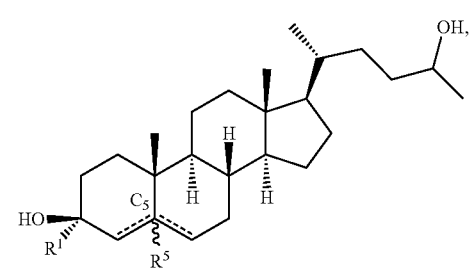
(III)

or a pharmaceutically acceptable salt thereof.

In some embodiments, the compound of Formula (III) is a compound of Formula (III-A) or Formula (III-B):

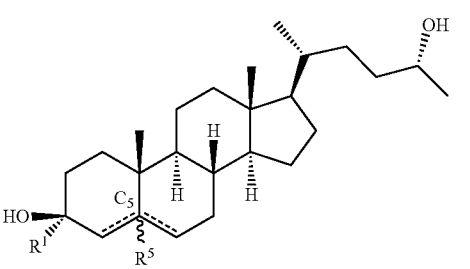
(III-A)

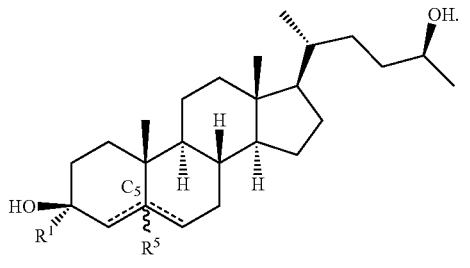
(III-B)

In some embodiments, the compound of Formula (I) is a compound of Formula (IV):

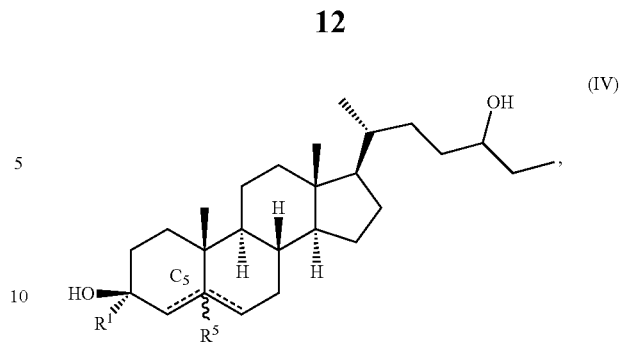
(IV)

or a pharmaceutically acceptable salt thereof.

In some embodiments, the compound of Formula (IV) is a compound of Formula (IV-A) or Formula (IV-B):

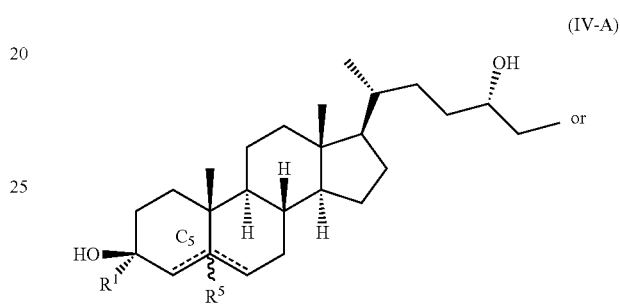
(IV-A)

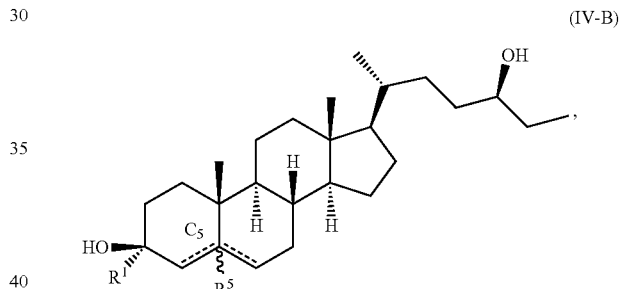
(IV-B)

or a pharmaceutically acceptable salt thereof.

In some embodiments, $R^2$ is carbocyclyl or heterocyclyl. In some embodiments, $R^2$ is carbocyclyl (e.g., cyclopropyl, cyclobutyl, cyclopentyl, cyclohexyl).

In some embodiments, $R^2$ is heterocyclyl. In some embodiments, $R^2$ is an oxygen-containing heterocycle (e.g., tetrahydropyran).

In some embodiments, the compound of Formula (I) is a compound of Formula (V):

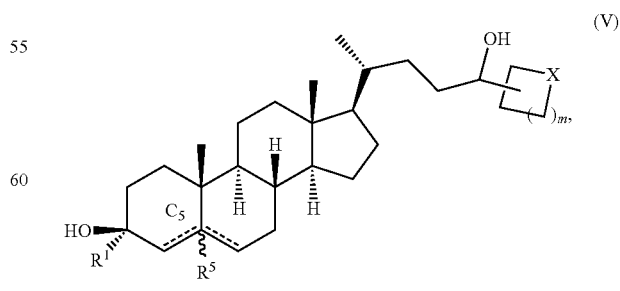
(V)

or a pharmaceutically acceptable salt thereof, wherein X is —$CH_2$—, —O—, —S—, or —$NR^4$—, and m is an integer selected from 0, 1, 2, 3, 4, or 5; wherein $R^A$ is hydrogen, alkyl, —C(O)$R^C$, —C(O)N($R^C$)$_2$, or —SO$_2$N($R^C$)$_2$; and each $R^C$ is independently hydrogen, alkyl, aryl, or heteroaryl.

In some embodiments, X is —CH$_2$—, —O—, —S—, or —NH—.

In some embodiments, the compound of Formula (V) is a compound of Formula (V-A-i) or Formula (V-A-ii):

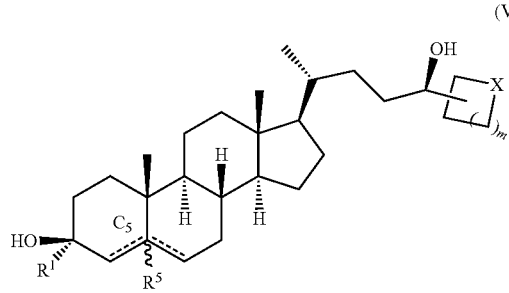

(V-A-i)

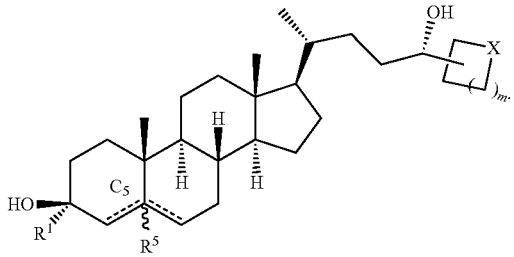

(V-A-ii)

In some embodiments, the compound of Formula (V) is a compound of Formula (V-B):

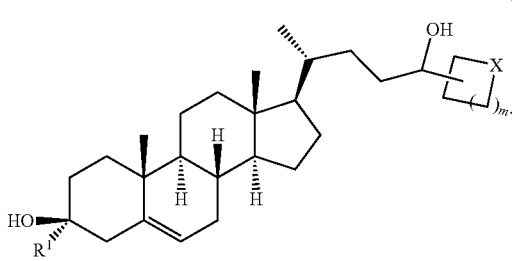

(V-B)

In some embodiments, X is —CH$_2$—.
In some embodiments, X is —O—.
In some embodiments, m is 0, 1, 2, or 3.
In some embodiments, the compound of Formula (V) is a compound of Formula (V-B-i):

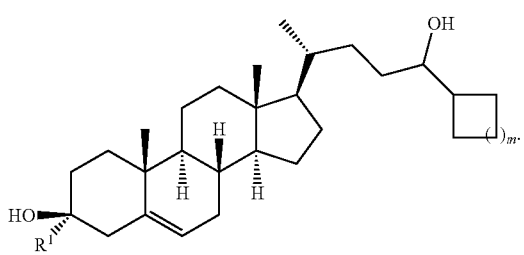

(V-B-i)

or a pharmaceutically acceptable salt thereof.

In some embodiments, the compound of Formula (V) is a compound of Formula (V-C):

(V-C)

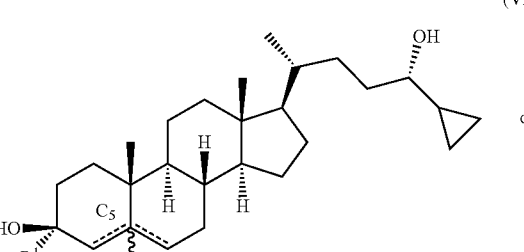

In some embodiments, the compound of Formula (I) is a compound of Formula (VI):

(VI)

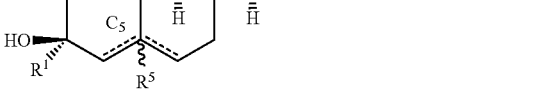

or a pharmaceutically acceptable salt thereof.

In some embodiments, the compound of Formula (I) is a compound of Formula (VI-A) or Formula (VI-B):

(VI-A)

or

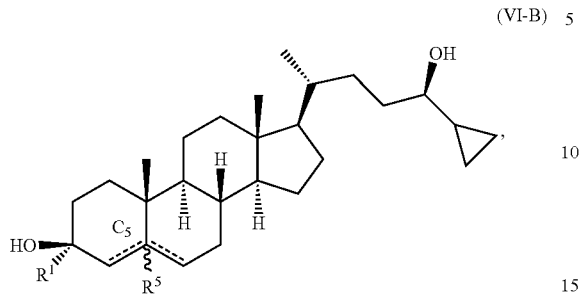

(VI-B)

or a pharmaceutically acceptable salt thereof.

In some embodiments, $R^1$ is $C_{1-6}$ alkyl. In some embodiments, $R^1$ is methyl (e.g., —$CH_3$, —$CF_3$ or —$CH_2OCH_3$), ethyl, or isopropyl. In some embodiments, $R^1$ is methyl, ethyl or isopropyl. In some embodiments, $R^1$ is methyl (e.g., —$CH_3$). In some embodiments, $R^1$ is ethyl (e.g., —$CH_2CH_3$).

In some embodiments, the compound of Formula (I) is selected from:

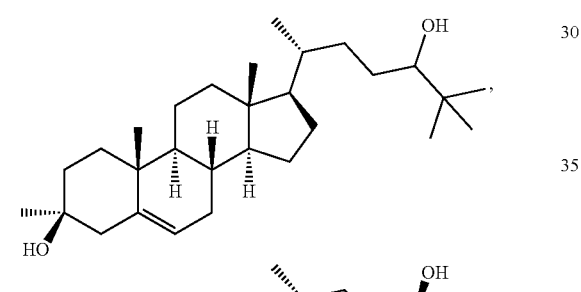

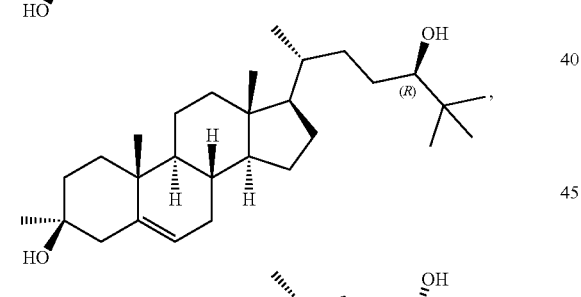

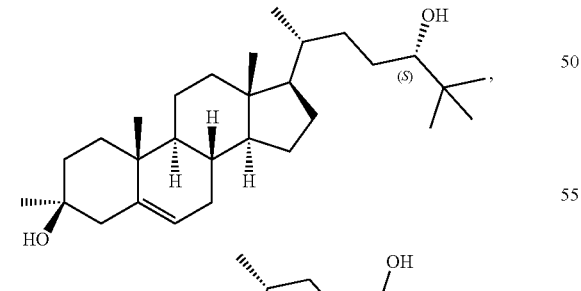

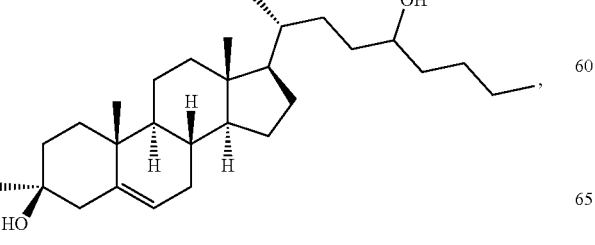

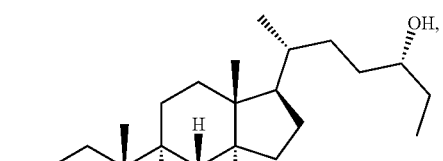

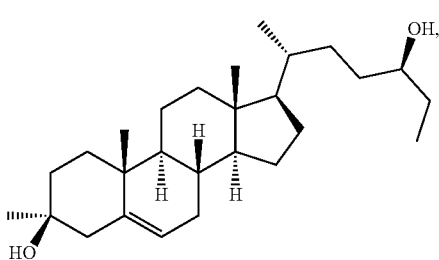

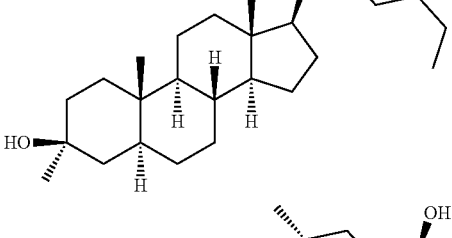

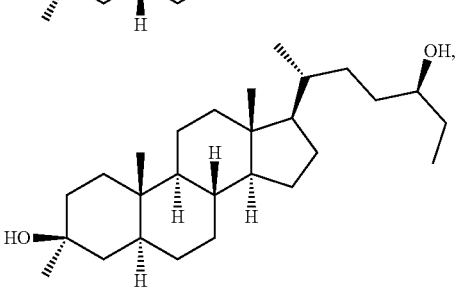

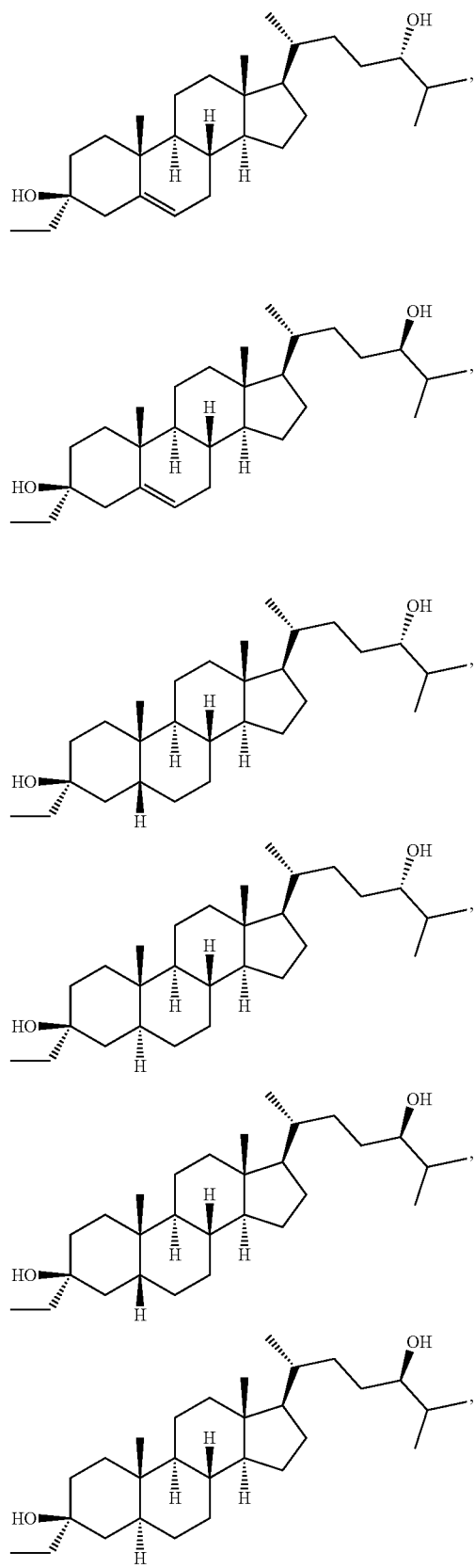
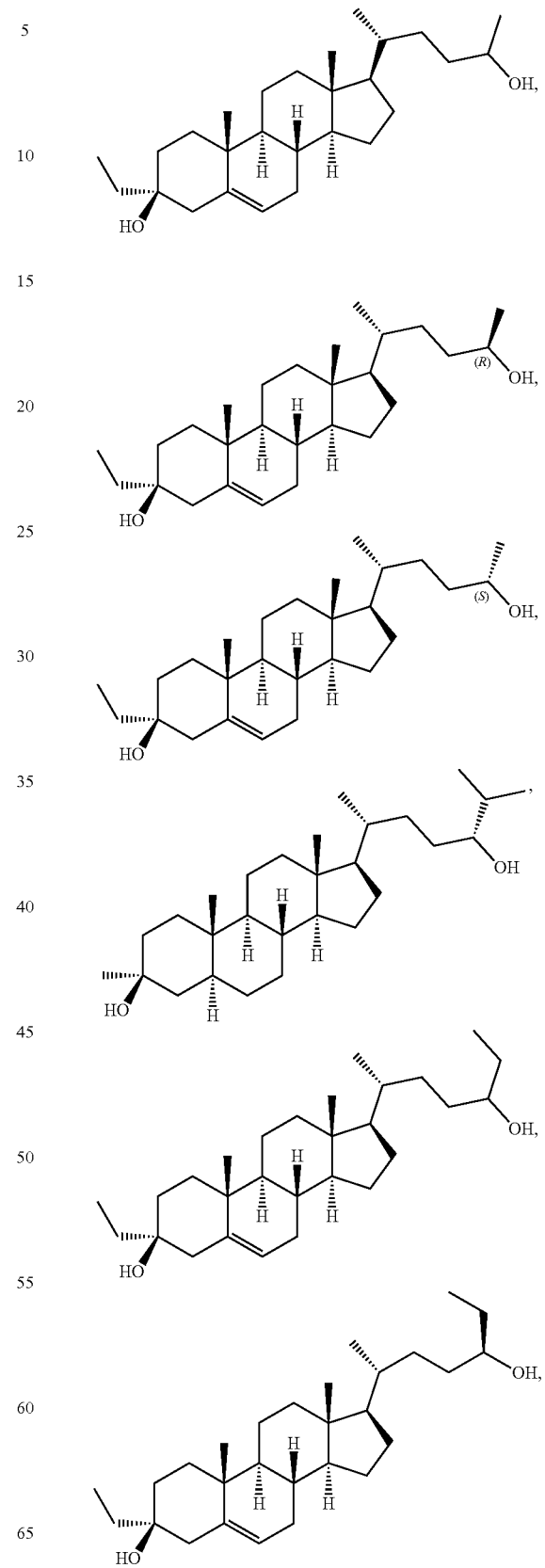

-continued
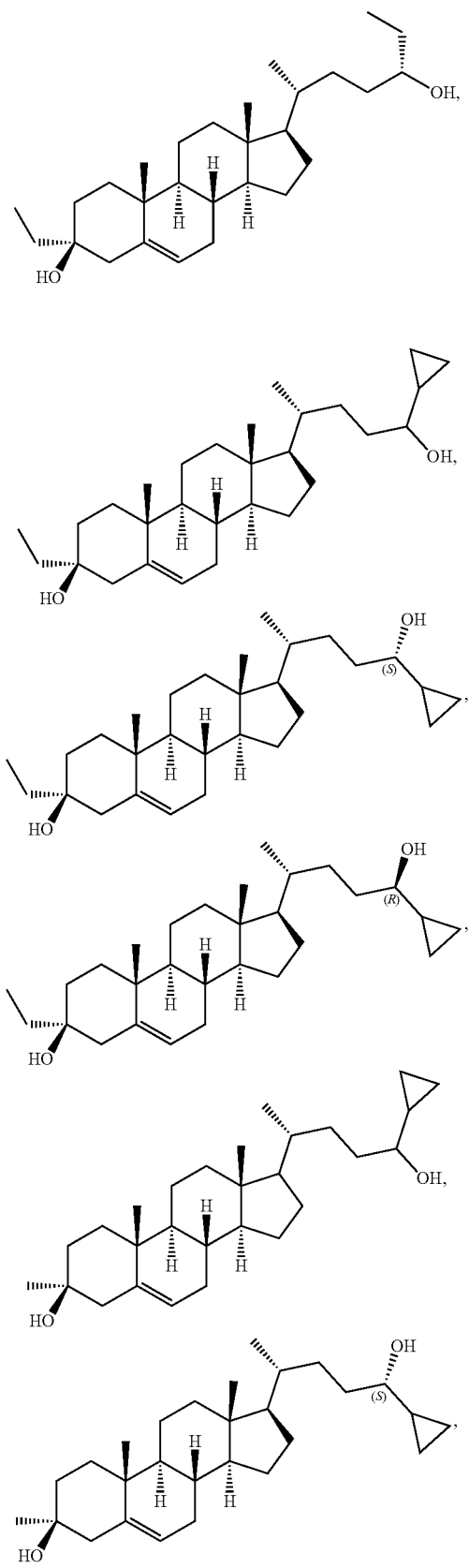
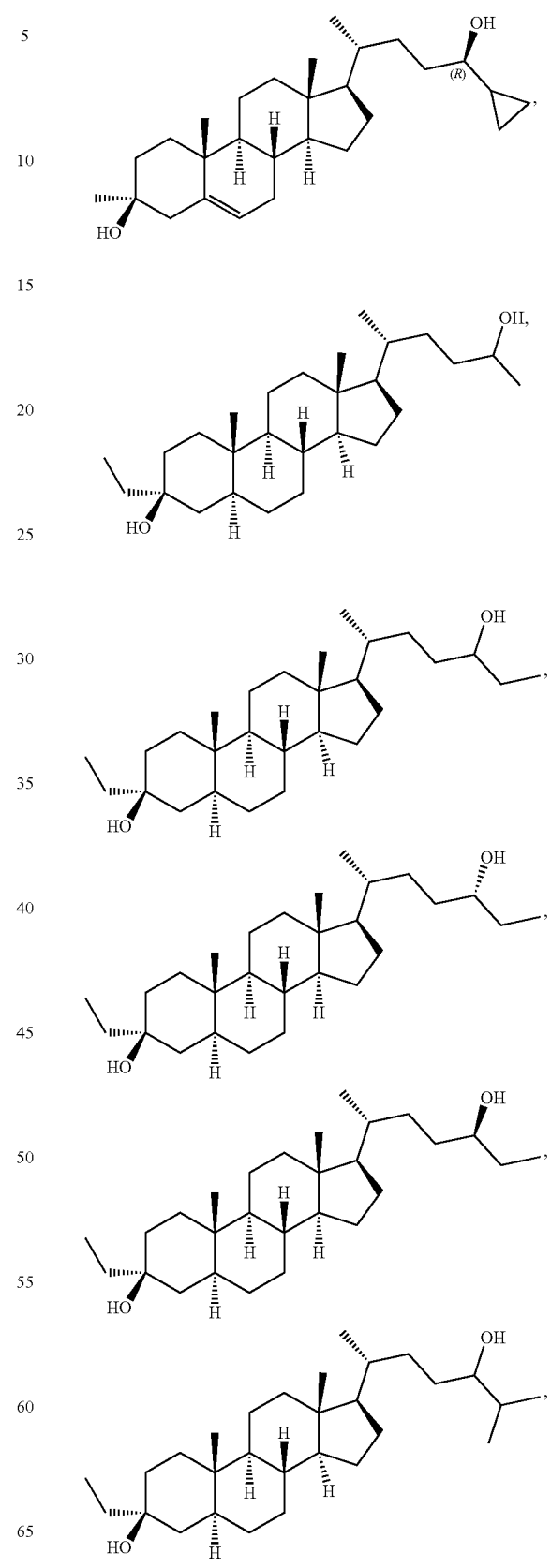

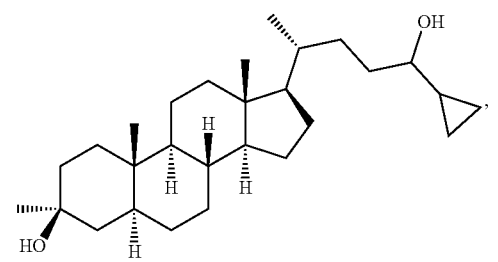
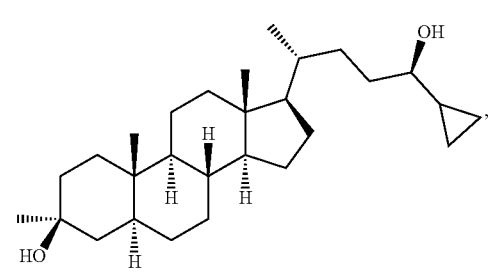
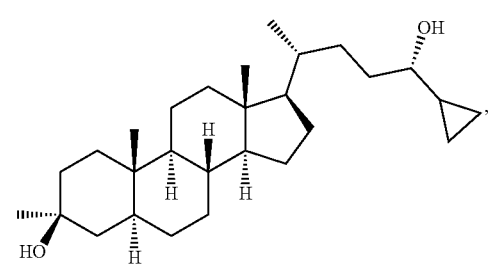
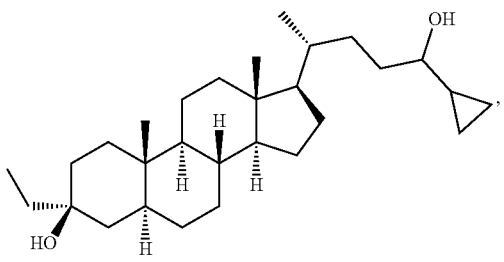
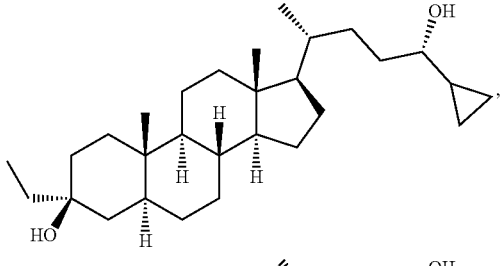
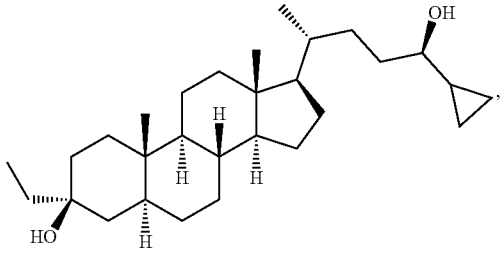
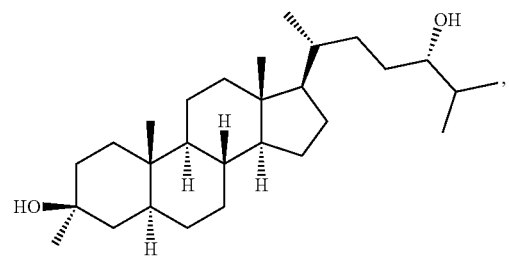
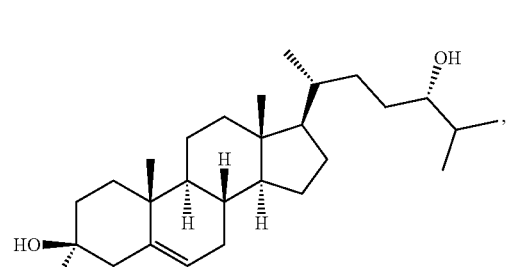
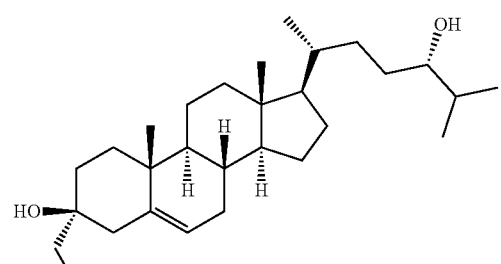
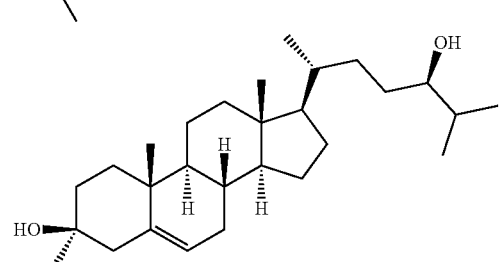
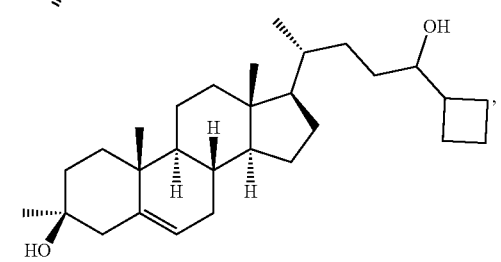
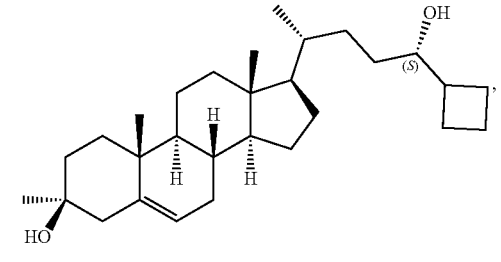

-continued
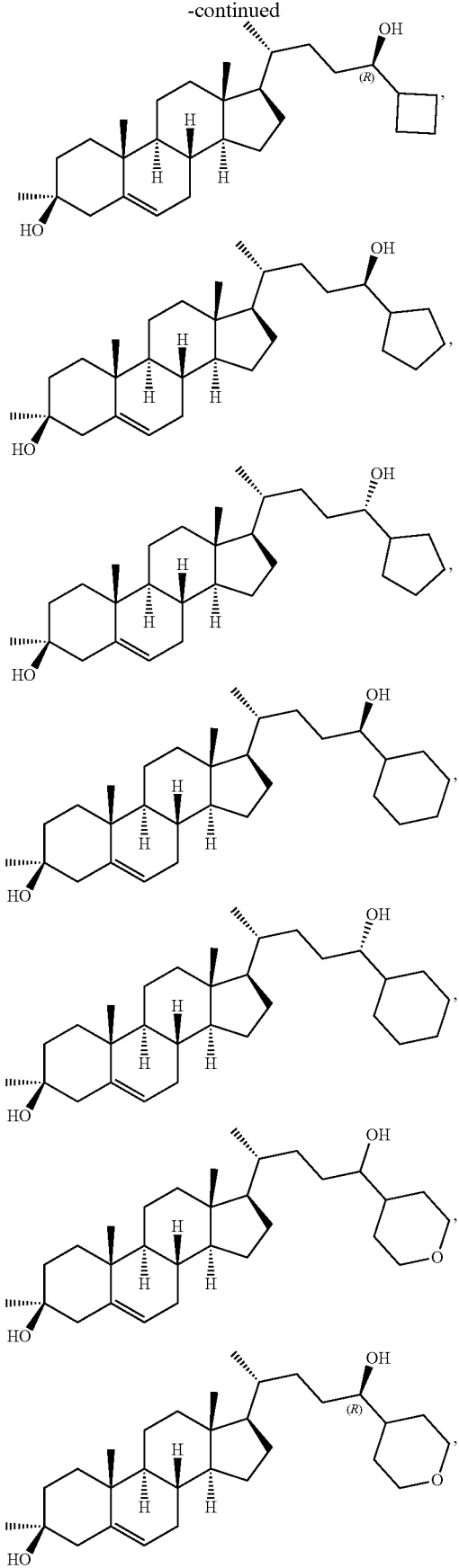
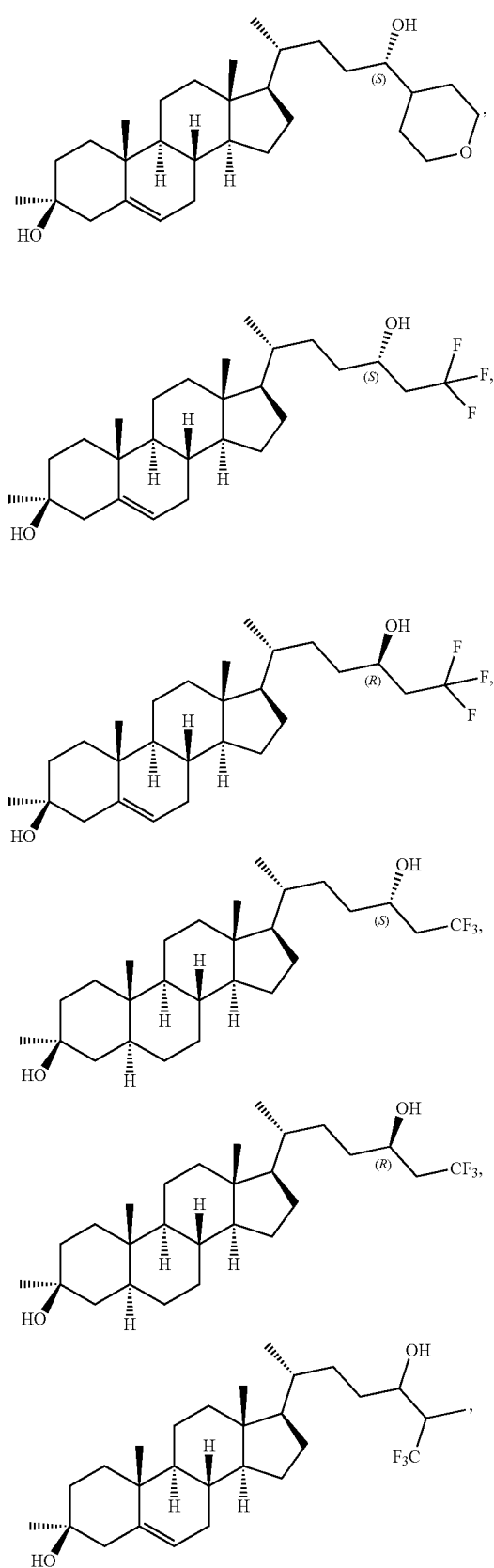

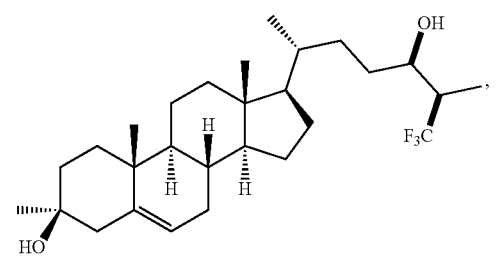
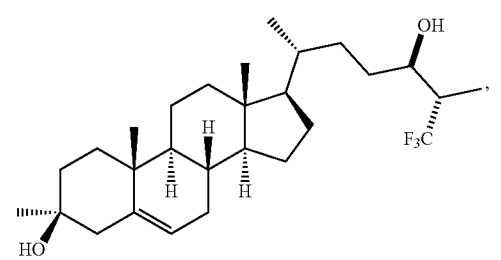
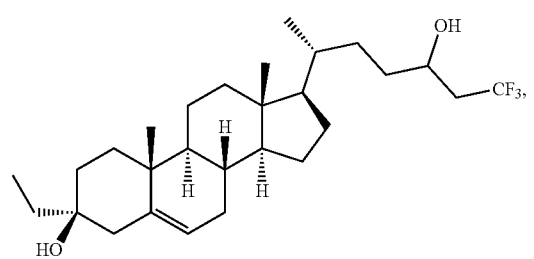
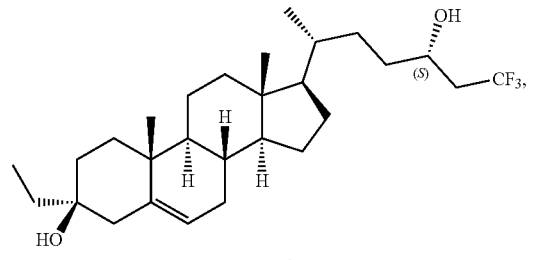
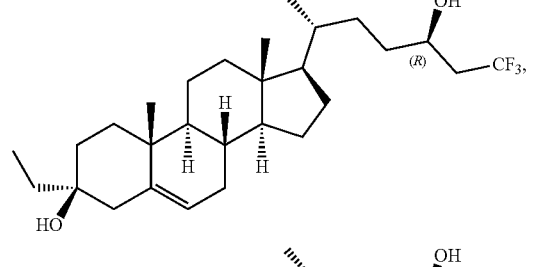
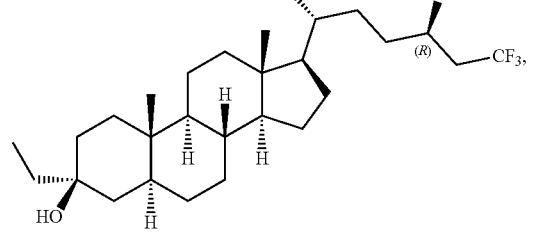
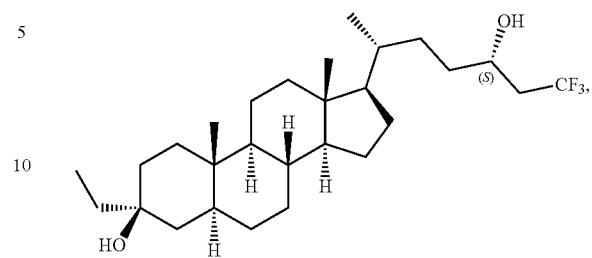
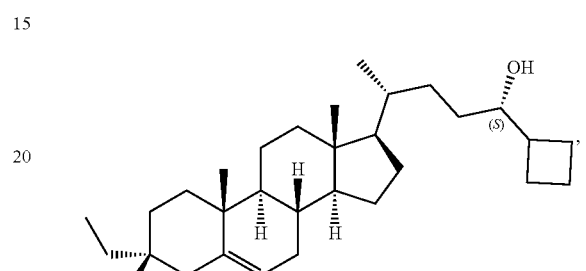
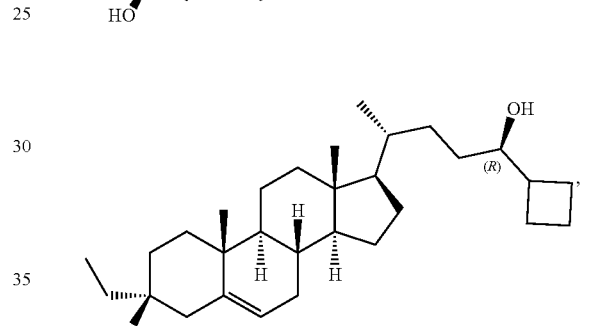
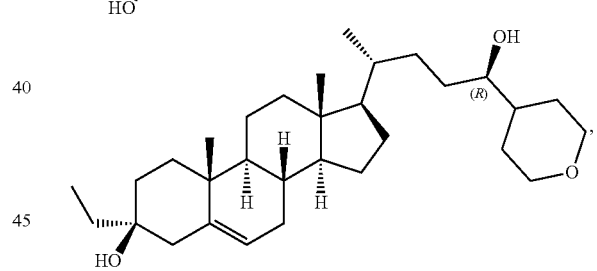
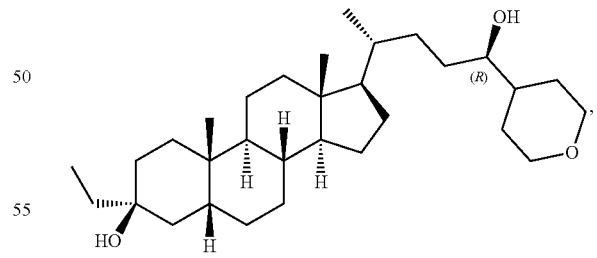
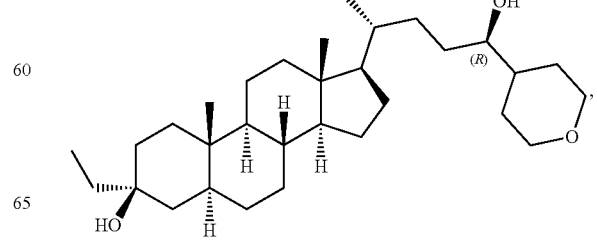

-continued

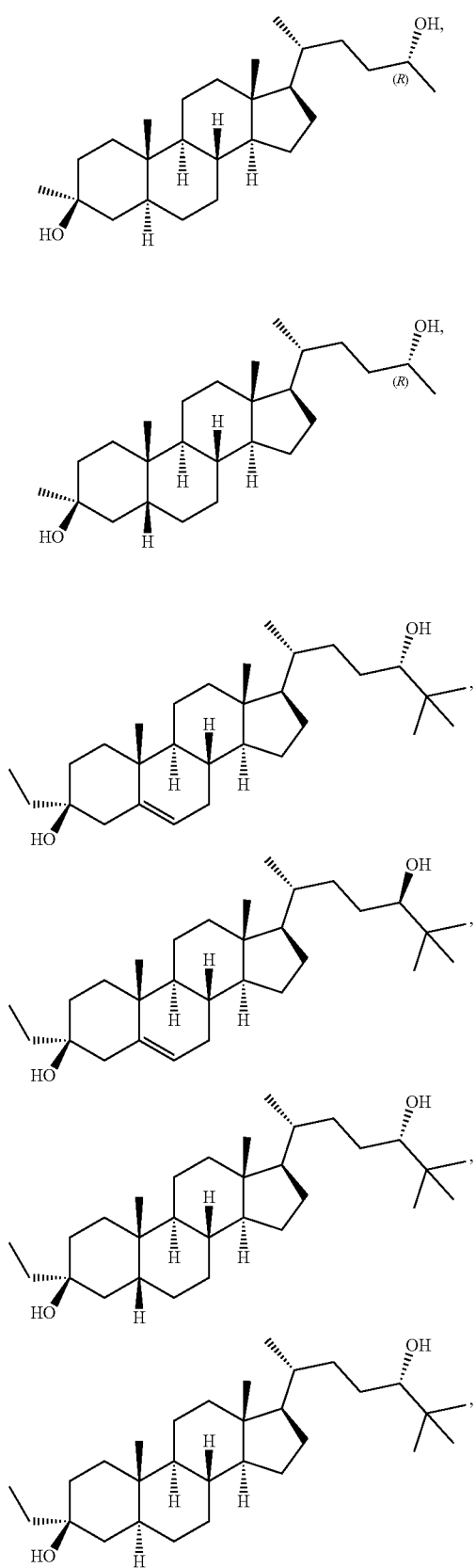

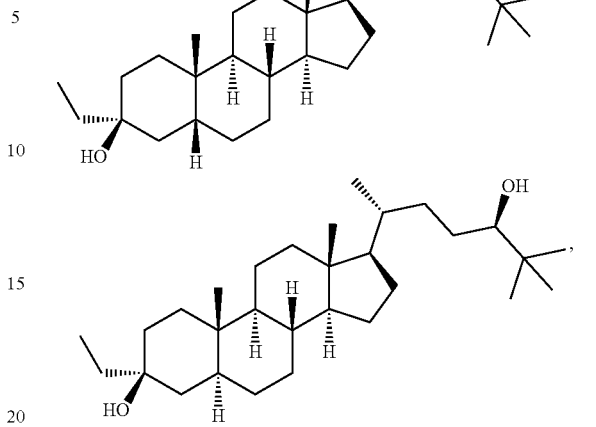

or a pharmaceutically acceptable salt thereof.

In an aspect, provided herein is a pharmaceutical composition comprising a compound described herein (e.g., a compound of Formula (I), or pharmaceutically acceptable salt thereof), and a pharmaceutically acceptable carrier.

In an aspect, provided herein is a method of inducing sedation or anesthesia comprising administering to a subject an effective amount of a compound described herein (e.g., a compound of Formula (I), or pharmaceutically acceptable salt thereof), or pharmaceutical composition thereof.

In an aspect, provided herein is a method for treating or preventing a disorder described herein, comprising administering to a subject in need thereof an effective amount of a compound described herein (e.g., a compound of Formula (I), or pharmaceutically acceptable salt thereof), or pharmaceutical composition thereof.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis.

In some embodiments, the disorder is inflammatory bowel disease.

In some embodiments, the disorder is cancer, diabetes, or a sterol synthesis disorder.

In an aspect, provided herein is a method for treating or preventing a CNS-related condition comprising administering to a subject in need thereof an effective amount of a compound described herein (e.g., a compound of Formula (I), or pharmaceutically acceptable salt thereof), or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, and tinnitus.

In some embodiments, the disorder is sterol synthesis disorder.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Compound described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —CH$_3$). In certain embodiments, the alkyl group is substituted $C_{1-10}$ alkyl. Common alkyl abbreviations include Me (—CH$_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$), or i-Bu (—CH$_2$CH(CH$_3$)$_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene,"

and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, (—$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—$CH=CH$—) and propenylene (e.g., —$CH=CHCH_2$—, —$CH_2$—$CH=CH$—). Exemplary substituted alkenylene groups, e.g., substituted with one or more alkyl (methyl) groups, include but are not limited to, substituted ethylene (—$C(CH_3)=CH$—, —$CH=C(CH_3)$—), substituted propylene (e.g., —$C(CH_3)=CHCH_2$—, —$CH=C(CH_3)CH_2$—, —$CH=CHCH(CH_3)$—, —$CH=CHC(CH_3)_2$—, —$CH(CH_3)$—$CH=CH$—, —$C(CH_3)_2$—$CH=CH$—, —$CH_2$—$C(CH_3)=CH$—, —$CH_2$—$CH=C(CH_3)$—), and the like.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_2$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and for 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and for 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and for 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

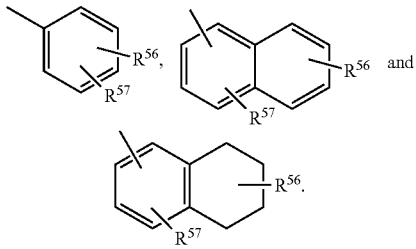

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}$ $NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

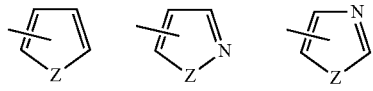

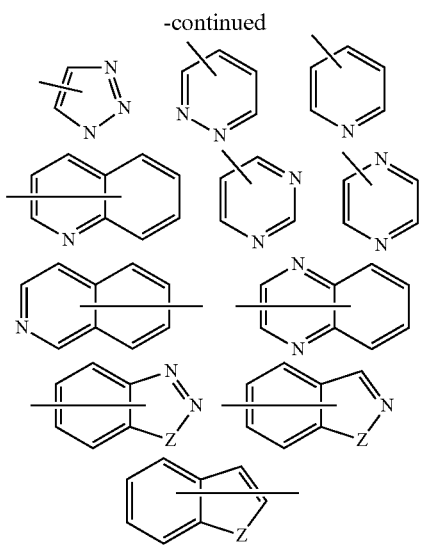

wherein each Z is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_5$ cycloalkyl"). In some embodiments, a cycloalkyl group has 5 to 10 ring carbon atoms ("C$_{5-10}$ cycloalkyl"). Examples of C$_5$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g,. heteroaryl, cycloalkenyl, e.g,. cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, $R^{21}$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —O$R^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted alkoxy, unsubstituted haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Substituted amino" refers to an amino group of the formula —N($R^{38}$)$_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or C$_1$-C$_8$ alkyl, substituted with halo or hydroxy; C$_3$-C$_8$ alkenyl, substituted with halo or hydroxy; C$_3$-C$_8$ alkynyl, substituted with halo or hydroxy, or —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), or —(CH$_2$)$_t$(4-10 membered heterocyclyl), wherein t is an integer between 0 and 8, each of which is substituted by unsubstituted C$_1$-C$_4$ alkyl, halo, unsubstituted C$_1$-C$_4$ alkoxy, unsubstituted haloalkyl, unsubstituted hydroxyalkyl, or unsubstituted C$_1$-C$_4$ haloalkoxy or hydroxy; or both $R^{38}$ groups are joined to form an alkylene group.

Exemplary "substituted amino" groups include, but are not limited to, —N$R^{39}$—C$_1$-C$_8$ alkyl, —N$R^{39}$—(CH$_2$)$_t$(C$_6$-C$_{10}$ aryl), —N$R^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$ (4-10 membered heterocyclyl), wherein t is an integer from 0 to 4, for instance 1 or 2, each R$^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted C$_1$-C$_4$ alkyl, halo, unsubstituted alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, SH, —SR$^{aa}$, —C(=O)R$^{aa}$, —CO$_2$H, —CHO, —C(OR$^{aa}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O) (NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR", —ON(R$^{ff}$)$_2$, —N(R$^{ff}$)$_2$, —N(R$^{ff}$)$_3{}^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_1$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HSO$_4{}^-$, SO$_4{}^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols.

Compounds

In one aspect, the present invention features a compound of Formula (I):

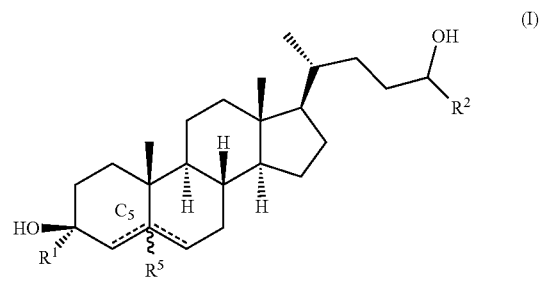

or a pharmaceutically acceptable salt thereof, wherein: $R^1$ is hydrogen or $C_{1-6}$ alkyl; $R^2$ is $C_{1-6}$ alkyl, carbocyclyl, or heterocyclyl; $R^5$ is absent or hydrogen; and ═ represents a single or double bond, wherein when one ═ is a double bond, the other ═ is a single bond and $R^5$ is absent.

In some embodiments, $R^1$ is hydrogen. In some embodiments, the compound of Formula (I) is a compound of Formula (X):

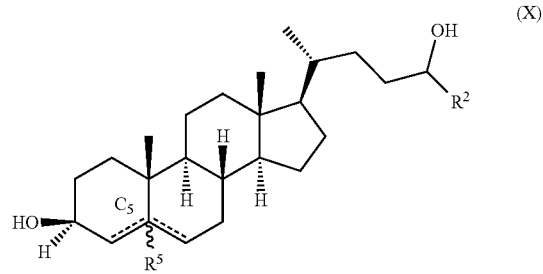

or a pharmaceutically acceptable salt thereof, wherein: $R^2$ is $C_{1-6}$ alkyl, carbocyclyl, or heterocyclyl; $R^5$ is absent or hydrogen; and ═ represents a single or double bond, wherein when one ═ is a double bond, the other ═ is a single bond and $R^5$ is absent.

In some embodiments, $R^1$ is $C_{1-6}$ alkyl. In some embodiments, $R^1$ is substituted $C_{1-6}$ alkyl. In some embodiments, $R^1$ is unsubstituted $C_{1-6}$ alkyl. In some embodiments, $R^1$ is methyl (e.g., —$CH_3$, —$CF_3$ or —$CH_2OCH_3$), ethyl, or isopropyl.

In some embodiments, $R^1$ is methyl (e.g., —$CH_3$) or ethyl (e.g., —$CH_2CH_3$).

In some embodiments, $R^2$ is $C_{1-6}$ alkyl or carbocyclyl. In some embodiments, $R^2$ is substituted $C_{1-6}$ alkyl. In some embodiments, $R^2$ is unsubstituted $C_{1-6}$ alkyl. In some embodiments, $R^2$ is methyl (e.g., —$CH_3$), ethyl (e.g., —$CH_2CH_3$, —$CH_2CF_3$, —$CH(CH_3)(CF_3)$), isopropyl, tertbutyl, or cyclopropyl. In some embodiments, $R^2$ is haloalkyl. In some embodiments, $R^2$ is —CH$_2$CF$_3$ or —CH(CH$_3$)(CF$_3$). In some embodiments, $R^1$ and $R^2$ are C$_{1-6}$ alkyl. In some embodiments, $R^1$ is C$_{1-6}$ alkyl and $R^2$ is C$_{1-6}$ alkyl, carbocyclyl, or heterocyclyl. In some embodiments, $R^1$ is methyl or ethyl, and $R^2$ is unsubstituted or substituted C$_{1-6}$ alkyl (e.g., haloalkyl). In some embodiments, $R^1$ is methyl or ethyl, and $R^2$ is carbocyclyl, or heterocyclyl.

In some embodiments, ═══ represents a single bond.

In some embodiments, the compound of Formula (I) is a compound of Formula (I-A) or Formula (I-B):

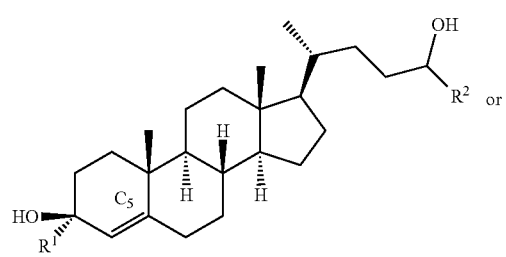
(I-A)

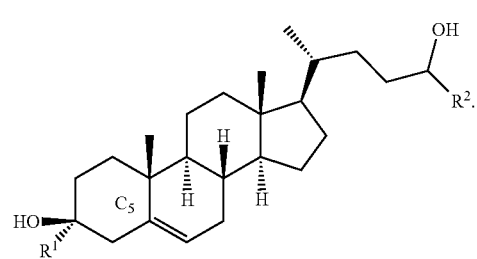
(I-B)

In some embodiments, the compound of Formula (I) is a compound of Formula (I-B-i) or Formula (I-B-ii):

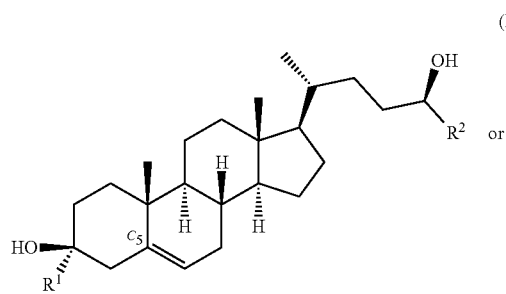
(I-B-i)

(I-B-ii)

In some embodiments, the compound of Formula (I) is a compound of Formula (I-C):

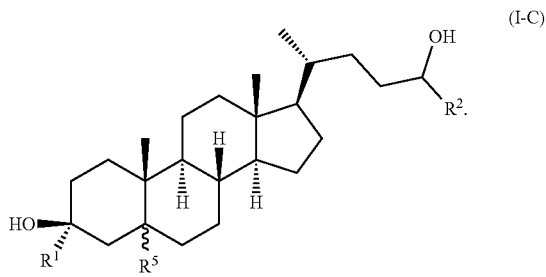
(I-C)

In some embodiments, the compound of Formula (I-C) is a compound of Formula (I-C-i) or (I-C-ii):

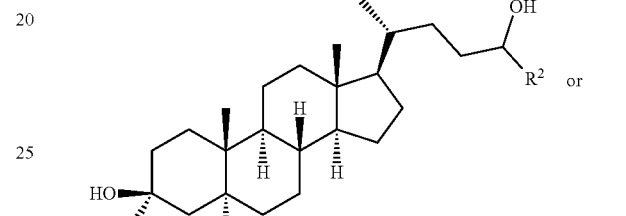
(I-C-i)

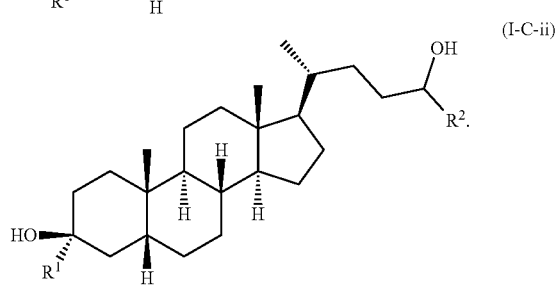
(I-C-ii)

In some embodiments, the compound of Formula (I-C-i) is a compound of Formula (I-C-i-a) or (I-C-i-b):

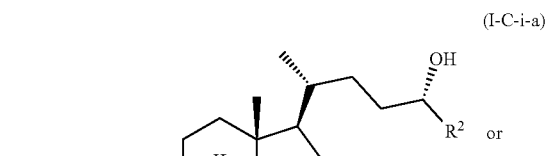
(I-C-i-a)

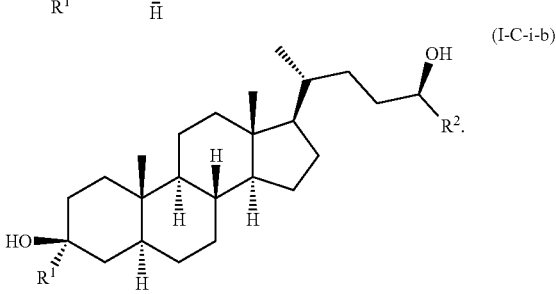
(I-C-i-b)

In some embodiments, the compound of Formula (I-C-ii) is a compound of Formula (I-C-ii-a) or (I-C-ii-b):

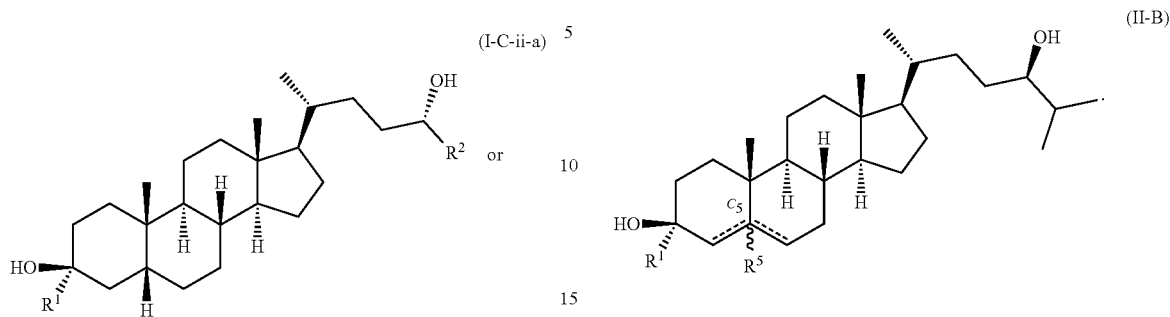

(I-C-ii-a)

(I-C-ii-b)

In some embodiments, $R^2$ is $C_{1-6}$ alkyl. In some embodiments, $R^2$ is substituted $C_{1-6}$ alkyl. In some embodiments, the compound of Formula (I) is a compound of Formula (II):

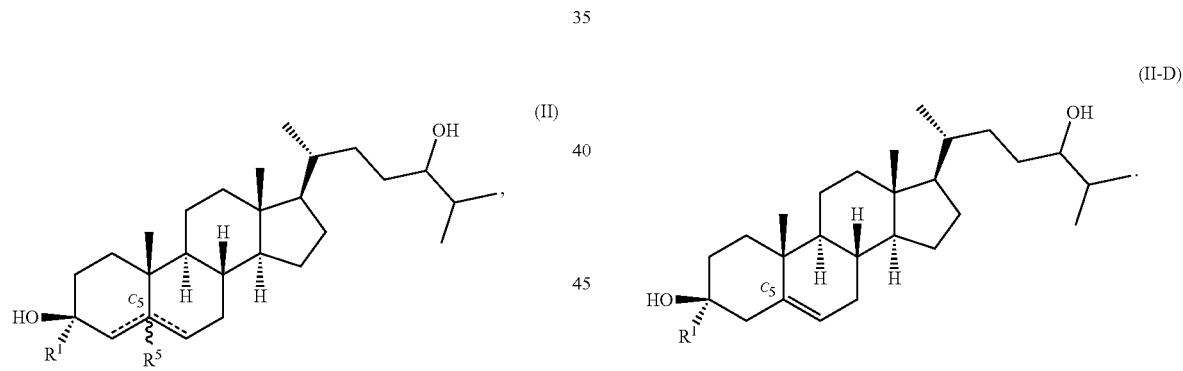

(II)

or a pharmaceutically acceptable salt thereof.

In some embodiments, the compound of Formula (II) is a compound of Formula (II-A) or Formula (II-B):

(II-A)

-continued (II-B)

In some embodiments, the compound of Formula (II) is a compound of Formula (II-C) or Formula (II-D):

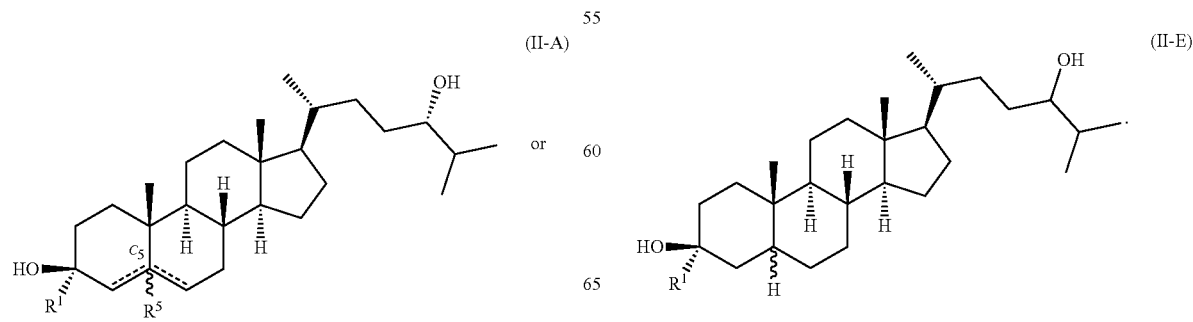

(II-C)

(II-D)

In some embodiments, the compound of Formula (II) is a compound of Formula (II-E):

(II-E)

In some embodiments, the compound of Formula (II-E) is a compound of Formula (II-E-i) or Formula (II-E-ii):

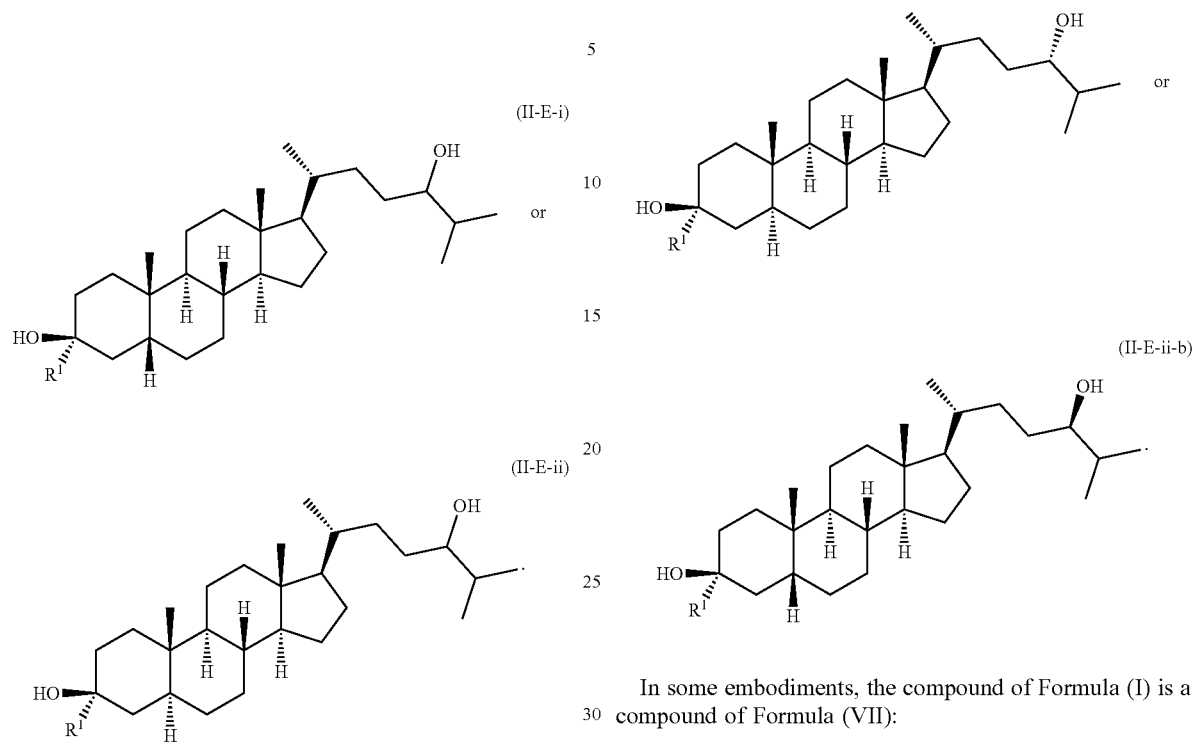

In some embodiments, the compound of Formula (II-E-i) is a compound of Formula (II-E-i-a) or Formula (II-E-i-b):

In some embodiments, the compound of Formula (II-E-ii) is a compound of Formula (II-E-ii-a) or Formula (II-E-ii-b):

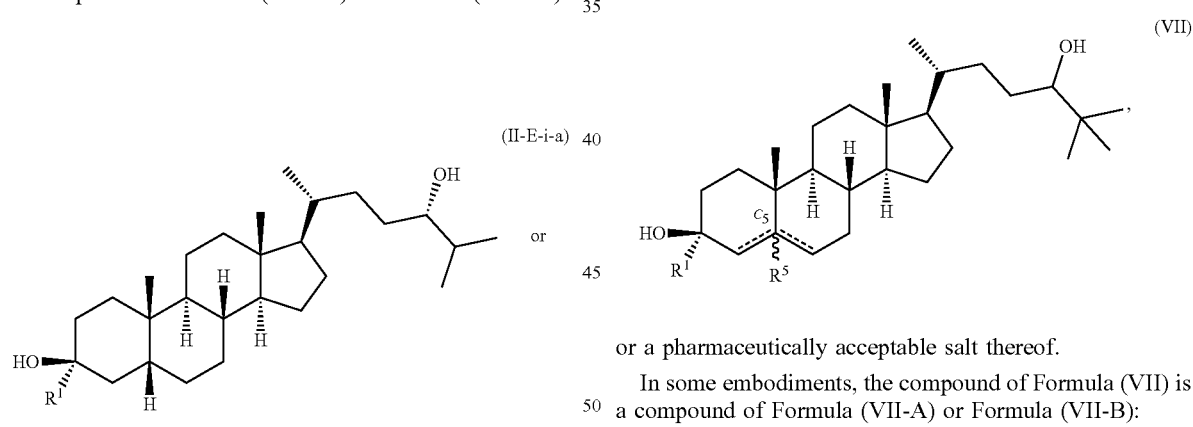

In some embodiments, the compound of Formula (I) is a compound of Formula (VII):

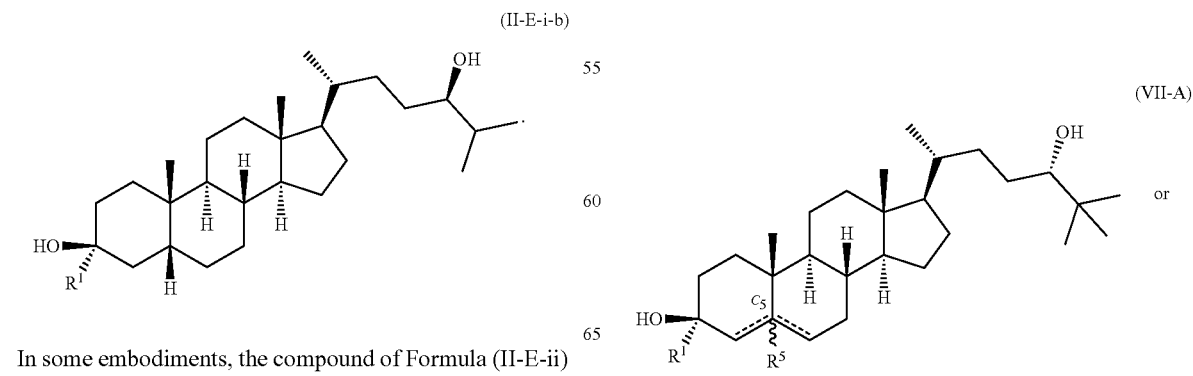

or a pharmaceutically acceptable salt thereof.

In some embodiments, the compound of Formula (VII) is a compound of Formula (VII-A) or Formula (VII-B):

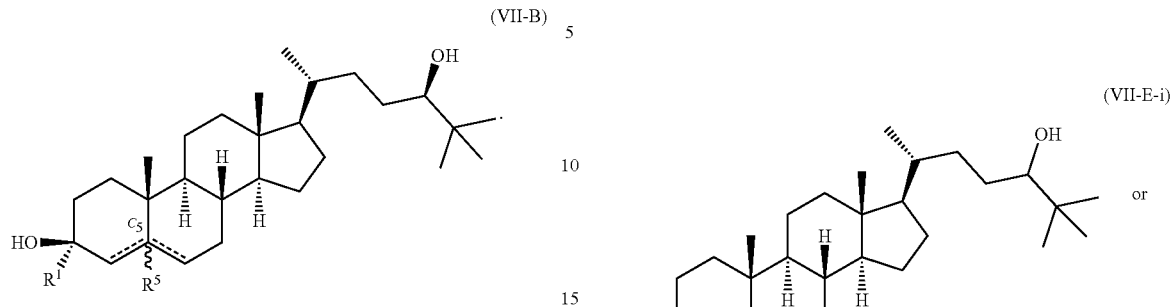

(VII-B)

In some embodiments, the compound of Formula (VII) is a compound of Formula (VII-C) or Formula (VII-D):

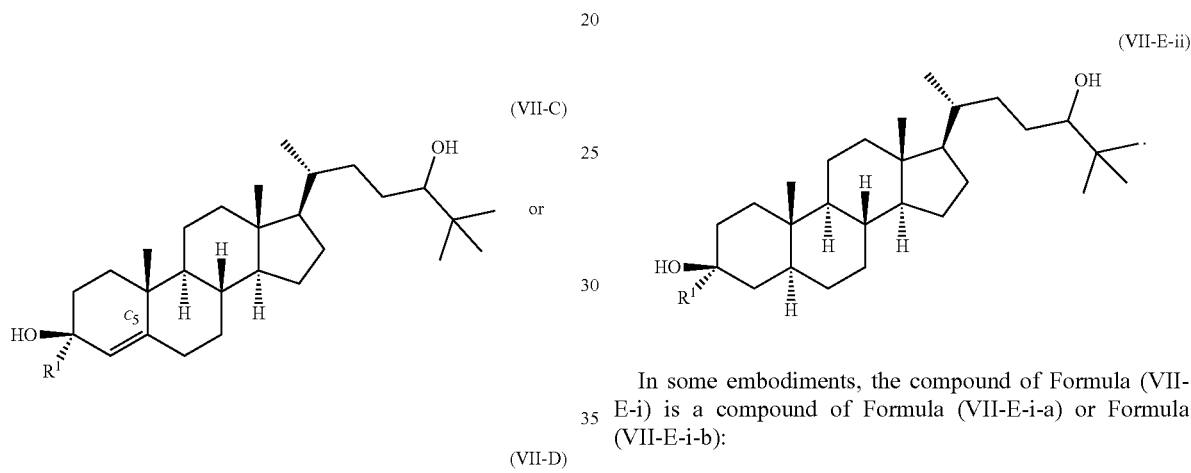

In some embodiments, the compound of Formula (VII) is a compound of Formula (VII-E):

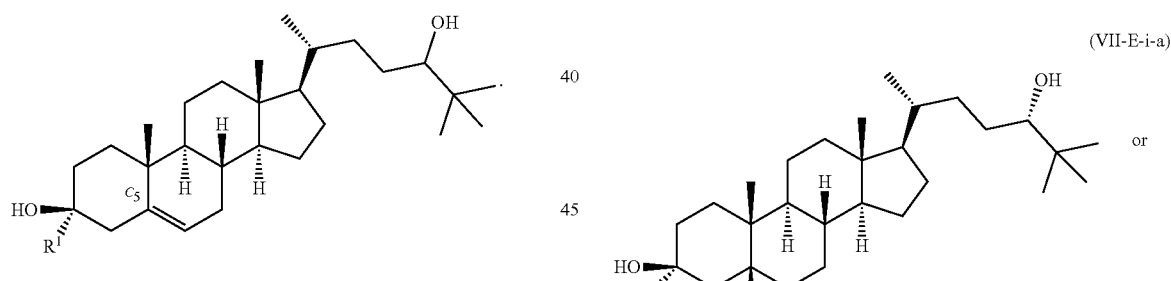

In some embodiments, the compound of Formula (VII-E) is a compound of Formula (VII-E-i) or Formula (VII-E-ii):

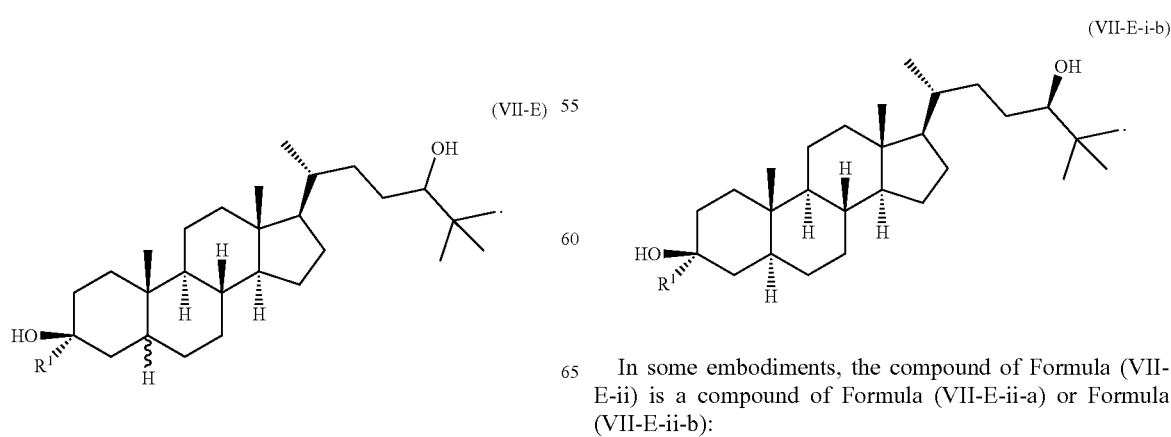

In some embodiments, the compound of Formula (VII-E-i) is a compound of Formula (VII-E-i-a) or Formula (VII-E-i-b):

In some embodiments, the compound of Formula (VII-E-ii) is a compound of Formula (VII-E-ii-a) or Formula (VII-E-ii-b):

(VII-E-ii-a)

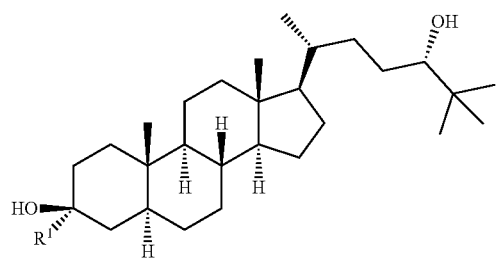

or (VII-E-ii-b)

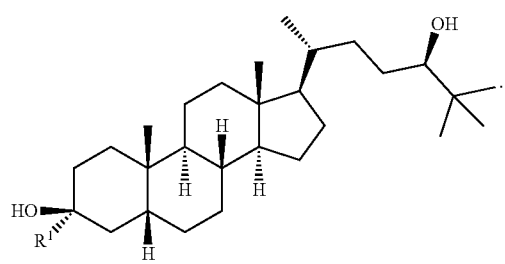

In some embodiments, the compound of Formula (I) is a compound of Formula (III):

(III)

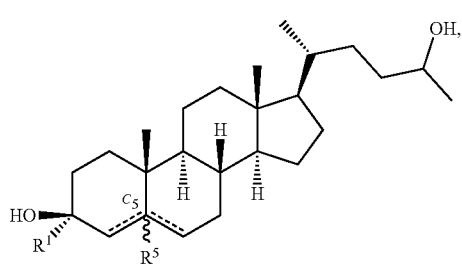

or a pharmaceutically acceptable salt thereof.

In some embodiments, the compound of Formula (III) is a compound of Formula (III-A) or Formula (III-B):

(III-A)

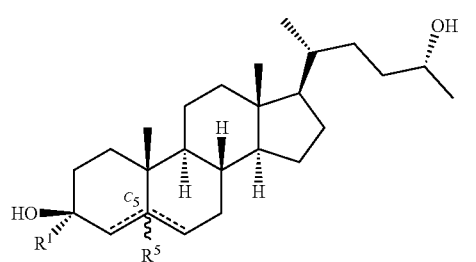

or (III-B)

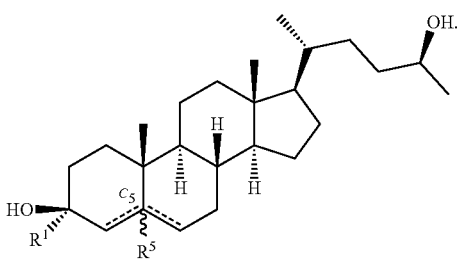

In some embodiments, the compound of Formula (I) is a compound of Formula (IV):

(IV)

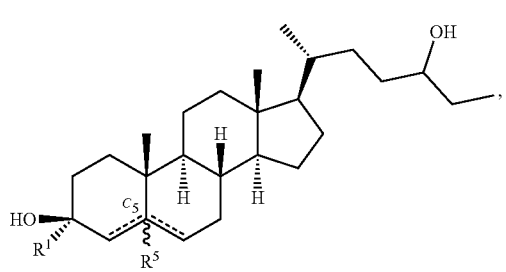

or a pharmaceutically acceptable salt thereof.

In some embodiments, the compound of Formula (IV) is a compound of Formula (IV-A) or Formula (IV-B):

(IV-A)

or (IV-B)

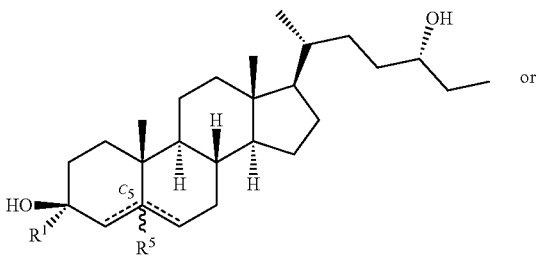

or a pharmaceutically acceptable salt thereof.

In some embodiments, $R^2$ is carbocyclyl or heterocyclyl. In some embodiments, $R^2$ is carbocyclyl (e.g., cyclopropyl, cyclobutyl, cyclopentyl, cyclohexyl).

In some embodiments, $R^2$ is heterocyclyl. In some embodiments, $R^2$ is an oxygen-containing heterocycle (e.g., tetrahydropyran).

In some embodiments, the compound of Formula (I) is a compound of Formula (V):

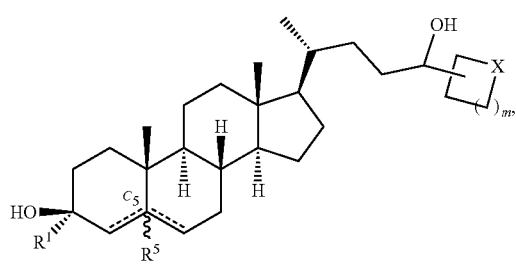

(V)

or a pharmaceutically acceptable salt thereof, wherein X is —CH$_2$—, —O—, —S—, or —NR$^A$—, and m is an integer selected from 0, 1, 2, 3, 4, or 5; wherein R$^A$ is hydrogen, alkyl, —C(O)R$^C$, —C(O)N(R$^C$)$_2$, or —SO$_2$N(R$^C$)$_2$; and each R$^C$ is independently hydrogen, alkyl, aryl, or heteroaryl. In some embodiments, X is —CH$_2$—, —O—, —S—, or —NH—.

In some embodiments, the compound of Formula (V) is a compound of Formula (V-A-i) or Formula (V-A-ii):

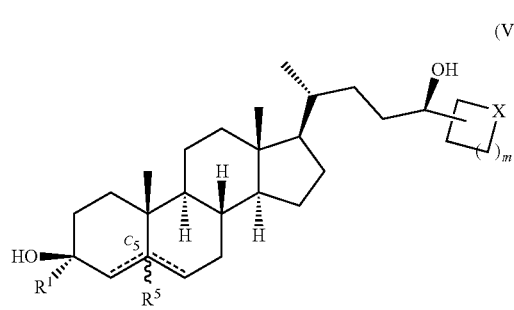

(V-A-i)

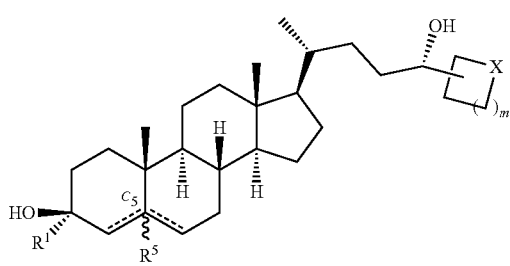

(V-A-ii)

In some embodiments, the compound of Formula (V) is a compound of Formula (V-B):

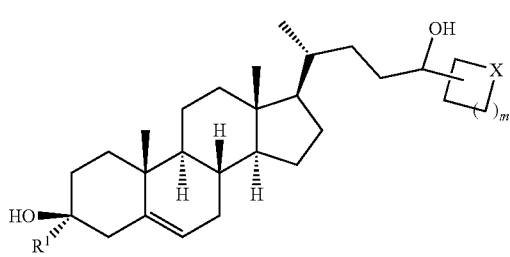

(V-B)

In some embodiments, X is —CH$_2$—.
In some embodiments, X is —O—.
In some embodiments, m is 0, 1, 2, or 3.

In some embodiments, the compound of Formula (V) is a compound of Formula (V-B-i):

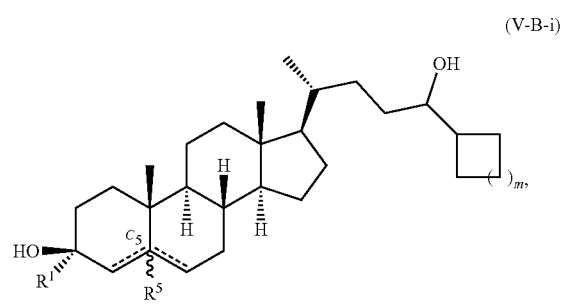

(V-B-i)

or a pharmaceutically acceptable salt thereof.

In some embodiments, the compound of Formula (V) is a compound of Formula (V-C):

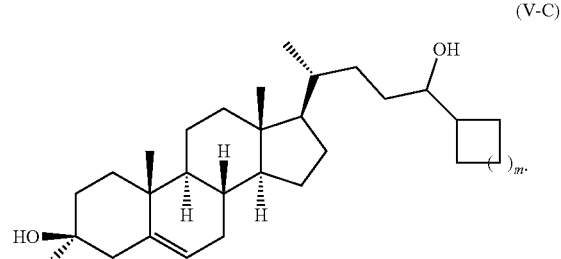

(V-C)

In some embodiments, the compound of Formula (I) is a compound of Formula (VI):

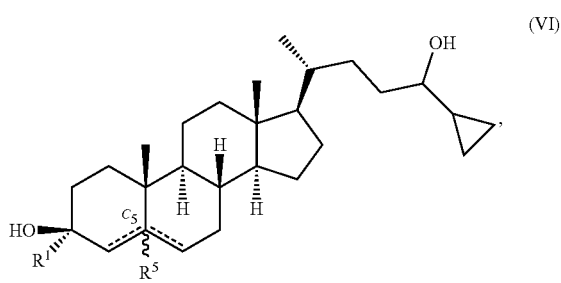

(VI)

or a pharmaceutically acceptable salt thereof.

In some embodiments, the compound of Formula (VI) is a compound of Formula (VI-A) or Formula (VI-B):

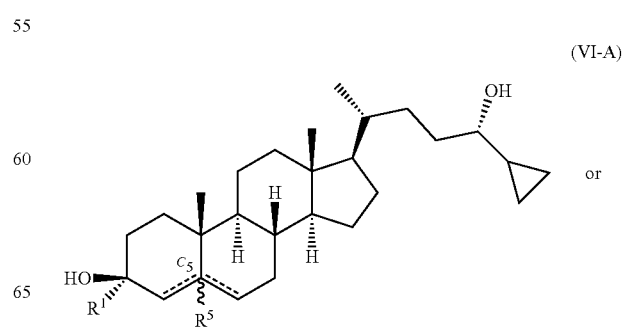

(VI-A) or

-continued
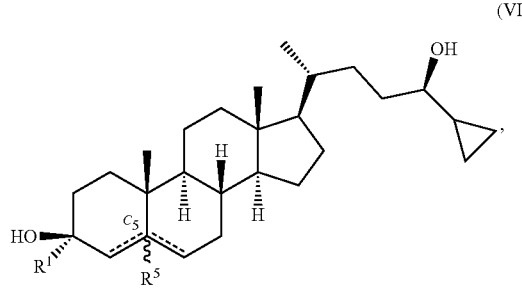
or a pharmaceutically acceptable salt thereof.
In some embodiments, $R^1$ is $C_{1-6}$ alkyl. In some embodiments, $R^1$ is methyl (e.g., —$CH_3$, —$CF_3$ or —$CH_2OCH_3$), ethyl, or isopropyl.
In some embodiments, $R^1$ is methyl, ethyl, or isopropyl.
In some embodiments, the compound of Formula (I) is selected from:
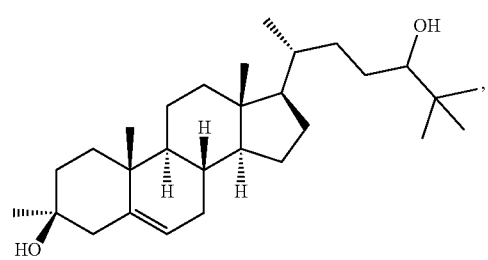
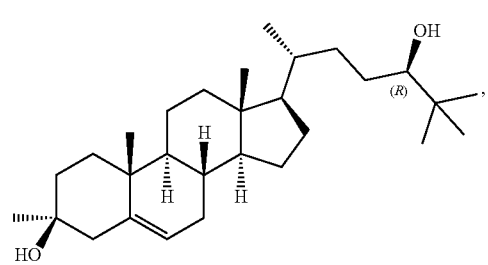
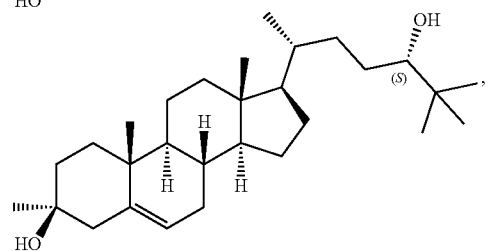
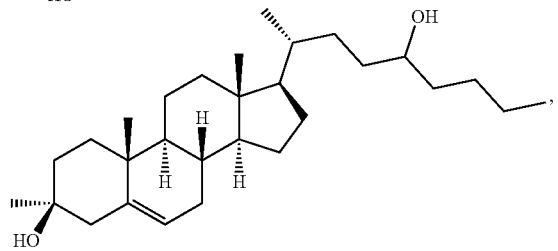
-continued
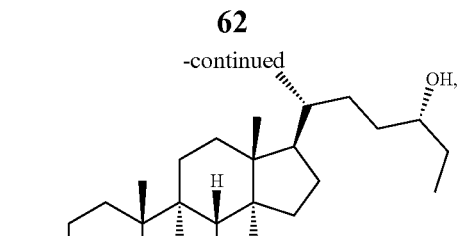
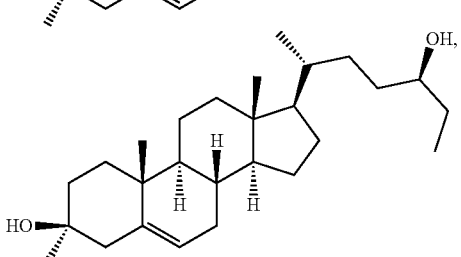
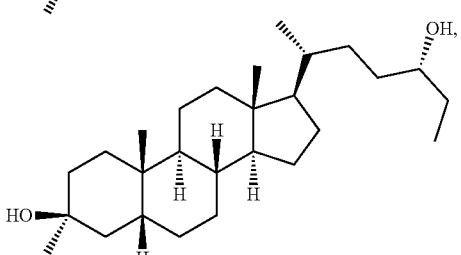
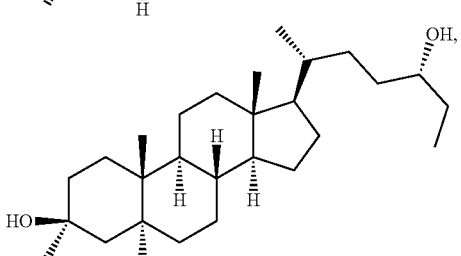
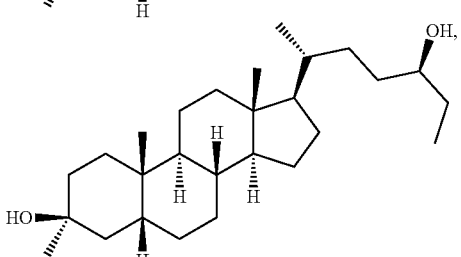
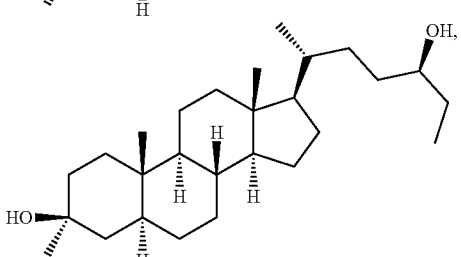
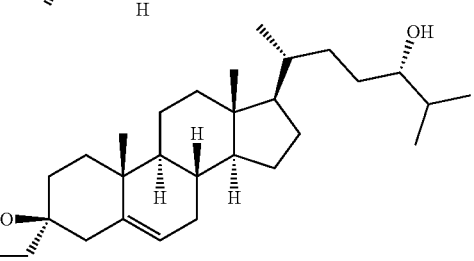

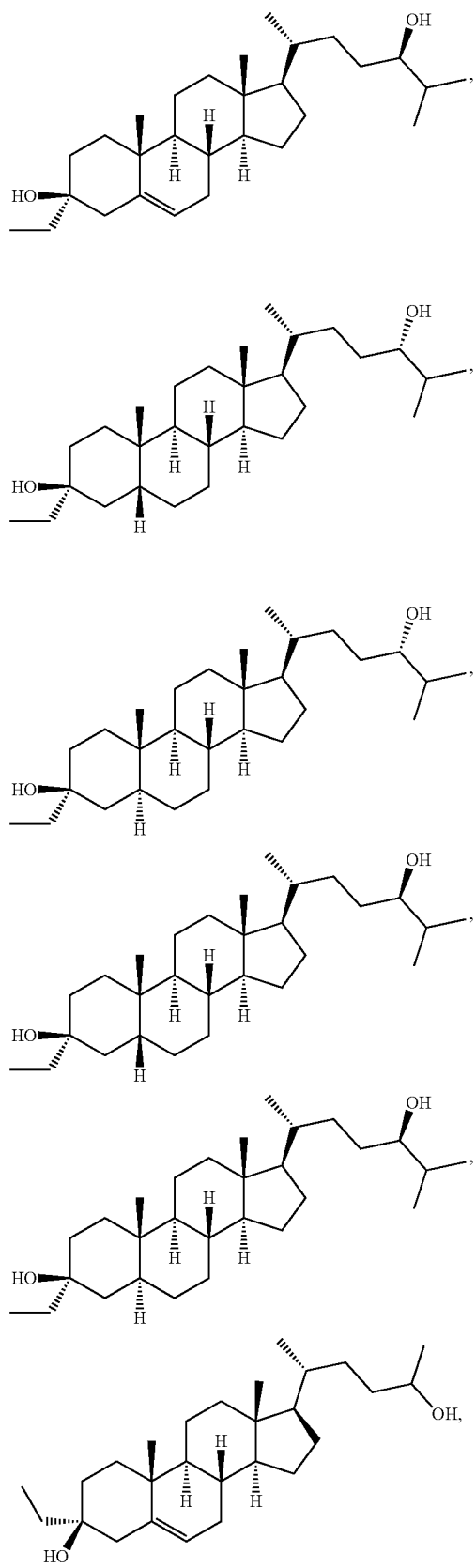
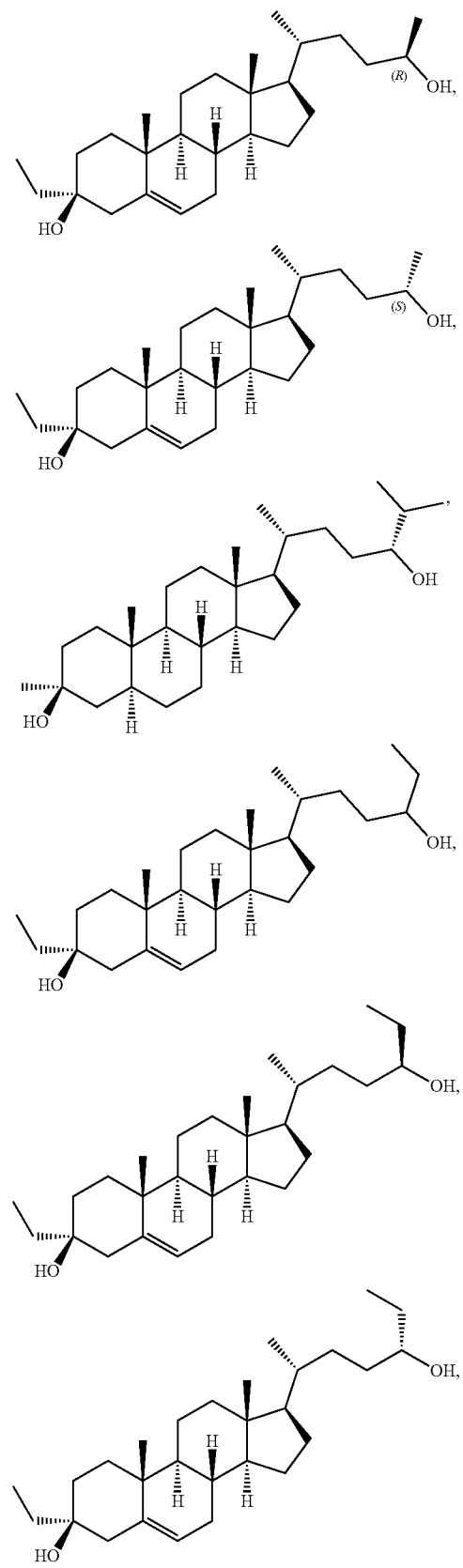

-continued
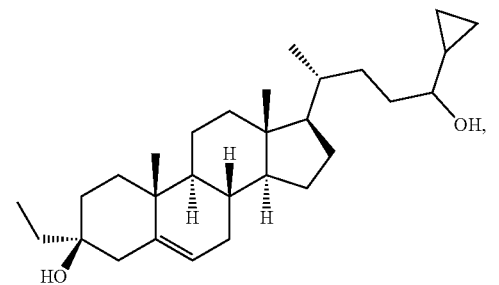
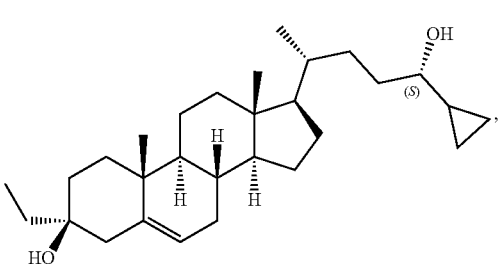
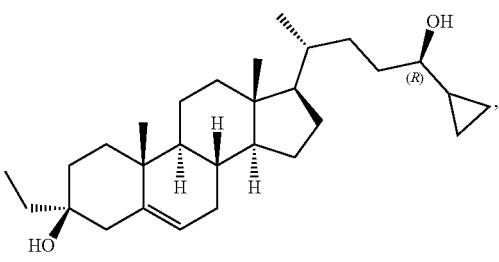
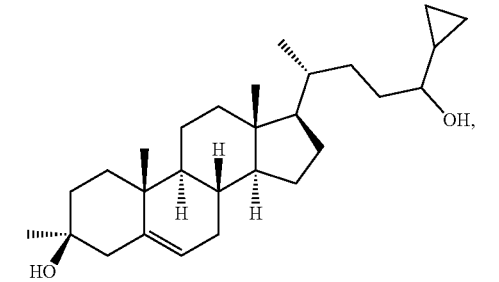
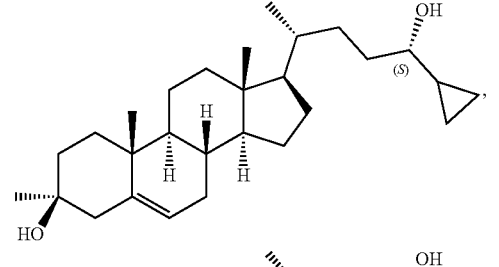
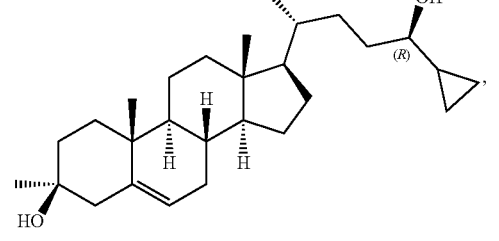
-continued
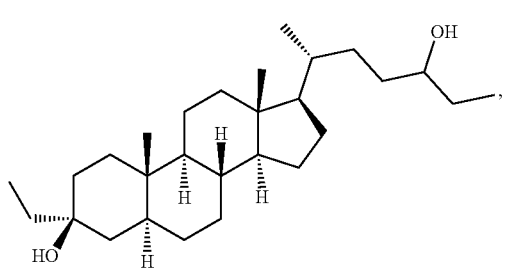
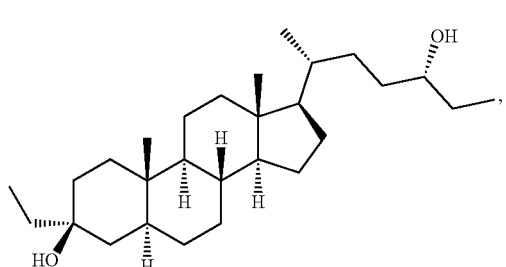
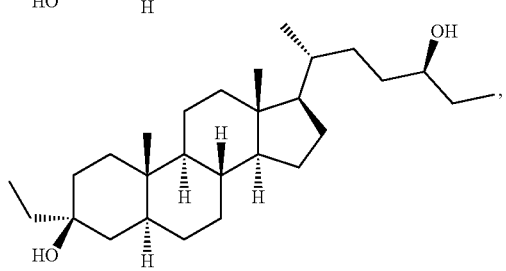
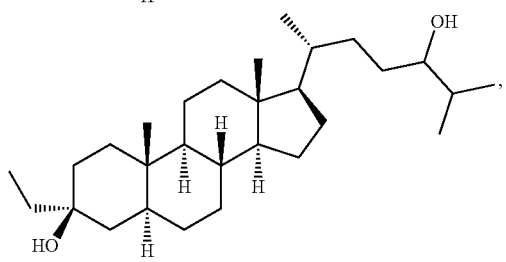
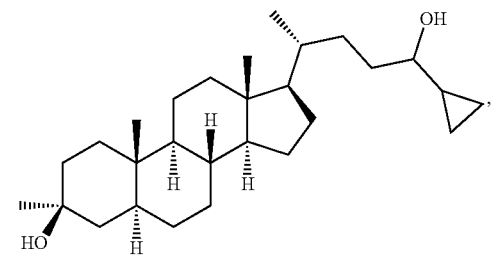

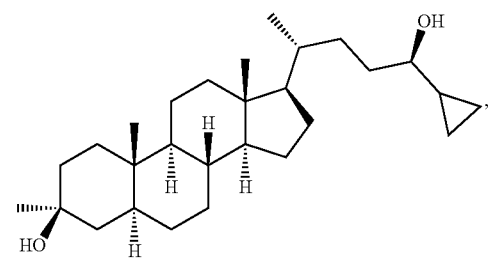
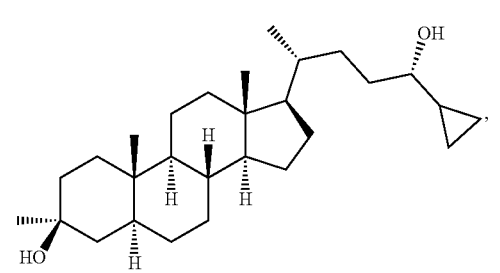
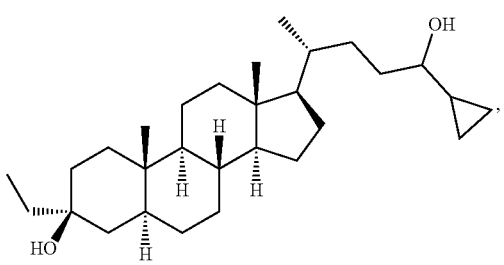
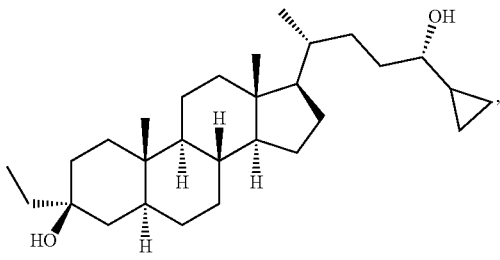
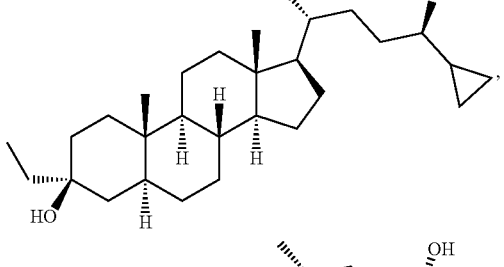
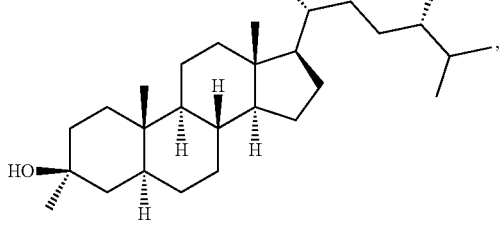
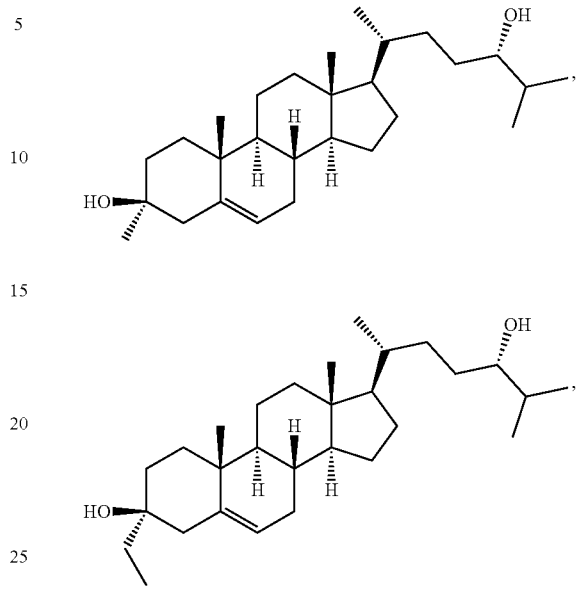
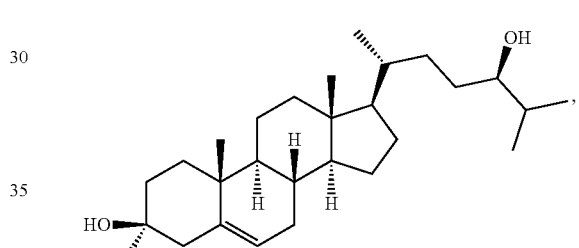
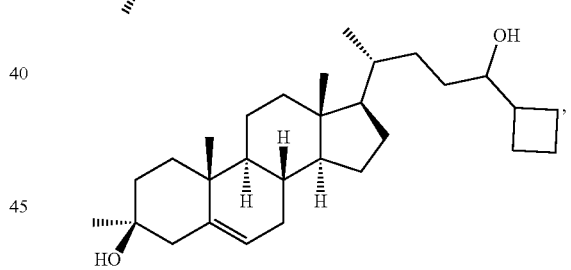
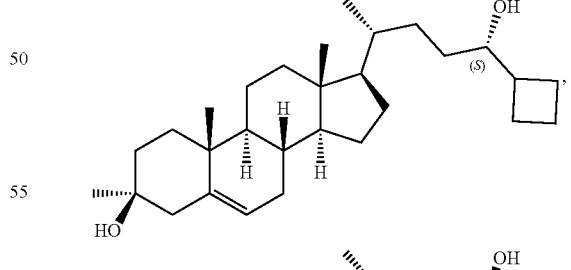
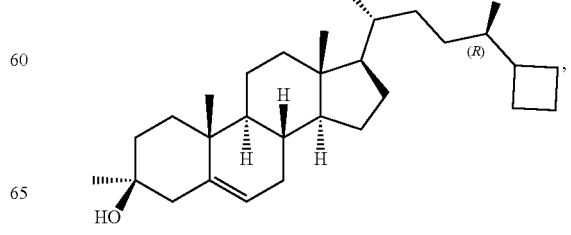

69
-continued
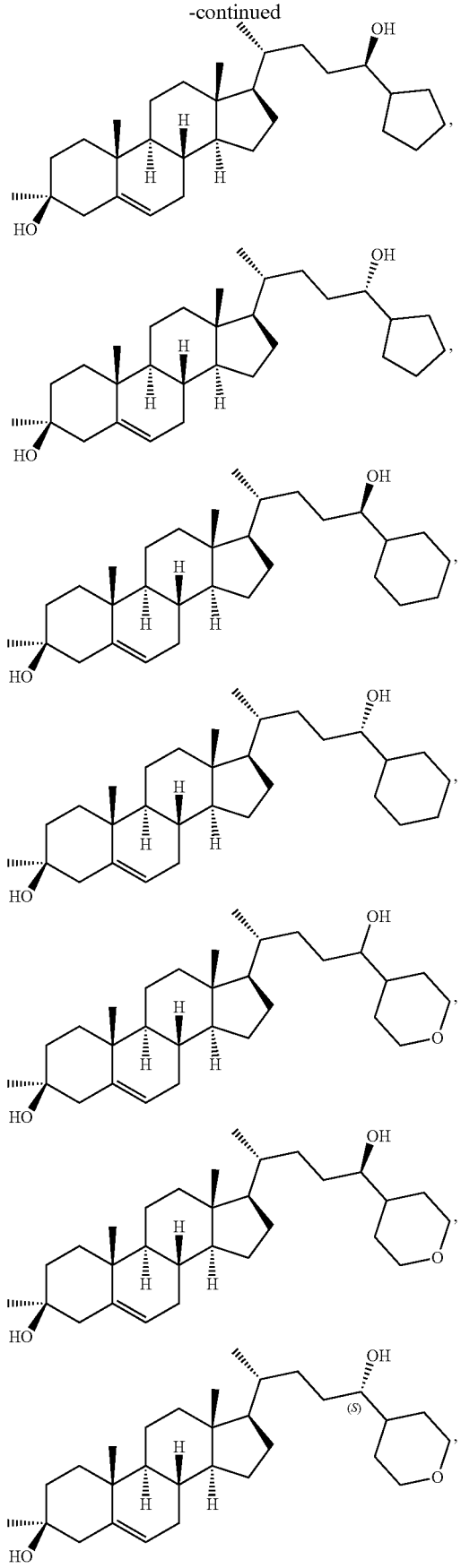
70
-continued
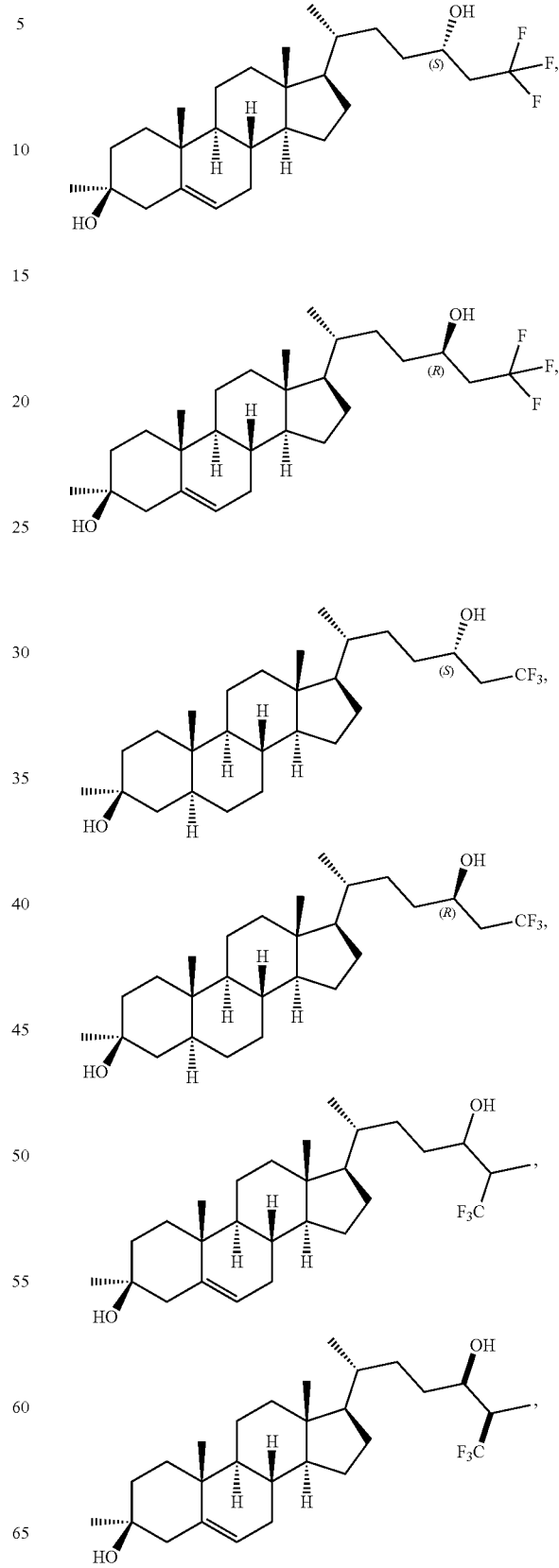

71
-continued
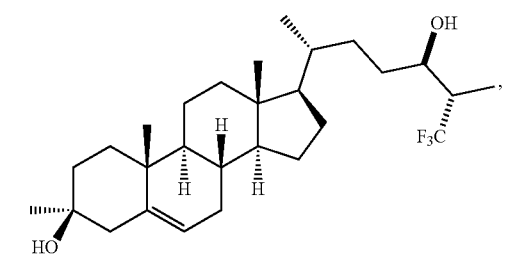
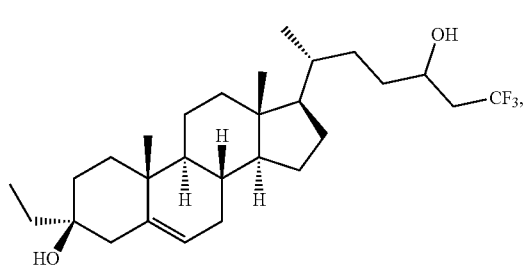
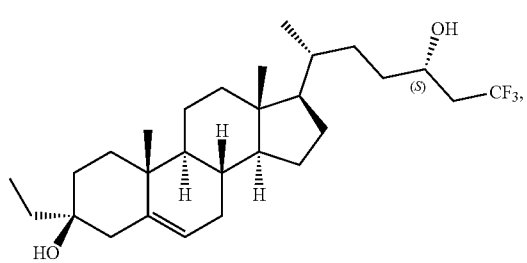
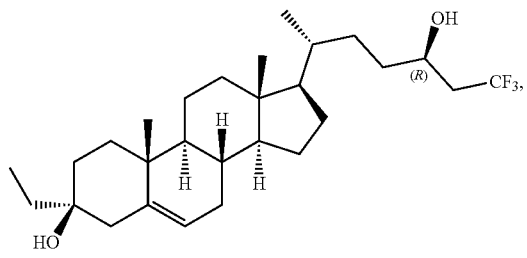
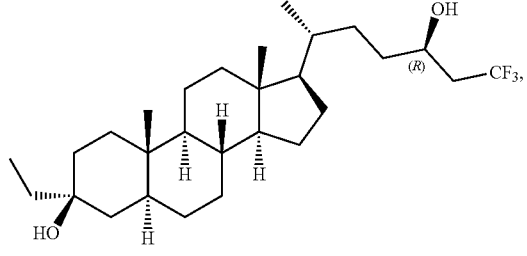
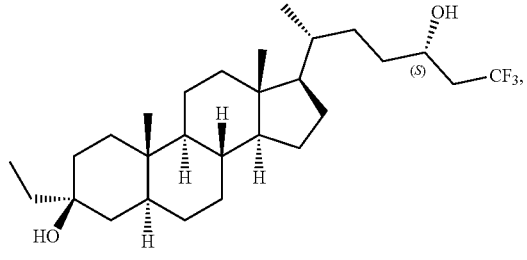
72
-continued
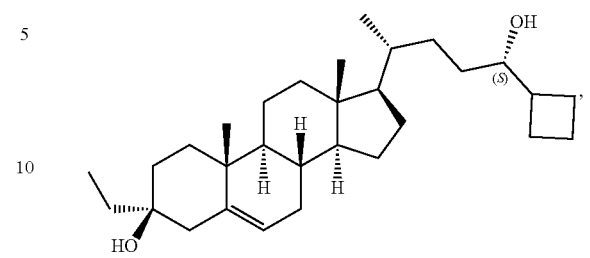
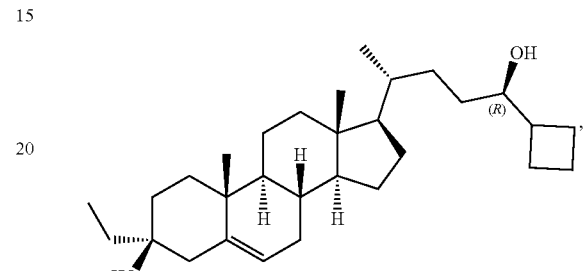
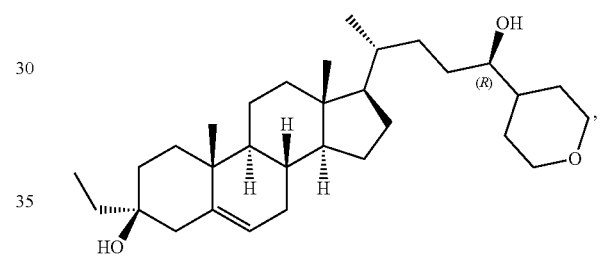
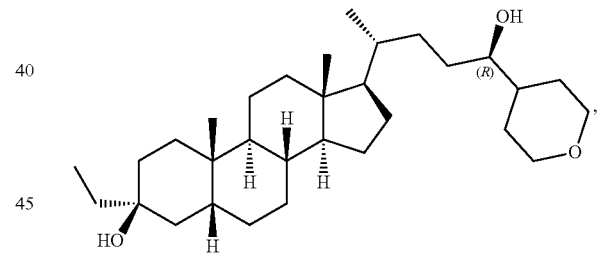
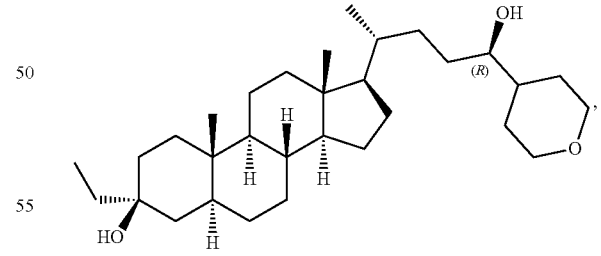
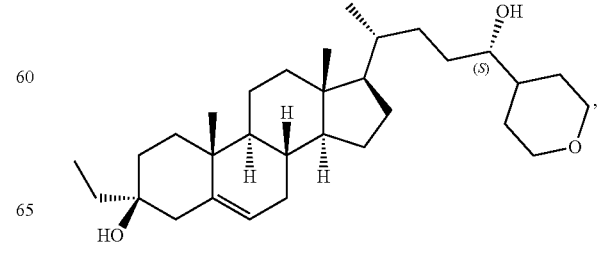

73
-continued
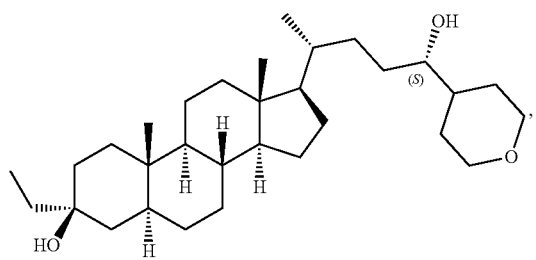
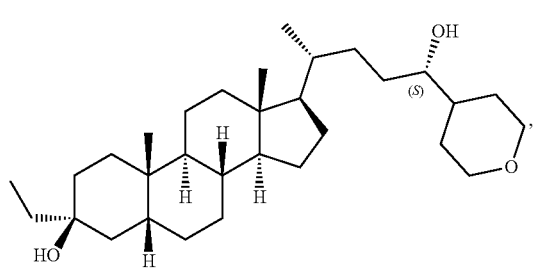
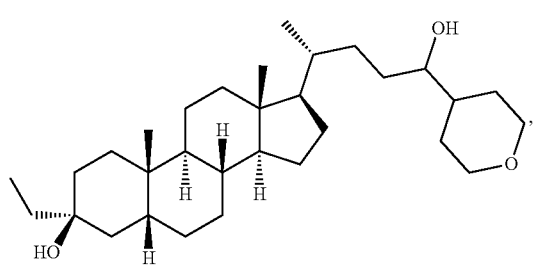
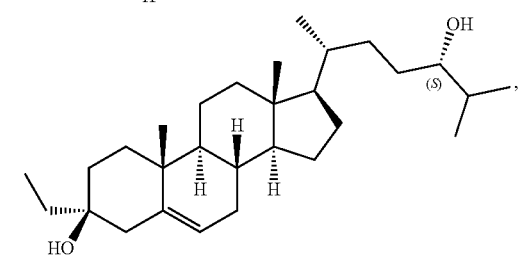
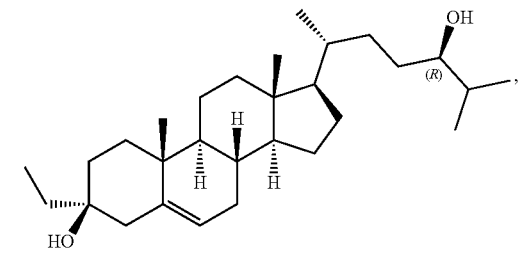
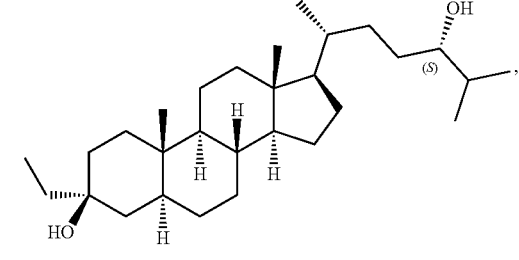
74
-continued
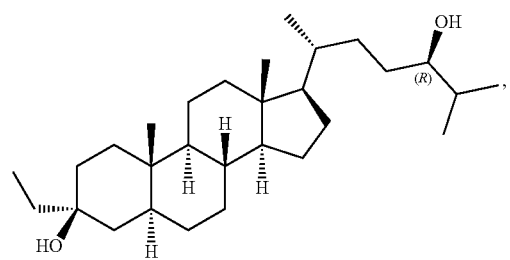
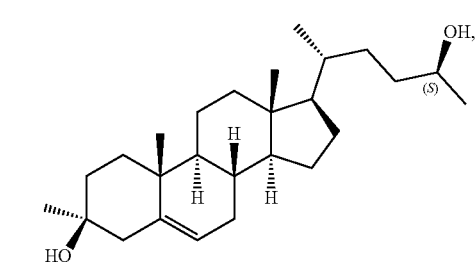
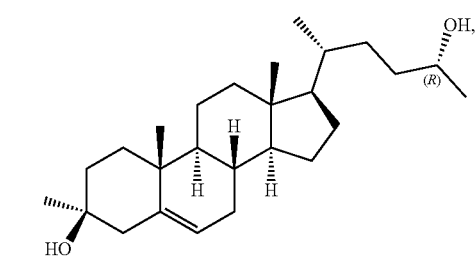
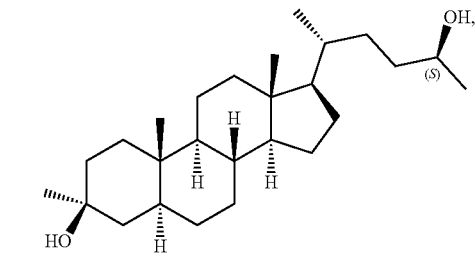
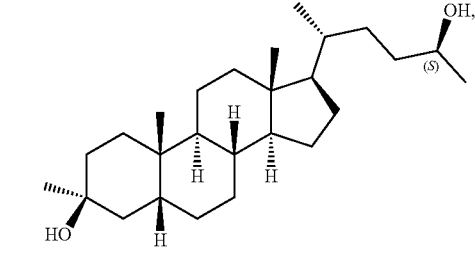
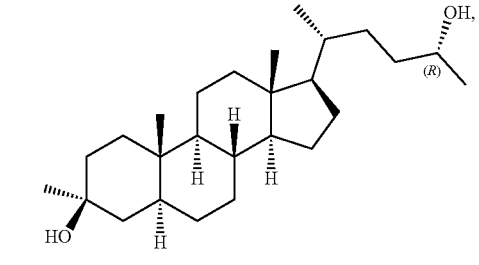

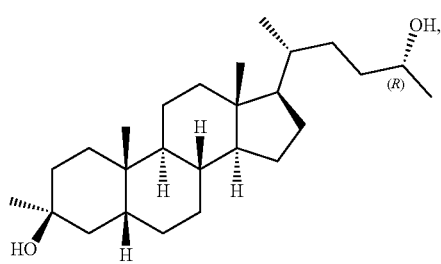
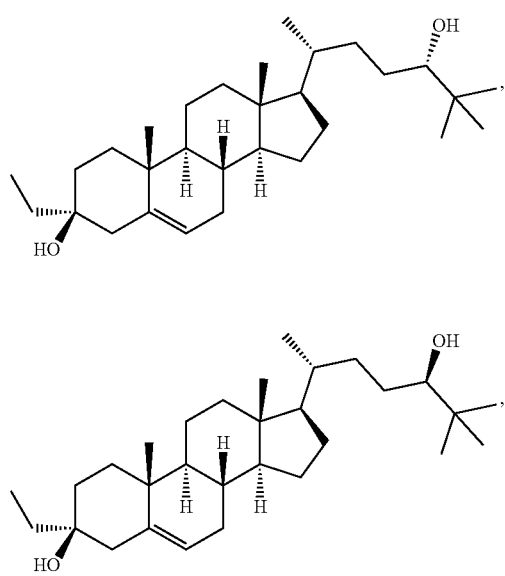
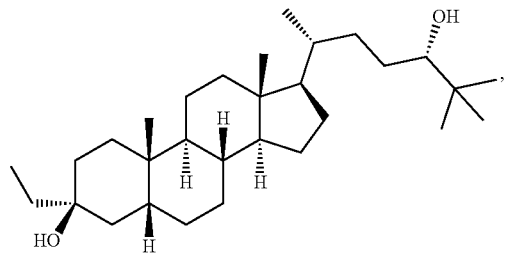
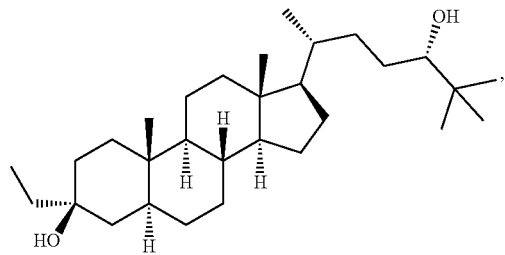
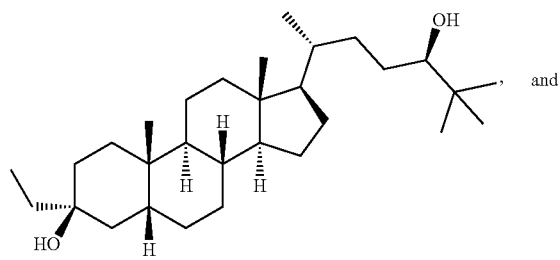
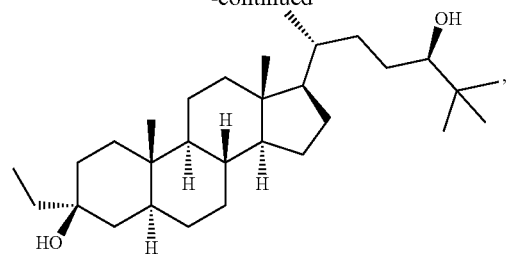
or a pharmaceutically acceptable salt thereof.
In some embodiments, the compound of Formula (I) is selected from:
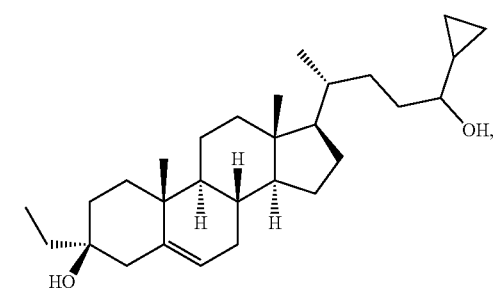
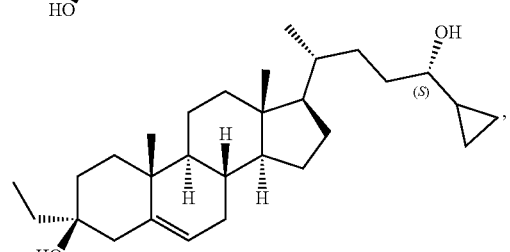
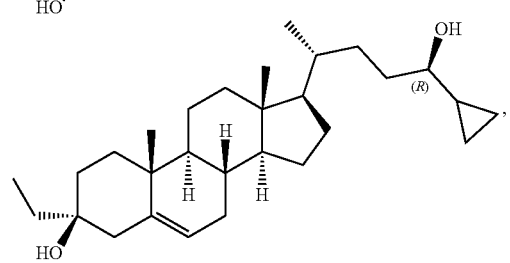
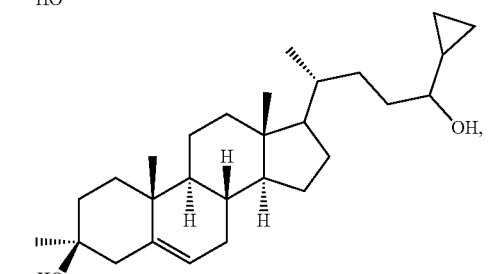
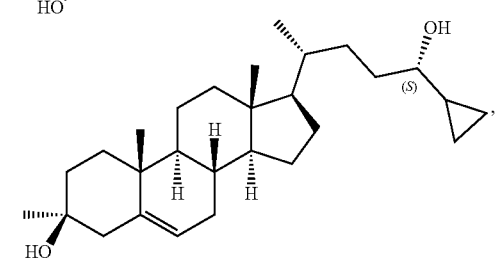

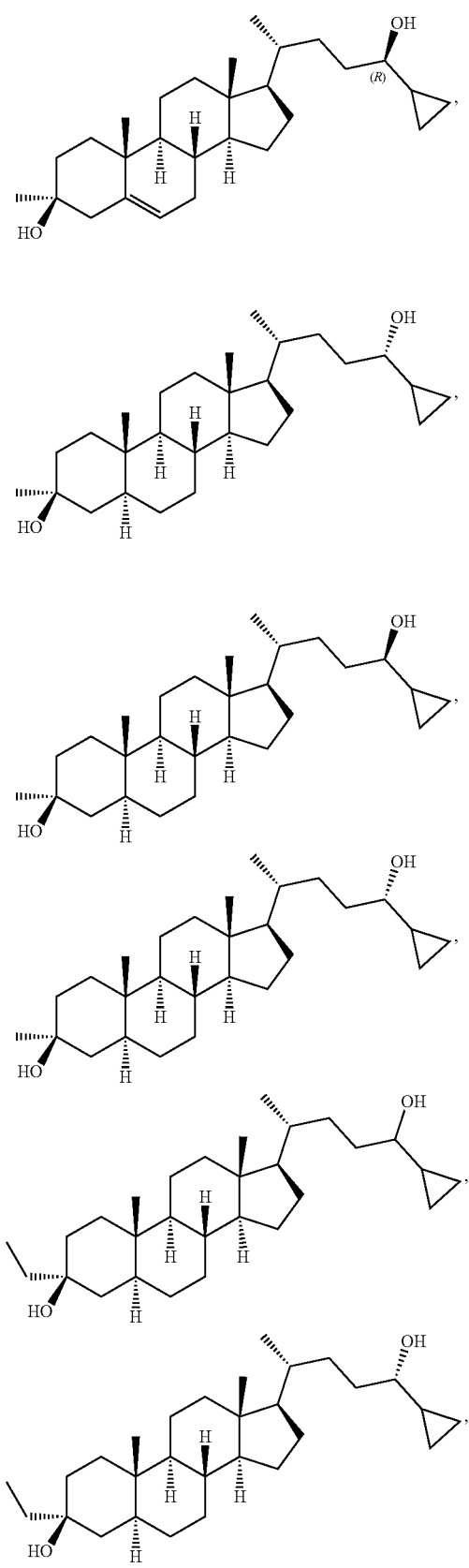
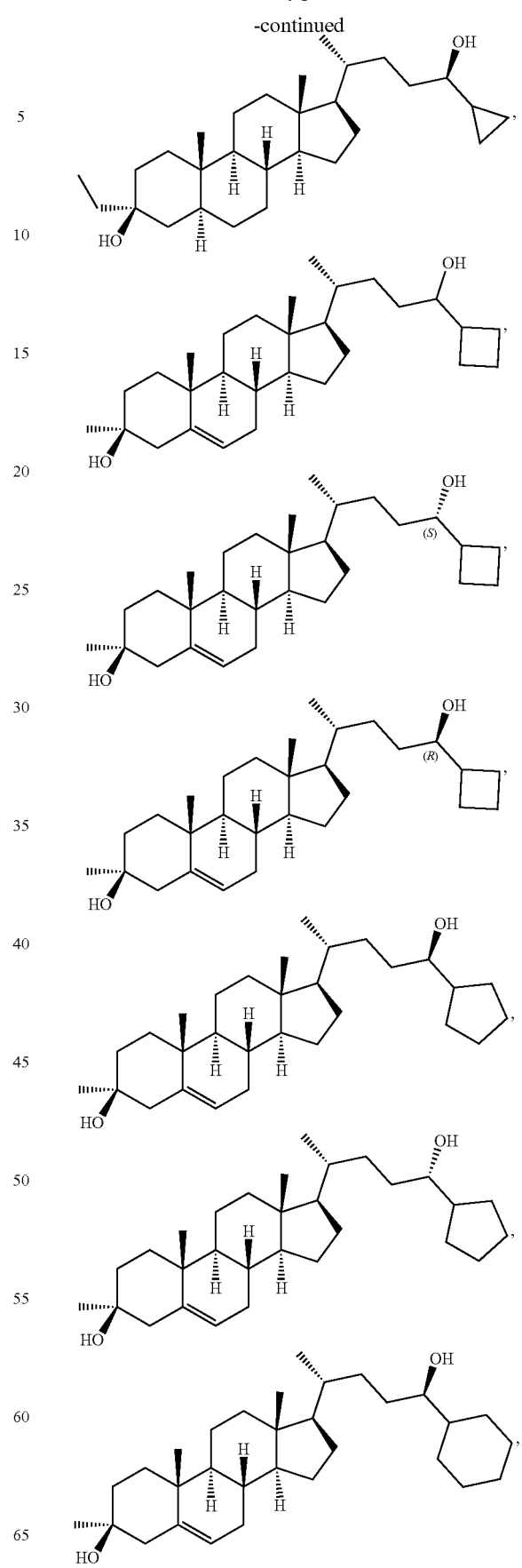

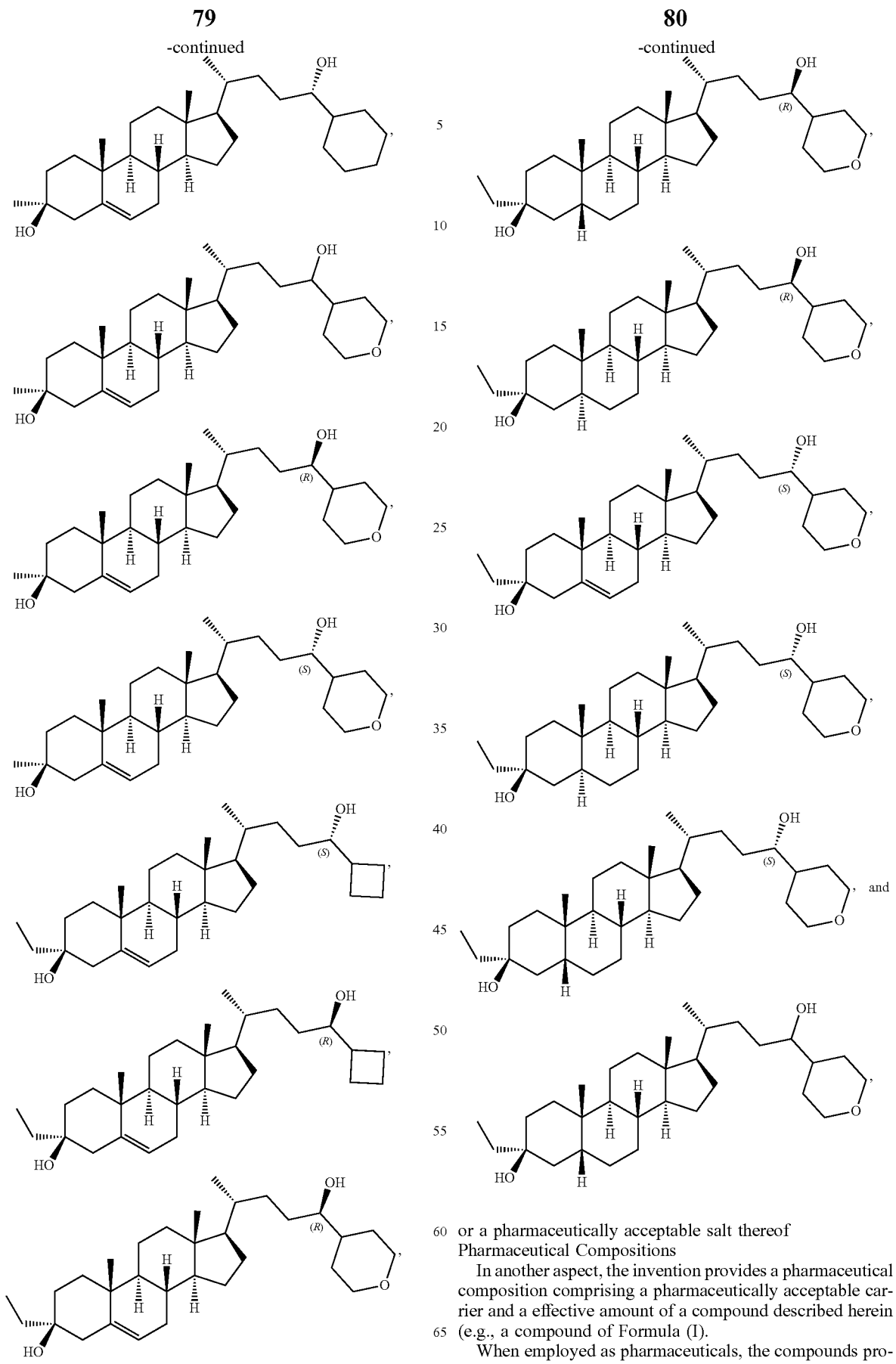

or a pharmaceutically acceptable salt thereof

Pharmaceutical Compositions

In another aspect, the invention provides a pharmaceutical composition comprising a pharmaceutically acceptable carrier and a effective amount of a compound described herein (e.g., a compound of Formula (I)).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound described herein (e.g., a compound of Formula (I), or pharmaceutical composition thereof) for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, PRIMOGEL® (primrose oil), or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound described herein (e.g., a compound of Formula (I)). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, CAPTISOL® (sulfobutylether-β-cyclodextrin). See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound described herein (e.g., a compound of Formula (I)). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound described herein (e.g., a compound of Formula (I), or pharmaceutically acceptable salt thereof), may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound described herein (e.g., a compound of Formula (I), or pharmaceutically acceptable salt thereof), may be admixed as a dry powder with a starch diluent in an approximate 1:1 weight ratio. The mixture is filled into 250 mg capsules (125 mg of active compound per capsule).

Exemplary Formulation 3—Liquid: A compound described herein (e.g., a compound of Formula (I), or pharmaceutically acceptable salt thereof), (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound described herein (e.g., a compound of Formula (I) or pharmaceutically acceptable salt thereof), may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound described herein (e.g., a compound of Formula (I), or pharmaceutically acceptable salt thereof), may be dissolved or suspended in a buffered sterile saline injectable aqueous medium to a concentration of approximately 5 mg/mL.

Exemplary Formulation 6—Tablets: A compound described herein (e.g., a compound of Formula (I) or pharmaceutically acceptable salt thereof), may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound described herein (e.g., a compound of Formula (I) or pharmaceutically acceptable salt thereof), may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound described herein (e.g., a compound of Formula (I), or pharmaceutically acceptable salt thereof), may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound described herein (e.g., a compound of Formula (I) or pharmaceutically acceptable salt thereof), may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound described herein (e.g., a compound of Formula (I), or pharmaceutically acceptable salt thereof), may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention (e.g., a compound of Formula (I), and pharmaceutically acceptable salts thereof), as described herein, are generally designed to modulate NMDA function, and therefore to act as oxysterols for the treatment and prevention of, e.g., CNS-related conditions in a subject. In some embodiments, the compounds described herein (e.g., a compound of Formula (I), and pharmaceutically acceptable salts thereof), as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound described herein (e.g., a compound of Formula (I), and pharmaceutically acceptable salts thereof), may act as a negative allosteric modulator (NAM) of NMDA, and inhibit NMDA receptor function. In certain embodiments, the present invention, e.g., a compound of Formula (I), or pharmaceutically acceptable salt thereof, may act as positive allosteric modulators (PAM) of NMDA, and potentiate NMDA receptor function. In certain embodiments, the compound described herein (e.g., a compound of Formula (I), and pharmaceutically acceptable salts thereof), modulates NMDA function, but does not act as a negative allosteric modulator (NAM) or positive allosteric modulator (PAM) of NMDA.

In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis. In some embodiments, the disorder is inflammatory bowel disease.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketomuria.

Exemplary conditions related to NMDA-modulation includes, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary CNS conditions related to NMDA-modulation include, but are not limited to, adjustment disorders, anxiety disorders (including obsessive-compulsive disorder, post-traumatic stress disorder, social phobia, generalized anxiety disorder), cognitive disorders (including Alzheimer's disease and other forms of dementia (e.g., frontotemporal dementia)), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, pain (including acute and chronic pain; headaches, e.g., migraine headaches), seizure disorders (including status epilepticus and monogenic forms of epilepsy such as Dravet's disease, and Tuberous Sclerosis Complex (TSC)), stroke, traumatic brain injury, movement disorders (including Huntington's disease and Parkinson's disease) and tinnitus. In certain embodiments, the compound of the present invention, e.g., a compound of Formula (I), and pharmaceutically acceptable salts thereof, can be used to induce sedation or anesthesia. In certain embodiments, the compound described herein (e.g., a compound of Formula (I), and pharmaceutically acceptable salts thereof), is useful in the treatment or prevention of adjustment disorders, anxiety disorders, cognitive disorders, dissociative disorders, eating disorders, mood disorders, schizophrenia or other psychotic disorders, sleep disorders, substance-related disorders, personality disorders, autism spectrum disorders, neurodevelopmental disorders, sterol synthesis disorders, pain, seizure disorders, stroke, traumatic brain injury, movement disorders and vision impairment, hearing loss, and tinnitus. In some embodiments, the disorder is Huntington's disease. In some embodiments, the disorder is Parkinson's disease. In some embodiments, the disorder is an inflammatory disease (e.g., lupus).

In another aspect, provided is a method of treating or preventing brain excitability in a subject susceptible to or afflicted with a condition associated with brain excitability, comprising administering to the subject an effective amount of a compound of the present invention, e.g., a compound of Formula (I) or a pharmaceutically acceptable salt thereof.

In yet another aspect, the present invention provides a combination of a compound of the present invention, e.g., a compound of Formula (I), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Diseases and Disorders

Described herein are methods of treating a sterol synthesis disorder. Exemplary disorders are described herein. The methods include administering to a subject, e.g., a subject suffering from a sterol synthesis disorder such as SLOS, a NMDA receptor modulating compound. Exemplary compounds are described herein.

Sterol Synthesis Disorders

In one aspect, described herein are methods for treating a sterol synthesis disorder. Cholesterol has an essential rule in growth and development. It is a membrane lipid and a precursor to many molecules that play important roles in cellular growth and differentiation, protein glycosylation, and signaling pathways. Biosynthesis of cholesterol involves a number of enzymes and intermediates. Disorders resulting from a deficiency in any of the enzymes involved in cholesterol biosynthesis lead to the accumulation of intermediates and imbalance in biomolecules, resulting in disorders including congenital skeletal malformations, dysmorphic facial features, psychomotor retardation, and failure to thrive. In an embodiment, a sterol synthesis disorder or symptom of a sterol synthesis disorder can be treated by administering to a subject suffering from a sterol synthesis disorder a compound described herein, such as a NMDA receptor modulating compound as described herein. Additional disorders are described below.

Smith-Lemli-Opitz Syndrome

In one aspect, described herein are methods for treating Smith-Lemli-Opitz Syndrome (or SLOS, or 7-dehydrocholesterol reductase deficiency). SLOS is an inborn error of cholesterol synthesis. In addition to microcephaly, moderate to severe intellectual disability, sensory hypersensitivity, stereotyped behaviors, dysmorphic facial features, and syndactyly of the second/third toes, a feature of the disease is reduced cerebrosterol (24(S)-hydroxycholesterol) levels. SLOS is an autosomal recessive genetic condition resulting from deficiency in the final enzyme of the cholesterol synthesis pathway, and causes low or low-normal plasma cholesterol levels and increased 7- and 8-dehydrocholesterol (DHC; 7DHC and 8DHC) levels. Common therapies currently used include dietary cholesterol supplementation, treatment with 3-hydroxy-3-methylglutaryl coenzyme A reductase inhibitors (HMG CoA reductase inhibitors, also known as statins), and treatment with agents that enhance cholesterol production and/or accretion; and to decrease the accumulation of 7DHC and 8DHC, the potentially toxic precursors of cholesterol.

Desmosterolosis

Desmosterolosis is a deficiency in desmosterol reductase and has a similar phenotype to SLOS. In one aspect, described herein are methods for treating desmosterolosis with compounds described herein.

Sitosterolemia

Sitosterolemia is a rare autosomal recessive disorder caused by mutations in two ATP-binding cassette (ABC) transporter genes (ABCG5 and ABCG8). Sitosterolemia enhances the absorption of plant sterols and cholesterol from the intestines. Patients typically present with tendon and tuberous xanthomas and premature coronary artery disease. In one aspect, described herein are methods for treating sitosterolemia with compounds described herein.

Cerebrotendinous Xanthomatosis (CTX)

In one aspect, described herein are methods for treating cerebrotendinous xanthomatosis (also referred to as cerebral cholesterosis, or Van Bogaert-Scherer-Epstein syndrome) with compounds described herein. CTX can be caused by a mutation in the CYP27A1 gene, which produces the sterol 27-hydroxylase enzyme. Sterol 27-hydroxylase metabolizes cholesterol into bile acids (e.g., chenodeoxycholic acid) that are important in the absorption of fats in the intestine. Enzyme dysfunction can lead to cholesterol accumulation in tissues. CTX is characterized by childhood diarrhea, cataracts, tendon xanthomas, reduced mental capability and abnormal movements in adults.

Mevalonate Kinase Deficiency Syndromes (MKD)

Mevalonate Kinase Deficiency (also referred to as mevalonic aciduria (a more severe form of MKD), or Hyper IgD Syndrome (HIDS, or hyperimmunoglobulinemia D) with period fever syndrome (a more benign form of MKD)) causes an accumulation of mevalonic acid in the urine as a result of insufficient activity of mevalonate kinase. MKD can result in developmental delay, hypotonia, anemia, hepatosplenomegaly, dysmorphic features, mental retardation, and overall failure to thrive. Mevalonic aciduria is characterized by delayed physical and mental development, failure to thrive, recurrent episodes of fever with vomiting and diarrhea, enlarged liver, spleen and lymph nodes, microcephaly (small head size), cataract, low muscle tone, short statute, distinct facial features, ataxia, and anemia. HIDS is characterized by recurrent episodes of fever associated with swollen lymph nodes, joint pain, gastrointestinal issues and skin rash. In one aspect, described herein are methods for treating MKD with the compounds described herein.

SC4MOL Gene Mutation (SMO Deficiency)

SC4MOL gene deficiency is a genetic disorder in the cholesterol biosynthesis pathway (e.g., mutations in the SC4MOL gene encoding a novel sterol oxidase). SC$MOL deficiency is characterized by the accumulation of dimethyl and monomethyl sterols that can be detected in blood, skin flakes or primary skin fibroblasts. In one aspect, described herein are methods for treating SMO deficiency with compounds described herein.

Niemann-Pick Disease

Niemann-Pick disease is a lysosomal storage disease resulting from a genetic mutation that affects metabolism. Niemann-Pick disease leads to abnormal accumulation of cholesterol and other fatty substances (lipids) due to an inability of the body to transport the substances. The accumulation damages the affected areas.

Autism

In one aspect, described herein are methods for treating autism spectrum disorder or autism. Autism spectrum disorder (ASD) and autism refer to a group of complex disorders of brain development. Autism is typically characterized by difficulties in social interaction, for example in verbal and nonverbal communication. Repetitive behaviors are also often seen in individuals having autism. Autism can be associated with intellectual disability, difficulties in motor coordination and attention and physical health issues, e.g., sleep and gastrointestinal disturbances. Individuals having autism can also excel in visual skills, music, math and art. Autism can refer to autistic disorder, childhood disintegrative disorder, pervasive developmental disorder—not otherwise specified (PDD-NOS), and Asperger syndrome. Autism also refers to monogenetic causes of autism such as synaptophathy's, e.g., Rett syndrome, Fragile X syndrome, Angelman syndrome.

Disorders Associated with Phenylketonuria

In one aspect, described herein are methods for treating disorders associated with phenylketonuria (e.g., cognitive disorders) with compounds described herein. Phenylketonuria can lead to hypochesterolemia and lowered vitamin D status. Total and low-density cholesterols and 25-hydroxy vitamin D have been found to be decreased in subjects suffering from phenylketonuria as compared with subjects not suffering from phenylketonuria (Clin. Chim. Acta 2013, 416: 54-59). 24S-hydroxycholesterol and 27S-hydroxycholesterol and 7α-hydroxycholesterol (e.g., representing peripheral and hepatic cholesterol elimination, respectively) have been shown to be significantly decreased in subjects suffering from phenylketonuria, while 7β-hydroxycholesterol (e.g., reflecting oxidative stress) was increased significantly in subjects suffering from phenylketonuria. Changes in the levels of 24S-OHC and 7β-hydroxycholesterol correlate with phenylalanine level, and 27S-hydroxycholesterol levels may correlate with the 25-hydroxy vitamin D level in subjects suffering from phenylketonuria.

EXAMPLES

In order that the invention described herein may be more fully understood, the following examples are set forth. Synthetic methods or intermediates may be found, for example in WO2014/160480*. The synthetic and biological examples described in this application are offered to illustrate the compounds, pharmaceutical compositions, and methods provided herein and are not to be construed in any way as limiting their scope.

The stereochemistry assigned herein (e.g., the assignment of "R" or "S" to the C24 position of the steroid) may be tentatively (e.g., randomly) assigned. For example, a C24 position may be drawn in the "R" configuration when the absolute configuration is "S." A C24 position may also be drawn in the "S" configuration when the absolute configuration is "R.".

Abbreviation List

Me: methyl; Ac: acetyl; Bu: butyl; t-Bu: tert-butyl; Ph: phenyl; THF: tetrahydrofuran; $Na_2SO_4$: sodium sulfate; $NaHCO_3$: sodium bicarbonate; $Na_2S_2O_3$: sodium thiosulfate; PE: petroleum ether; DCM: dichloromethane; DMF: N,N-dimethylformamide; Et: ethyl; EtOAc: ethylacetate; EtOH: ethanol; MeOH: methyl alcohol; t-BuLi: tert-butyl lithium; MTBE: methyl tert-butyl ether; HMPA: hexamethylphosphoric triamide; n-BuLi: n-butyllithium; TsCl: 4-methylbenzene-1-sulfonyl chloride; $Ph_3PMeBr$: methyltriphenylphosphonium bromide; PCC: pyridinium chlorochromate; t-BuOK: potassium tert-butoxide; TBAF: tetra-n-butylammonium fluoride; TBSCl: tert-Butyl(chloro)dimethylsilane; $AlMe_3$: trimethylaluminum; DMP: Dess-Martin periodinane; $(i-PrO)_4Ti$: titanium tetraisopropoxide; LAH: lithium aluminium hydride; LDA: lithium diisopropylamide; MAD: methyl aluminum bis(2,6-di-t-butyl-4- methylphenoxide); n-BuLi: normal-butyl lithium; BHT: 2,6-di-t-butyl-p-cresol (butylated hydroxytoluene); DIEA: diisopropylethylamine; NCS: N-chlorosuccinimide; iPrMgBr: isopropylmagnesium bromide.
Synthetic Methods
Example 1. Synthesis of Compound 1
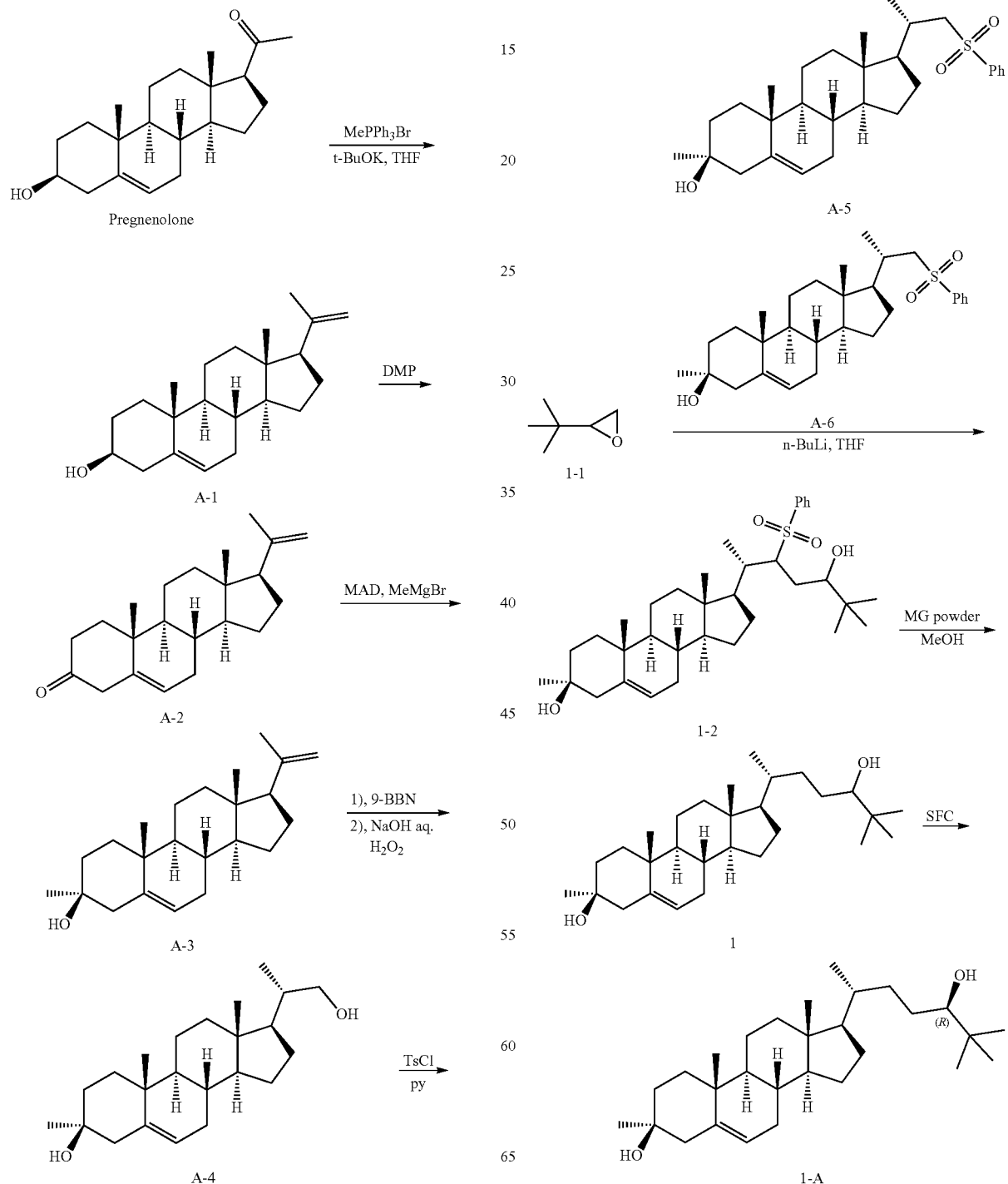

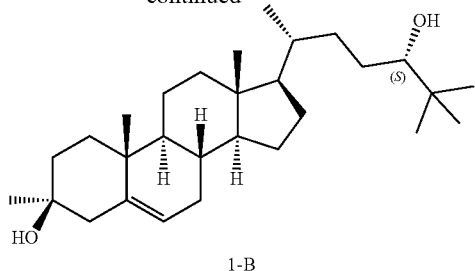

1-B

Step 1. Synthesis of Intermediate A-1. To a suspension of PPh₃MeBr (2.13 kg, 5.97 mol) in THF (3000 mL) was added t-BuOK (688 g, 6.14 mol) at 20° C. The color of the suspension was turned to yellow. After stirring at 50° C. for 1 h, Pregnenolone (630 g, 2.05 mol) was added at 50° C. The reaction mixture was stirred at 50° C. for 2 h. After cooling to 20° C., the mixture was treated with NH₄Cl (10% aq., 5 L) and heptane (3.5 L), stirred for 15 minutes. The organic layer was separated, concentrated in vacuum to give a crude material as a thick oil, which was poured into MTBE (10 L) with violent stirring and the mixture was stirred at room temperature for 16 hours. An off-white solid was formed and collected by filtration and washed with MTBE (3 L). The combined filtrate was mixed with MeOH (10 L) and concentrated to 6 L in vacuum. An off-white solid was formed, which was collected by filtration, washed with MeOH (3 L), dried in air to give 700 g of wet off-white solid. The combined MeOH filtrate was concentrated in vacuum to give a thick oil. The oil was poured into MTBE (3 L) with violent stirring and the mixture was stirred for 3 hours. An off-white solid was formed and collected by filtration, washed with MTBE (1 L). The combined filtrate was mixed with MeOH (3 L) and concentrated to 1.5 L in vacuum. An off-white solid was formed which was collected by filration, washed with MeOH (500 mL), dried in air to give 150 g of a wet off-white solid. The previous 700 g and 150 g batch were combined, dried in vacuum to give A-1 (552 g, 88%) as an off-white solid. $^1$H NMR (400 MHz, CDCl₃) δ 5.40-5.30 (m, 1H), 4.85 (s, 1H), 4.71 (s, 1H), 3.60-3.50 (m, 1H), 2.36-2.18 (m, 2H), 2.08-1.96 (m, 2H), 1.92-1.78 (m, 3H), 1.76 (s, 3H), 1.73-1.48 (m, 9H), 1.38-1.03 (m, 4H), 1.01 (s, 3H), 1.00-0.91 (m, 1H), 0.58 (s, 3H).

Step 2. Synthesis of Intermediate A-2. To a solution of A-1 (184 g, 585 mmol) in DCM (2000 mL) was added DMP (496 g, 1.17 mol) at 25° C. in portions, followed by adding water (42 mL). The mixture was stirred at 25° C. for 30 min the water (1500 mL) and NaHCO₃ (750 g) were added in portions with gas evolution. The mixture was then filtered through a pad of celite and the solid was washed with DCM (500 mL). The organic layer of the filtrate was separated, washed with Na₂S₂O₃ (1000 mL, sat.), dried over Na₂SO₄, filtered and concentrated in vacuum below 30° C. to give A-2 (250 g, crude) of a light yellow gum. The crude was used in the next step directly.

Step 3. Synthesis of Intermediate A-3. To a solution of BHT (769 g, 3.49 mol) in toluene (1500 mL) was added AlMe₃ (870 mL, 2M in toluene, 1.74 mol) at 0° C. After stirring at 0° C. for 1 h, the reaction mixture was cooled to −78° C. and a solution of A-2 (250 g crude, theoretical mass: 182 g, 582 mmol) in toluene (1000 mL) was added. After stirring at −78° C. for 1 h, MeMgBr (580 mL, 3 M in ether, 1.74 mmol) was added at −78° C. and the mixture was stirred at −78° C. for another 1 h. The mixture was quenched by pouring into citric acid (4000 mL, 20% aq.) in portions with gas released. Another two batches were conducted and combined together. The mixture was extracted with EtOAc (10 L). The organic layer was separated, washed with brine (5 L, 10%), NaHCO₃ (5 L, sat. aq.), brine (5 L, sat.), dried over Na₂SO₄ and concentrated in vacuum. The crude product was purified by silica gel column (eluting PE to EtOAc) to give crude A-3 (440 g) as a light yellow solid. To a solution of crude A-3 (440 g) in DCM (6 L) was added DMAP (24.4 g) and Ac₂O (51 g). The mixture was stirred at 20° C. for 1 h. To the mixture was added NaHCO₃ (1 L, sat. aq.) and stirred for 10 min. The organic layer was separated, concentrated in vacuum and the residue was triturated with PE (2 L). The solid was washed with PE (3×500 mL) and dried in vacuum to give A-3 (262 g) as an off-white solid. The combined filtrate was concentrated, purified by silica gel column (PE/EtOAc=50/1 to 8/1) and triturated with PE (1 L) give A-3 (30 g). 1H NMR (400 MHz, CDCl₃) δ 5.35-5.28 (m, 1H), 4.85 (s, 1H), 4.71 (s, 1H), 2.48-2.37 (m, 1H), 2.08-1.94 (m, 3H), 1.92-1.85 (m, 1H), 1.82-1.33 (m, 14H), 1.29-1.08 (m, 7H), 1.02 (s, 3H), 1.00-0.93 (m, 1H), 0.59 (s, 3H).

Step 4. Synthesis of Intermediate A-4. A-3 (100 g, 304 mmol) was dissolved in 9-BBN (1.21 L, 0.5 M in THF, 608 mmol) at 0° C. under N₂. The solution was stirred at 65° C. for 1 hour and re-cooled to 10° C. An off-white solid was precipitated. Ethanol (279 g, 6080 mmol) and aqueous NaOH (304 mL, 5 M, 1520 mmol) were added drop-wise to the mixture below 10° C. to give a clear solution. Then hydrogen peroxide (343 g, 30% in water, 3040 mmol) was added drop-wise below 10° C. The reaction mixture was stirred at 75° C. for 1 hour. After re-cooling to 20° C., a white solid was precipitated and collected by filtration. The filter cake was washed with water (3×500 mL), dried under vacuum to give a white solid, which was triturated in ethanol (1.5 L) at reflux to give A-4 (92 g, 88%) as an off-white solid. 1H NMR (400 MHz, CDCl₃) δ 5.31-5.29 (m, 1H), 3.65-3.63 (m, 1H), 3.38-3.37 (m, 1H), 2.42 (d, J=12.4, 1H), 2.05-1.92 (m, 3H), 1.88-1.63 (m, 4H), 1.63-1.40 (m, 8H), 1.40-0.90 (m, 16H), 0.70 (s, 3H).

Step 5. Synthesis of Intermediate A-5. To a solution of A-4 (124.5 g, 357 mmol) in chloroform (1 L) and pyridine (700 mL) was added TsCl (204 g, 1071 mmol) at 15° C. The mixture was stirred at 15° C. for 2 hrs. The mixture was concentrated under vacuum to remove most of the chloroform. The pyridine mixture was added into water (6 L). An off-white solid was produced and collected by filtration, which was washed with water (6×1 L). The off-white solid was dissolved in DCM (3.5 L), dried over Na₂SO₄, filtered and concentrated under vacuum to give A-5 (163 g, 92%) as an off-white solid. $^1$H NMR (400 MHz, CDCl₃) δ 7.78 (d, J=8.0 Hz, 2H), 7.34 (d, J=8.4 Hz, 2H), 5.29-5.28 (m, 1H), 3.96 (dd, J=3.2, 9.6 Hz, 1H), 3.79 (dd, J=6.4, 9.2 Hz, 1H), 2.45 (s, 3H), 2.41 (d, J=13.6 Hz, 1H), 1.99-1.91 (m, 3H), 1.77-1.39 (m, 11H), 1.26-0.86 (m, 16H), 0.64 (s, 3H).

Step 6. Synthesis of Compound A-6. To a solution of A-5 (163 g, 325 mmol) in DMF (1.7 L) was added KI (258 g, 1560 mmol) at 15° C. and the mixture was stirred at 60° C. for 2 hours. Sodium benzenesulfinate (195 g, 975 mmol) was added and the mixture was stirred at 60° C. for 2 hours. The reaction mixture was cooled to 25° C. and combined with another batch from 83 g of A-5. The combined mixture was poured into water (20 L) and some yellow solid was produced. The mixture was filtered and the filter cake was washed with water (3×2 L). The resulting filter cake was dissolved in DCM (5 L), washed with water (2×1 L), brine (2×1 L), dried over Na₂SO₄, filtered and concentrated in vacuum to give the crude product as a yellow solid, which was re-crystallized in toluene (2.5 L) to give A-6 (150 g, 65%) as a light yellow solid. The re-crystallization filtrate was concentrated under vacuum to give additional crude A-6 (30 g) as a yellow solid. $^1$H NMR (400 MHz, CDCl$_3$) δ 7.91 (d, J=7.2 Hz, 2H), 7.69-7.61 (m, 1H), 7.60-7.50 (m, 2H), 5.28-5.27 (m, 1H), 3.14 (d, J=14.0 Hz, 1H), 2.85 (dd, J=9.6, 14.0 Hz, 1H), 2.41 (d, J=12.8 Hz, 1H), 2.17-2.03 (m, 1H), 2.02-1.87 (m, 3H), 1.81-1.65 (m, 3H), 1.60-1.32 (m, 8H), 1.25-0.85 (m, 15H), 0.65 (s, 3H). LCMS Rt=2.057 min in 3.0 min chromatography, 30-90 AB, MS ESI calcd. for C$_{29}$H$_{41}$O$_2$S [M+H−H$_2$O]$^+$ 453, found 453.

Step 7. Synthesis of Compound 1-2. To THF (2 mL) under N$_2$ at −70° C. was added n-BuLi (1.69 mL, 4.24 mmol) and a suspension of A-6 (500 mg, 1.06 mmol) in THF (5 mL) was added drop-wise to give a light yellow suspension. After stirring at −70° C. for 30 mins, a solution of Compound 1-1 (212 mg, 2.12 mmol) in THF (2 mL) was added. The reaction was stirred at −70° C. for 10 mins and stirred at 25° C. for 16 hrs. The reaction mixture was quenched with water (10 mL) and extracted with EtOAc (3×50 mL). The combined organic phase was washed with brine (100 mL), dried over Na$_2$SO$_4$, filtered and concentrated under vacuum to give the crude product, which was purified by a silica gel column (PE/EtOAc=10/1) to give Compound 1-2 (500 mg, crude) as a yellow solid, which was used directly.

Step 8. Synthesis of Compound 1. To a solution of Compound 1-2 (500 mg, 0.876 mmol) in MeOH (10 mL) was added Mg powder (630 mg, 26.3 mmol) at 60° C. The mixture was stirred at 60° C. for 2 hrs and another batch of Mg powder (630 mg, 26.3 mmol) was added. The reaction was stirred at 60° C. for another 16 hrs. After cooling, the mixture was quenched with HCl (100 mL, 1M) until the reaction became clear and extracted with DCM (2×30 mL). The combined organic phase was dried over Na$_2$SO$_4$, filtered, concentrated and purified by a silica gel column (PE/EtOAc=10/1 to 8/1) to give Compound 1 (104 mg, 28%) as an off-white solid.

Compound 1: $^1$H NMR (400 MHz, CDCl$_3$) δ 5.31-5.30 (m, 1H), 3.19-3.05 (m, 1H), 2.44-2.40 (m, 1H), 2.08-1.91 (m, 3H), 1.91-1.57 (m, 6H), 1.52-1.35 (m, 11H), 1.74-1.12 (m, 10H), 1.11-1.01 (m, 5H), 0.90 (s, 9H), 0.68 (s, 3H). LCMS Rt=1.564 min in 2 min chromatography, 10-80 AB, MS ESI calcd. for C$_{29}$H$_{47}$ [M+H−2H$_2$O]$^+$ 395, found 395.

Step 9. Compound 1 (0.83 g) was purified by SFC (Column: AD (250 mm*30 mm, 5 um), 0.1% NH$_3$H$_2$O ETOH, Gradient: from 30% to 100%, FlowRate (ml/min): 60 mL/min, 25° C.) to afford Compound 1-A (379 mg, 46%) and Compound 1-B (338 mg, 41%) as an off white solid.

Compound 1-A: $^1$H NMR (400 MHz, CDCl$_3$) δ 5.33-5.28 (m, 1H), 3.12-3.06 (m, 1H), 2.45-2.40 (m, 1H), 2.05-1.92 (m, 3H), 1.91-1.64 (m, 5H), 1.63-1.57 (m, 3H), 1.52-1.38 (m, 6H), 1.37-1.24 (m, 3H), 1.21-1.09 (m, 5H), 1.09-1.03 (m, 2H), 1.02-1.00 (m, 4H), 0.99-0.96 (m, 1H), 0.94 (d, J=6.8 Hz, 3H), 0.90 (s, 9H), 0.68 (s, 3H). LCMS Rt=1.361 min in 2.0 min chromatography, 30-90 AB, MS ESI calcd. for C$_{29}$H$_{47}$ [M+H−2H$_2$O]$^+$ 395, found 395.

Compound 1-B: $^1$H NMR (400 MHz, CDCl$_3$) δ 5.32-5.30 (m, 1H), 3.16-3.14 (m, 1H), 2.45-2.40 (m, 1H), 2.05-1.92 (m, 3H), 1.90-1.66 (m, 4H), 1.63-1.57 (m, 2H), 1.52-1.38 (m, 6H), 1.37-1.24 (m, 5H), 1.21-1.09 (m, 5H), 1.09-0.95 (m, 5H), 0.94 (d, J=6.4 Hz, 3H), 0.90 (s, 9H), 0.69 (s, 3H). LCMS Rt=1.361 min in 2.0 min chromatography, 30-90 AB, MS ESI calcd. for C$_{29}$H$_{47}$ [M+H−2H$_2$O]$^+$ 395, found 395.

Example 2. Synthesis of Compound 2

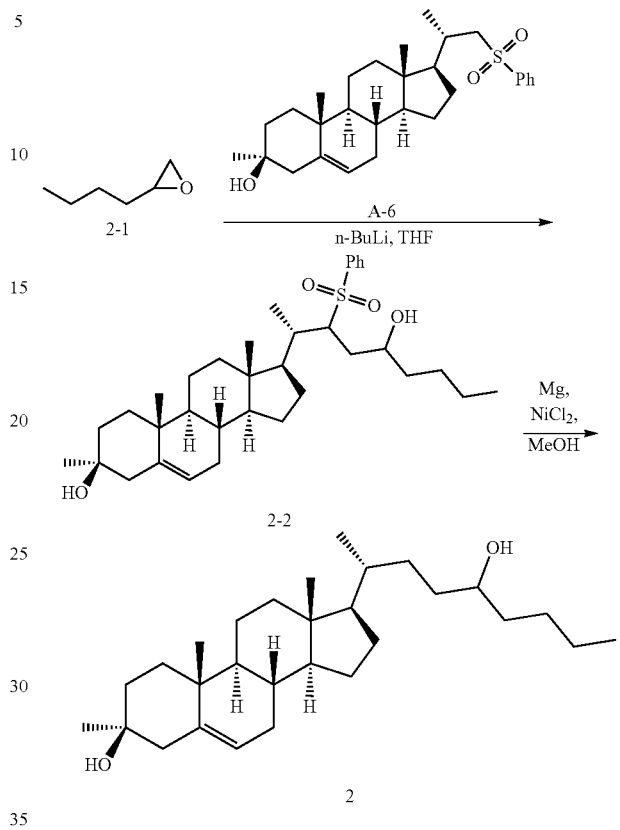

Synthesis of Compound 2-2. To THF (6 mL) was added n-BuLi (2.5 M, 2.65 mmol, 1.05 mL, 2.5 eq) under N$_2$ at −70° C. and a suspension of A-6 (1.06 mmol, 500 mg, 1.0 eq.) in THF (3 mL) was added dropwise to give a light yellow suspension. After stirring at −70° C. for 30 mins, a solution of Compound 2-1 (1.27 mmol, 127 mg, 1.2 eq.) in THF (1 mL) was added dropwise. The reaction was stirred at 15° C. for 12 hrs. The reaction was quenched with sat·NH$_4$Cl (30 mL) and extracted with EtOAc (3×10 mL). The combined organic layers were dried over Na$_2$SO$_4$, filtered and concentrated to give Compound 2-2 (560 mg, crude) as a light yellow foam, which was used directly in the next step.

Synthesis of Compound 2. To a solution of Compound 2-2 (560 mg, 0.98 mmol) in MeOH (10 mL) was added NiCl$_2$ (127 mg, 0.980 mmol). After heating to 55° C., Mg turnings (938 mg) were added and the mixture was stirred at 55° C. for 30 minutes. After that, another batch of Mg turnings (938 mg) was added and the reaction was stirred at 55° C. for 16 hrs. After cooling, the mixture was quenched with HCl (100 mL, 1N) until the reaction became clear and extracted with DCM (2×30 mL). The combined organic phase was dried over Na$_2$SO$_4$, filtered and concentrated. The crude residue was purified by flash column (0-10% of EtOAc in PE/DCM (v/v=2/1)) to give Compound 2 (26 mg, 6%) as an off-white solid. $^1$H NMR (400 MHz, CDCl$_3$) δ 5.30-5.29 (m, 1H), 3.54-3.52 (m, 1H), 2.44-2.40 (m, 1H), 2.05-1.90 (m, 3H), 1.85-1.58 (m, 4H), 1.56-1.24 (m, 18H), 1.23-0.92 (m, 19H), 0.68 (s, 3H). LCMS Rt=1.359 min in 2.0 min chromatography, 30-90AB_ELSD, MS ESI calcd. for C$_{29}$H$_{47}$ [M+H−2H$_2$O]$^+$ 395, found 395.

Example 3. Synthesis of Compounds 3 and 4

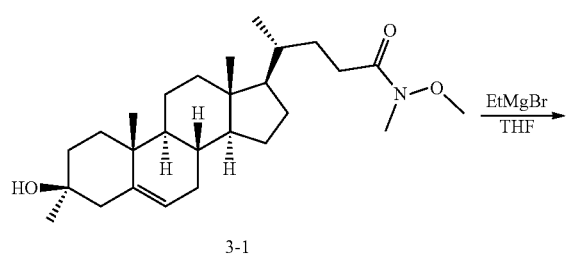

3-1

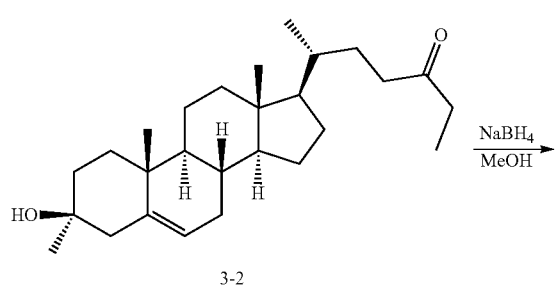

3-2

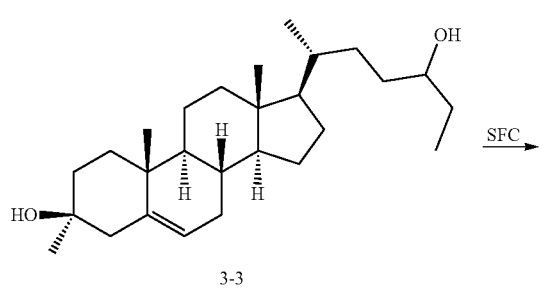

3-3

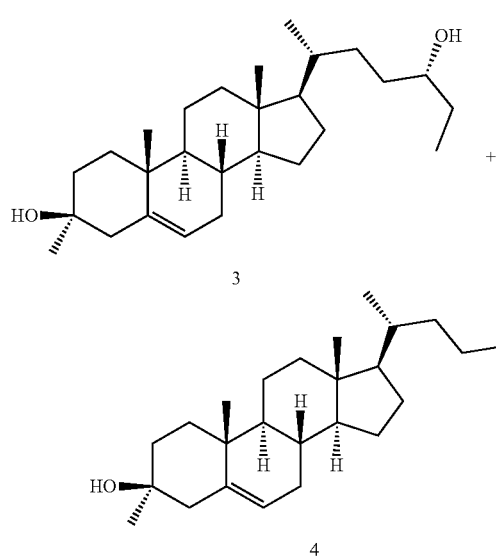

3

4

Synthesis of Compound 3-2. To a solution of Compound 3-1* (7.0 g, 16.2 mmol) in THF (70 mL) was added dropwise ethylmagnesium bromide (26.9 mL, 80.9 mmol, 3M in Et$_2$O) at 0° C. under Nitrogen atmosphere. The reaction mixture was stirred at 25° C. for 12 h. The mixture was quenched with saturated aqueous NH$_4$Cl (100 mL) and extracted with EtOAc (2×200 mL). The combined organic phase was washed with brine (200 mL), dried over anhydrous Na$_2$SO$_4$, concentrated in vacuum. The residue was purified by column. chromatography on silica del (PE/EtOAc=20/1) to afford Compound 3-2 (500 mg, 8%) as an off-white solid. 1H NMR (400 MHz, CDCl$_3$) δ 5.30-5.28 (m, 1H), 2.42-2.39 (m, 5H), 1.98-1.63 (m, 8H), 1.53-0.84 (m, 27H), 0.66 (s, 3H).

Synthesis of Compound 3-3. To a solution of Compound 3-2 (500 mg, 1.24 mmol) in MeOH (10 mL) was added NaBH$_4$ (93.8 mg, 2.48 mmol) in portions. The reaction mixture was stirred at 25° C. for 2 h. The reaction mixture was quenched with saturated aqueous NH$_4$Cl (10 mL) and extracted with EtOAc (2×30 mL). The combined organic phase was washed with brine (30 mL) and concentrated in vacuum. The residue was purified by column chromatography on silica gel (PE/EtOAc=20/1) to afford Compound 3-3 (500 mg, crude), which was purified by preparative HPLC to afford Compound 3-3 (60 mg, 12%) as an off-white solid. $^1$H NMR (400 MHz, CDCl3) δ 5.33-5.28 (m, 1H), 3.48-3.47 (m, 1H), 2.45-2.38 (m, 1H), 2.02-1.57 (m, 14H), 1.57-0.92 (m, 26H), 0.67 (s, 3H).

Synthesis of Compounds 3 and 4. Compound 3-3 (60 mg, 149 μmol) in MeOH (5 mL) was separated by SFC (Column: AD (250 mm*30 mm, 5 um); Condition: Base-EtOH) to afford peak 1 as Compound 3 (33.6 mg, 56%) and peak 2 as Compound 4 (18.3 mg, 31%) as an off-white solid. Compound 3: $^1$H NMR (400 MHz, CDCl$_3$) δ 5.32-5.28 (m, 1H), 3.48-3.46 (m, 1H), 2.46-2.39 (m, 1H), 2.02-1.57 (m, 11H), 1.54-0.92 (m, 29H), 0.67 (s, 3H). LCMS Rt=1.443 min in 2.0 min chromatography, 10-80 AB, MS ESI calcd. for C$_{27}$H$_{45}$O [M−H$_2$O+H]$^+$ 385, found 385. Compound 4: $^1$H NMR (400 MHz, CDCl$_3$) δ 5.33-0.28 (m, 1H), 3.48-3.46 (m, 1H), 2.45-2.41 (m, 1H), 2.02-1.57 (m, 11H), 1.54-0.92 (m, 29H), 0.68 (s, 3H). LCMS Rt=1.446 min in 2.0 min chromatography, 10-80 AB, MS ESI calcd. C$_{27}$H$_{45}$O [M−H$_2$O+H]$^+$ 385, found 385.

Example 4. Synthesis of Compounds 6 and 7

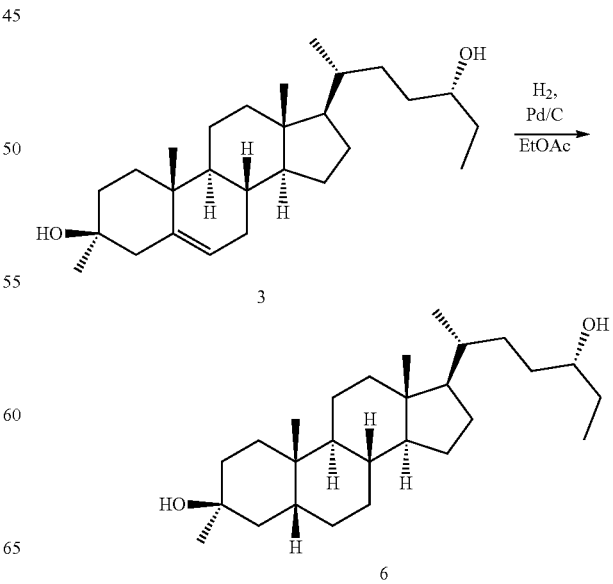

3

6

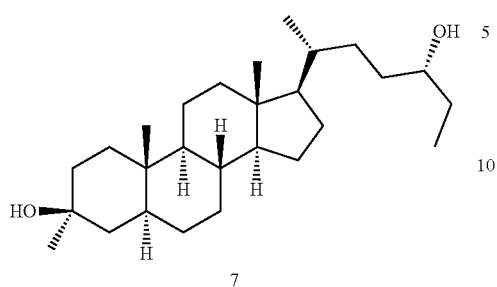

7

To a solution of Compound 3 (90 mg, 223 μmol) in EtOAc (10 mL) was added Pd/C (100 mg, 10%, dry), then the mixture was stirred under hydrogen (50 psi) at 50° C. for 12 h. The mixture was filtered through a pad of celite and the filtrate was evaporated under reduced pressure. The residue was purified by column chromatography on silica gel (PE/EtOAc 20/1 to 10/1) to afford Compound 6 (4.8 mg, 5%) and Compound 7 (44.5 mg, 49%) as off white solids. Compound 6: $^1$H NMR (400 MHz, CDCl$_3$) δ 3.47-3.46 (m, 1H), 2.05-1.82 (m, 4H), 1.79-1.57 (m, 2H), 1.55-0.90 (m, 38H), 0.64 (s, 3H). LCMS Rt=1.484 min in 2.0 min chromatography, 10-80 AB, MS ESI calcd. for C$_{27}$H$_{45}$ [M−2H$_2$O+H]$^+$ 369, found 369. Compound 7: $^1$H NMR (400 MHz, CDCl$_3$) δ 3.49-3.46 (m, 1H), 1.97-1.90 (m, 1H), 1.90-1.55 (m, 1H), 1.55-1.62 (m, 4H), 1.53-1.24 (m, 19H), 1.23-0.82 (m, 15H), 0.80 (s, 3H), 0.64-0.63 (m, 4H). LCMS Rt=1.474 min in 2.0 min chromatography, 10-80 AB, MS ESI calcd. for C$_{27}$H$_{45}$ [M−2H$_2$O+H]$^+$ 369, found 369.

Example 5. Synthesis of Compounds 8 and 9

9

To a solution of Compound 4 (90 mg, 223 umol) in EtOAc (10 mL) was added Pd/C (100 mg, 10%, dry), then the mixture was stirred under hydrogen (50 psi) at 50° C. for 12 h. The mixture was filtered through a pad of celite and the filtrate was evaporated under reduced pressure. The residue was purified by column chromatography on silica gel (PE/EtOAc=20/1 to 10/1) to afford Compound 8 (5.5 mg, 6%) and Compound 9 (64.7 mg, 72%) as off white solids. Compound 8: $^1$H NMR (400 MHz, CDCl$_3$) δ 3.47-3.46 (m, 1H), 1.86-1.75 (m, 4H), 1.65-0.90 (m, 40H), 0.64 (s, 3H). LCMS Rt=1.484 min in 2.0 min chromatography, 10-80 AB, MS ESI calcd. for C$_{27}$H$_{45}$ [M−2H$_2$O+H]$^+$ 369, found 369.

Compound 9: $^1$H NMR (400 MHz, CDCl$_3$) δ 3.47-3.46 (m, 1H), 1.97-1.90 (m, 1H), 1.90-1.78 (m, 1H), 1.70-1.58 (m, 6H), 1.50-0.90 (m, 35H), 0.64-0.63 (m, 4H). LCMS Rt=1.472 min in 2.0 min chromatography, 10-80 AB, MS ESI calcd. for C$_{27}$H$_{45}$ [M−2H$_2$O+H]$^+$ 369, found 369.

Example 6. Synthesis of Compounds 10 and 11

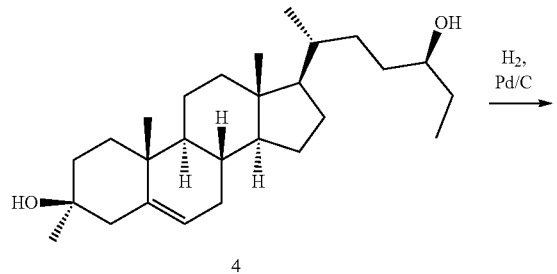

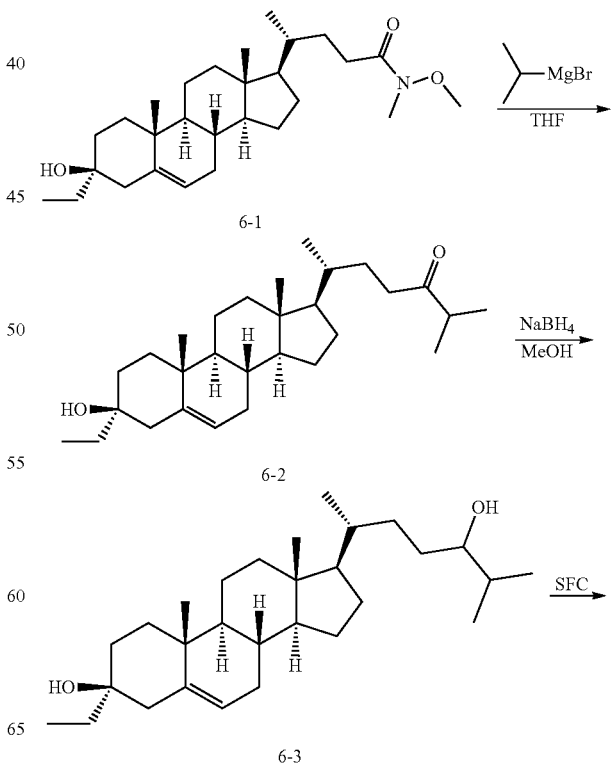

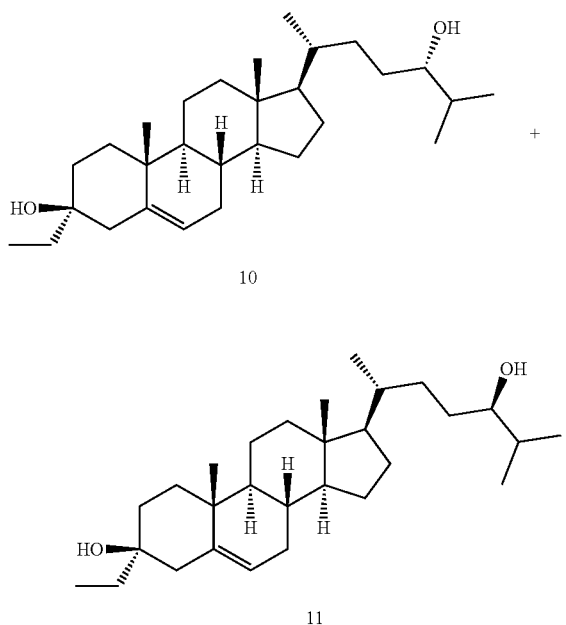

10

11

Synthesis of Compound 6-2. To a solution Compound 6-1* (3.6 g, 8.07 mmol) in THF (50 mL) was added dropwise isopropylmagnesium bromide (16.1 mL, 32.2 mmol, 2M in THF) at 0° C. under nitrogen atmosphere. The reaction mixture was stirred at 25° C. for 12 h. The mixture was quenched with saturated aqueous NH$_4$Cl (50 mL) and extracted with EtOAc (2×100 mL). The combined organic phase was washed with brine (50 mL). dried over anhydrous Na$_2$SO$_4$ and concentrated in vacuum. The residue was purified by column chromatography on silica gel (PE/EtOAc=20/1) to afford Compound 6-2 (600 mg, 17%) as an off-white solid. $^1$H NMR (400 MHz, CDCl$_3$) δ 5.30-5.26 (m, 1H), 2.61-2.51 (m, 1H), 2.38-2.34 (m, 3H), 2.01-1.59 (m, 8H), 1.55-1.25 (m, 11H), 1.23-0.83 (m, 21H), 0.67 (s, 3H).

Synthesis of Compound 6-3. To a suspension of Compound 6-2 (500 mg, 1.16 mmol) in MeOH (8 mL) was added NaBH$_4$ (87.7 mg, 2.32 mmol) in portions. The reaction mixture was stirred at 25° C. for 2 h. The reaction mixture was quenched with saturated aqueous NH$_4$Cl (10 mL) and H$_2$O (30 mL) was added. An off-white solid was precipitated, filtered, collected and dried by vacuum to give Compound 6-3 (500 mg, 100%) as an off-white solid. $^1$H NMR (400 MHz, CDCl$_3$) δ 5.30-5.26 (m, 1H), 3.31-3.30 (m, 1H), 2.40-2.30 (m, 1H), 2.04-1.63 (m, 7H), 1.55-1.25 (m, 15H), 1.23-0.84 (m, 22H), 0.67 (s, 3H).

Synthesis of Compounds 10 and 11. Compound 6-3 (500 mg, 1.16 mmol) in MeOH (10 mL) was separated by basic conditions SFC (Column: AD (250 mm*30 mm, 5 um); Condition: Base-MeOH) to afford peak 1 as Compound 10 and peak 2 as Compound 11 (230 mg, 46%) as an off-white solid. Compound 10: $^1$H NMR (400 MHz, CDCl$_3$) δ 5.30-5.24 (m, 1H), 3.32-3.31 (m, 1H), 2.40-2.34 (m, 1H), 2.04-1.90 (m, 3H), 1.90-1.57 (m, 10H), 1.55-1.25 (m, 9H), 1.23-0.82 (m, 22H), 0.67 (s, 3H). LCMS Rt=1.648 min in 2.0 min chromatography, 10-80 AB, MS ESI calcd. for C$_{29}$H$_{49}$O [M−H$_2$O+H]$^+$ 413, found 413. Compound 11: $^1$H NMR (400 MHz, CDCl$_3$) δ 5.29-5.25 (m, 1H), 3.32-3.31 (m, 1H), 2.40-2.32 (m, 1H), 2.04-1.57 (m, 6H), 1.54-1.25 (m, 17H), 1.23-0.84 (m, 21H), 0.68 (s, 3H) LCMS Rt=1.641 min in 2.0 min chromatography, 10-80 AB, MS ESI calcd. for C$_{29}$H$_{49}$O [M−H$_2$O+H]$^+$ 413, found 413.

Example 7. Synthesis of Compounds 12 and 13

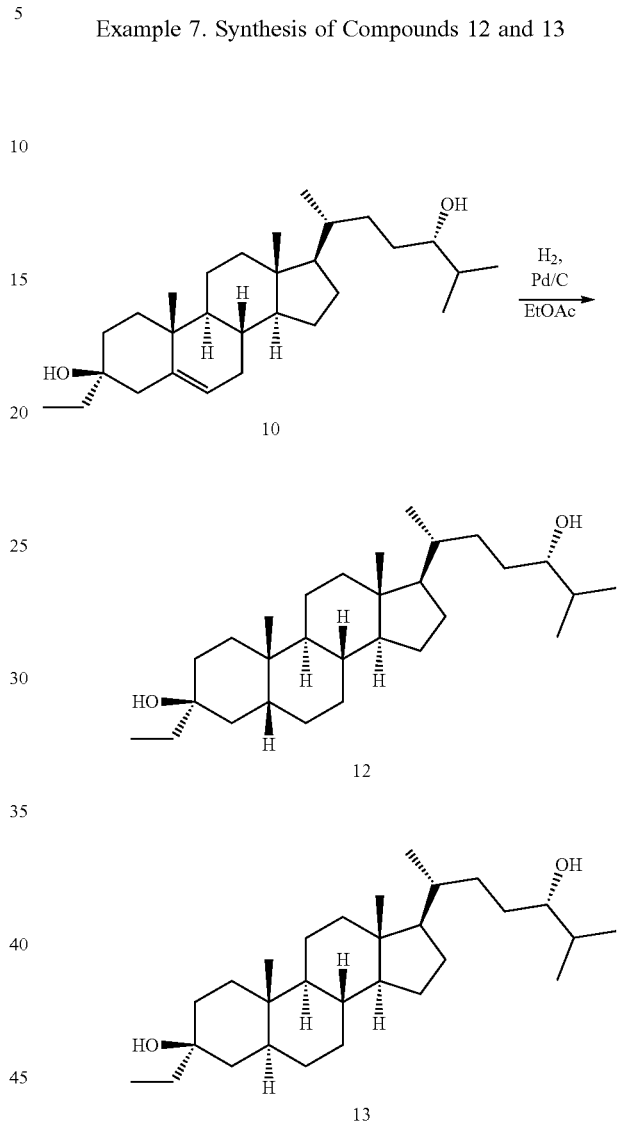

To a solution of Compound 10 (150 mg, 348 μmol) in EtOAc (15 mL) was added Pd/C (200 mg, 10%, dry), then the mixture was stirred under hydrogen (50 psi) at 50° C. for 12h. The mixture was filtered through a pad of celite and the filtrate was evaporated under reduced pressure. The residue was purified by column chromatography on silica gel (PE/EtOAc=30/1 to 20/1) to afford Compound 12 (10.8 mg, 7%) and Compound 13 (82.7 mg, 55%) as off white solids. Compound 12: $^1$H NMR (400 MHz, CDCl$_3$) δ 3.31-3.30 (m, 1H), 1.95-1.58 (m, 5H), 1.50-1.10 (m, 22H), 1.10-0.88 (m, 21H), 0.64 (s, 3H). LCMS Rt=1.680 min in 2.0 min chromatography, 10-80 AB, MS ESI calcd. for C$_{29}$H$_{49}$ [M−2H$_2$O+H]$^+$ 397, found 397. Compound 13: $^1$H NMR (400 MHz, CDCl$_3$) δ 3.31-3.30 (m, 1H), 1.97-1.80 (m, 1H), 1.80-1.75 (m, 1H), 1.75-1.58 (m, 4H), 1.58-1.25 (m, 17H), 1.25-0.82 (m, 24H), 0.64-0.63 (m, 4H). LCMS Rt=1.682 min in 2.0 min chromatography, 10-80 AB, MS ESI calcd. for C$_{29}$H$_{49}$ [M−2H$_2$O+H]$^+$ 397, found 397.

Example 8. Synthesis of Compounds 14 and 15

Example 9. Synthesis of Compounds 16 and 17

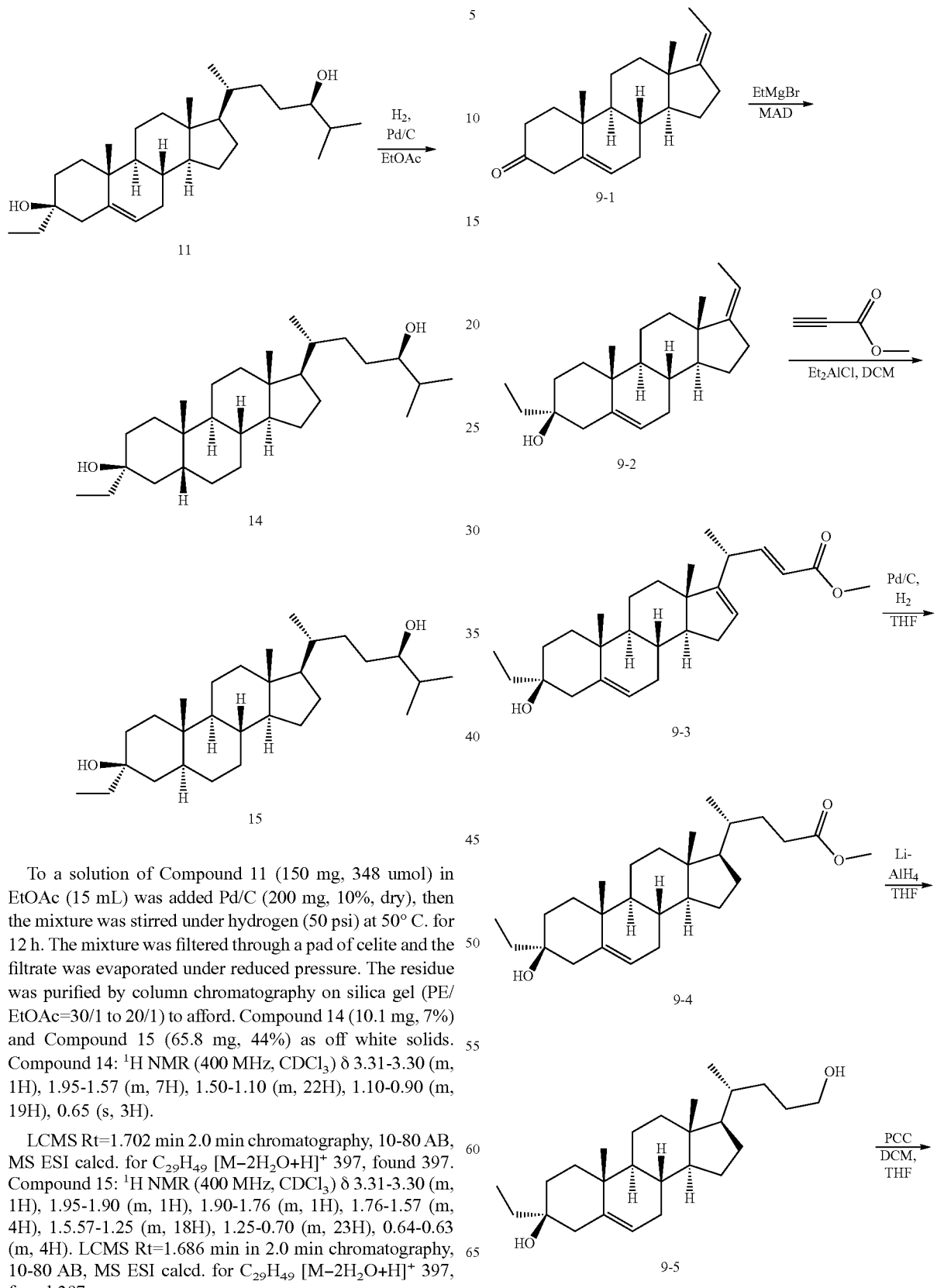

To a solution of Compound 11 (150 mg, 348 umol) in EtOAc (15 mL) was added Pd/C (200 mg, 10%, dry), then the mixture was stirred under hydrogen (50 psi) at 50° C. for 12 h. The mixture was filtered through a pad of celite and the filtrate was evaporated under reduced pressure. The residue was purified by column chromatography on silica gel (PE/EtOAc=30/1 to 20/1) to afford. Compound 14 (10.1 mg, 7%) and Compound 15 (65.8 mg, 44%) as off white solids. Compound 14: $^1$H NMR (400 MHz, CDCl$_3$) δ 3.31-3.30 (m, 1H), 1.95-1.57 (m, 7H), 1.50-1.10 (m, 22H), 1.10-0.90 (m, 19H), 0.65 (s, 3H).

LCMS Rt=1.702 min 2.0 min chromatography, 10-80 AB, MS ESI calcd. for $C_{29}H_{49}$ [M−2H$_2$O+H]$^+$ 397, found 397. Compound 15: $^1$H NMR (400 MHz, CDCl$_3$) δ 3.31-3.30 (m, 1H), 1.95-1.90 (m, 1H), 1.90-1.76 (m, 1H), 1.76-1.57 (m, 4H), 1.5.57-1.25 (m, 18H), 1.25-0.70 (m, 23H), 0.64-0.63 (m, 4H). LCMS Rt=1.686 min in 2.0 min chromatography, 10-80 AB, MS ESI calcd. for $C_{29}H_{49}$ [M−2H$_2$O+H]$^+$ 397, found 397.

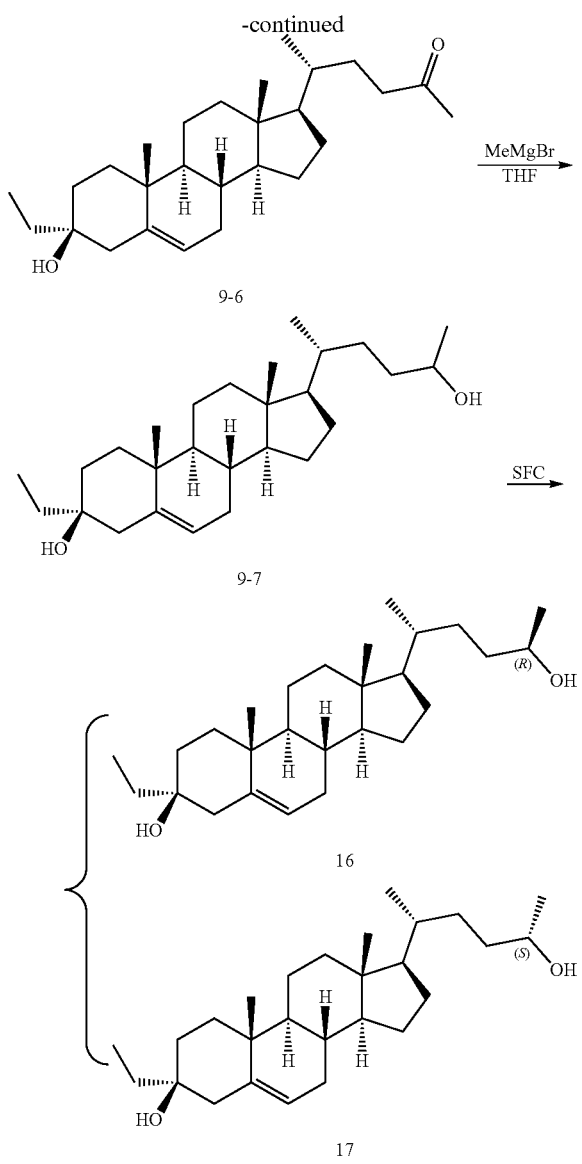

Synthesis of Compound 9-2. To a solution of 2,6-di-tert-butyl-4-methylphenol (220 g, 1.0 mol) in toluene (250 mL) was added AlMe₃ (250 mL, 501 mmol, 2 M in toluene) dropwise below 25° C. The solution was stirred at 25° C. for 1 h. Then a solution of Compound 9-1 (50 g, 167 mmol) in DCM (400 mL) was added dropwise at −78° C. After stirring at the −78° C. for 1 h, EtMgBr (167 mL, 501 mmol, 3M in ethyl ether) was added dropwise at −78° C. The resulting solution was stirred at −78° C. to −50° C. for 3 h. The reaction was quenched by saturated citric acid (100 mL) at −78° C. After stirring at 25° C. for 0.5 h, the resulting mixture was filtered and the filtrate was extracted with DCM (3×100 mL). The combined organic layer was dried over Na₂SO₄, filtered and concentrated in vacuum. The reaction was conducted in parallel for 2 times. The crude product was combined and purified by a silica gel column (PE/EtOAc=5/1) to give 38 g of the crude product as white solid, which was recrystallized from PE to give a Compound 9-2 as an off white solid (13.5 g, 13%). $^1$H NMR (CDCl₃) 400 MHz δ 5.33-5.26 (m, 1H), 5.23-5.10 (m, 1H), 2.45-1.90 (m, 6H), 1.78-0.70 (m, 28H).

Synthesis of Compound 9-3. To a solution of Compound 9-2 (13 g, 39.5 mmol) and methyl propiolate (8.29 g, 98.7 mmol) in anhydrous DCM (100 mL) under N₂ at 0° C. was added diethylaluminum chloride (1 M in hexane, 158 mL, 158 mmol) dropwise. The mixture was stirred at 20° C. for 16 hours. The reaction mixture was poured into ice-water, extracted with DCM (3×300 mL). The extracts were dried over anhydrous sodium sulfate, filtered and concentrated. The residue was purified by column chromatography on silica gel (PE/EtOAc=5/1) to give Compound 9-3 (14 g, 86%) as an off white solid. $^1$H NMR (CDCl₃) 400 MHz δ 6.93 (dd, J=15.6 Hz, 8.0 Hz, 1H), 5.81 (d, J=8.0 Hz, 1H), 5.42-5.38 (m, 1H), 5.33-5.24 (m, 1H), 3.73 (s, 3H), 3.05-2.95 (m, 1H), 2.40-2.30 (m, 1H), 2.10-1.95 (m, 3H), 1.90-1.65 (m, 4H), 1.60-1.25 (m, 9H), 1.88 (d, J=7.2 Hz, 3H), 1.15-0.95 (m, 6H), 0.84 (t, J=7.6 Hz, 3H), 0.78 (s, 3H).

Synthesis of Compound 9-4. To a solution of Compound 9-3 (9 g, 21.8 mmol) in THF (100 mL) was added Pd/C (2 g, wet 10%) at 15° C. After degassing and back-fill with H₂ for three times, the reaction mixture was stirred for 16 h at 15° C. with H₂ balloon. The mixture was filtered through a pad of celite. The filtrated was concentrated in vacuum to give crude Compound 9-4 (8.7 g, crude) as an off white solid. $^1$H NMR (CDCl₃) 400 MHz δ 5.35-5.25 (m, 1H), 3.69 (s, 3H), 2.40-2.15 (m, 4H), 2.10-1.40 (m, 17H), 2.15-0.80 (m, 16H), 0.70 (s, 3H).

Synthesis of Compound 9-5. To a solution of Compound 9-4 (5 g, 12.0 mmol) in THF (100 mL) was added lithium aluminium hydride (1.13 g, 30.0 mmol) at 0° C. Then the reaction was stirred at 25° C. for 5 min. Then the reaction was quenched by aqueous NH₄Cl solution (50 mL) and aqueous citric acid (30 mL) to pH=4-5. Then the reaction solution was extracted with EtOAc (3×100 mL). The combined organic layers were dried over Na₂SO₄, filtered and concentrated in vacuum to give crude product Compound 9-5 (4 g, 80%) as an off white solid. $^1$H NMR (CDCl₃) 400 MHz δ 5.35-5.25 (m, 1H), 3.18-3.05 (m, 2H), 2.40-2.32 (m, 1H), 2.08-1.80 (m, 18H), 1.80-0.80 (m, 19H), 0.68 (s, 3H).

Synthesis of Compound 9-6. To a solution of Compound 9-5 (1 g, 2.57 mmol) in DCM (15 mL) and THF (15 mL) was added PCC (1.10 g, 5.14 mmol). The resulting reaction mixture was stirred at 25° C. for 2 hours. The combined organic phase was dried, concentrated and purified by combi-flash (0-15% of EtOAc in PE) to give Compound 9-6 (700 mg, 70%) as an off-white solid. $^1$H NMR (CDCl₃) 400 MHz δ 9.77 (s, 1H), 5.30-5.26 (m, 1H), 2.46-2.35 (m, 2H), 2.04-1.57 (m, 12H), 1.50-0.83 (m, 23H), 0.68 (m, 3H).

Synthesis of Compound 9-7. To a solution of Compound 9-6 (100 mg, 0.258 mmol) in THF (5 mL) was added methylmagnesium bromide (0.513 ml, 1.54 mmol) under N₂. The resulting reaction mixture was stirred at 25° C. for 1 hour. The reaction mixture was quenched with saturated NH₄Cl solution (10 mL) and then concentrated to give a residue which was extracted with EtOAc (3×10 mL). The combined organic phase was dried, concentrated and purified by combi-flash (0~15% of EtOAc in PE) to give Compound 9-7 (10 mg, 10%) as an off-white solid. $^1$H NMR (CDCl₃) 400 MHz δ 5.30-5.24 (m, 1H), 3.80-3.74 (m, 1H), 2.38-2.35 (m, 1H), 2.05-0.83 (m, 40H), 0.68 (m, 3H). LCMS MS ESI calcd. for C₂₇H₄₅O [M−H₂O+H]⁺ 385, found 385.

Synthesis of Compounds 16 and 17. Compound 9-7 (150 mg, 0.372 mmol) was purified by SFC (Column: AD (250 mm*30 mm, 10 um), Condition: Base-MEOH) to give Compound 16 (10.6 mg, 7%) and Compound 17 (25.2 mg, 17%) as off-white solids. Compound 16: $^1$H NMR (400 MHz, CDCl₃) δ 5.29-5.27 (m, 1H), 3.75-3.71 (m, 1H), 2.38-2.34 (m, 1H), 2.05-0.80 (m, 40H), 0.67 (s, 3H). LCMS $t_R$=1.221 min in 2 min chromatography, 30-90AB_ELSD, MS ESI calcd. for $C_{27}H_{45}O$ [M−H$_2$O+H]$^+$ 385, found 385. Compound 17: $^1$H NMR (400 MHz, CDCl$_3$) δ 5.29-5.27 (m, 1H), 3.75-3.71 (m, 1H), 2.38-2.34 (m, 1H), 2.05-0.80 (m, 40H), 0.67 (s, 3H). LCMS $t_R$=1.216 min in 2 min chromatography, 30-90AB_ELSD, MS ESI calcd. for $C_{27}H_{45}O$ [M−H$_2$O+H]$^+$ 385, found 385.

Example 10. Synthesis of Compounds 18 and 19

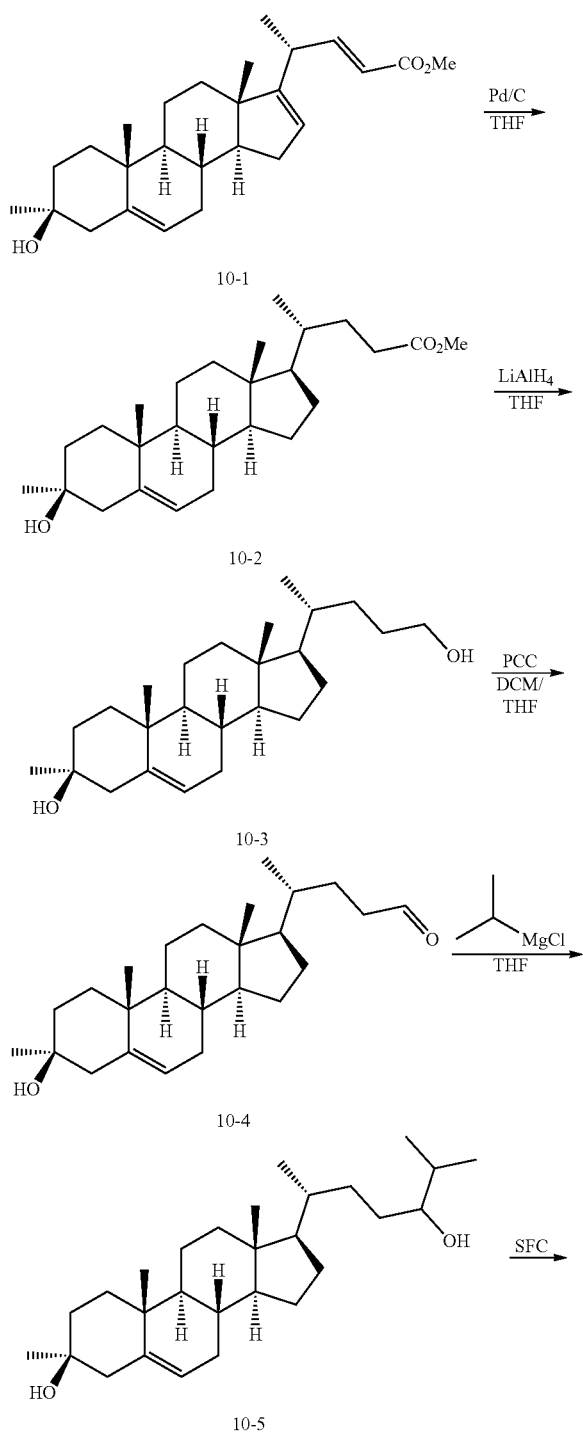

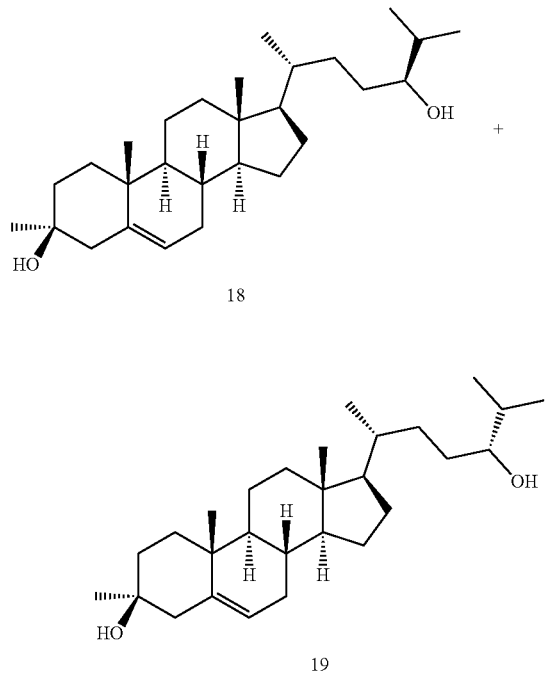

Synthesis of Compound 10-2. To a solution of Compound 10-1* (2 g, 5.01 mmol) and Pd/C (200 mg, 10%) in THF (30 mL) was hydrogenated under 15 psi of hydrogen at 25° C. for 3 h. The mixture was filtered through a pad of celite and the filtrate was concentrated in vacuum to afford Compound 10-2 (1.8 g, crude) as an off-white solid.

Synthesis of Compound 10-3. To a solution of Compound 10-2 (1.8 g, 4.47 mmol) in THF (25 mL) was added a solution LiAlH$_4$ (339 mg, 8.94 mmol) in THF (5 mL) drop wise below 15° C. The solution was stirred at 15° C. for 2 h. The reaction was quenched by the addition of saturated aqueous NH$_4$Cl (20 mL) at 0° C. The resulting mixture was extracted with EtOAc (2×50 mL). The combined organic layer was washed with brine (2×30 mL) and concentrated in vacuum to afford Compound 10-3 (1.6 g, crude) as a light yellow solid.

Synthesis of Compound 10-4. A mixture of Compound 10-3 (1.6 g, 4.27 mmol) in DCM (10 mL) and THF (10 mL) was added PCC (2.27 g, 10.6 mmol) at 25° C. The reaction was stirred at 25° C. for 3 hrs. The solution was filtered and the filter cake was washed with DCM (25 mL). The combined filtrate was concentrated in vacuum. The residue was purified by silica gel column, eluting with PE/EtOAc=8/1 to give Compound 10-4 (0.9 g, 54%) as an off-white solid.

Synthesis of Compound 10-5. To a solution of Compound 10-4 (0.9 g, 2.41 mmol) in THF (30 mL) was added drop wise isopropyl magnesium chloride (3.61 mL, 7.23 mmol, 2M in THF) at −78° C. The mixture was stirred at −78° C. for 2 hrs. Then, the mixture was allowed to warm up to 25° C. and stirred for 3 hrs. The reaction was poured into water (100 mL) and extracted with EtOAc (2×30 mL). The combined organic layer was washed with brine (50 mL), dried over Na$_2$SO$_4$ and concentrated in vacuum. The residue was purified by silica gel column, eluting with PE/EtOAc=5/1 to afford Compound 10-5 (0.6 g, 57%) as an off-white solid.

Synthesis of Compounds 18 and 19. Compound 10-5 (0.6 g) was purified by base conditions SFC (Column: AD (250 mm*30 mm, 5 um); Condition: Base-MEOH) to afford peak 1 as Compound 18 (140 mg, 23%) as an off-white solid and peak 2 Compound 19 (220 mg, 37%) as a light yellow solid. Compound 18: $^1$H NMR (400 MHz, CDCl$_3$) δ 5.35-5.27 (m, 1H), 3.38-3.26 (m, 1H), 2.52-2.37 (m, 1H), 2.07-1.92 (m, 3H), 1.90-1.59 (m, 6H), 1.56-1.35 (m, 7H), 1.33-1.21 (m, 3H), 1.18-1.10 (m, 7H), 1.03-1.00 (m, 6H), 0.97-0.87 (m, 10H), 0.68 (s, 3H). LCMS R$_t$=1.298 min in 2 min chromatography, 30-90AB, MS ESI calcd. for C$_{28}$H$_{47}$O [M−H$_2$O+H]$^+$ 399, found 399. Compound 19: $^1$H NMR (400 MHz, CDCl$_3$) δ 5.33-5.25 (m, 1H), 3.30 (br. s., 1H), 2.41 (d, J=13.2 Hz, 1H), 2.05-1.90 (m, 3H), 1.90-1.55 (m, 6H), 1.51-1.04 (m, 19H), 1.03-0.96 (m, 4H), 0.95-0.85 (m, 10H), 0.67 (s, 3H). LCMS Rt=1.294 min in 2 min chromatography, 30-90AB, MS ESI calcd. for C$_{28}$H$_{47}$O [M−H$_2$O+H]$^+$ 399, found 399.

Example 11. Synthesis of Compound 20

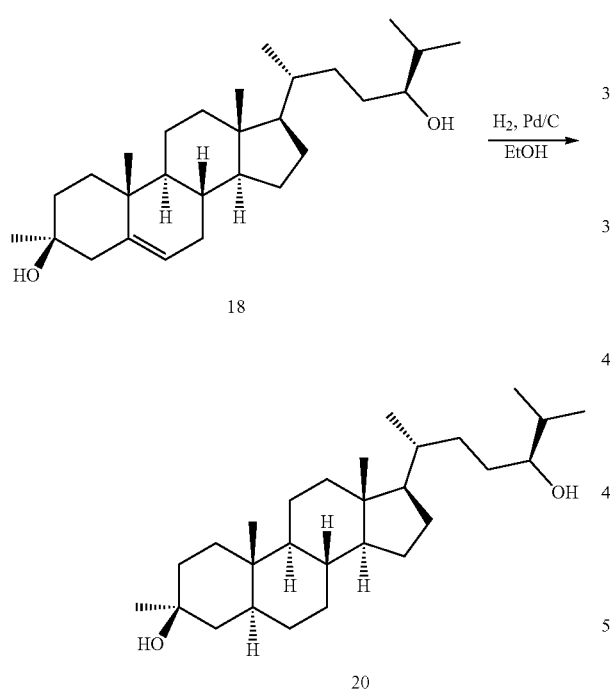

A mixture of Compound 18 (50 mg, 119 μmol) and Pd/C (50 mg, 10%) in EtOH (10 mL) was hydrogenated for 12 h at 50° C. under H$_2$ (50 psi). The reaction mixture was filtered through a pad of celite and the pad was washed with EtOAc (2×20 mL). The combined filtrates were concentrated. The residue was purified by column chromatography on silica gel (PE/EtOAc=20/1 to 10/1) to afford Compound 20 (38.5 mg, 76%) as an off-white powder. 1H NMR (400 MHz, CDCl$_3$) δ 3.31-3.30 (m, 1H), 1.96-1.90 (m, 1H), 1.90-1.75 (m, 1H), 1.75-1.57 (m, 4H), 1.54-0.80 (m, 39H), 0.65-064 (m, 4H). LCMS Rt=1.578 min in 2.0 min chromatography, 10-80 AB, MS ESI calcd. for C$_{28}$H$_{47}$ [M−2H$_2$O+H]$^+$ 383, found 383.

Example 12. Synthesis of Compound 21

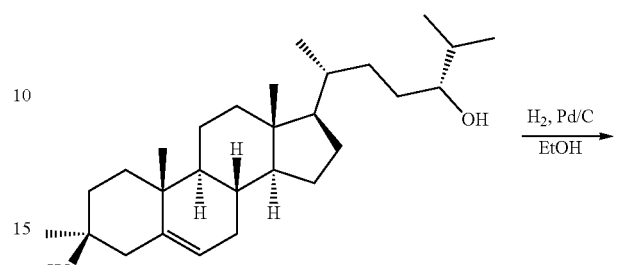

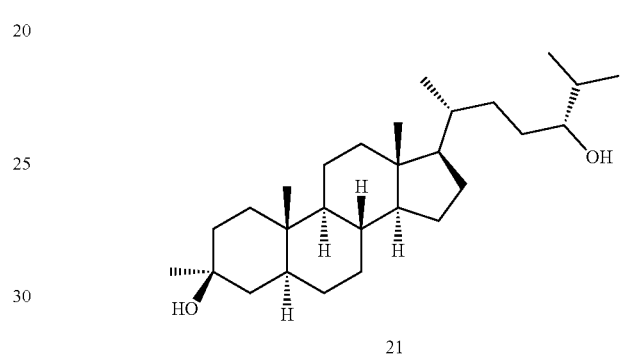

A mixture of Compound 19 (50 mg, 119 μmol) and Pd/C (50 mg, 10%) in EtOH (10 mL) was hydrogenated for 12 h at 50° C. under H$_2$ (50 psi). The reaction mixture was filtered through a pad of celite and the pad was washed with EtOAc (20 mL×2). The combined filtrates were concentrated. The residue was purified by column chromatography on silica gel (PE/EtOAc=20/1 to 10/1) to afford Compound 21 (9.8 mg, 20%) as an off-white powder. $^1$H NMR (400 MHz, CDCl$_3$) δ 3.31-3.30 (m, 1H), 1.97-1.92 (m, 1H), 1.92-1.75 (m, 1H), 1.75-1.57 (m, 27H), 1.54-0.80 (m, 16H), 0.65-064 (m, 4H). LCMS Rt=1.535 min in 2.0 min chromatography, 10-80 AB, MS ESI calcd. for C$_{28}$H$_{47}$ [M−2H$_2$O+H]$^+$ 383, found 383.

Example 13. Synthesis of Compounds 22 and 23

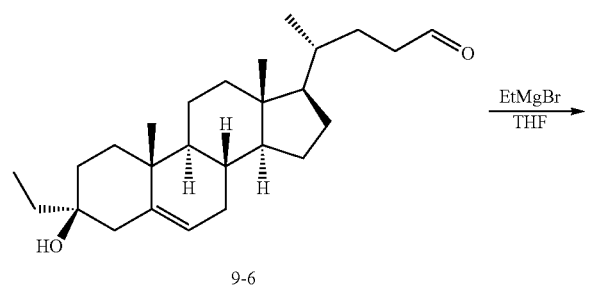

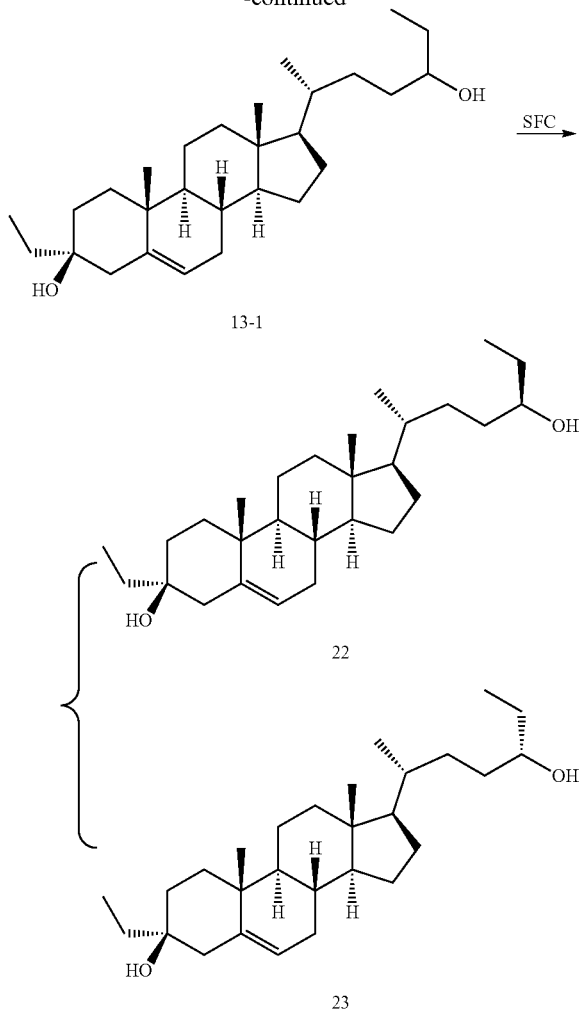

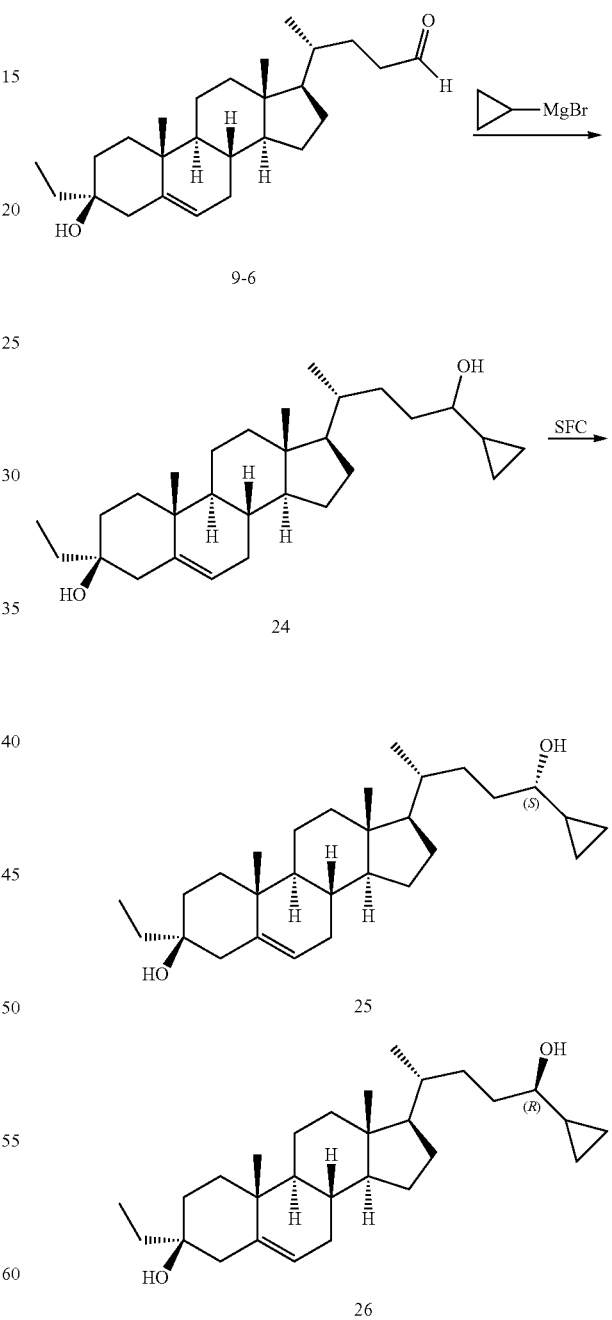

5.32 (br. s., 1H), 3.51 (br. s., 1H), 2.39 (d, J=13.1 Hz, 1H), 2.11-1.95 (m, 3H), 1.93-1.82 (m, 1H), 1.75 (d, J=13.3 Hz, 1H), 1.69-1.35 (m, 18H), 1.33-1.24 (m, 3H), 1.23-0.91 (m, 13H), 0.87 (t, J=7.4 Hz, 3H), 0.70 (s, 3H). LCMS $R_t$=2.340 min in 4 min chromatography, 50-100AB, MS ESI calcd. for $C_{28}H_{47}O$ $[M-H_2O+H]^+$ 399, found 399.

Example 14. Synthesis of Compounds 24, 25, and 26

Synthesis of Compounds 22 and 23. To a solution of Compound 9-6 (340 mg, 879 μmol) in THF (20 mL) at 0° C. was added ethylmagnesium bromide (876 μL, 3.0 M, 2.63 mmol). The reaction mixture was stirred at 15° C. for 2 hours then was quenched with saturated NH$_4$Cl (10 mL) and extracted with ethyl acetate (3×50 mL). The combined organic phases were washed with brine (60 mL), dried over Na$_2$SO$_4$, filtered and concentrated in vacuum to give Compound 13-1 as an off-white solid (240 mg). The solid was purified by SFC (Column: AD (250 mm*30 mm, 5 um); Condition: Base-MeOH) to afford peak 1 as Compound 22 (13 mg, 4%) as an off-white solid and peak 2 as Compound 23 (54.0 mg, impure) as an off-white solid. Compound 22: $^1$H NMR (400 MHz, CDCl$_3$) δ 5.31 (d, J=5.0 Hz, 1H), 3.49 (br. s., 1H), 2.39 (d, J=11.0 Hz, 1H), 2.09-1.94 (m, 3H), 1.92-1.80 (m, 1H), 1.78-1.71 (m, 1H), 1.69-1.37 (m, 16H), 1.35-1.23 (m, 4H), 1.22-0.92 (m, 14H), 0.87 (t, J=7.5 Hz, 3H), 0.70 (s, 3H). LCMS Rt=2.334 min in 4 min chromatography, 50-100AB, MS ESI calcd. for $C_{28}H_{47}O$ $[M-H_2O+H]^+$ 399, found 399.

Further Purification of Compound 23. Compound 23 (54 mg, 129 μmol, impure) was purified by SFC (Column: AD (250 mm*30 mm, 5 um); Condition: Base-MEOH) to give a light yellow solid (34 mg), which was further purified by trituration from n-hexane to afford Compound 23 (8.5 mg, 16%) as an off-white solid. $^1$H NMR (400 MHz, CDCl$_3$) δ

Synthesis of Compound 24: To a solution of Compound 9-6 (0.7 g, 1.80 mmol) in THF (10 mL) was added cyclopropylmagnesium bromide (180 mL, 90 mmol, 0.5M in THF) in portions. The mixture was stirred at 15° C. for 16 hours. The mixture was quenched with saturated NH₄Cl solution (100 mL) and then extracted with EtOAc (2×30 mL). The combined organic phase was dried, concentrated and purified by preparative HPLC to give Compound 24 (50 mg, 6%) as an off-white solid. ¹H NMR (400 MHz, CDCl₃) δ 5.29-5.27 (m, 1H), 2.81 (s, 1H), 2.38-2.34 (m, 1H), 2.05-0.85 (m, 38H), 0.67 (s, 3H), 0.60-0.45 (m, 2H), 0.30-0.15 (m, 2H). LCMS R$_t$=1.284 min in 2 min chromatography, 30-90AB_ELSD, MS ESI calcd. for C₂₉H₄₅ [M−2H₂O+H]⁺ 393, found 393.

Synthesis of Compounds 25 and 26: 90 mg of Compound 24 (90 mg, 0.209 mmol) was purified by SFC (Column: AD (250 mm*30 mm, 5 um); Condition: Base-MEOH) to give peak 1 as Compound 25 (24.0 mg, 27%) and peak 2 as Compound 26 (11.1 mg, 12%) as an off-white solid. Compound 25: ¹H NMR (400 MHz, CDCl₃) δ 5.29-5.27 (m, 1H), 2.82-2.79 (m, 1H), 2.43-2.40 (m, 1H), 2.05-0.80 (m, 38H), 0.67 (s, 3H), 0.55-0.40 (m, 2H), 0.30-0.15 (m, 2H). LCMS t$_R$=1.280 min in 2 min chromatography, 30-90AB_ELSD, MS ESI calcd. for C₂₉H₄₅ [M−2H₂O+H]⁺ 393, found 393. Compound 26: ¹H NMR (400 MHz, CDCl₃) δ 5.29-5.27 (m, 1H), 2.82-2.79 (m, 1H), 2.43-2.40 (m, 1H), 2.05-0.80 (m, 38H), 0.67 (s, 3H), 0.55-0.40 (m, 2H), 0.30-0.15 (m, 2H). LCMS R$_t$=1.282 min in 2 min chromatography, 30-90AB_ELSD, MS ESI calcd. for C₂₉H₄₅ [M−2H₂O+H]⁺ 393, found 393.

Example 15. Synthesis of Compounds 27, 28, and 29

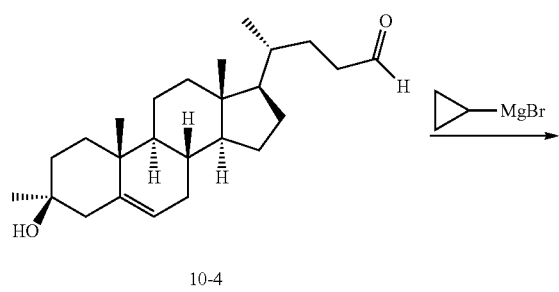

10-4

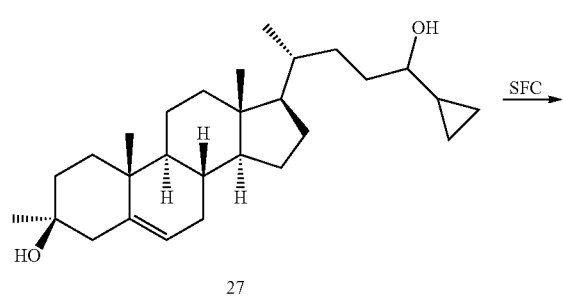

27

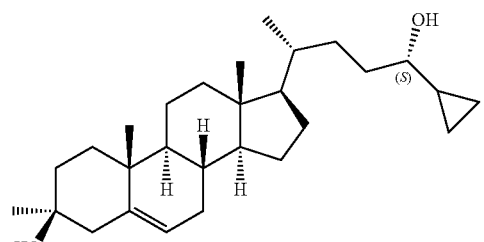

28

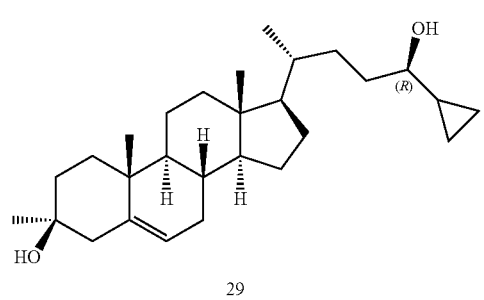

29

To a solution of Compound 10-4 (4 g, 10.7 mmol) in THF (50 mL) was added cyclopropylmagnesium bromide (428 mL, 214 mmol, 0.5M in THF) in portions. The mixture was stirred at 15° C. for 16 hours. The mixture was quenched with saturated NH₄Cl solution (500 mL) and then extracted with EtOAc (2×100 mL). The combined organic phase was dried, concentrated and purified by combi-flash (0~20% of EtOAc in PE) to give Compound 27 (2 g, 45%) as an off-white solid. Compound 27: ¹H NMR (400 MHz, CDCl₃) δ 5.30-5.29 (m, 1H), 2.80 (s, 1H), 2.43-2.40 (m, 1H), 2.02-1.43 (m, 16H), 1.40-0.80 (m, 20H), 0.67 (s, 3H), 0.55-0.40 (m, 2H), 0.30-0.15 (m, 2H). LCMS Rt=1.231 min in 2 min chromatography, 30-90AB_ELSD, MS ESI calcd. for C₂₈H₄₃ [M−2H₂O+H]⁺ 379, found 379.

Synthesis of Compounds 28 and 29. 0.17 g of Compound 27 (170 mg, 0.409 mmol) was purified by SFC (Column: AY (250 mm*30 mm, 10 um); Condition: Base-IPA) to give peak 1 as Compound 28 (37 mg, 22%) and peak 2 as Compound 29 (50 mg, 30%) as an off-white solid. Compound 28: ¹H NMR (400 MHz, CDCl₃) δ 5.30-5.29 (m, 1H), 2.82-2.79 (m, 1H), 2.43-2.40 (m, 1H), 2.05-0.80 (m, 36H), 0.67 (s, 3H), 0.55-0.40 (m, 2H), 0.30-0.15 (m, 2H). LCMS Rt=1.217 min in 2 min chromatography, 30-90AB_ELSD, MS ESI calcd. for C₂₈H₄₃ [M−2H₂O+H]⁺ 379, found 379. Compound 29: ¹H NMR (400 MHz, CDCl₃) δ 5.30-5.29 (m, 1H), 2.82-2.79 (m, 1H), 2.43-2.40 (m, 1H), 2.05-0.80 (m, 36H), 0.68 (s, 3H), 0.55-0.40 (m, 2H), 0.30-0.15 (m, 2H). LCMS Rt=1.218 min in 2 min chromatography, 30-90AB_ELSD, MS ESI calcd. for C₂₈H₄₃ [M−2H₂O+H]⁺ 379, found 379.

Example 16. Synthesis of Compound 30

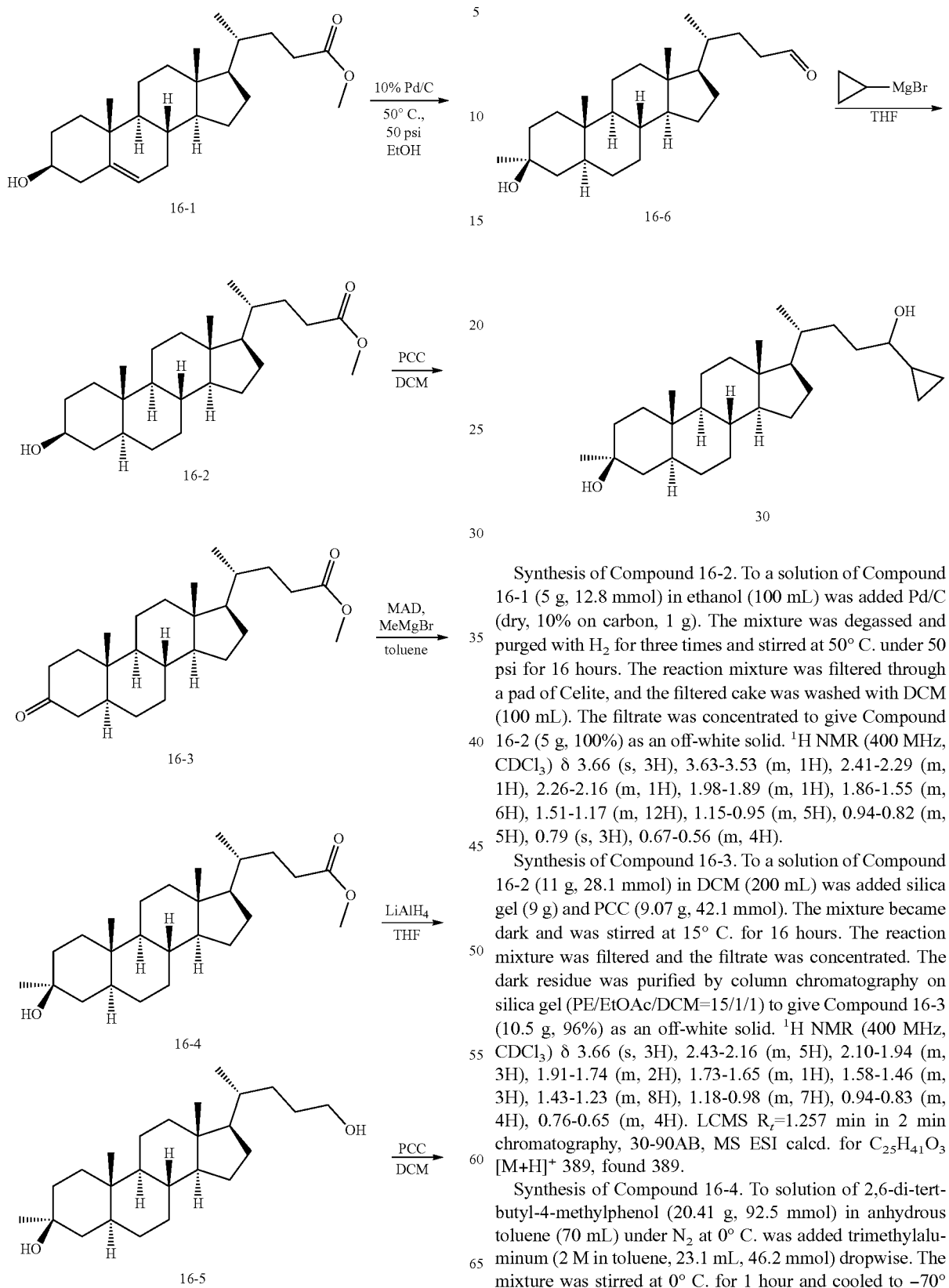

Synthesis of Compound 16-2. To a solution of Compound 16-1 (5 g, 12.8 mmol) in ethanol (100 mL) was added Pd/C (dry, 10% on carbon, 1 g). The mixture was degassed and purged with $H_2$ for three times and stirred at 50° C. under 50 psi for 16 hours. The reaction mixture was filtered through a pad of Celite, and the filtered cake was washed with DCM (100 mL). The filtrate was concentrated to give Compound 16-2 (5 g, 100%) as an off-white solid. $^1$H NMR (400 MHz, $CDCl_3$) δ 3.66 (s, 3H), 3.63-3.53 (m, 1H), 2.41-2.29 (m, 1H), 2.26-2.16 (m, 1H), 1.98-1.89 (m, 1H), 1.86-1.55 (m, 6H), 1.51-1.17 (m, 12H), 1.15-0.95 (m, 5H), 0.94-0.82 (m, 5H), 0.79 (s, 3H), 0.67-0.56 (m, 4H).

Synthesis of Compound 16-3. To a solution of Compound 16-2 (11 g, 28.1 mmol) in DCM (200 mL) was added silica gel (9 g) and PCC (9.07 g, 42.1 mmol). The mixture became dark and was stirred at 15° C. for 16 hours. The reaction mixture was filtered and the filtrate was concentrated. The dark residue was purified by column chromatography on silica gel (PE/EtOAc/DCM=15/1/1) to give Compound 16-3 (10.5 g, 96%) as an off-white solid. $^1$H NMR (400 MHz, $CDCl_3$) δ 3.66 (s, 3H), 2.43-2.16 (m, 5H), 2.10-1.94 (m, 3H), 1.91-1.74 (m, 2H), 1.73-1.65 (m, 1H), 1.58-1.46 (m, 3H), 1.43-1.23 (m, 8H), 1.18-0.98 (m, 7H), 0.94-0.83 (m, 4H), 0.76-0.65 (m, 4H). LCMS $R_t$=1.257 min in 2 min chromatography, 30-90AB, MS ESI calcd. for $C_{25}H_{41}O_3$ $[M+H]^+$ 389, found 389.

Synthesis of Compound 16-4. To solution of 2,6-di-tert-butyl-4-methylphenol (20.41 g, 92.5 mmol) in anhydrous toluene (70 mL) under $N_2$ at 0° C. was added trimethylaluminum (2 M in toluene, 23.1 mL, 46.2 mmol) dropwise. The mixture was stirred at 0° C. for 1 hour and cooled to −70° C. To the above solution was added a solution of Compound 16-3 (6 g, 15.4 mmol) in anhydrous toluene (100 mL) dropwise. The mixture was stirred at −70° C. for 1 hour and then methylmagnesium bromide (3 M in diethyl ether, 15.4 mL, 46.2 mmol) was added dropwise. The resultant mixture was stirred at −70° C. for 2 hours. The reaction mixture was quenched with aqueous citric acid (200 mL), extracted with EtOAc and THF (200 mL/50 mL) three times. The combined organic layers were dried over anhydrous sodium sulfate, filtered and concentrated. The residue was purified by column chromatography on silica gel (PE/EtOAc/THF=20/1/1) to give Compound 16-4 (6 g, 96%) as an off-white solid. $^1$H NMR (400 MHz, CDCl$_3$) δ 3.66 (s, 3H), 2.40-2.16 (m, 2H), 1.99-1.90 (m, 1H), 1.89-1.73 (m, 2H), 1.68-0.83 (m, 29H), 0.80 (s, 3H), 0.70-0.60 (m, 4H). LCMS Rt=1.273 min in 2 min chromatography, 30-90AB, MS ESI calcd. for $C_{26}H_{43}O_2$ [M−H$_2$O+H]$^+$ 387, found 387.

Synthesis of Compound 16-5. To a solution of Compound 16-4 (3 g, 7.41 mmol) in anhydrous THF (50 mL) at 0° C. was added LiAlH$_4$ (421 mg, 11.1 mmol) in portions. The mixture was stirred at 0° C. for 30 minutes. The reaction mixture was quenched with water (5 mL) and aqueous NaOH (10%, 5 mL) dropwise then filtered through a pad of Celite. The filter cake was washed with THF (5×20 mL). The filtrate was dried over anhydrous sodium sulfate, filtered and concentrated to give Compound 16-5 (2.5 g, 90% yield) as an off-white solid. $^1$H NMR (400 MHz, CDCl$_3$) δ 3.61 (s, 2H), 1.97-1.94 (m, 1H), 1.89-1.75 (m, 1H), 1.68-1.52 (m, 6H), 1.50-1.18 (m, 16H), 1.17-0.84 (m, 11H), 0.80 (s, 3H), 0.70-0.60 (m, 4H). LCMS Rt=1.137 min in 2 min chromatography, 30-90AB, MS ESI calcd. for $C_{25}H_{43}O$ [M−H$_2$O+H]$^+$ 359, found 359.

Synthesis of Compound 16-6. To a solution of Compound 16-5 (2 g, 5.31 mmol) in anhydrous DCM (30 mL) was added silica gel (2.5 g) and PCC (2.28 g, 10.6 mmol). The mixture was stirred at 15° C. for 16 hours. The reaction mixture was filtered and the filtrate was concentrated. The residue was purified by column chromatography on silica gel (PE/EtOAc/THF=20/1/1) to give Compound 16-6 (1.3 g, 66%) as an off-white solid. $^1$H NMR (400 MHz, CDCl$_3$) δ 9.76 (s, 1H), 2.51-2.26 (m, 2H), 1.99-1.73 (m, 3H), 1.69-1.18 (m, 19H), 1.17-0.83 (m, 10H), 0.80 (s, 3H), 0.72-0.59 (m, 4H). LCMS Rt=1.212 min in 2 min chromatography, 30-90AB, MS ESI calcd. for $C_{25}H_{39}$ [M−2H$_2$O+H−]$^+$ 339, found 339.

Synthesis of Compound 30. To a solution of cyclopropylmagnesium bromide (0.5 M in THF, 21.2 mL, 10.6 mmol) under N$_2$ was added Compound 16-6 (200 mg, 0.533 mmol) at 25° C. The mixture was stirred at 50° C. for 16 hours. The reaction mixture was quenched with aqueous NH$_4$Cl (50 mL), extracted with EtOAc (3×50 mL), dried over anhydrous sodium sulfate, filtered and concentrated. The residue was purified by column chromatography on silica gel (PE/EtOAc=20/1) to give Compound 30 (100 mg, 45%) as an off-white solid. $^1$H NMR (400 MHz, CDCl$_3$) δ 2.85-2.75 (m, 1H), 2.00-1.93 (m, 1H), 1.93-1.73 (m, 1H), 1.73-0.83 (m, 34H), 0.80 (s, 3H), 0.70-0.59 (m, 4H), 0.57-0.43 (m, 2H), 0.30-0.16 (m, 2H) LCMS Rt=1.443 min in 2 min chromatography, 10-80AB, MS ESI calcd. for $C_{28}H_{45}$ [M−2H$_2$O+H]$^+$ 381, found 381.

Example 17. Synthesis of Compounds 31 and 32

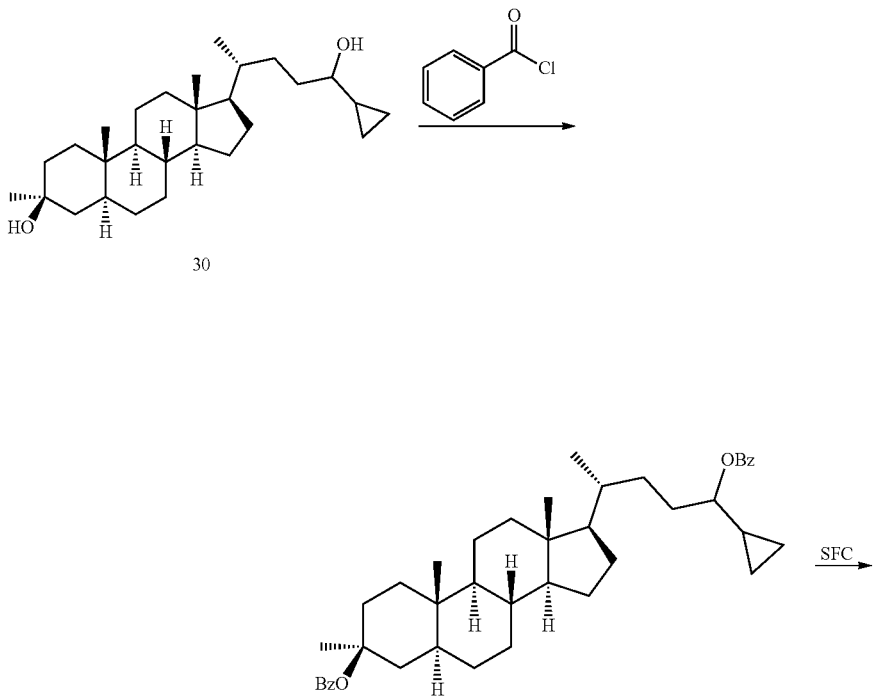

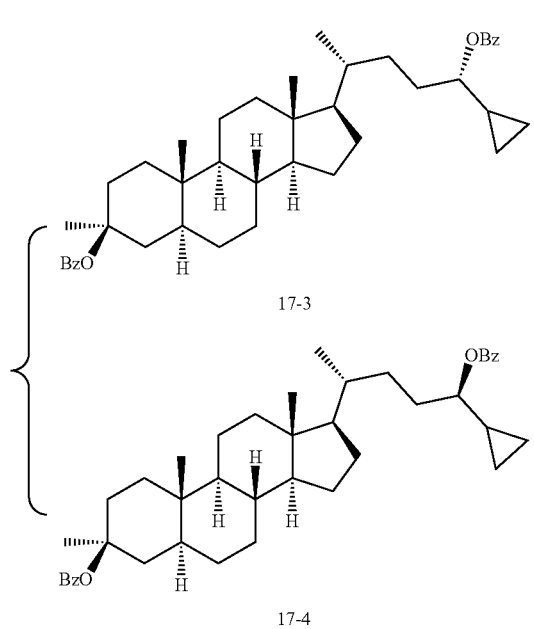

17-3

17-4

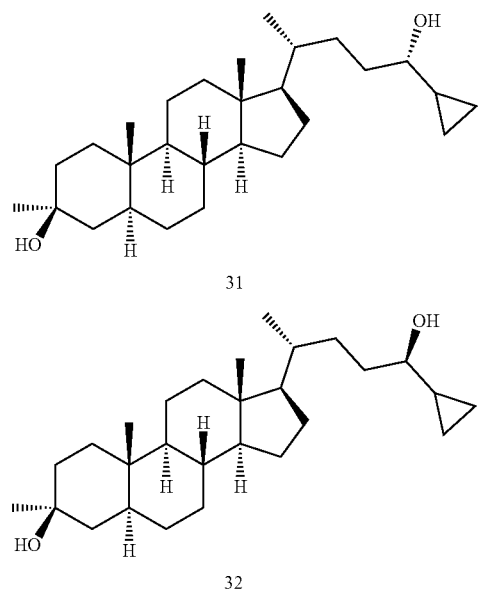

31

32

Synthesis of Compound 17-2. To a solution of Compound 30 (440 mg, 1.05 mmol) in pyridine (10 mL) was added benzoyl chloride (295 mg, 2.10 mmol) at 25° C. Then the reaction was stirred at 50° C. for 16 h. The reaction was quenched by adding water (10 mL) and extracted with EtOAc (2×10 mL). The combined organic layers were dried over $Na_2SO_4$, filtered and concentrated in vacuum. The crude product was purified by a silica gel column (PE/EtOAC=40/1) to give Compound 17-2 (420 mg, 64%) as yellow oil.

Synthesis of Compounds 17-3 and 17-4. A mixture of Compound 17-2 was purified by SFC separation (column: AD (250 mm*30 mm, 10 um) gradient: B in A (A=$NH_3·H_2O$, B=EtOH), flow rate: 30 mL/min) to give peak 1 as Compound 17-3 (170 mg, 41%) as an off-white solid and peak 2 as Compound 17-4 (160 mg, 38%) as an off-white solid. Compound 17-3: $^1$H NMR (400 MHz, $CDCl_3$) δ 8.06 (d, J=8.8 Hz, 2H), 7.99 (d, J=8.4 Hz, 2H), 7.58-7.48 (m, 2H), 7.48-7.38 (m, 4H), 4.55-4.45 (m, 1H), 2.11-0.77 (m, 37H), 0.73-0.55 (m, 5H), 0.52-0.45 (m, 2H), 0.39-0.31 (m, 1H). Compound 17-3: $^1$H NMR (400 MHz, $CDCl_3$) δ 8.06 (d, J=8.8 Hz, 2H), 7.99 (d, J=8.4 Hz, 2H), 7.58-7.48 (m, 2H), 7.48-7.38 (m, 4H), 4.55-4.45 (m, 1H), 2.11-0.77 (m, 37H), 0.73-0.55 (m, 5H), 0.52-0.45 (m, 2H), 0.39-0.31 (m, 1H).

Synthesis of Compound 31. To a solution of Compound 17-3 (50 mg, 0.08 mmol) in THF (1 mL) and MeOH (1 mL) was added NaOH (63.5 mg, 1.59 mmol) and $H_2O$ (1 mL) at 25° C. The solution was stirred at 50° C. for 16 h. The reaction solution was extracted with EtOAc (2×5 mL). The combined organic layers were dried over $Na_2SO_4$, filtered and concentrated in vacuum. The crude product was purified by a silica gel column (PE/EtOAc=3/1) to give the desired product Compound 31 (4.0 mg, 12%) as an off-white solid. $^1$H NMR (400 MHz, $CDCl_3$) 2.85-2.75 (m, 1H), 1.98-1.93 (m, 1H), 1.93-1.76 (m, 1H), 1.76-0.75 (m, 37H), 0.70-0.60 (m, 4H), 0.58-0.45 (m, 2H), 0.30-0.15 (m, 2H). LCMS Rt=1.437 min in 2 min chromatography, 10-80AB, MS ESI calcd. for $C_{28}H_{45}$ 381 ([M–2$H_2O$+H]$^+$), found 381.

Synthesis of Compound 32. To a solution of Compound 17-4 (50 mg, 0.08 mmol) in THF (1 mL) and MeOH (1 mL) was added NaOH (63.5 mg, 1.59 mmol) and $H_2O$ (1 mL) at 25° C. The reaction solution was extracted with EtOAc (5 mL×2). The combined organic layers were dried over $Na_2SO_4$, filtered and concentrated in vacuum. The crude product was purified by a silica gel column (PE/EtOAc=3/1) to give the desired product Compound 32 (8.0 mg, 24%) as an off-white solid. $^1$H NMR (400 MHz, $CDCl_3$) δ 2.84-2.76 (m, 1H), 1.96-1.92 (m, 1H), 1.90-1.73 (m, 1H), 1.73-0.83 (m, 34H), 0.81 (s, 3H), 0.70-0.61 (m, 4H), 0.58-0.44 (m, 2H), 0.29-0.19 (m, 2H). LCMS Rt=1.436 min in 2 min chromatography, 10-80AB, MS ESI calcd. for $C_{28}H_{45}$ 381 ([M–2$H_2O$+H]$^+$), found 381.

Example 18. Synthesis of Compound 33

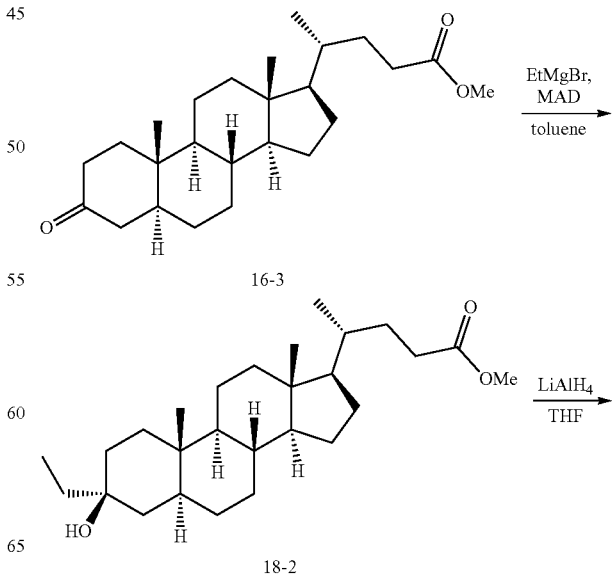

16-3

18-2

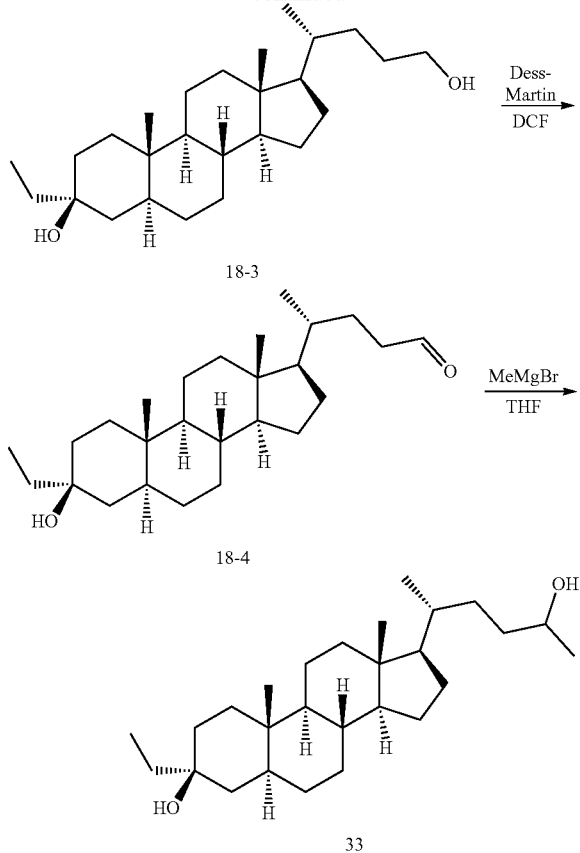

Synthesis of Compound 18-2. To a solution of 2,6-di-tert-butyl-4-methylphenol (17 g, 77.1 mmol) in toluene (50 mL) was added trimethylaluminum (19.2 mL, 2M in toluene) at 10° C. The mixture was stirred at 20° C. for 1 h. To the solution was added a solution of Compound 16-3 (5 g, 12.8 mmol) in toluene (20 mL) dropwise at −70° C. dropwise under $N_2$. The mixture was stirred at −70° C. for 1 hour. A solution of EtMgBr (12.7 mL, 3M) was added dropwise at −70° C. The mixture was stirred at −70° C. for another 3 hours and then the reaction mixture was quenched with citric acid (150 mL, sat. aq.). The reaction was warmed to 25° C. The organic layer was separated and concentrated in vacuum. The crude product was purified by column chromatography on silica gel (PE/EtOAc=200/1 to 10/1) to give Compound 18-2 (3.8 g) as an off-white solid.

$^1$H NMR (400 MHz, CDCl$_3$) δ 3.66 (s, 3H), 2.41-2.30 (m, 1H), 2.26-2.15 (m, 1H), 1.94 (td, J=3.3, 12.5 Hz, 1H), 1.90-1.73 (m, 2H), 1.69-1.58 (m, 3H), 1.56-0.84 (m, 28H), 0.82 (s, 3H), 0.64 (s, 4H).

Synthesis of Compound 18-3. LiAlH$_4$ (500 mg, 13.17 mmol) was added to THF (50 mL) under $N_2$ at 0° C. To the mixture was added a solution of Compound 18-2 (1.5 g, 3.58 mmol) in THF (15 mL) at 0° C. The mixture was stirred at 0° C. for 20 min. Water (1 mL) in THF (1 mL) was added and an off-white solid was formed from the solution. The mixture was filtered, concentrated in vacuum to give Compound 18-3 (700 mg, crude) as an off-white solid. $^1$H NMR (400 MHz, CDCl$_3$) δ3.70-3.55 (brs, 2H), 1.98-1.90 (m, 1H), 1.90-1.72 (m, 1H), 1.72-0.72 (m, 39H), 0.64 (s, 3H).

Synthesis of Compound 18-4. To a solution of Compound 18-3 (100 mg, crude) in DCM (5 mL) was added Dess Martin reagent (215 mg) at 0° C. under $N_2$. The mixture was stirred at 20° C. for 2 h. A solution of NaHCO$_3$ (215 mg) and Na$_2$S$_2$O$_3$ (348 mg) in water (10 mL) was added.

The mixture was extracted with petroleum ether (3×10 mL). The organic layer was separated, washed with water (20 mL), dried over Na$_2$SO$_4$, filtered and concentrated in vacuum to afford the crude product, which was purified by column chromatography on silica gel (PE/EtOAc=100/1 to 8/1) to give Compound 18-4 (52 mg) as an off-white solid.

$^1$H NMR (400 MHz, CDCl$_3$) δ 9.76 (s, 1H), 2.51-2.24 (m, 2H), 1.98-1.90 (m, 1H), 1.89-1.73 (m, 2H), 1.68-1.59 (m, 3H), 1.54-0.77 (m, 30H), 0.65 (s, 5H).

Synthesis of Compound 33. To a solution of Compound 18-4 (52 mg, 0.134 mmol) in THF (1 mL) was added methylmagnesium bromide (0.5 mL, 1.5 mmol, 3M in ether) at −70° C. under $N_2$. The mixture was stirred at 20° C. for 20 min and then saturated NH$_4$Cl (4 mL), EtOAc (5 mL) and H$_2$O (3 mL) was added. The mixture was extracted with EtOAc (3×6 mL), washed with saturated NaCl (2×15 mL), dried over Na$_2$SO$_4$, filtered and concentrated in vacuum to afford the crude product, which was purified by column chromatography on silica gel (PE/EtOAc=100/1 to 12/1) to give Compound 33 (18.4 mg, 30%) as an off-white solid. $^1$H NMR (400 MHz, CDCl$_3$) δ 3.78-3.70 (m, 1H), 1.99-1.91 (m, 1H), 1.89-1.76 (m, 1H), 1.68-0.80 (m, 41H), 0.65 (s, 4H). LCMS R$_t$=1.448 min in 2 min chromatography, 10-80AB_E, MS ESI calcd. for C$_{27}$H$_{45}$ [M−2H$_2$O+H]$^+$ 369, found 369.

Example 19. Synthesis of Compound 34

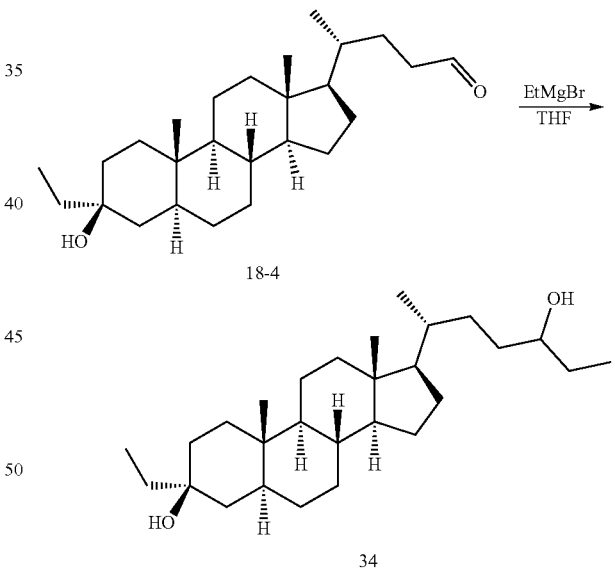

Synthesis of Compound 34. To a solution of Compound 18-4 (250 mg, crude) in THF (20 mL) was added ethylmagnesium bromide (2.2 mL, 6.6 mmol, 3M in ether) at −70° C. under $N_2$. The mixture was stirred at 20° C. for 1 h and then saturated NH$_4$Cl (20 mL), EtOAc (20 mL) and H$_2$O (10 mL) was added. The mixture was extracted with EtOAc (20 mL×3), washed with saturated NaCl (60 mL×2), dried over Na$_2$SO$_4$, filtered and concentrated in vacuum to afford the crude product, which was purified by column chromatography on silica gel (PE/EtOAc=100/1 to 12/1) to give Compound 34 (80 mg) as an off-white solid. $^1$H NMR (400 MHz, CDCl$_3$) δ 3.53-3.42 (m, 1H), 2.00-1.92 (m, 1H), 1.89-1.75

(m, 1H), 1.69-1.58 (m, 3H), 1.56-0.84 (m, 37H), 0.82 (s, 3H), 0.68-0.59 (m, 4H). LCMS $R_f$=1.526 min in 2 min chromatography, 10-80AB_E, MS ESI calcd. for $C_{28}H_{47}$ [M−2H$_2$O+H]$^+$ 383, found 383.

Example 20. Synthesis of Compounds 35 and 36

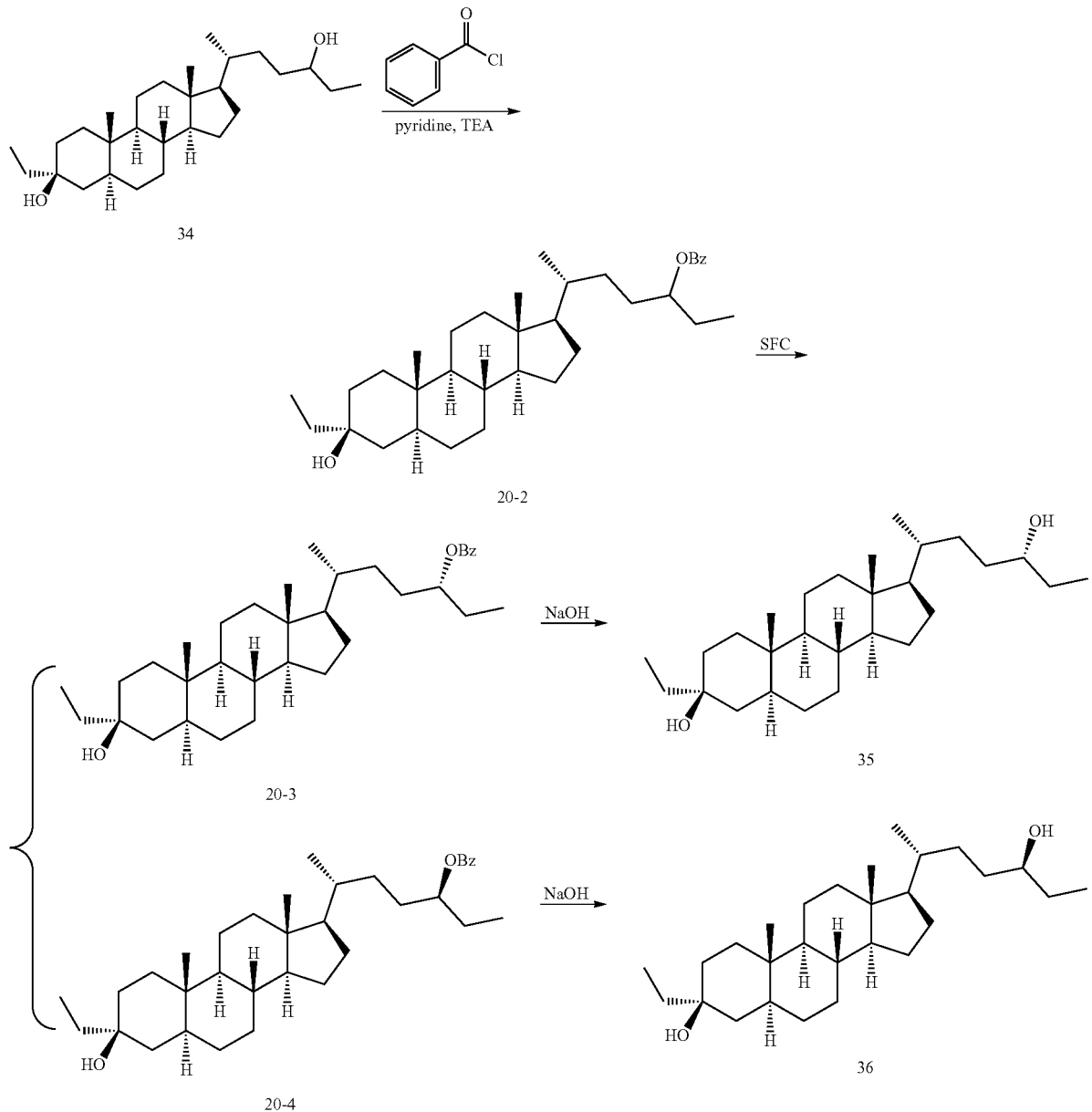

(70 mg, crude). LCMS $R_f$=1.257 min in 1.5 min chromatography, 5-95AB, MS ESI calcd. for $C_{28}H_{47}$ [M−BzOH—H$_2$O+H]$^+$ 383, found 383.

Synthesis of Compounds and 20-3 and 20-4. (SFC). Compound 20-2 (70 mg, crude) was separated by SFC (column: IC (250 mm*30 mm, 10 um); Condition: Base-IPA; Gradient: 35% B; flow rate: 80 mL/min) to give Compound 20-3 (18 mg, $R_t$=5.988 min) and Compound 20-4 (30 mg, Rt=6.229 min).

Synthesis of Compound 20-2. To a solution of Compound 34 (64 mg, 0.153 mmol) in pyridine (3 mL) was added benzoyl chloride (32.2 mg, 0.229 mmol) and triethylamine (23.1 mg, 0.229 mmol). The mixture was stirred at 25° C. for 5h and then the reaction mixture was quenched with saturated NH$_4$Cl (6 mL). The mixture was extracted with EtOAc (3×6 mL), washed with Sat·NaCl (2×15 mL), dried over Na$_2$SO$_4$, filtered, concentrated in vacuum to give a crude product, which was purified by column chromatography on silica gel (PE/EtOAc=50/1 to 10/1) to give Compound 20-2

Synthesis of Compound 35. To a solution of Compound 20-3 (18 mg, 0.03442 mmol) in THF (1 mL) and MeOH (1 mL) was added aq. NaOH (1 mL, 20%). The mixture was stirred at 20° C. for 20 h. The mixture was concentrated in vacuum, extracted with EtOAc (2×2 mL), washed with NaHCO$_3$ (3×4 mL) and brine (2×3 mL), dried over Na$_2$SO$_4$, filtered, concentrated in vacuum to give Compound 35 (8.5 mg, 59%) as an off-white solid. ¹H NMR (400 MHz, CDCl₃) δ 3.55-3.40 (m, 1H), 2.00-1.90 (m, 1H), 1.85-1.75 (m, 1H), 1.65-1.55 (m, 4H), 1.50-0.85 (m, 36H), 0.82 (s, 3H), 0.65-0.60 (m, 4H). LCMS $t_R$=1.322 min in 2 min chromatography, 30-90AB_E, MS ESI calcd. for $C_{28}H_{47}$ $[M-2H_2O+H]^+$ 383, found 383.

Synthesis of Compound 36. To a solution of Compound 20-4 (30 mg, 0.057 mmol) in THF (1 mL) and MeOH (1 mL) was added aq. NaOH (1 mL, 20%). The mixture was stirred at 20° C. for 20 h. The mixture was concentrated in vacuum, extracted with EtOAc (2×2 mL), washed with NaHCO₃ (3×4 mL) and brine (2×3 mL), dried over Na₂SO₄, filtered, concentrated in vacuum to give Compound 36 (5.2 mg, 22%) as an off-white solid. ¹H NMR (400 MHz, CDCl₃) δ 3.55-3.40 (m, 1H), 2.00-1.90 (m, 1H), 1.85-1.75 (m, 1H), 1.65-1.55 (m, 4H), 1.50-0.85 (m, 36H), 0.82 (s, 3H), 0.65-0.60 (m, 4H) LCMS $t_R$=1.507 min in 2 min chromatography, 30-90AB_E, MS ESI calcd. for $C_{28}H_{47}$ $[M-2H_2O+H]^+$ 383, found 383.

Example 21. Synthesis of Compound 37

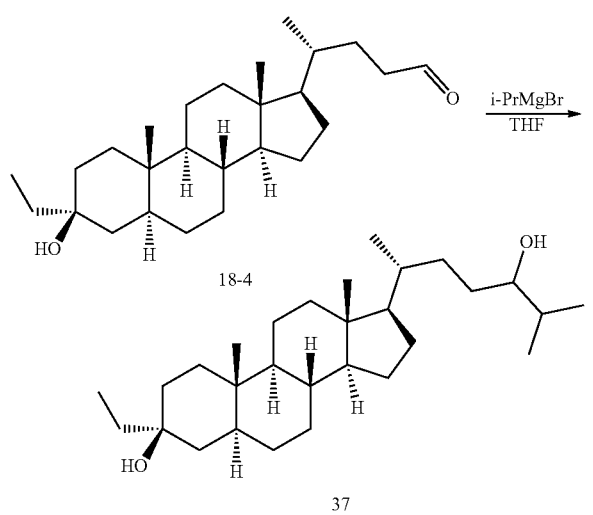

To a solution of Compound 18-4 (50 mg, crude) in THF (20 mL) was added isopropylmagnesium bromide (3.2 mL, 6.4 mmol, 2 M in THF) at −70° C. under N₂. The mixture was stirred at 20° C. for 1 h. To the mixture was added saturated NH₄Cl (20 mL), EtOAc (20 mL) and H₂O (10 mL). The mixture was extracted with EtOAc (3×20 mL), washed with saturated NaCl (2×60 mL), dried over Na₂SO₄, filtered and concentrated in vacuum to give the crude product, which was purified by column chromatography on silica gel (PE/EtOAc=100/1 to 12/1) to give Compound 37 (5.3 mg) as an off-white solid. ¹H NMR (400 MHz, CDCl₃) δ 3.35-3.27 (m., 1H), 1.96 (d, J=12.8 Hz, 1H), 1.88-1.76 (m, 1H), 1.73-1.58 (m, 5H), 1.53-0.84 (m, 37H), 0.82 (s, 3H), 0.68-0.59 (m, 4H). LCMS $t_R$=1.371 min in 2 min chromatography, 30-90AB_E, MS ESI calcd. for $C_{29}H_{49}$ $[M-2H_2O+H]^+$ 397, found 397.

Example 22. Synthesis of Compound 38

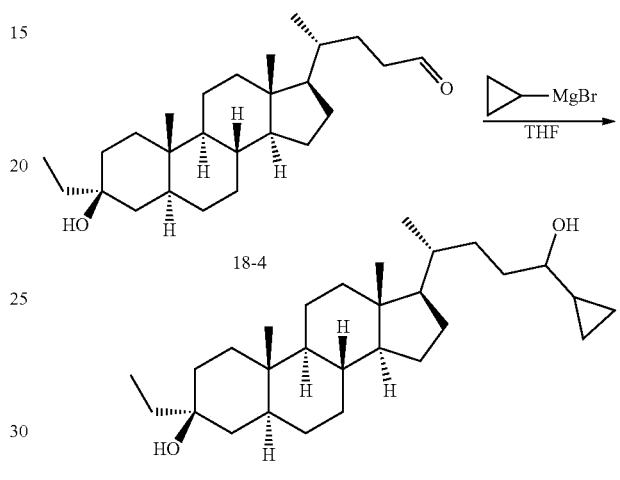

A solution of Compound 18-4 (250 mg, crude) in THF (20 mL) was added to cyclopropylmagnesium bromide (12.8 mL, 6.4 mmol, 0.5 M in THF) at −70° C. under N₂. The mixture was stirred at 20° C. for 1 h. To the mixture was added saturated. NH₄Cl (20 mL), EtOAc (20 mL) and H₂O (10 mL). The mixture was extracted with EtOAc (3×20 mL), washed with saturated NaCl (2×60 mL), dried over Na₂SO₄, filtered, concentrated in vacuum to give the crude product, which was purified by column chromatography on silica gel (PE/EtOAc=100/1 to 12/1) to give Compound 38 (110 mg, 40%) as an off-white solid. ¹H NMR (400 MHz, CDCl₃) δ 2.85-2.75 (m, 1H), 2.00-1.92 (m, 1H), 1.89-1.76 (m, 1H), 1.69-1.59 (m, 4H), 1.55-0.85 (m, 32H), 0.82 (s, 3H), 0.65 (s, 4H), 0.56-0.43 (m, 2H), 0.29-0.16 (m, 2H). LCMS $t_R$=1.518 min in 2 min chromatography, 10-80AB_E, MS ESI calcd. for $C_{29}H_{47}$ $[M-2H_2O+H]^+$ 395, found 395.

Example 23. Synthesis of Compounds 39 and 40

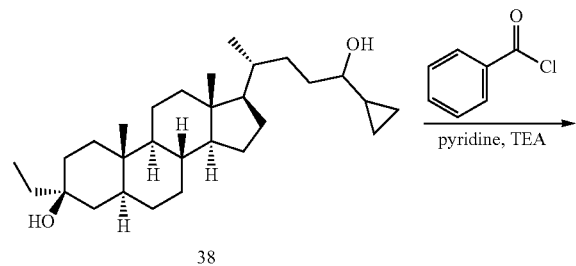

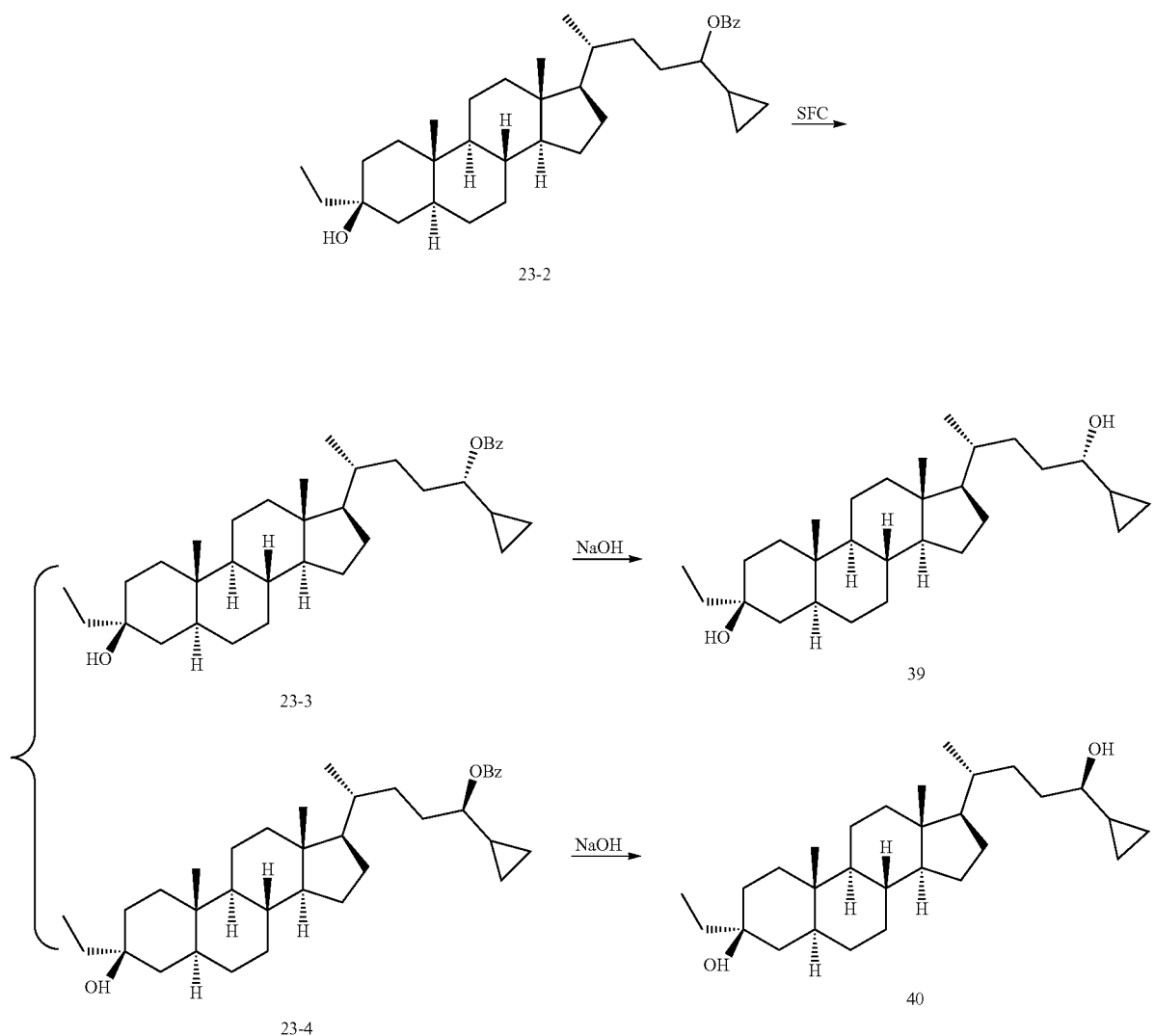

Synthesis of Compound 23-2. To a solution of Compound 38 (80 mg, 0.186 mmol) in pyridine (3 mL) was added benzoyl chloride (39.1 mg, 0.279 mmol) and triethylamine (28.1 mg, 0.279 mmol). The mixture was stirred at 25° C. for 5h. The reaction mixture was quenched with saturated NH$_4$Cl (6 mL). The mixture was extracted with EtOAc (3×6 mL), washed with saturated NaCl (2×15 mL), dried over Na$_2$SO$_4$, filtered, concentrated in vacuum to give the crude product, which was purified by column chromatography on silica gel (PE/EtOAc=50/1 to 10/1) to give Compound 23-2 (80 mg, crude). LCMS t$_R$=1.247 min in 1.5 min chromatography, 5-95 AB_E, MS ESI calcd. for C$_{29}$H$_{47}$ [M−BzOH−H$_2$O+H]$^+$ 395, found 395.

Synthesis of Compounds 23-3 and 23-4. Compound 23-2 (80 mg, crude) was separated by SFC (column: IC (250 mm*30 mm, 10 um); Condition: Base-IPA; Gradient: 30% B; flow rate: 50 mL/min) to give Compound 23-3 (23 mg, R$_t$=6.153) and Compound 23-4 (35 mg, Rt=6.357).

Synthesis of Compound 39. To a solution of Compound 23-3 (23 mg, 0.04 mmol) in THF (1 mL) and MeOH (1 mL) was added aq. NaOH (2 mL, 20%). The mixture was stirred at 20° C. for 20 h. The mixture was concentrated in vacuum, extracted with EtOAc (2×2 mL), washed with NaHCO$_3$ (3×4 mL) and brine (2×3 mL), dried over Na$_2$SO$_4$, filtered and concentrated in vacuum to give a solid, which was purified by column chromatography on silica gel (PE/EtOAc=100/1 to 8/1) to give Compound 39 (9 mg, 49%) as an off-white solid. $^1$H NMR (400 MHz, CDCl$_3$) δ 2.85-2.75 (m, 1H), 2.00-1.92 (m, 1H), 1.89-1.76 (m, 1H), 1.75-1.59 (m, 6H), 1.55-0.89 (m, 30H), 0.82 (s, 3H), 0.70-0.60 (m, 4H), 0.56-0.43 (m, 2H), 0.29-0.16 (m, 2H) LCMS t$_R$=1.484 min in 2 min chromatography, 30-90AB_E, MS ESI calcd. for C$_{29}$H$_{47}$ [M−2H$_2$O+H]$^+$ 395, found 395.

Synthesis of Compound 40. To a solution of Compound 23-4 (35 mg, 0.065 mmol) in THF (1 mL) and MeOH (1 mL) was added aq. NaOH (2 mL, 20%). The mixture was stirred at 20° C. for hrs. The mixture was concentrated in vacuum, extracted with EtOAc (2×2 mL), washed with NaHCO$_3$ (3×4 mL) and brine (2×3 mL), dried over Na$_2$SO$_4$, filtered and concentrated in vacuum to give Compound 40 (14 mg, 50%) as an off-white solid. $^1$H NMR (400 MHz, CDCl$_3$) δ 2.85-2.75 (m, 1H), 2.00-1.92 (m, 1H), 1.89-1.76 (m, 1H), 1.69-1.59 (m, 2H), 1.55-0.85 (m, 34H), 0.82 (s, 3H), 0.65 (m, 4H), 0.56-0.43 (m, 2H), 0.29-0.16 (m, 2H) LCMS t$_R$=1.510 min in 2 min chromatography, 30-90AB_E, MS ESI calcd. for C$_{29}$H$_{47}$ [M−2H$_2$O+H]$^+$ 395, found 395.

Example 24. Synthesis of Compound 41

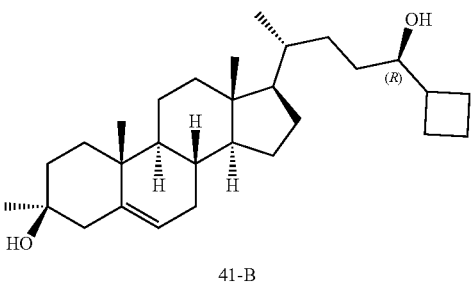

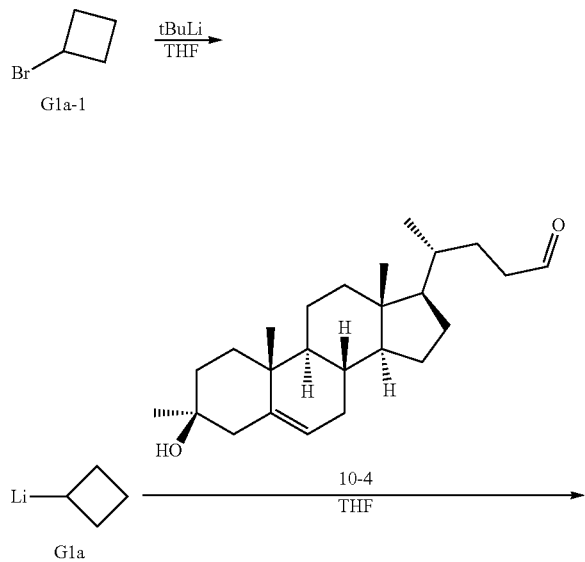

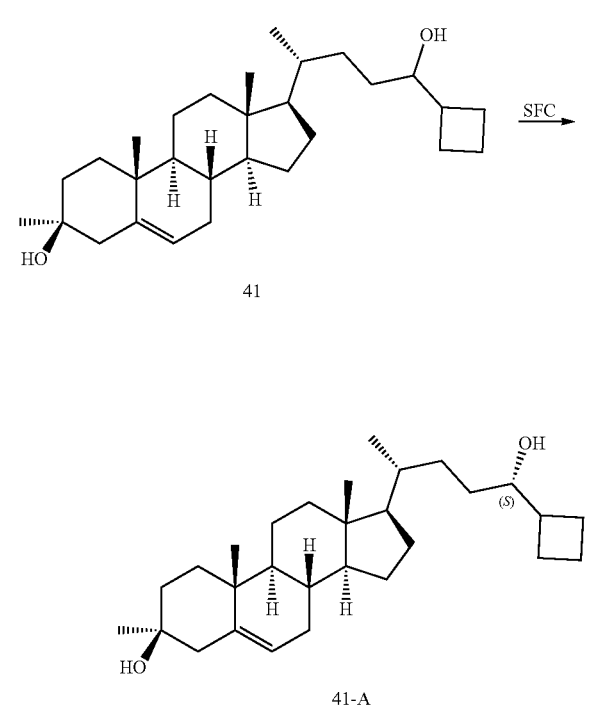

Step 1. To a solution of G1a-1 (1 g, 7.4 mmol) in THF (7 mL) under N$_2$ was added $^t$BuLi (9.25 mL, 1.6 M in pentanes, 14.8 mmol) dropwise at −60° C. After addition, the mixture was warmed to −40° C. slowly for 0.5 h to give a solution of G1a in THF, which was used for the next step directly.

Step 2. To THF (2 mL) under N$_2$ was added G1a (0.87 mL, 0.46 M in THF and pentanes, 0.402 mmol) at −70° C. After stirring at −70° C. for 5 min, a solution of Compound 10-4 (50 mg, 0.314 mmol) in THF (3 mL) was added. The reaction mixture was warmed gradually to 15° C. for 10 hrs. The mixture was quenched with 10 mL of sat·NH$_4$Cl and extracted with 50 mL of EtOAc. The separated organic phase was washed with 10 mL of brine, dried over Na$_2$SO$_4$, filtered and concentrated. The residue was purified by silica gel chromatography eluting with PE/EtOAc=10/1~2/1 to give Compound 41 (7.3 mg, 13%) as an off-white solid.

$^1$H NMR (400 MHz, CDCl$_3$) δ. 5.35-5.25 (m, 1H), 3.49-3.32 (m, 1H), 2.48-2.38 (m, 1H), 2.38-2.25 (m, 1H), 2.05-1.71 (m, 12H), 1.50-0.86 (m, 29H), 0.72-0.63 (m, 3H). LCMS Rt=1.300 min in 2 min chromatography, 30-90AB_E.M, MS ESI calcd. for C$_{29}$H$_{45}$ [M−2H$_2$O+H]$^+$ 393, found 393.

Step 3. Compound 41 (800 mg, 1.86 mmol) was separated by SFC (Column: AD (250 mm*30 mm, 5 um). condition: 0.1% NH$_3$H$_2$O ETOH. Gradient: 40% B. Flow rate: 40 mL/min) to give Compound 41-A (123 mg, 15%) as an off white solid and Compound 41-B (109 mg, 14%) as an off white solid.

Compound 41-A: $^1$H NMR (400 MHz, CDCl$_3$) δ 5.32-5.28 (m, 1H), 3.46-3.38 (m, 1H), 2.46-2.27 (m, 2H), 2.02-1.67 (m, 13H), 1.55-1.36 (m, 8H), 1.31-1.22 (m, 2H), 1.19-1.06 (m, 8H), 1.05-0.89 (m, 10H), 0.67 (s, 3H). LCMS Rt=1.321 min in 2.0 min chromatography, 30-90 AB, MS ESI calcd. for C$_{29}$H$_{45}$ [M+H−2H$_2$O]$^+$ 393, found 393.

Compound 41-B: $^1$H NMR (400 MHz, CDCl$_3$) δ 5.33-5.28 (m, 1H), 3.49-3.42 (m, 1H), 2.45-2.39 (m, 1H), 2.36-2.28 (m, 1H), 2.04-1.66 (m, 12H), 1.53-1.22 (m, 10H), 1.20-0.98 (m, 12H), 0.96-0.77 (m, 7H), 0.68 (s, 3H). LCMS Rt=1.316 min in 2.0 min chromatography, 30-90 AB, MS ESI calcd. for C$_{29}$H$_{45}$ [M+H−2H$_2$O]$^+$ 393, found 393.

Example 25. Synthesis of Compound 42

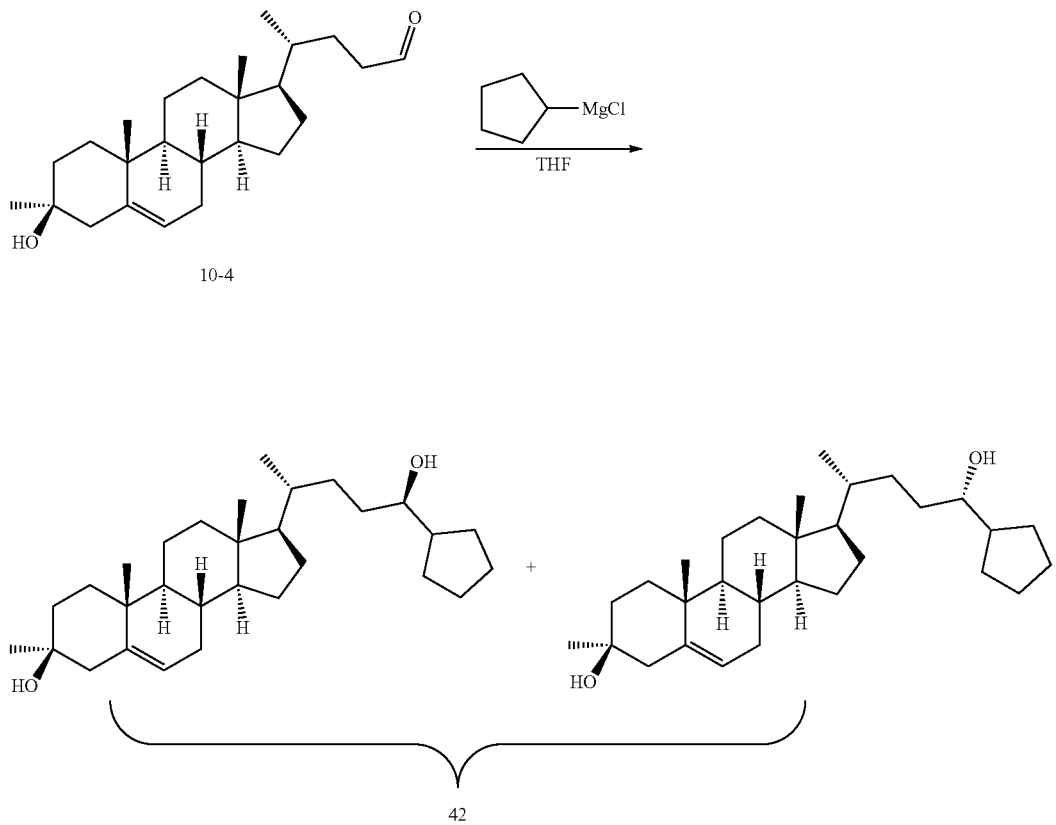

To THF (1 mL) under $N_2$ was added cyclopentylmagnesium chloride (0.402 mL, 1.0 M in THF, 0.402 mmol) at −70° C. After stirring at −70° C. for 5 min, a solution of Compound 10-4 (50 mg, 0.134 mmol) in THF (4 mL) was added. The reaction mixture was gradually warmed to 15° C. for 18 hrs. The mixture was quenched with 10 mL of saturated $NH_4Cl$ and extracted with 50 mL of EtOAc. The separated organic phase was washed with 10 mL of brine, dried over $Na_2SO_4$, filtered and concentrated. The residue was purified by flash column eluting with PE/EtOAc=10/1~2/1 to give Compound 42 (4.1 mg, 7%) as an off-white solid.

$^1$H NMR (400 MHz, $CDCl_3$) δ. 5.35-5.25 (m, 1H), 3.40-3.29 (m, 1H), 2.46-2.37 (m, 1H), 2.05-1.60 (m, 12H), 1.55-0.82 (m, 32H), 0.72-0.61 (m, 3H). LCMS Rt=1.389 min in 2 min chromatography, 30-90AB_E.M, MS ESI calcd. for $C_{30}H_{47}$ $[M-2H_2O+H]^+$ 407, found 407.

Example 26. Synthesis of Compound 43

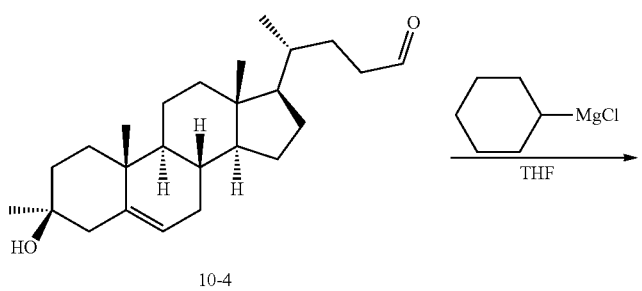

131 132

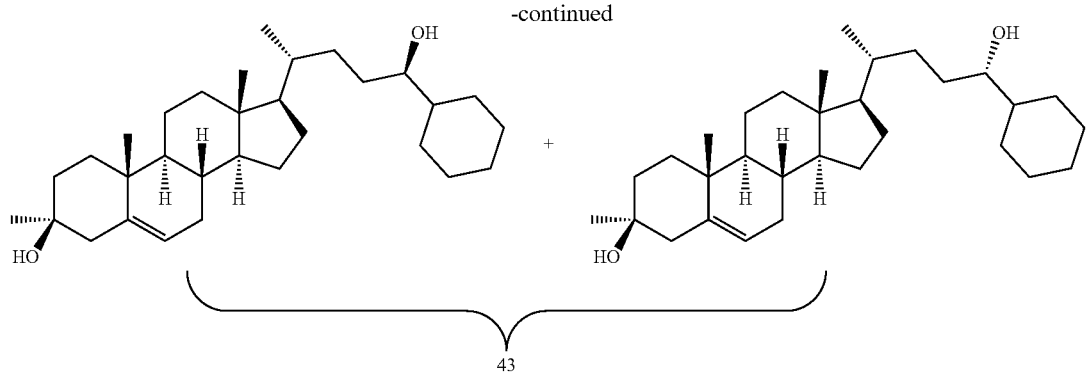

43

To THF (1 mL) under N₂ was added cyclohexylmagnesium chloride (0.402 mL, 2.0 M in THF, 0.804 mmol) at −70° C. After stirring at −70° C. for 5 min, a solution of Compound 10-4 (100 mg, 0.268 mmol) in THF (1 mL) was added. The reaction mixture was gradually warmed to 15° C. for 18 hrs. The mixture was quenched with 10 mL of sat·NH₄Cl and extracted with 50 mL of EtOAc. The separated organic phase was washed with 10 mL of brine, dried over Na₂SO₄, filtered and concentrated. The residue was purified by flash column eluting with PE/EtOAc, 10/1 to 2/1 to give Compound 43 (20 mg, 16%) as an off-white solid.

¹H NMR (400 MHz, CDCl₃) δ. 5.40-5.25 (m, 1H), 3.40-3.26 (m, 1H), 2.51-2.30 (m, 1H), 2.09-1.91 (m, 3H), 1.90-1.59 (m, 10H), 1.55-0.85 (m, 33H), 0.68 (s, 3H). LCMS Rt=1.490 min in 2 min chromatography, 30-90AB_E.M, MS ESI calcd. for $C_{31-149}$ [M−2H₂O+H]⁺ 421, found 421.

Example 27. Synthesis of Compound 44

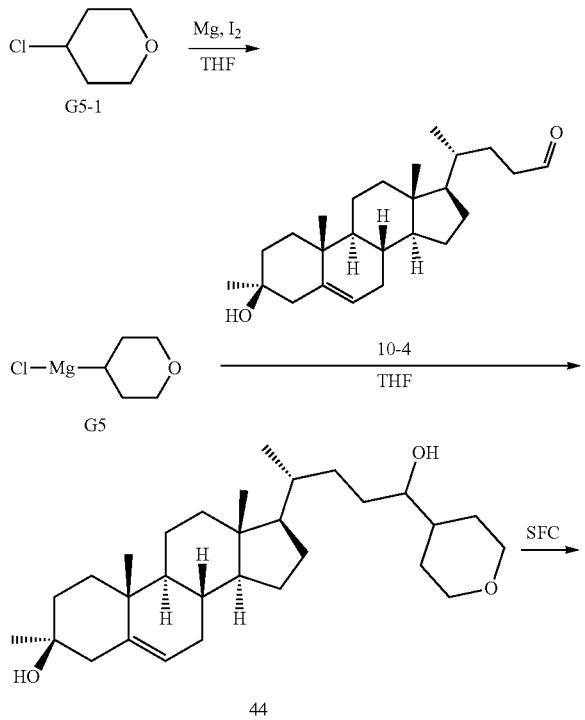

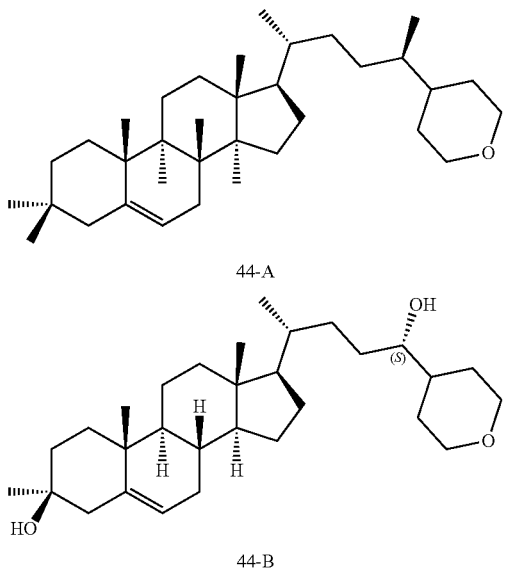

Step 1. To a vigorously stirred suspension of Mg turnings (602 mg, 24.8 mmol) and iodine (31.3 mg, 0.124 mmol) in THF (5 mL) under N₂ was added G5-1 (0.15 g, 1.24 mmol). The mixture was heated to 60° C. After the reaction was initiated, G5-1 (1.35 g, 11.16 mmol) in THF (6 mL) was added slowly. After addition, the mixture was stirred at 60° C. for 2 hrs to give a gray suspension of G5 in THF, which was used for the next step directly.

Step 2. To THF (2 mL) under N₂ was added G5 (0.402 mL, 1.0 M in THF, 0.402 mmol) at −70° C. After stirring at −70° C. for 5 mins, a solution of Compound 10-4 (50 mg, 0.314 mmol) in THF (3 mL) was added. The reaction mixture was gradually warmed to 15° C. and stirred for 18 hrs. The mixture was quenched with 10 mL of saturated NH₄Cl and extracted with 50 mL of EtOAc. The separated organic phase was washed with 10 mL of brine, dried over Na₂SO₄ and concentrated. The residue was purified by flash column eluting with PE/EtOAc=10/1 to 2/1 to give Compound 44 (10 mg, 16%) as an off-white solid.

¹H NMR (400 MHz, CDCl₃) δ 5.38-5.25 (m, 1H), 4.11-3.89 (m, 2H), 3.42-3.24 (m, 3H), 2.47-2.36 (m, 1H), 2.04-1.91 (m, 3H), 1.90-1.59 (m, 6H), 1.53-1.45 (m, 14H), 1.40-0.86 (m, 17H), 0.68 (s, 3H). LCMS Rt=1.187 min in 2 min chromatography, 30-90AB_E.M, MS ESI calcd. for $C_{30}H_{49}O_2$ $[M-H_2O+H]^+$ 441, found 441.

Step 3. The product Compound 44 (830 mg, 1.80 mmol) was purified by SFC (Column: AD (250 mm*30 mm, 5 um); Condition: 0.1% $NH_3H_2O$ IPA; Gradient 40% B; Gradient Time (min): 30; FlowRate (ml/min): 60.) to afford Compound 44-A (142 mg, 17%) as white solid and Compound 44-B (220 mg, 27%) as white solid.

Compound 44-A: $^1$H NMR (400 MHz, CDCl$_3$) δ 5.33-5.28 (m, 1H), 4.05-3.96 (m, 2H), 3.43-3.30 (m, 3H), 2.46-2.38 (m, 1H), 2.05-1.92 (m, 3H), 1.91-1.66 (m, 4H), 1.65-1.57 (m, 2H), 1.54-1.41 (m, 10H), 1.40-1.20 (m, 5H), 1.19-1.06 (m, 7H), 1.05-0.88 (m, 9H), 0.68 (s, 3H). LCMS Rt=1.167 min in 2 min chromatography, 30-90AB_2 MIN_E.M, MS ESI calcd. for $C_{30}H_{49}O_2$ $[M+H-H_2O]^+$ 441, found 441.

Compound 44-B: $^1$H NMR (400 MHz, CDCl$_3$) δ 5.34-5.27 (m, 1H), 4.06-3.97 (m, 2H), 3.43-3.28 (m, 3H), 2.47-2.38 (m, 1H), 2.04-1.92 (m, 3H), 1.89-1.66 (m, 4H), 1.64-1.57 (m, 5H), 1.53-1.35 (m, 9H), 1.33-1.21 (m, 3H), 1.21-1.07 (m, 7H), 1.06-0.90 (m, 9H), 0.68 (s, 3H). LCMS Rt=1.163 min in 2 min chromatography, 30-90AB_2 MIN_E.M, MS ESI calcd. for $C_{30}H_{49}O_2$ $[M+H-H_2O]^+$ 441, found 441.

Example 28. Synthesis of Compounds 45 and 46

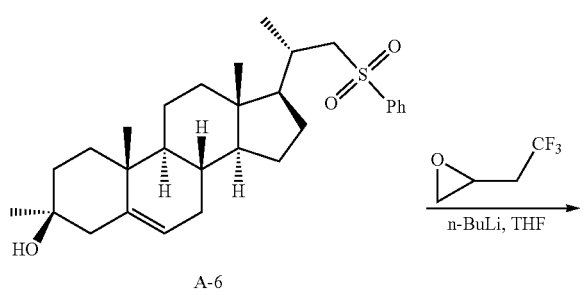

A-6 n-BuLi, THF

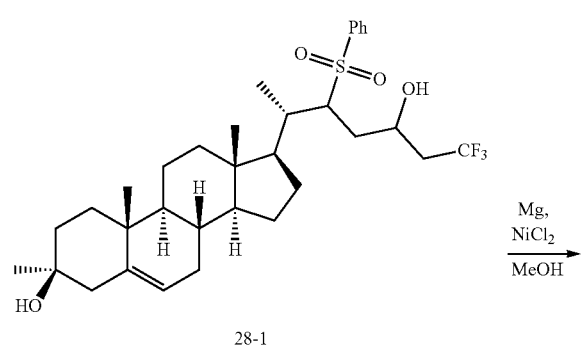

28-1

Mg, NiCl$_2$
MeOH

-continued

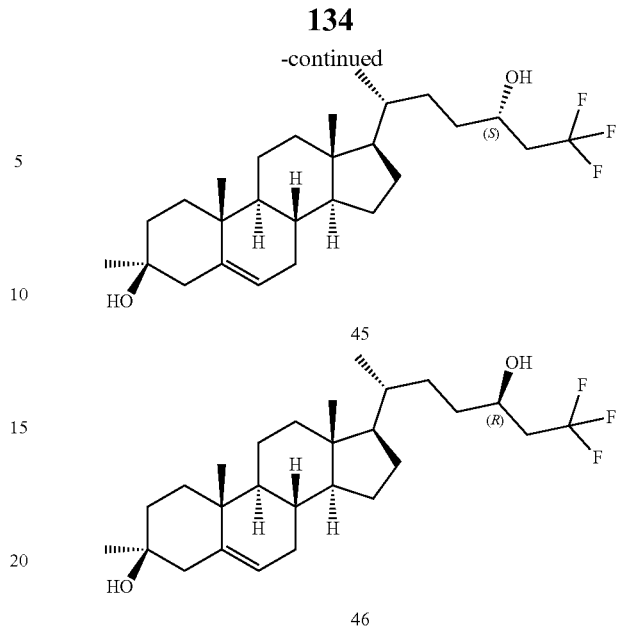

45

46

Synthesis of Compound 28-1. To THF (5 mL) under N$_2$ at −70° C. was added n-BuLi (2.96 mL, 2.5 M in hexane, 7.42 mmol). After that, a suspension of A-6 (1 g, 2.12 mmol) in THF (8 mL) was added dropwise to give a light yellow suspension. After stirring at −70° C. for 30 mins, a solution of 2-(2,2,2-trifluoroethyl)oxirane (320 mg, 2.52 mmol) in THF (5 mL) was added. The reaction mixture was stirred at −70° C. for 10 mins, warmed to 15° C. and stirred for 16 hrs. The reaction was quenched with saturated NH$_4$Cl (40 mL), extracted with EtOAc (100 mL×3). The combined organic layers were dried over Na$_2$SO$_4$, filtered and concentrated to give Compound 28-1 (1.15 g, crude) as a light yellow solid, which was used in the next step directly. Synthesis of Compounds 45 and 46. To a solution of Compound 28-1 (1.15 g, 1.92 mmol) in 25 mL of dry MeOH was added under N$_2$ magnesium turnings (0.2 g, 8.22 mmol) (activated with 0.5% aqueous HCl, water, dry EtOH, and MTBE) and NiCl$_2$ (49.7 mg, 0.384 mmol) with stirring at 50° C. to initiate continuous hydrogen generation. After ten batches of 0.2 g of magnesium turnings were added, the reaction mixture was quenched by 2M HCl (250 mL) at 10° C. until the solid was dissolved. The mixture was extracted with EtOAc (400 mL). The organic layer was washed with saturated NaHCO$_3$ (50 mL), brine (50 mL), dried over Na$_2$SO$_4$, filtered and concentrated. The residue was purified by flash column, eluting with PE:EtOAc=20:1-5:1 to give 300 mg of impure product as an off-white solid. The impure product was further purified by SFC (Column: Chiralpak AD-3 150×4.6 mm I.D., 3 um Mobile phase: A: CO$_2$ B: methanol (0.05% DEA) Gradient: from 5% to 40% of B in 5 min and hold 40% for 2.5 min, then 5% of B for 2.5 min Flow rate: 2.5 mL/min Column temp.: 35° C.) to give Compound 45 (99.9 mg, 11%) and Compound 46 (84 mg, 10%).

Compound 45: $^1$H NMR (400 MHz, CDCl$_3$) δ 5.38-5.25 (m, 1H), 4.06-3.88 (m, 1H), 2.48-2.35 (m, 1H), 2.32-2.18 (m, 2H), 2.08-1.90 (m, 3H), 1.87-1.63 (m, 4H), 1.60-1.45 (m, 12H), 1.40-0.83 (m, 16H), 0.68 (s, 3H). LCMS Rt=1.203 min in 2 min chromatography, 30-90AB_2 MIN_E.M, MS ESI calcd. for $C_{27}H_{42}F_3O$ $[M+H-H_2O]^+$ 439, found 439. SFC Rt=4.933 min in 10 min chromatography, AD_3_MeOH_DEA_5_40_25 ML.

Compound 46: $^1$H NMR (400 MHz, CDCl$_3$) δ 5.35-5.25 (m, 1H), 4.01-3.88 (m, 1H), 2.45-2.35 (m, 1H), 2.32-2.18

(m, 2H), 2.05-1.91 (m, 3H), 1.90-1.60 (m, 4H), 1.60-1.45 (m, 12H), 1.40-0.83 (m, 16H), 0.69 (s, 3H). LCMS Rt=1.205 min in 2 min chromatography, 30-90AB_2 MIN_E.M, MS ESI calcd. for $C_{27}H_{42}F_3O$ $[M+H-H_2O]^+$ 439, found 439. SFC $R_t$=5.640 min in 10 min chromatography, AD_3_MeOH_DEA_5_40_25 ML.

Example 29. Synthesis of Compound 47

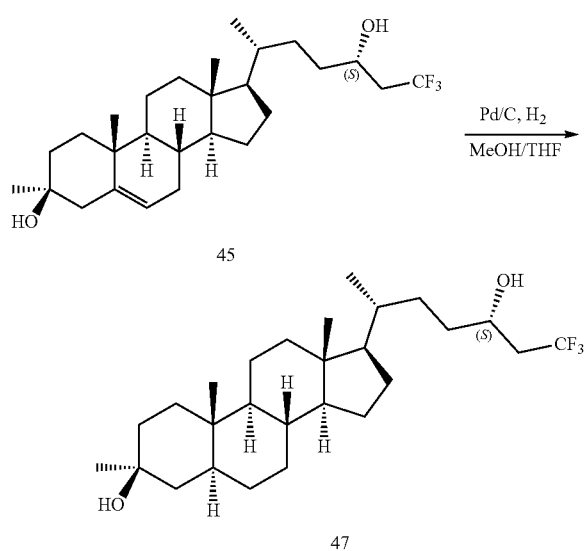

To a solution of Compound 45 (140 mg, 0.307 mmol) in MeOH/THF (10 mL/1 mL) was added Pd/C (dry, 10%, 350 mg) under Ar. After degassing for three times with $N_2$, the reaction mixture was degassed for three times with $H_2$. The reaction mixture was stirred for 16 hrs at 55° C. in $H_2$ atmosphere (50 Psi). The catalyst was removed by suction, and the filtrate was concentrated to give crude product, which was purified by a silica gel column (EtOAc in PE, 10%-15%) to give Compound 47 (30 mg, 21%) as a white solid.

$^1$H NMR (400 MHz, CDCl$_3$) δ 3.96-3.94 (m, 1H), 2.30-2.21 (m, 2H), 1.97-1.93 (m, 1H), 1.92-1.81 (m, 2H), 1.80-1.58 (m, 4H), 1.55-1.26 (m, 6H), 1.24-1.20 (m, 11H), 1.19-0.93 (m, 11H), 0.80 (s, 3H), 0.66-0.62 (m, 4H). LCMS Rt=1.220 min in 2 min chromatography, 30-90 AB, MS ESI calcd. For $C_{27}H_{44}F_3O$ $[M+H-H_2O]^+$ 441, found 441.

Example 30. Synthesis of Compound 48

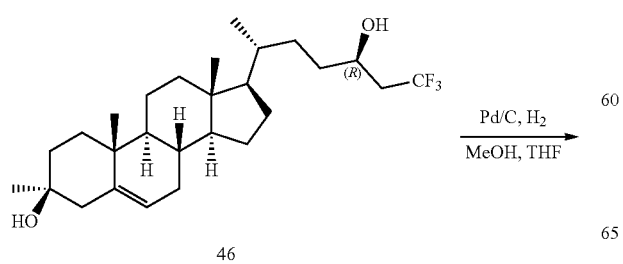

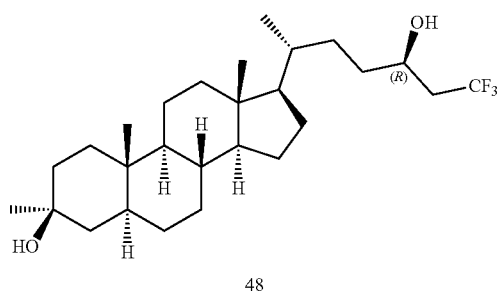

To a solution of Compound 46 (102 mg, 0.223 mmol) in MeOH/THF (10 mL/1 mL) was added Pd/C (dry, 10%, 350 mg) under Ar. After degassing for three times with $N_2$, the reaction mixture was degassed for three times with $H_2$. The reaction mixture was stirred for 16 hrs at 55° C. under $H_2$ atmosphere (50 Psi). The catalyst was removed by suction, and the filtrate was concentrated to give crude product, which was purified by a silica gel column (EtOAc in PE, 10%-15%) to give Compound 48 (25 mg, 24%) as a white solid.

$^1$H NMR (400 MHz, CDCl$_3$) δ 4.00-3.95 (m, 1H), 2.29-2.26 (m, 2H), 1.97-1.93 (m, 1H), 1.92-1.81 (m, 2H), 1.80-1.58 (m, 4H), 1.55-1.26 (m, 6H), 1.24-1.20 (m, 11H), 1.19-0.93 (m, 11H), 0.80 (s, 3H), 0.66-0.64 (m, 4H). LCMS Rt=1.218 min in 2 min chromatography, 30-90 AB, MS ESI calcd. For $C_{27}H_{44}F_3O$ $[M+H-H_2O]^+$ 441, found 441.

Example 31. Synthesis of Compounds 49, 50 and 51

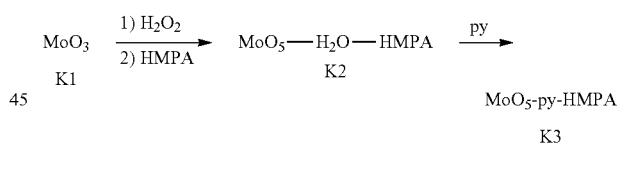

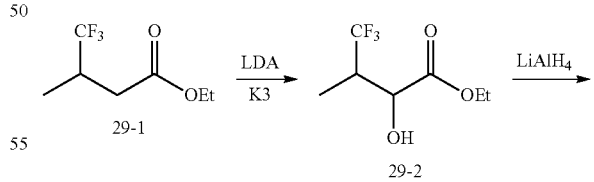

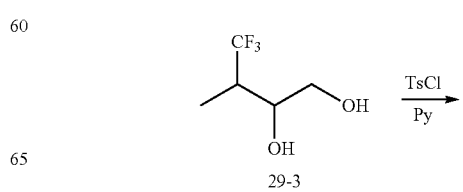

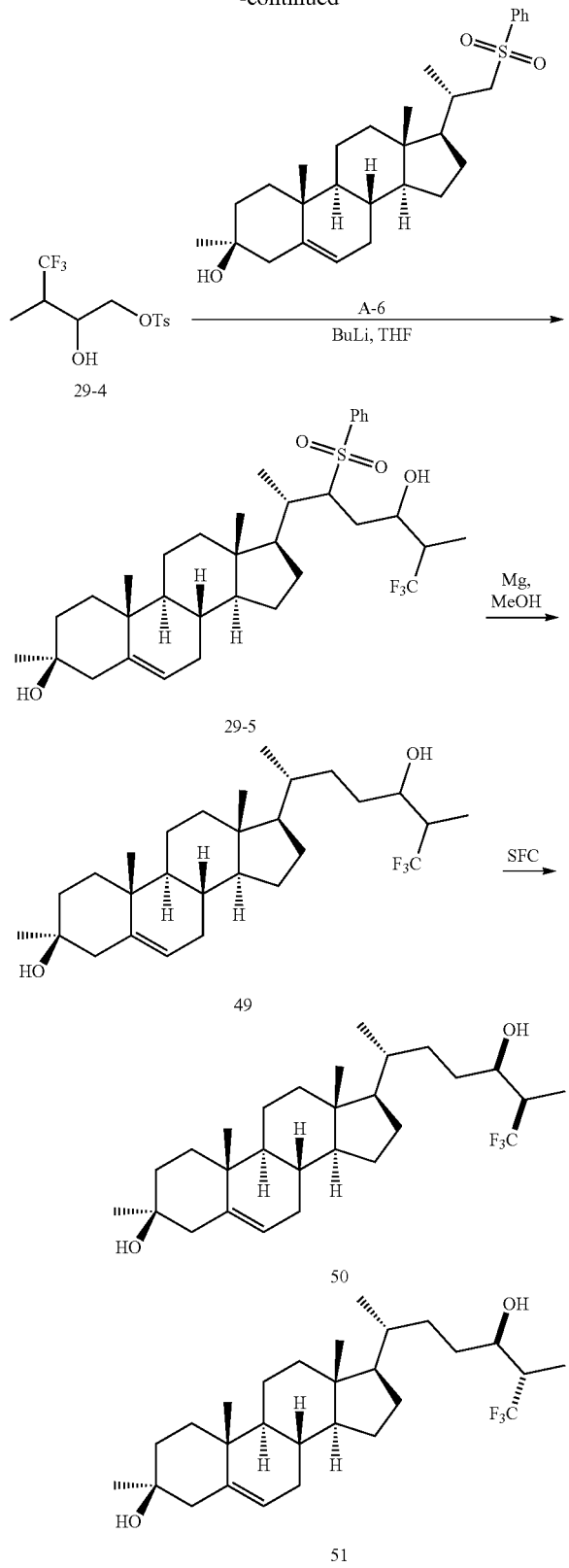

filtered through a 1-cm mat of Celite. The yellow filtrate is cooled to 10° C. (with an ice bath and magnetic stirring) and HMPA (37.2 g, 208 mmol) was added dropwise. A yellow crystalline precipitate was produced. After filtration, the yellow product was recrystallized from 100 mL of EtOH at −20° C. to give 52 g of crude K2 as a yellow solid.

Synthesis of K3. K2 (52 g, 138 mmol) was dried over $P_2O_5$ in vacuum for 6 hrs to give 50 g of a yellow solid. The yellow solid was dissolved in 150 mL of THF at 20° C. Pyridine (11.1 g, 140 mmol) was added. After stirring at 20° C. for 10 mins, a yellow crystalline solid was obtained. After filtration, the filtered cake was washed with THF (50 mL), MTBE (200 mL) and dried in vacuum to give 48 g of crude K3 as a yellow solid, which was used directly.

Synthesis of Compound 29-2. To a solution of diisopropylamine (1.81 mL, 12.9 mmol) in THF (80 mL) under $N_2$ at −70° C. was added a solution of n-BuLi (5.15 mL, 12.9 mmol, 2.5 M in hexane) dropwise. After stirring at −70° C. for 10 mins, the reaction mixture was warmed to 10° C. gradually for 0.5 h. After cooling to −70° C., a solution of Compound 29-1 (2 g, 10.8 mmol) in THF (20 mL) was added. The reaction mixture was stirred for 0.5 h. K3 (7.06 g, 16.2 mmol) was added. After stirring at −20° C. for 3 hrs, the mixture was quenched with 200 mL of saturated $Na_2SO_3$ and extracted with MTBE (2×200 mL). The combined organic phase was washed with 100 mL of brine, dried over $NaSO_4$, filtered and concentrated to give 2.1 g of crude product as brown oil.

$^1$H NMR (400 MHz, $CDCl_3$) δ. 4.55 (s, 1H), 4.37-4.24 (m, 2H), 3.16-3.03 (m, 1H), 2.78-2.66 (m, 1H), 1.32 (t, J=6.8 Hz, 3H), 1.09 (d, J=6.8 Hz, 3H).

Synthesis of Compound 29-3. To a solution of Compound 29-2 (2.1 g, 10.4 mmol) in THF (100 mL) was added $LiAlH_4$ (789 mg, 20.8 mmol) in portions at −10° C. under $N_2$. The reaction mixture was stirred at 15° C. for 2 hrs. The reaction was quenched with water (1 mL), 15% NaOH aqueous solution (1 mL) and water (3 mL) dropwise at 0° C. After stirring at 15° C. for 15 mins, 2 g of $MgSO_4$ was added at 15° C. The mixture was stirred at this temperature for 1 h. After filtering through celite under vacuum and washing with DCM (2×100 mL), the organic layer was concentrated under vacuum to give 2 g of crude product as a yellow oil.

$^1$H NMR (400 MHz, $CDCl_3$) δ. 4.09-4.03 (m, 1H), 3.69-3.61 (m, 2H), 2.39-2.27 (m, 1H), 2.21 (d, J=4.0 Hz, 1H), 1.20 (d, J=7.2 Hz, 3H).

Synthesis of Compound 29-4. To a solution of Compound 29-3 (2 g, 12.6 mmol) in pyridine (15 mL) was added TsCl (2.87 g, 15.1 mmol) in portions during 5 minutes at 0° C. The reaction solution was stirred at 15° C. for 16 hrs. The reaction mixture was quenched with 2N HCl (95 mL) to pH=1-2 at 0° C. The inner temperature was maintained below 30° C. and the mixture was extracted with MTBE (2×250 mL). The combined organic layer was dried over $Na_2SO_4$, filtered, concentrated and purified by column (0-20% of EtOAc in PE) to give Compound 29-4 (2.1 g, 53%) as light yellow oil.

$^1$H NMR (400 MHz, $CDCl_3$) δ. 7.80 (d, J=8.4 Hz, 2H), 7.37 (d, J=8.4 Hz, 2H), 4.22-4.15 (m, 1H), 4.06-3.97 (m, 2H), 2.47 (s, 3H), 2.41-2.29 (m, 1H), 2.18 (d, J=4.8 Hz, 1H), 1.14 (d, J=7.2 Hz, 3H).

Synthesis of Compound 29-5. To THF (3.5 mL) under $N_2$ at −70° C. was added diisopropylamine (2.35 mmol, 237 mg), followed by an addition of n-BuLi (2.22 mmol, 0.89 mL, 2.5M in hexane). The reaction was allowed to warm to 15° C. and re-cooled to −70° C. A suspension of A-6 (0.637 mmol, 300 mg) in THF (1.5 mL) was added dropwise to give a light yellow suspension. After stirring at −70° C. for 30

Synthesis of K2. To 150 mL of 30% $H_2O_2$ in water was added $MoO_3$ (3 g, 208 mmol). The mixture was stirred at 40° C. for 5 hrs to form a yellow solution containing a suspended white solid. After cooling to 20° C., the suspension was mins, a solution of Compound 29-4 (700 µmol, 218 mg) in THF (1.5 mL) was added over 5 min (slightly exothermic, keeping internal T←−70° C.). The reaction was stirred at 15° C. for 12 hrs. The reaction was quenched with saturated NH₄Cl (30 mL) and extracted with EtOAc (3×10 mL). The combined organic layers were dried over Na₂SO₄, filtered and concentrated to give Compound 29-5 (400 mg, crude) as light yellow foam, which was used in the next step directly.

Synthesis of Compound 49. To a solution of Compound 29-5 (400 mg, 0.654 mmol) in MeOH (5 mL) was added Mg powder (940 mg, 39.2 mmol) at 55° C. The mixture was stirred at 55° C. for 16 hrs. The mixture was quenched with HCl (30 mL, 1N) until the mixture became clear and was extracted with DCM (3×10 mL). The combined organic phase was washed with saturated NaHCO₃ (20 mL), dried over Na₂SO₄, filtered, concentrated and purified by combi-flash (0-15% of EtOAc in PE) to give Compound 49 (80 mg, 26%) as an off-white solid.

¹H NMR (400 MHz, CDCl₃) δ. 5.31-5.30 (m, 1H), 3.96-3.95 (m, 1H), 2.43-2.40 (m, 1H), 2.23-2.15 (m, 1H), 2.05-1.91 (m, 3H), 1.90-1.62 (m, 4H), 1.61-1.58 (m, 3H), 1.56-1.42 (m, 7H), 1.41-1.36 (m, 1H), 1.33-1.22 (m, 2H), 1.20-1.16 (m, 5H), 1.15-1.10 (m, 4H), 1.09-1.07 (m, 1H), 1.06-1.03 (m, 4H), 1.02-0.93 (m, 4H), 0.68 (s, 3H). LCMS Rt=1.295 min in 2 min chromatography, 30-90AB_ELSD, MS ESI calcd. for $C_{28}H_{44}F_3O$ $[M+H-H_2O]^+$ 453, found 453.

Synthesis of Compounds 50 and 51. Compound 49 (55 mg, 0.116 mmol) was separated by SFC (column: AD (250 mm*30 mm, 5 um), gradient: (A=0.05% NH₃/H₂O, B=MeOH) flow rate: 120 mL/min) to give Compound 50 (15 mg, 27%) and Compound 51 (11 mg, 20%) as off white solids.

Compound 50: ¹H NMR (400 MHz, CDCl₃) δ. 5.31-5.30 (m, 1H), 3.96-3.95 (m, 1H), 2.43-2.40 (m, 1H), 2.23-2.15 (m, 1H), 2.05-1.91 (m, 3H), 1.90-1.58 (m, 3H), 1.56-1.45 (m, 7H), 1.44-1.35 (m, 5H), 1.34-1.20 (m, 1H), 1.19-1.11 (m, 10H), 1.10-0.85 (m, 9H), 0.68 (s, 3H). LCMS Rt=1.292 min in 2 min chromatography, 30-90AB_ELSD, MS ESI calcd. for $C_{28}H_{44}F_3O$ $[M+H-H_2O]^+$ 453, found 453. SFC Rt=5.077 min in 10 min chromatography, AD_3_MeOH_DEA_5_40_25 ML, (UV 210 nm).

Compound 51: ¹H NMR (400 MHz, CDCl₃) δ. 5.31-5.30 (m, 1H), 3.96-3.95 (m, 1H), 2.43-2.40 (m, 1H), 2.23-2.15 (m, 1H), 2.05-1.91 (m, 3H), 1.90-1.58 (m, 6H), 1.56-1.36 (m, 8H), 1.35-1.22 (m, 3H), 1.20-1.11 (m, 9H), 1.10-0.97 (m, 5H), 0.96-0.90 (m, 4H), 0.68 (s, 3H). LCMS Rt=1.294 min in 2 min chromatography, 30-90AB_ELSD, MS ESI calcd. for $C_{28}H_{44}F_3O$ $[M+H-H_2O]^+$ 453, found 453. SFC Rt=5.412 min in 10 min chromatography, AD_3_MeOH_DEA_5_40_25 ML, (UV 210 nm).

Example 32. Synthesis of Compounds 52, 53, and 54

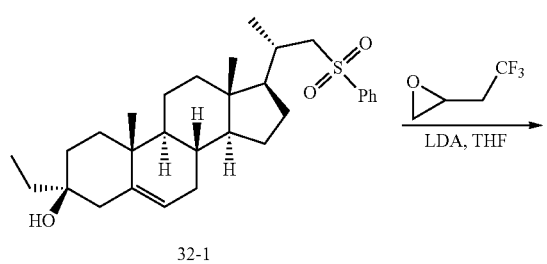

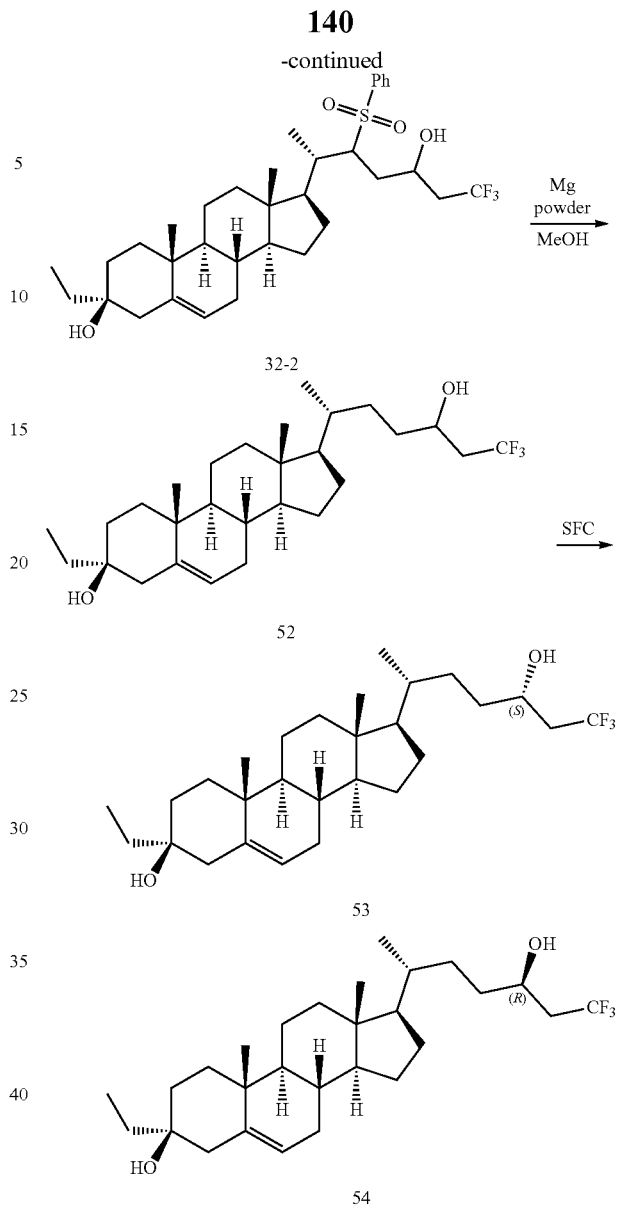

Step 1. To a solution of diisopropylamine (781 mg, 7.72 mmol) in THF (8 mL) was added a solution of n-BuLi (2.8 mL, 2.5 M in hexane, 7.10 mmol) dropwise under N₂ at −78° C. The mixture was warmed to 0° C. To a suspension of 32-1 (1.5 g, 3.09 mmol) in THF (15 mL) was added the fresh prepared LDA solution dropwise under N₂ at −78° C. The mixture was stirred at −78° C. for 30 mins. A solution of 2-(2,2,2-trifluoroethyl)oxirane (583 mg, 4.63 mmol) in THF (6 mL) was added. The mixture was stirred at −78° C. for 30 mins and allowed to warm to 25° C. and stirred for 48 hrs. The reaction mixture was quenched by water (100 mL) and HCl (1 M, aq.) until pH=5 at 15° C. The mixture was extracted with EtOAc (500 mL). The separated organic phase was washed with brine, dried over Na₂SO₄, filtered and concentrated. The crude product was purified by flash column (10~50% of EtOAc in PE) to give 32-2 (1.4 g, 74%) as an off white solid, which was used directly.

Step 2. To a solution of 32-2 (1.4 g, 2.29 mmol) in 20 mL of dry MeOH was added Mg powder (1.64 g, 68.7 mmol) under N₂ at 60° C. The reaction mixture was quenched by 2 M HCl (250 mL) at 10° C. until the solid was dissolved.

After extracted with EtOAc (400 mL), the organic layer was washed with Sat. NaHCO₃ (50 mL), brine (50 mL), dried over Na₂SO₄, filtered and concentrated. The residue was purified by flash column eluted with PE/EtOAc=20:1-5:1 to give Compound 52 (510 mg, 47%) as an off white solid.

¹H NMR (400 MHz, CDCl₃) δ 5.30-5.28 (m, 1H), 3.98-3.96 (m, 1H), 2.35-2.25 (m, 3H), 2.05-2.00 (m, 6H), 1.96-1.60 (m, 8H), 1.57-1.04 (m, 11H), 1.03-0.92 (m, 6H), 0.86-0.83 (m, 6H), 0.68 (s, 3H). LCMS Rt=1.299 min in 2 min chromatography, 30-90 AB, MS ESI calcd. For C₂₈H₄₄F₃O [M+H–H₂O]⁺ 453, found 453.

Step 3. The Compound 52 (510 mg, 1.08 mmol) was purified by SFC separation (Column: AD (250 mm*30 mm, 5 um); Mobile phase: Supercritical CO₂/MeOH+ NH₃H₂O=40/40; Flow rate: 60 ml/min; Wavelength: 220 nm) to give Compound 53 (208 mg, 41%) as an off white solid and Compound 54 (212 mg, 42%) as an off white solid.

Compound 53: ¹H NMR (400 MHz, CDCl₃) δ 5.29-5.27 (m, 1H), 3.96-3.93 (m, 1H), 2.40-2.20 (m, 3H), 2.06-1.92 (m, 3H), 1.88-1.59 (m, 6H), 1.52-1.34 (m, 8H), 1.33-1.22 (m, 2H), 1.05-1.00 (m, 10H), 0.96-0.93 (m, 5H), 0.85 (t, J=7.6 Hz, 3H), 0.68 (s, 3H)

LCMS Rt=1.304 min in 2 min chromatography, 30-90AB, MS ESI calcd. For C₂₈H₄₄F₃O [M+H–H₂O]⁺ 453, found 453.

Compound 54: ¹H NMR (400 MHz, CDCl₃) δ 5.29-5.27 (m, 1H), 4.00-3.95 (m, 1H), 2.41-2.16 (m, 3H), 2.08-1.79 (m, 4H), 1.77-1.68 (m, 2H), 1.67-1.56 (m, 4H), 1.52-1.34 (m, 9H), 1.32-1.16 (m, 3H), 1.16-0.96 (m, 8H), 0.94-0.92 (m, 4H), 0.85 (t, J=7.6 Hz, 3H), 0.68 (s, 3H). LCMS Rt=1.305 min in 2 min chromatography, 30-90 AB, MS ESI calcd. for C₂₈H₄₄F₃O [M+H–H₂O]⁺ 453, found 453.

Example 33. Synthesis of Compound 55

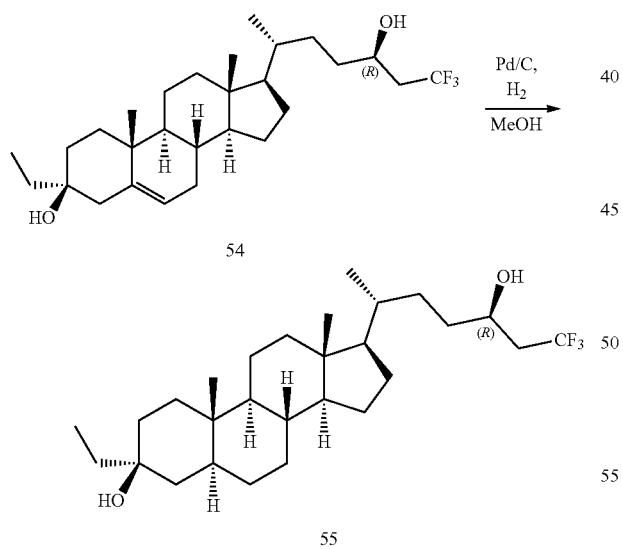

To a solution of Compound 54 (186 mg, 0.395 mmol) in MeOH (20 mL) was added Pd/C (dry, 10%, 350 mg) under Ar. After degassing for three times with N₂, the reaction mixture was degassed for three times with H₂. The reaction mixture was stirred for 16 hrs at 55° C. under H₂ atmosphere (50 Psi). The catalyst was removed by suction, and the filtrate was concentrated to give crude product, which was purified by a silica gel column (EtOAc in PE, 10%-15%) to give Compound 55 (26 mg, 13%) as an off white solid. ¹H NMR (400 MHz, CDCl₃) δ 4.00-3.94 (m, 1H), 2.33-2.22 (m, 2H), 1.97-1.93 (m, 1H), 1.92-1.81 (m, 2H), 1.80-1.58 (m, 4H), 1.55-1.26 (m, 8H), 1.24-1.20 (m, 11H), 1.19-0.93 (m, 11H), 0.82 (s, 3H), 0.67-0.61 (m, 4H). LCMS Rt=1.273 min in 2 min chromatography, 30-90 AB, MS ESI calcd. For C₂₈H₄₆F₃O [M+H–H₂O]⁺ 455, found 455.

Example 34. Synthesis of Compound 56

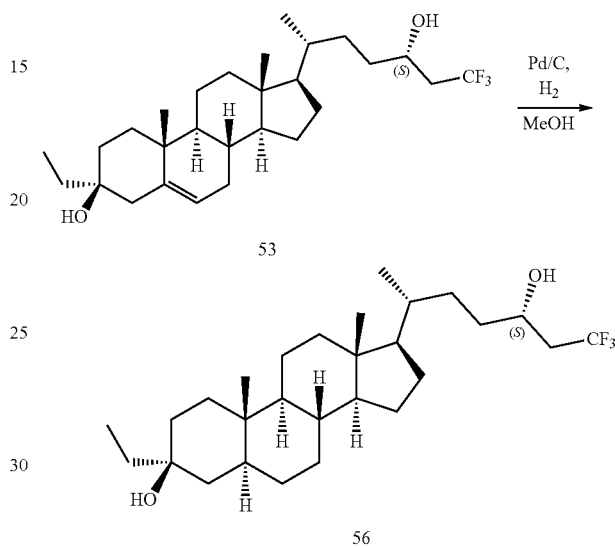

To a solution of Compound 53 (183 mg, 0.389 mmol) in MeOH (20 mL) was added Pd/C (dry, 10%, 350 mg) under Ar. After degassing for three times with N₂, the reaction mixture was degassed for three times with H₂. The reaction mixture was stirred for 16 hrs at 55° C. under H₂ atmosphere (50 Psi). The catalyst was removed by suction, and the filtrate was concentrated to give the crude product which was purified by a silica gel column (EtOAc in PE, 10%-15%) to give Compound 56 (20 mg, 10%) as an off-white solid.

¹H NMR (400 MHz, CDCl₃) δ 3.96-3.93 (m, 1H), 2.30-2.20 (m, 2H), 1.97-1.93 (m, 1H), 1.92-1.81 (m, 2H), 1.80-1.58 (m, 4H), 1.55-1.26 (m, 8H), 1.24-1.20 (m, 11H), 1.19-0.93 (m, 11H), 0.82 (s, 3H), 0.66-0.64 (m, 4H). LCMS Rt=1.268 min in 2 min chromatography, 30-90 AB, MS ESI calcd. For C₂₈H₄₆F₃O [M+H–H₂O]⁺ 455, found 455.

Example 35. Synthesis of Compounds 57 and 58

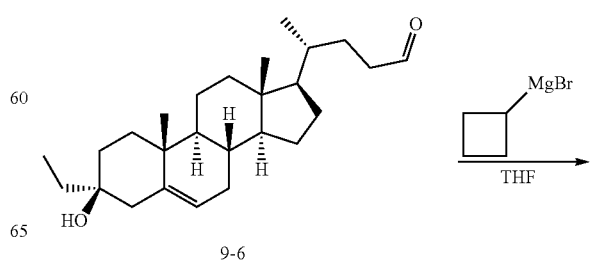

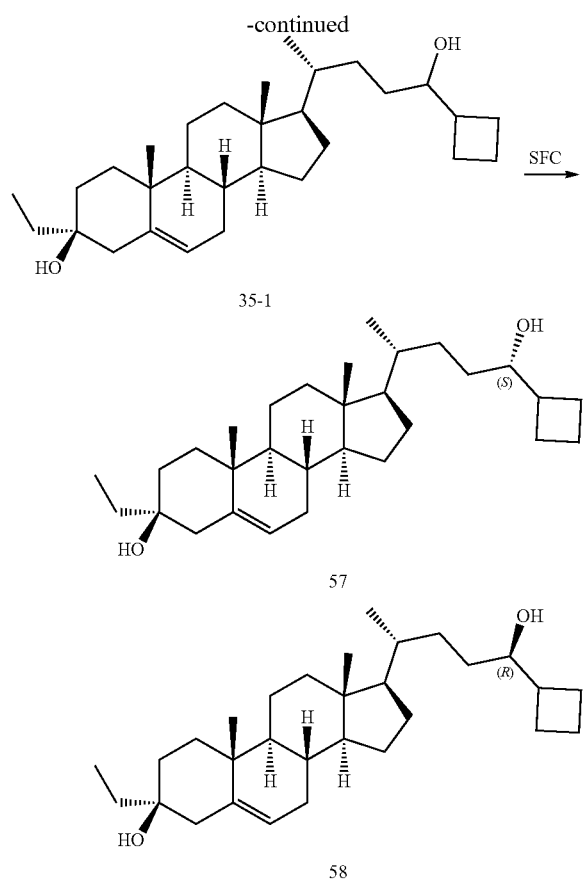

Step 1. To a suspension of Mg (1 g, 41.1 mmol) and 12 (10 mg) in THF (1 mL) was added a solution of bromocyclobutane (2.5 g, 18.5 mmol) in THF (4 mL) at 60° C. dropwise. The mixture was stirred at 60° C. for 1 h. The cyclobutylmagnesium bromide (18.55 mmol in 15 mL THF) solution was then added to a solution of 9-6 (0.5 g, 1.29 mmol) in THF (10 mL) at 0° C. The mixture was stirred at 0° C. for 1 h and quenched with NH$_4$Cl (10 mL, sat. aq.). The mixture was extracted with EtOAc (30 mL). The organic layer was separated, concentrated in vacuum, purified by silica gel (PE/EtOAc=10/1 to 7/1) to give a crude product, which was re-crystallized from MeCN (50 mL) to give 35-1 (100 mg, 18%, 50 mg delivered) as a off-white solid. 1H NMR (400 MHz, CDCl$_3$) δ 5.33-5.21 (m, 1H), 3.50-3.38 (m, 1H), 2.42-2.24 (m, 2H), 2.09-1.61 (m, 13H), 1.55-1.21 (m, 13H), 1.20-0.89 (m, 14H), 0.85 (t, J=7.6 Hz, 3H), 0.70-0.64 (m, 3H). LCMS Rt=1.612 min in 2.0 min chromatography, 30-90AB_E, weak MS. MS MS ESI calcd. for C$_{30}$H$_{49}$O [M+H−H$_2$O]$^+$ 425.3778, found 425.3779.

Step 2. 440 mg of 35-1 was separated by SFC (Instrument: SFC-14; Method: Column: AD (250 mm*30 mm, 5 um); Condition: 0.1% NH$_3$H$_2$O EtOH; Begin B: 40%; End B: 40%; Gradient Time (min): 100% B Hold Time (min): FlowRate (ml/min): 60 ML/MIN; Injections: 160) to give Compound 57 (100 mg, 23%, 50 mg delivered) and Compound 58 (130 mg, SFC impure). The impure Compound 57 (130 mg) was purified by SFC (Column: AD (250 mm*30 mm, 5 um); Condition: 0.1% NH$_3$H$_2$O ETOH, 40% B; FlowRate (ml/min): 60) to give Compound 58 (112 mg, 26%) as a off-white solid.

Compound 57: $^1$H NMR (400 MHz, CDCl$_3$) δ 5.35-5.22 (m, 1H), 3.480-3.37 (m, 1H), 2.40-2.28 (m, 2H), 2.09-1.61 (m, 13H), 1.55-1.21 (m, 13H), 1.20-0.89 (m, 14H), 0.85 (t, J=7.6 Hz, 3H), 0.67 (s, 3H). HPLC Rt=5.51 min in 8.0 min chromatography, 50-100_AB_E. MS MS ESI calcd. for C$_{30}$H$_{49}$O [M+H−H$_2$O]$^+$ 425.3778, found 425.3770.

Compound 58: $^1$H NMR (400 MHz, CDCl$_3$) δ 5.35-5.22 (m, 1H), 3.480-3.37 (m, 1H), 2.40-2.28 (m, 2H), 2.09-1.61 (m, 13H), 1.55-1.21 (m, 14H), 1.20-0.89 (m, 13H), 0.85 (t, J=7.6 Hz, 3H), 0.68 (s, 3H). LCMS Rt=1.361 min in 2.0 min chromatography, 30-90 AB_E, MS ESI calcd. for C30H47 [M+H−2H$_2$O]$^+$ 407, found 407.

Example 36. Synthesis of Compounds 36-6, 59, 59-A, 59-B, 60, 60-A, and 60-B

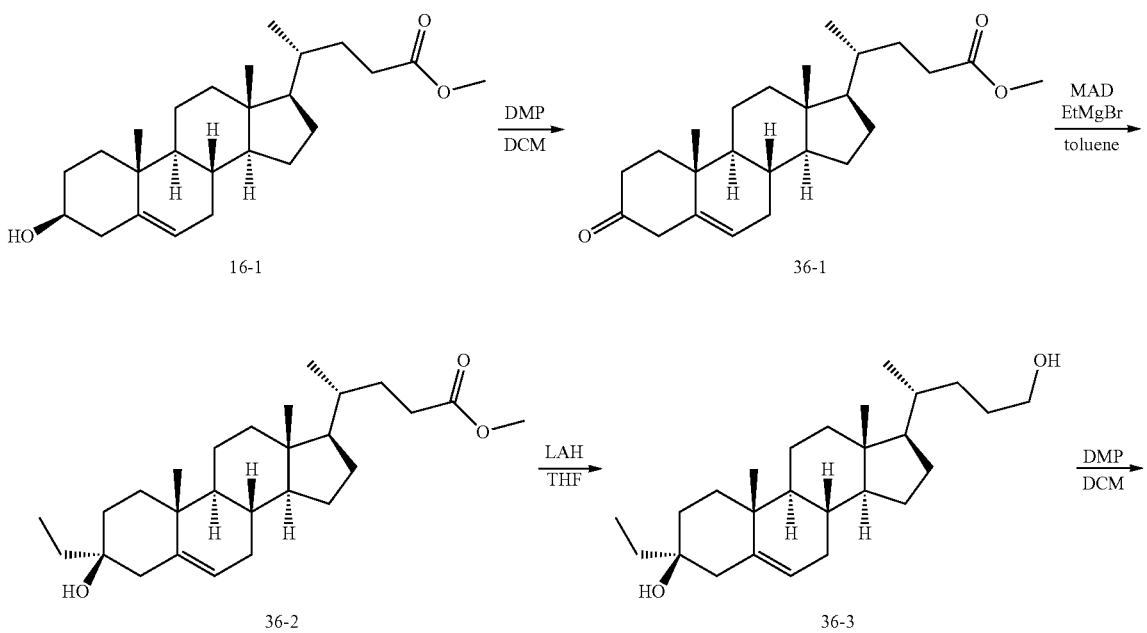

-continued
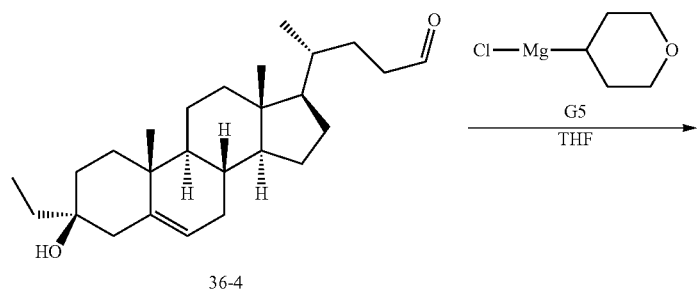
36-4
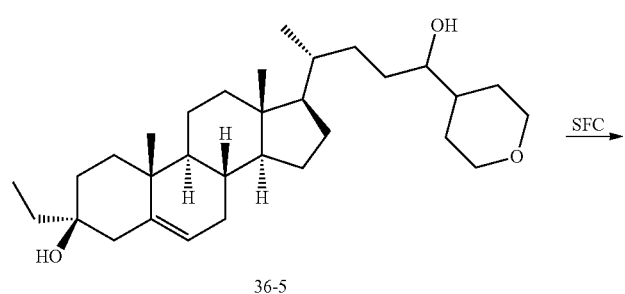
36-5
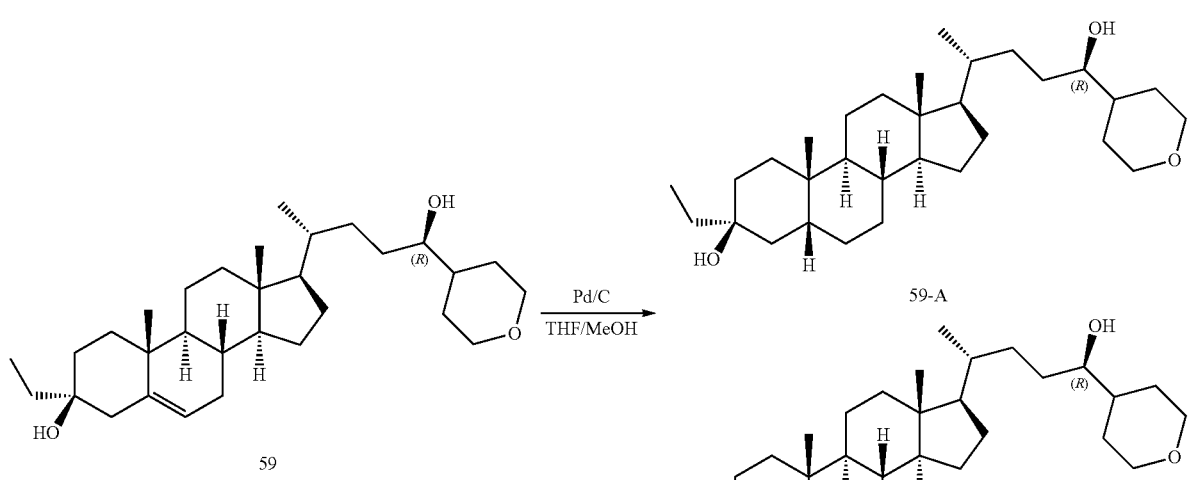
59
60
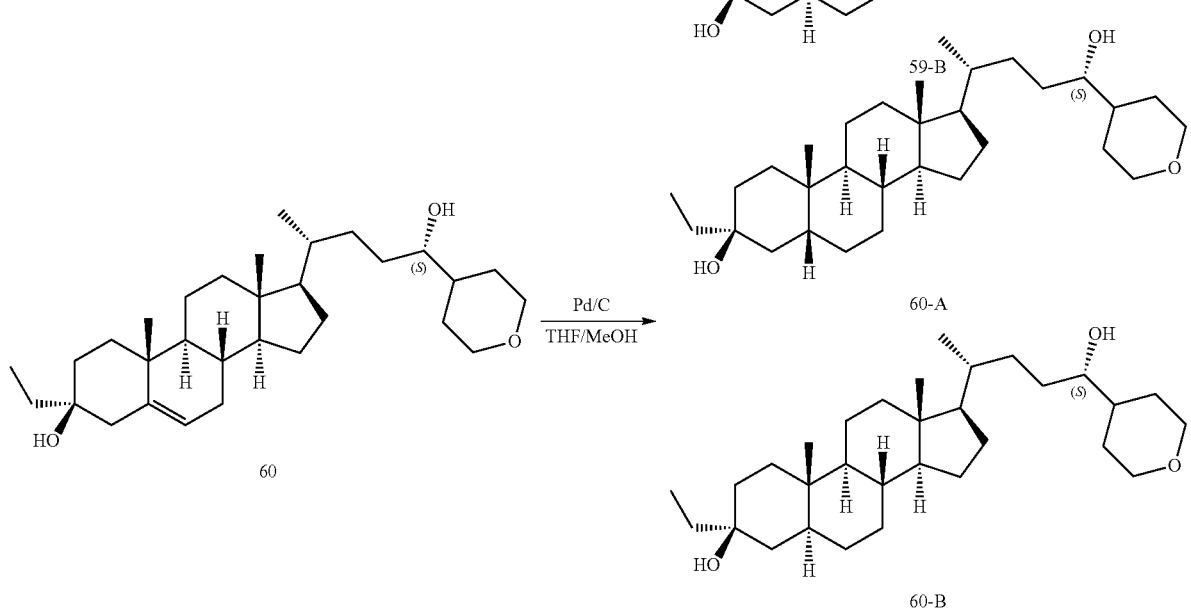
59-A
59-B
60-A
60-B

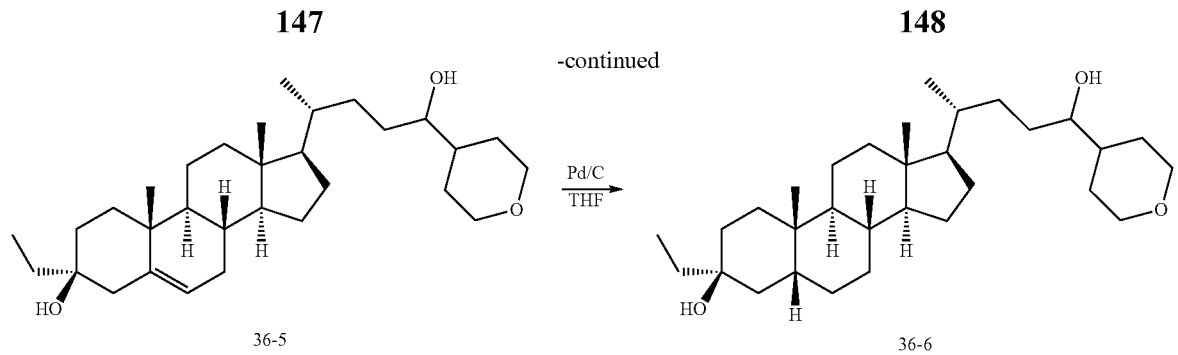

36-5 → 36-6 (Pd/C, THF)

Step 1. To a solution of 16-1 (20 g, 51.4 mmol) in DCM (200 mL) was added DMP (43.2 g, 102 mmol) at 30° C. The reaction mixture was stirred at 30° C. for 1 h. The reaction mixture was quenched with Saturated NaHCO$_3$ aqueous (100 mL). The mixture was filtered. DCM layer was separated and the aqueous phase was extracted with DCM (100 mL). The combined organic phase was washed with saturated Na$_2$S$_2$O$_3$ aqueous (150 mL), brine (150 mL), dried over Na$_2$SO$_4$, filtered and concentrated to give 36-1 (20 g, crude) as a yellow solid. 1H NMR (400 MHz, CDCl$_3$) δ 5.37-5.31 (m, 1H), 3.66 (s, 3H), 3.32-3.24 (m, 1H), 2.86-2.78 (m, 1H), 2.49-2.19 (m, 5H), 2.08-2.02 (m, 3H), 1.91-1.75 (m, 2H), 1.55-1.39 (m, 5H), 1.38-1.27 (m, 5H), 1.20-1.01 (m, 5H), 0.94-0.91 (m, 3H), 0.73-0.66 (m, 4H).

Step 2. To a solution of BHT (73.9 g, 336 mmol) in anhydrous toluene (100 mL) under N$_2$ at 0° C. was added trimethylaluminum (2 M in toluene, 77.5 mL, 155 mmol) drop-wise. The mixture was stirred at 15° C. for 1 hour and cooled to −70° C. A solution of 36-1 (20 g, 51.7 mmol) in toluene (50 mL) was added below −60° C. The resulting mixture was stirred at −70° C. for 1 hour. Ethylmagnesium bromide (51.6 mL, 3.0 M in diethyl ether, 155 mmol) was added drop-wise below −60° C. The reaction mixture was stirred at −70° C. for another 1 hour. The reaction mixture was quenched by saturated citric acid (400 mL) at −70° C. The mixture was warmed to 15° C. slowly, and extracted with ethyl acetate (3×400 mL). The combined organic layer was washed with brine (500 mL), dried over Na$_2$SO$_4$, filtered and concentrated. The residue was purified by Combi-flash (0%~20% of EtOAc in PE) to afford 36-2 (13 g, 60%) as off-white solid. 1H NMR (400 MHz, CDCl$_3$) δ 5.31-5.25 (m, 1H), 3.66 (s, 3H), 2.47-2.16 (m, 4H), 2.07-1.69 (m, 6H), 1.66-1.59 (m, 3H), 1.55-1.38 (m, 6H), 1.36-1.23 (m, 4H), 1.20-1.00 (m, 7H), 0.98-0.81 (m, 7H), 0.67 (s, 3H).

Step 3. To a solution of 36-2 (25 g, 60.0 mmol) in THF (500 mL) under N$_2$ at 0° C. was added LiAlH$_4$ (3.41 g, 90.0 mmol) in portions. The reaction was stirred at 0° C. for 30 min. The reaction was quenched with 1 M HCl (300 mL) at 0° C. and extracted with EtOAc (3×300 mL). The combined organic phase was washed with brine (500 mL), dried over Na$_2$SO$_4$, filtered and concentrated. The residue was purified by Combi-flash (0%~20% of EtOAc in PE/DCM (v/v=1/1)) to afford 36-3 (3 g, pure) and (10 g, impure) as off-white solid. $^1$H NMR (400 MHz, CDCl$_3$) δ 5.34-5.24 (m, 1H), 3.67-3.55 (m, 2H), 2.41-2.30 (m, 1H), 2.07-1.91 (m, 3H), 1.88-1.60 (m, 5H), 1.55-1.33 (m, 10H), 1.30-1.20 (m, 3H), 1.17-1.01 (m, 8H), 1.00-0.89 (m, 5H), 0.85 (t, J=7.4 Hz, 3H), 0.68 (s, 3H).

Step 4. To a solution of 36-3 (3 g, 7.71 mmol) in DCM (100 mL) was added DMP (6.52 g, 15.4 mmol) at 20° C. The reaction mixture was stirred at 20° C. for 10 min. The reaction mixture was quenched with Saturated NaHCO$_3$ aqueous (100 mL) at 20° C. The mixture was filtered. The DCM layer was separated and the aqueous phase was extracted with DCM (50 mL). The combined organic phase was washed with saturated Na$_2$S$_2$O$_3$ aqueous (150 mL), brine (150 mL), dried over Na$_2$SO$_4$, filtered and concentrated to give 36-4 (3 g, crude) as off-white solid. 1H NMR (400 MHz, CDCl$_3$) δ 9.80-9.73 (m, 1H), 5.32-5.24 (m, 1H), 2.51-2.29 (m, 3H), 2.07-1.93 (m, 3H), 1.88-1.70 (m, 3H), 1.65-1.57 (m, 4H), 1.50-1.24 (m, 10H), 1.21-1.04 (m, 5H), 1.02-0.96 (m, 1H), 0.98-0.82 (m, 8H), 0.68 (s, 3H).

Step 5. To a vigorously stirred suspension of Mg (1.76 g, 72.8 mmol) turnings and iodine (46.1 mg, 0.182 mmol) in THF (2 mL) under N$_2$ was added 1,2-dibromoethane (68.3 mg, 0.364 mmol) and 10% of a solution of 4-chlorotetrahydro-2H-pyran (4.4 g, 36.4 mmol) in THF (18 mL). The mixture was heated to 60° C. and as the reaction mixture turned clear and Grignard initiated took place, the remainder of the solution of 4-chlorotetrahydro-2H-pyran in THF was added slowly over 30 min. The reaction mixture was stirred at 65° C. for 2h to give a solution of (tetrahydro-2H-pyran-4-yl)magnesium chloride in THF (~2M). The Grignard solution was used without any further purification. The solution of 36-4 (800 mg, 2.06 mmol) in THF (150 mL) under N$_2$ was added to Grignard reagent at 15° C. in one portion. After stirring at 15° C. for 2 min, the mixture was quenched by 200 mL of sat·NH$_4$Cl and extracted with 200 mL of EtOAc. The separated organic phase was washed with 200 mL of brine, dried over Na$_2$SO$_4$, filtered and concentrated. The residue was purified by Combi-flash (0%~30% of EtOAc in PE/DCM (v/v=1/1)) to afford 36-5 (550 mg, 56%) as off-white solid, and 50 mg of 36-5 was delivered. 1H NMR (400 MHz, CDCl$_3$) δ 5.32-5.25 (m, 1H), 4.06-3.96 (m, 2H), 3.42-3.29 (m, 3H), 2.39-2.33 (m, 1H), 2.07-1.79 (m, 6H), 1.77-1.60 (m, 7H), 1.51-1.38 (m, 10H), 1.35-1.21 (m, 4H), 1.16-1.01 (m, 8H), 0.97-0.90 (m, 4H), 0.85 (t, J=7.4 Hz, 3H), 0.71-0.66 (m, 3H). LCMS Rt=1.212 min in 2 min chromatography, 30-90AB_2 MIN_E.M, MS ESI calcd. for C$_{31}$H$_{51}$O$_2$ [M+H−H$_2$O]$^+$ 455, found 455.

Step 5. 36-5 (500 mg, 1.05 mmol) was purified by SEC (Column: AD (250 mm*30 mm, 5 um); Condition: 0.1% NH$_3$H$_2$O IPA; Gradient 40% B; Gradient Time (min): 30; FlowRate (ml/min): 60.) to afford Compound 59 (210 mg, 42%, 50 mg delivered) as off-white solid and Compound 60 (200 mg, 40%, 45 mg delivered) as off-white solid.

Compound 59 (peak1): $^1$H NMR (400 MHz, CDCl$_3$) δ 5.32-5.25 (m, 1H), 4.06-3.96 (m, 2H), 3.43-3.29 (m, 3H), 2.40-2.32 (m, 1H), 2.07-1.79 (m, 4H), 1.77-1.60 (m, 4H), 1.55-1.35 (m, 14H), 1.34-1.17 (m, 5H), 1.15-0.90 (m, 12H), 0.85 (t, J=7.4 Hz, 3H), 0.68 (s, 3H). LCMS Rt=1.221 min in 2 min chromatography, 30-90AB_2 MIN_E.M, MS ESI calcd. for C$_{31}$H$_{51}$O$_2$ [M+H−H$_2$O]$^+$ 455, found 455.

Compound 60 (peak2): $^1$H NMR (400 MHz, CDCl$_3$) δ 5.31-5.26 (m, 1H), 4.06-3.96 (m, 2H), 3.43-3.29 (m, 3H), 2.40-2.33 (m, 1H), 2.07-1.93 (m, 4H), 1.88-1.61 (m, 9H), 1.54-1.38 (m, 9H), 1.34-1.06 (m, 8H), 1.05-0.90 (m, 9H), 0.85 (t, J=7.4 Hz, 3H), 0.68 (s, 3H). LCMS Rt=1.218 min in 2 min chromatography, 30-90AB_2 MIN_E.M, MS ESI calcd. for C$_{31}$H$_{51}$O$_2$ [M+H–H$_2$O]$^+$ 455, found 455.

Step 6. To a solution of Compound 59 (150 mg, 0.317 mmol) in MeOH (5 mL) and THF (5 mL) was added dry Pd/C (300 mg) at 15° C. The mixture was degassed and purged with H$_2$ several times and then stirred under 50 psi of H$_2$ at 55° C. for 72 hours. The reaction mixture was filtered through a pad of Celite and washed with THF (2×5 mL). The filtrate was concentrated. The residue was purified by Combi-flash (0-30% of EtOAc in PE/DCM (v/v=1/1)) to afford Compound 59-A (20 mg, 13%) as an off-white solid. $^1$H NMR (400 MHz, CDCl$_3$) δ 4.06-3.94 (m, 2H), 3.43-3.27 (m, 3H), 2.00-1.67 (m, 6H), 1.55-1.48 (m, 4H), 1.45-1.32 (m, 13H), 1.29-1.12 (m, 11H), 1.07-0.89 (m, 12H), 0.65 (s, 3H). LCMS Rt=1.261 min in 2.0 min chromatography, 30-90 AB, MS ESI calcd. for C$_{31}$H$_{51}$O [M+H–2H$_2$O]$^+$ 439, found 439.

Step 7. To a solution of Compound 59 (50 mg, 0.105 mmol) in MeOH (5 mL) and THF (5 mL) was added dry Pd(OH)$_2$ (300 mg) at 15° C. The mixture was degassed and purged with H$_2$ several times, stirred under 50 psi of H$_2$ at 55° C. for 72 hours. The reaction mixture was filtered through a pad of Celite and washed with THF (2×5 mL). The filtrate was concentrated. The residue was purified by Combi-flash (0%~30% of EtOAc in PE/DCM (v/v=1/1)) to afford Compound 59-B (10 mg, 20%) as an off-white solid. $^1$H NMR (400 MHz, CDCl$_3$) δ 4.05-3.95 (m, 2H), 3.42-3.29 (m, 3H), 1.99-1.91 (m, 1H), 1.89-1.58 (m, 6H), 1.56-1.35 (m, 14H), 1.33-1.16 (m, 8H), 1.14-0.95 (m, 6H), 0.94-0.80 (m, 10H), 0.69-0.58 (m, 4H). LCMS Rt=1.253 min in 2.0 min chromatography, 30-90 AB, MS ESI calcd. for C$_{31}$H$_{51}$O [M+H–2H$_2$O]$^+$ 439, found 439.

Step 8. To a solution of Compound 60 (150 mg, 0.317 mmol) in MeOH (5 mL) and THF (5 mL) was added dry Pd/C (300 mg) at 15° C. The mixture was degassed and purged with H$_2$ several times, stirred under 50 psi H$_2$ at 55° C. for 72 hours. The reaction mixture was filtered through a pad of Celite and washed with THF (2×5 mL). The filtrate was concentrated. The residue was purified by Combi-flash (0%~30% of EtOAc in PE/DCM (v/v=1/1)) to afford Compound 60-A (33 mg) as a off-white solid. $^1$H NMR (400 MHz, CDCl$_3$) δ 4.06-3.95 (m, 2H), 3.43-3.26 (m, 3H), 2.00-1.59 (m, 9H), 1.53-1.35 (m, 11H), 1.34-1.10 (m, 13H), 1.08-0.84 (m, 13H), 0.65 (s, 3H). LCMS Rt=1.261 min in 2.0 min chromatography, 30-90 AB, MS ESI calcd. for C$_{31}$H$_{51}$O [M+H–2H$_2$O]$^+$ 439, found 439.

Step 9. To a solution of Compound 60 (150 mg, 0.317 mmol) in MeOH (5 mL) and THF (5 mL) was added dry Pd/C (300 mg) at 15° C. The mixture was degassed and purged with H$_2$ several times, stirred under 50 psi H$_2$ at 55° C. for 72 hours. The reaction mixture was filtered to remove Pd/C, the filtrate was concentrated. The residue was purified by Combi-flash (0%~30% of EtOAc in PE/DCM (v/v=1/1)) to afford Compound 60-B (40 mg, 26%) as a off-white solid. $^1$H NMR (400 MHz, CDCl$_3$) δ 4.06-3.95 (m, 2H), 3.43-3.27 (m, 3H), 2.03-1.91 (m, 1H), 1.86-1.74 (m, 1H), 1.72-1.57 (m, 8H), 1.54-1.34 (m, 10H), 1.33-1.15 (m, 8H), 1.15-0.96 (m, 7H), 0.94-0.79 (m, 10H), 0.72-0.56 (m, 4H). LCMS Rt=1.250 min in 2.0 min chromatography, 30-90 AB, MS ESI calcd. for C$_{31}$H$_{51}$O [M+H–2H$_2$O]$^+$ 439, found 439.

Step 10. To a solution of 36-5 (150 mg, 0.317 mmol) in MeOH (5 mL) and THF (5 mL) was added dry Pd/C (300 mg) at 15° C. The mixture was degassed and purged with H$_2$ several times, stirred under 50 psi of H$_2$ at 55° C. for 72 hours. The reaction mixture was filtered through a pad of Celite and washed with THF (2×5 mL). The filtrate was concentrated. The residue was purified by Combi-flash (0%~30% of EtOAc in PE/DCM (v/v=1/1)) to afford 36-6 (30 mg) as a off-white solid. $^1$H NMR (400 MHz, CDCl$_3$) δ 4.07-3.94 (m, 2H), 3.43-3.25 (m, 3H), 2.00-1.59 (m, 7H), 1.50-1.36 (m, 11H), 1.34-1.10 (m, 15H), 1.07-0.82 (m, 13H), 0.65 (s, 3H). LCMS Rt=1.261 min in 2.0 min chromatography, 30-90 AB, MS ESI calcd. for C$_{31}$H$_{51}$O [M+H–2H$_2$O]$^+$ 439, found 439.

Example 37. Alternative Synthesis of 10, 11, 13, and 15

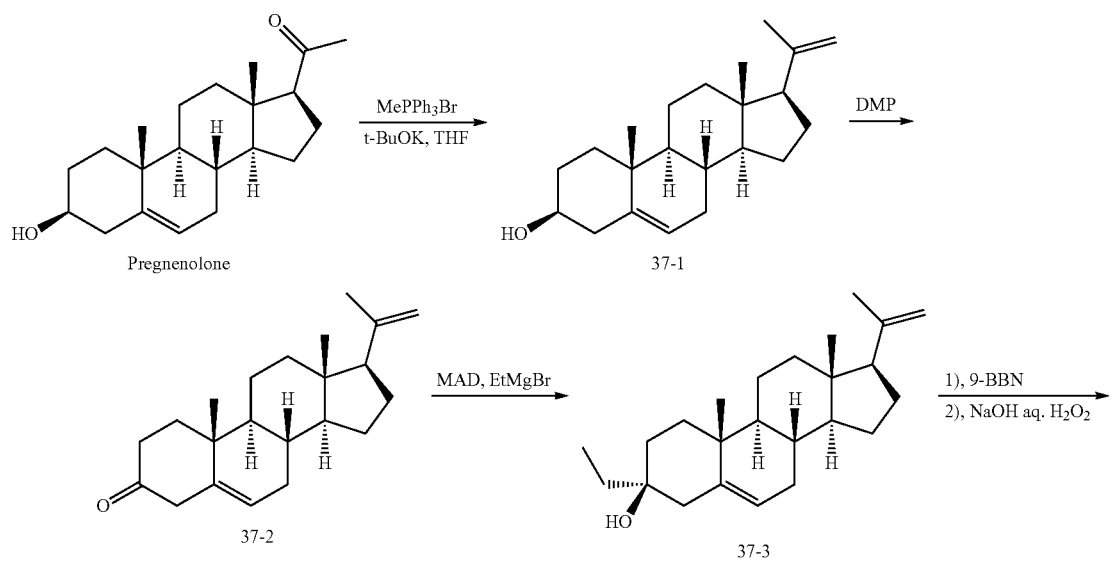

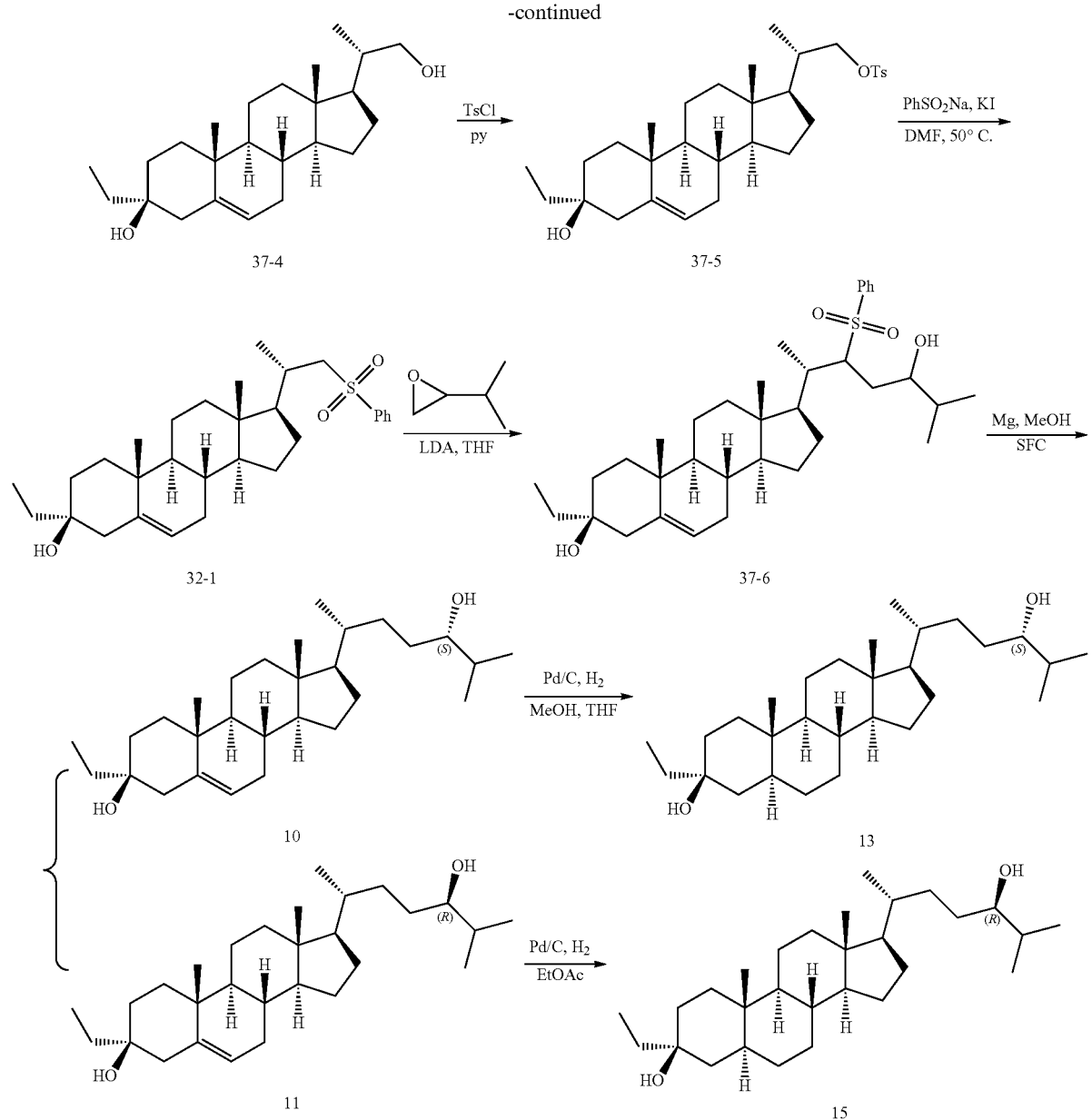

Step 2. To a mixture of DMP (539 g, 1271 mmol) in DCM (800 mL) was added 37-1 (200 g, 636 mmol) in DCM (2.2 L) at 30° C. The reaction mixture was stirred at 40° C. for 1 h. The reaction mixture was quenched with saturated NaHCO$_3$ aqueous (1.2 L) at 10° C. The mixture was filtered. The DCM phase in filtrate was separated and washed with saturated NaHCO$_3$/Na$_2$S$_2$O$_3$ aqueous (1:1, 2×1 L), brine (1 L), dried over Na$_2$SO$_4$, filtered and concentrated under vacuum to give a yellow solid, which was triturated in MeCN (700 mL) to give 37-2 (115 g, 58%) as a off-white solid.

$^1$H NMR (400 MHz, CDCl$_3$) δ 5.38-5.31 (m, 1H), 4.86 (s, 1H), 4.72 (s, 1H), 3.28 (dd, J=2.8, 16.8 Hz, 1H), 2.82 (dd, J=1.6, 16.8 Hz, 1H), 2.56-2.40 (m, 1H), 2.35-2.24 (m, 1H), 2.11-1.99 (m, 3H), 1.95-1.85 (m, 1H), 1.85-1.77 (m, 1H), 1.76 (s, 3H), 1.73-1.61 (m, 3H), 1.56-1.39 (m, 3H), 1.31-1.19 (m, 2H), 1.19 (s, 3H), 1.18-0.99 (m, 3H), 0.61 (s, 3H).

Step 3. To a mixture of BHT (405 g, 1839 mmol) in toluene (400 mL) was added AlMe$_3$ (459 mL, 2 M, 919 mmol) drop-wise at 0° C. The resulting mixture was stirred at 15° C. for 1 h. 37-2 (115 g, 368 mmol) in toluene (500 mL) was added dropwise at −70° C. The mixture was stirred at −70° C. for 1 h. EtMgBr (368 mL, 3 M, 1104 mmol) was added drop-wise at −70° C. The reaction mixture was stirred at −70° C. for 1 h. The reaction mixture was poured into saturated critic acid aqueous (2 L). The aqueous was extracted with ethyl acetate (2×1.5 L). The combined organic was washed with brine (2 L), dried over Na$_2$SO$_4$, filtered and concentrated under vacuum to give a off-white solid, which was purified by re-crystallization in MeCN (900 mL) to give 37-3 (80 g, 63%) as a off-white solid. The filtrate was concentrated under vacuum to give a solid, which was purified by silica gel chromatography (PE:E-tOAc=20:1) to give a off-white solid, which was further purified by re-crystallization in MeCN (150 mL) to give 37-3 (17 g, 14%) as a off-white solid. $^1$H NMR (400 MHz, CDCl$_3$) δ 5.34-5.24 (m, 1H), 4.85 (s, 1H), 4.71 (s, 1H), 2.40-2.33 (m, 1H), 2.07-1.94 (m, 3H), 1.91-1.82 (m, 3H), 1.82-1.73 (m, 4H), 1.73-1.52 (m, 8H), 1.50-1.32 (m, 4H), 1.29-1.05 (m, 5H), 1.05-0.90 (m, 1H), 0.85 (t, J=7.6 Hz, 3H), 0.58 (s, 3H).

Step 4. To a mixture of 37-3 (97 g, 283 mmol) and 9-BBN dimer (79 g, 324 mmol) was added THF (650 mL) at 15° C. under N$_2$. The reaction mixture was stirred at 30° C. for 1 h. The mixture was cooled to 15° C. Ethanol (129 g, 2.83 mmol) was added at 15° C. NaOH aqueous (478 mL, 5 M, 2390 mmol) was added drop-wise at 15° C. H$_2$O$_2$ (320 g, 30%, 2.83 mmol) was added drop-wise at 15° C. The obtained mixture was stirred at 60° C. for 1 h. The reaction mixture was cooled to 20° C. A off-white solid was produced. The solid was filtered and washed with water (2×800 mL). The combined solid was purified by triturated in MeCN (200 mL) to give 15-3a-1 (91 g, impure) as a off-white solid. 1H NMR (400 MHz, CDCl$_3$) δ 5.32-5.23 (m, 1H), 3.67-3.60 (m, 1H), 3.42-3.33 (m, 1H), 2.40-2.33 (m, 1H), 2.08-1.90 (m, 3H), 1.89-1.69 (m, 2H), 1.66-1.60 (m, 3H), 1.56-1.24 (m, 9H), 1.23-1.07 (m, 5H), 1.05 (d, J=6.8 Hz, 3H), 1.03 (s, 3H), 1.02-0.90 (m, 2H), 0.85 (t, J=7.2 Hz, 3H), 0.70 (s, 3H).

Step 5. To a solution of 37-4 (91 g, 252 mmol) in chloroform (500 mL) and pyridine (350 mL) was added TsCl (132.2 g, 694 mmol) at 15° C. The mixture was stirred at 15° C. for 2 hrs. The reaction mixture combined was concentrated under vacuum to remove most of chloroform. To the obtained pyridine mixture was added water (3 L). A off-white solid was produced, and filtered to give a off-white solid, which was washed with water (6×4 L). The off-white solid was dissolved in DCM (3.5 L), dried over Na$_2$SO$_4$, filtered and concentrated under vacuum to give 37-5 (127 g, 98%) as a off-white solid. $^1$H NMR (400 MHz, CDCl$_3$) δ 7.78 (d, J=8.4 Hz, 2H), 7.34 (d, J=8.0 Hz, 2H), 5.30-5.20 (m, 1H), 4.00-3.90 (m, 1H), 3.80-3.70 (m, 1H), 2.45 (s, 3H), 2.40-2.30 (m, 1H), 2.10-1.90 (m, 3H), 1.75-1.60 (m, 6H), 1.55-1.30 (m, 5H), 1.25-0.95 (m, 13H), 0.90-0.80 (m, 5H), 0.64 (s, 3H).

Step 6. To a solution of 37-5 (127 g, 246 mmol) in DMF (1 L) was added KI (196 g, 1.18 mol) at 15° C. The mixture was stirred at 50° C. for 1 h. To the resulting mixture was added PhSO$_2$Na (148 g, 737 mmol). The mixture was stirred at 50° C. for 16 hrs. The reaction mixture was poured into water (4 L) and some yellow solid was produced. The mixture was filtered. The filter cake was washed with water (3×2 L). The resulting filter cake was dissolved in DCM (3 L), washed with water (3×1 L), brine (2×2 L), dried over Na$_2$SO$_4$, filtered, concentrated in vacuum to give a crude product as a yellow solid, which was re-crystallization in MeCN (400 mL) to give 32-1 (45 g, 34%) as a light yellow solid. $^1$H NMR (400 MHz, CDCl$_3$) δ 7.95-7.88 (m, 2H), 7.68-7.62 (m, 1H), 7.61-7.53 (m, 2H), 5.30-5.22 (m, 1H), 3.20-3.08 (m, 1H), 2.91-2.79 (m, 1H), 2.40-2.30 (m, 1H), 2.09-1.87 (m, 4H), 1.74-1.60 (m, 4H), 1.50-1.36 (m, 7H), 1.24-0.98 (m, 13H), 0.90-0.80 (m, 4H), 0.65 (s, 3H).

Step 7. To a solution of diisopropylamine (7.28 g, 72.1 mmol) in THF (20 mL) under N$_2$ at −70° C., was added n-BuLi (27.1 mL, 2.5 M, 67.9 mmol). The resulting mixture was stirred at 0° C. for 30 min. The mixture was re-cooled to −70° C. To the mixture was added 32-1 (10 g, 20.6 mmol) in THF (50 mL) at −70° C. The reaction mixture was stirred at −70° C. for 1 h. 2-isopropyloxirane (2.12 g, 24.7 mmol) in THF (10 mL) was added at −70° C. The reaction mixture was warmed to 15° C. slowly, and stirred at 15° C. for 16 hrs. The reaction mixture was quenched with saturated NH$_4$Cl aqueous (100 mL) at 0° C. The mixture was extracted with EtOAc (2×200 mL). The combined organic phase was washed with brine (150 mL), dried over Na$_2$SO$_4$, filtered and concentrated under vacuum to give 37-6 (12 g, crude) as a yellow solid. LCMS Rt=3.784 & 3.859 min in 7 min chromatography, 30-90AB_7MIN_E.M, MS ESI calcd. for C$_{35}$H$_{53}$O$_3$S [M+H−H$_2$O]$^+$ 553, found 553.

Step 8. To a solution of 37-6 (12 g, 21.0 mmol) in 200 mL of anhydrous MeOH was added Mg powder (30.6 g, 1260 mmol) and NiCl$_2$ (27.0 mg, 0.21 mmol) with stirring under N$_2$ at 50° C. to initiate continuous hydrogen generation. The reaction mixture was quenched by 2 M HCl (100 mL) until solid was dissolved. The mixture was extracted with EtOAc (3×200 mL). The combined organic layer was washed with Sat. NaHCO$_3$ (50 mL), brine (50 mL), dried over Na$_2$SO$_4$, filtered and concentrated. The residue was purified by silica gel chromatography eluted with PE/EtOAc=20/1~8/1 to give 5.6 g of off-white solid, which was purified by SFC (Column: Chiralpak AD 250×30 mm I.D., 5 um Mobile phase: A: CO2 B: methanol (0.1% NH$_3$H$_2$O) Gradient: from 35% to 35% of B, Flow rate: 60 mL/min) to give Compound 10 (2.2 g, 24%), Compound 11 (2.2 g, 24%) as off-white solid.

Compound 10: $^1$H NMR (400 MHz, CDCl$_3$) δ 5.32-5.23 (m, 1H), 3.38-3.24 (m, 1H), 2.41-2.32 (m, 1H), 2.10-1.92 (m, 3H), 1.91-1.78 (m, 1H), 1.76-1.58 (m, 6H), 1.53-1.22 (m, 11H), 1.19-0.98 (m, 9H), 0.98-0.80 (m, 14H), 0.68 (s, 3H). LCMS Rt=1.346 min in 2 min chromatography, 30-90AB_2 MIN_E.M, MS ESI calcd. for C$_{29}$H$_{47}$ [M+H−2H$_2$O]$^+$ 395, found 395.

Compound 11: $^1$H NMR (400 MHz, CDCl$_3$) δ 5.32-5.23 (m, 1H), 3.38-3.24 (m, 1H), 2.41-2.32 (m, 1H), 2.10-1.92 (m, 3H), 1.91-1.78 (m, 1H), 1.76-1.55 (m, 6H), 1.50-1.22 (m, 11H), 1.19-0.98 (m, 9H), 0.98-0.80 (m, 14H), 0.68 (s, 3H). LCMS Rt=1.344 min in 2 min chromatography, 30-90AB_2 MIN_E.M, MS ESI calcd. for C$_{29}$H$_{47}$ [M+H−2H$_2$O]$^+$ 395, found 395.

Step 8A. To a solution of Compound 10 (1.6 g, 3.71 mmol) in MeOH/THF (130 mL/20 mL) was added Pd/C (dry, 10%, 5 g) under Ar. After degassing for three times with N$_2$, the reaction mixture was degassed for three times with H$_2$. The reaction mixture was stirred for 16 h at 55° C. in H$_2$ atmosphere (50 Psi). The catalyst was removed by suction, and the filtrate was concentrated to give crude product which was purified by a silica gel column (EtOAc in PE, 5%-10%) to give Compound 13 (815 mg, 50%) as off-white solid. $^1$H NMR (400 MHz, CDCl$_3$) δ 3.31-3.30 (m, 1H), 2.00-1.92 (m, 1H), 1.89-1.78 (m, 1H), 1.58 (m, 5H), 1.57-1.48 (m, 3H), 1.47-1.30 (m, 8H), 1.30-1.16 (m, 7H), 1.15-0.94 (m, 6H), 0.93-0.85 (m, 13H), 0.82 (s, 3H), 0.70-0.60 (m, 4H). LCMS Rt=1.392 min in 2 min chromatography, 30-90AB_2 MIN_E.M, MS ESI calcd. for C$_{29}$H$_{49}$ [M+H−2H$_2$O]$^+$ 397, found 397.

Step 8B. The mixture of Compound 11 (1.6 g, 3.71 mmol) and Pd/C (5 g, 10%, dry) in ethyl acetate (250 mL) was stirred at 50° C. under H$_2$ (50 psi) for 16 hrs. The reaction mixture was filtered. The filtrate cake was washed with THF (4×20 mL). The combined filtrate was concentrated under vacuum to give a solid, which was purified by silica gel chromatography (PE:EtOAc=20:1) to give Compound 15 (974 mg, 61%) as an off-white solid. $^1$H NMR (400 MHz, CDCl$_3$) δ 3.31-3.30 (m, 1H), 2.00-1.92 (m, 1H), 1.89-1.78 (m, 1H), 1.69-1.58 (m, 5H), 1.57-1.48 (m, 3H), 1.47-1.30 (m, 8H), 1.30-1.16 (m, 7H), 1.15-0.94 (m, 6H), 0.93-0.85 (m, 13H), 0.82 (s, 3H), 0.70-0.60 (m, 4H). LCMS Rt=1.389 min in 2 min chromatography, 30-90AB_2 MIN_E.M, MS ESI calcd. for $C_{29}H_{49}$ $[M+H-2H_2O]^+$ 397, found 397.

Example 38. Synthesis of Compounds 66, 67, 68, and 69

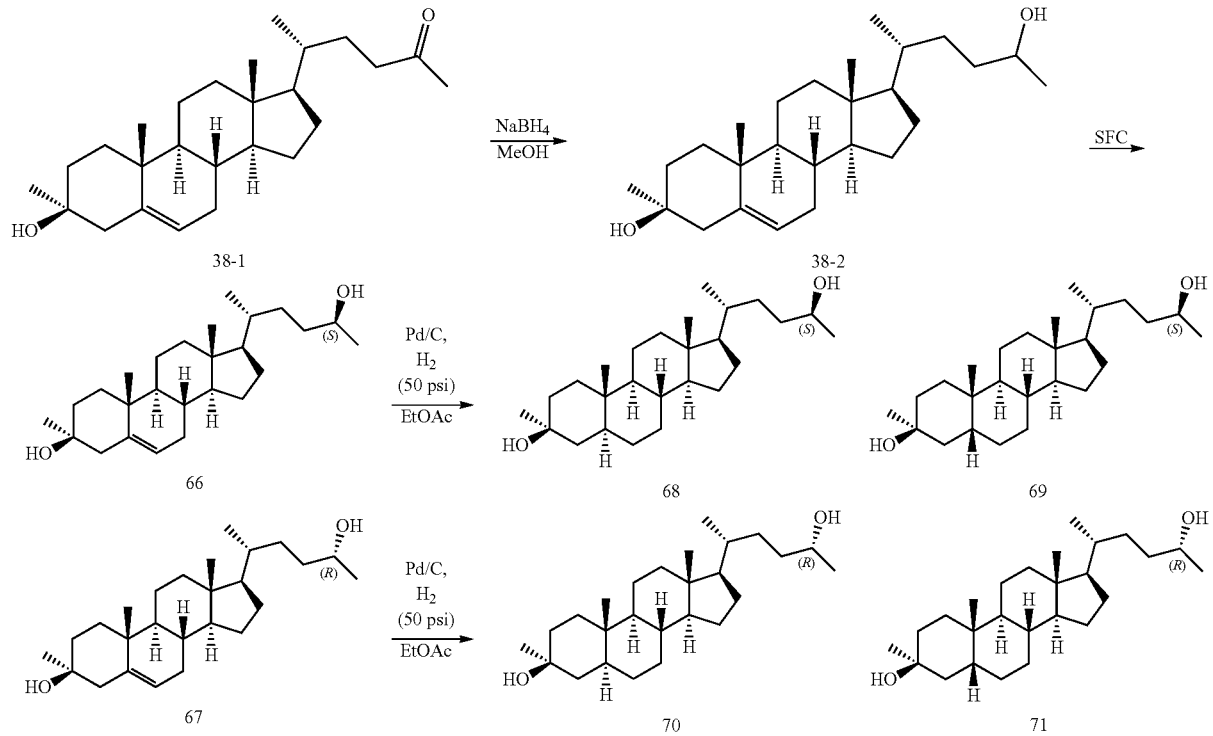

Step 1. To a solution of compound 38-1 (1.0 g, 2.60 mmol) in MeOH (15 mL) was added $NaBH_4$ (0.21 g, 5.7 mmol) in portions at 0° C. Then the reaction mixture was warmed to room temperature and stirred for 2 hours. The reaction mixture was quenched with aqueous saturated $NH_4Cl$ (5 mL) and extracted with $CH_2Cl_2$ (3×20 mL). The organic layer was washed with brine, dried over $Na_2SO_4$ and concentrated under reduced pressure. The crude product was purified by column chromatography on silica gel (PE/EtOAc=15/1 to 10/1) to give the desired product (0.82 g, 82%) as off-white powder. $^1H$ NMR (400 MHz, $CDCl_3$) δ 5.35-5.29 (m, 1H), 3.76-3.73 (m, 1H), 2.45-2.40 (m, 1H), 2.01-1.95 (m, 3H), 1.94-1.68 (m, 4H), 1.67-1.53 (m, 4H), 1.51.63-1.19 (m, 18H), 1.18 (s, 3H), 1.02 (s, 3H), 0.95 (d, J=6.4 Hz, 3H), 0.68 (s, 3H).

Step 2. A solution of 38-1 (0.6 g, 15.4 mmol) in MeOH (20 mL) was purified by prep-SFC to give the Compound 66 (180 mg, 30%) and Compound 67 (240 mg, 40%). The absolute configuration of Compound 66 and Compound 67 was confirmed by Mosher method.

$^1H$ NMR (Compound 66): (400 MHz, $CDCl_3$) δ 5.35-5.28 (m, 1H), 3.80-3.70 (m, 1H), 2.48-2.38 (m, 1H), 2.07-1.65 (m, 10H), 1.65-1.20 (m, 13H), 1.20-0.95 (m, 12H), 0.95 (d, J=6.8 Hz, 3H), 0.63 (s, 3H).

$^1H$ NMR (Compound 67): (400 MHz, $CDCl_3$) δ 5.34-5.28 (m, 1H), 3.80-3.70 (m, 1H), 2.47-2.40 (m, 1H), 2.04-1.93 (m, 2H), 1.93-1.68 (m, 2H), 1.68-1.21 (m, 15H), 1.20-0.96 (m, 16H), 0.95 (d, J=6.8 Hz, 3H), 0.68 (s, 3H).

Step 3A. To a solution of compound Compound 66 (140 mg, 0.36 mmol) in EtOAc (5 mL) was added 5% Pd/C (56 mg) under $N_2$. The suspension was degassed under vacuum and purged with $H_2$ several times. Then the mixture was stirred under $H_2$ (50 psi) at 50° C. for 12 hours. The mixture was filtered through a pad of celite and the pad was washed with EtOAc (2×5 mL). The combined filtrates were concentrated to dryness to give a crude product, which was purified by column chromatography on silica gel (PE/EtOAc/EtOAc=12/1 to 10/1) to afford the Compound 68 (80 mg, 57%) and Compound 69 (18 mg, 13%) as off-white powder.

$^1H$ NMR (Compound 68) (400 MHz, $CDCl_3$) δ 3.80-3.70 (m, 1H), 1.98-1.93 (m, 1H), 1.88-1.78 (m, 1H), 1.67-1.27 (m, 16H), 1.24-0.94 (m, 14H), 0.92 (d, J=6.4 Hz, 3H), 0.80 (s, 3H), 1.07 (s, 3H), 0.62 (m, 4H).

$^1H$ NMR (Compound 69) (400 MHz, $CDCl_3$) δ 3.80-3.70 (m, 1H), 1.98-1.95 (m, 1H), 1.95-1.79 (m, 3H), 1.64-1.23 (m, 18H), 1.23-1.00 (m, 14H), 0.96 (s, 3H) 0.92 (d, J=6.0 Hz, 3H), 0.62 (s, 3H).

Step 3B. To a solution of compound Compound 67 (120 mg, 0.30 mmol) in EtOAc (5 mL) was added 5% Pd/C (48 mg) under $N_2$. The suspension was degassed under vacuum and purged with $H_2$ several times. Then the mixture was stirred under $H_2$ (50 psi) at 50° C. for 12 hours. The mixture was filtered through a pad of celite and the pad was washed with EtOAc (2×5 mL). The combined filtrates were concentrated to dryness to give a crude product, which was purified by column chromatography on silica gel (PE/EtOAc/EtOAc=12/1 to 10/1) to afford the Compound 70 (78 mg, 65%) and Compound 71 (26 mg, 21%) as off-white powder.

Compound 70: $^1H$ NMR: (400 MHz, $CDCl_3$) δ 3.80-3.70 (m, 1H), 1.98-1.93 (m, 1H), 1.88-1.78 (m, 1H), 1.67-1.35 (m, 18H), 1.24-0.85 (m, 19H), 0.80 (s, 3H), 0.67-0.61 (m, 4H).

Compound 71: $^1H$ NMR: (400 MHz, $CDCl_3$) δ 3.80-3.70 (m, 1H), 2.00-1.93 (m, 1H), 1.93-1.77 (m, 3H), 1.67-1.25 (m, 19H), 1.25-0.80 (m, 18H), 0.64 (s, 3H).

Example 39. Synthesis of Compounds 72, 73, 74-A, 74-B, 75-A, and 75-B

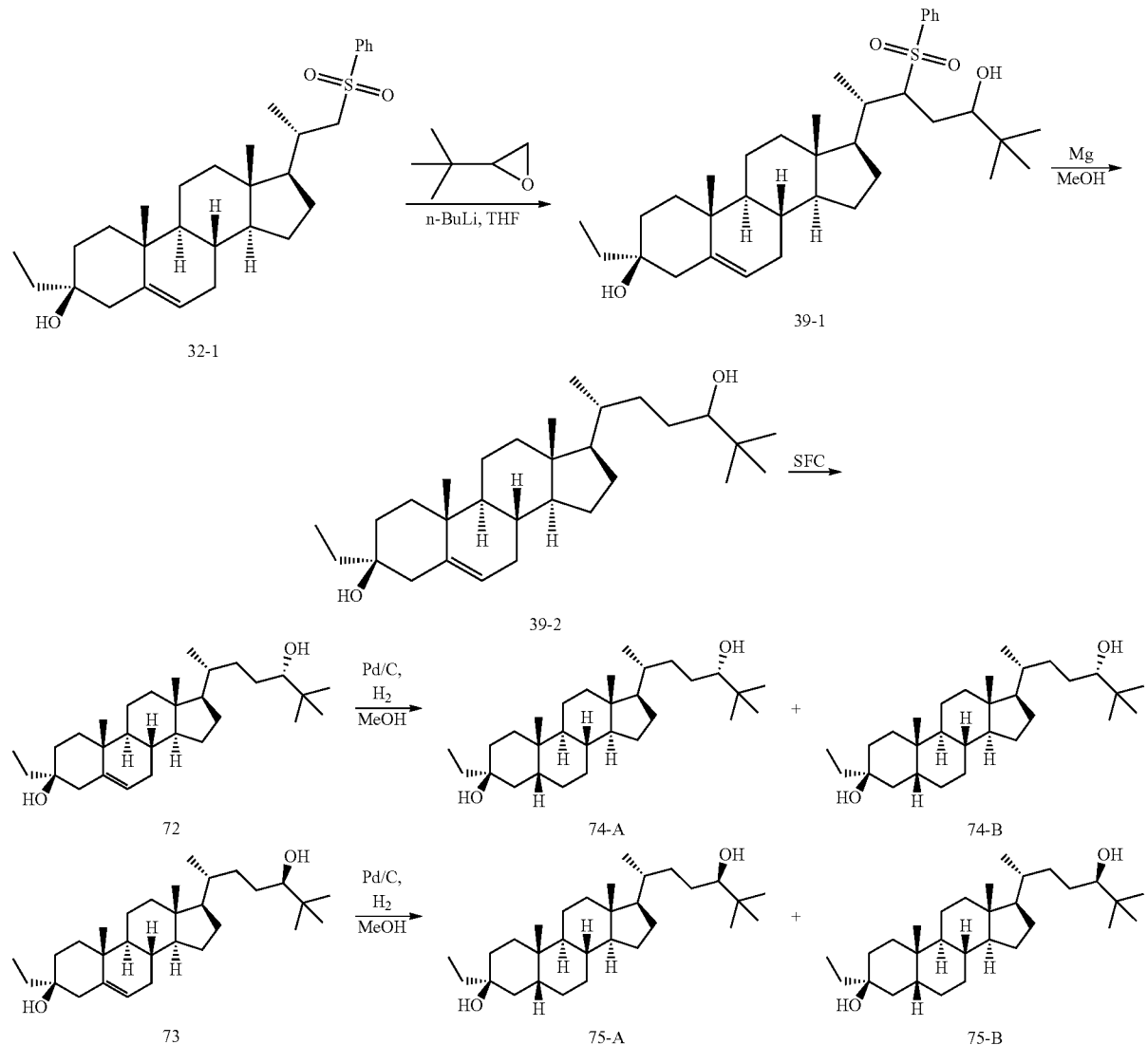

Step 1. nBuLi (2.06 mL, 2.5 M in hexane, 5.15 mmol) was added to THF (3 mL) dropwise under N₂ at −70° C., followed by adding a suspension of 32-1 (1 g, 2.06 mmol) in THF (5 mL). After stirring at −70° C. for 30 min, a solution of 2-(tert-butyl)oxirane (309 mg, 3.09 mmol) in THF (2 mL) was added dropwise. The mixture was stirred at −70° C. for 30 min and allowed to warm to 20° C. and stirred at 20° C. for 16 hrs. The reaction mixture was quenched by adding 30 mL of sat·NH₄Cl at 20° C. The organic layer was separated. The aqueous phase was extracted with EtOAc (2×30 mL). The combined organic layer dried over Na₂SO₄, filtered, concentrated and purified by combi-flash (0-15% of EtOAc in PE) to give impure 39-1 (700 mg, impure) as an off-white solid.

Step 2. A solution of 39-1 (700 mg, 1.19 mmol) in MeOH (30 mL) was heated at 55° C. Mg powder (1.15 g, 47.5 mmol) was added in one portion. The mixture was stirred at 55° C. for 2 hrs. The mixture was quenched with HCl (2 N, 100 mL) until the reaction became clear and extracted with DCM (3×50 mL). The combined organic phase was washed with sat·NaHCO₃ (100 mL), dried over Na₂SO₄, filtered, concentrated and purified by combi-flash (0-15% of EtOAc in PE) to give 39-2 (400 mg, 76%) as a off-white solid. $^1$H NMR (400 MHz, CDCl₃) δ 5.30-5.29 (m, 1H), 3.18-3.12 (m, 1H), 2.40-2.30 (m, 1H), 2.08-1.80 (m, 4H), 1.76-1.69 (m, 1H), 1.68-1.58 (m, 2H), 1.56-1.33 (m, 10H), 1.32-1.22 (m, 5H), 1.21-1.05 (m, 4H), 1.02 (s, 3H), 1.01-0.96 (m, 5H), 0.95-0.83 (m, 9H), 0.82-0.78 (m, 3H), 0.69 (s, 3H). LCMS $t_R$=1.375 min in 2 min chromatography, 30-90AB_ELSD, MS ESI calcd. for $C_{30}H_{49}$ [M+H−2H₂O]⁺ 409, found 409.

Step 3. 350 mg 39-2 was separated from SFC (column: AD (250 mm*30 mm, 5 um), gradient: 30-30% B (A=0.05% NH₃/H₂O, B=MeOH), flow rate: 60 mL/min) to give Compound 72 (160 mg, 46%) and Compound 73 (120 mg, 34%) as a off-white solid.

Compound 72: $^1$H NMR (400 MHz, CDCl₃) δ 5.30-5.29 (m, 1H), 3.18-3.12 (m, 1H), 2.40-2.30 (m, 1H), 2.08-1.80

(m, 4H), 1.76-1.69 (m, 1H), 1.68-1.58 (m, 2H), 1.56-1.33 (m, 10H), 1.32-1.22 (m, 5H), 1.21-1.05 (m, 4H), 1.02 (s, 3H), 1.01-0.96 (m, 5H), 0.95-0.83 (m, 9H), 0.82-0.78 (m, 3H), 0.69 (s, 3H). LCMS $t_R$=1.389 min in 2 min chromatography, 30-90AB_ELSD, MS ESI calcd. for $C_{30}H_{49}$ $[M+H-2H_2O]^+$ 409, found 409.

Compound 73: $^1$H NMR (400 MHz, CDCl$_3$) δ 5.30-5.29 (m, 1H), 3.18-3.12 (m, 1H), 2.40-2.30 (m, 1H), 2.08-1.80 (m, 4H), 1.76-1.69 (m, 1H), 1.68-1.58 (m, 2H), 1.56-1.33 (m, 10H), 1.32-1.22 (m, 5H), 1.21-1.05 (m, 4H), 1.02 (s, 3H), 1.01-0.96 (m, 5H), 0.95-0.83 (m, 9H), 0.82-0.78 (m, 3H), 0.69 (s, 3H). LCMS $t_R$=1.424 min in 2 min chromatography, 30-90AB_ELSD, MS ESI calcd. for $C_{30}H_{49}$ $[M+H-2H_2O]^+$ 409, found 409.

Step 4. Synthesis of Compounds 74-A and 74-B. To a solution of Compound 72 (110 mg, 0.247 mmol) in MeOH (30 mL) was added Pd/C (dry, 200 mg). The mixture was stirred at 50° C. for 72 hrs under H$_2$ (50 psi). The mixture was filtered, concentrated and purified by combi-flash (0-15% of EtOAc in PE) to give Compound 74-A (19 mg, 17%) as a off-white solid and Compound 74-B (18 mg, 16%) as an off-white solid.

Compound 74-A: $^1$H NMR (400 MHz, CDCl$_3$) δ 3.01-3.06 (m, 1H), 2.01-1.94 (m, 1H), 1.93-1.70 (m, 5H), 1.39-1.58 (m, 4H), 1.50-1.21 (m, 13H), 1.20-1.11 (m, 5H), 1.10-0.97 (m, 5H), 0.96 (s, 3H), 0.95-0.91 (m, 5H), 0.89 (s, 9H), 0.65 (s, 3H).

LCMS $t_R$=1.425 min in 2 min chromatography, 30-90AB_ELSD, purity 99.4%, MS ESI calcd. for $C_{30}H_{51}$ $[M+H-2H_2O]^+$ 411, found 411.

Compound 74-B: $^1$H NMR (400 MHz, CDCl$_3$) δ 3.11-3.07 (m, 1H), 1.98-1.94 (m, 1H), 1.88-1.58 (m, 6H), 1.56-1.40 (m, 5H), 1.39-1.15 (m, 10H), 1.13-1.02 (m, 5H), 1.01-0.96 (m, 3H), 0.95-0.92 (m, 4H), 0.91-0.83 (m, 12H), 0.81 (s, 3H), 0.70-0.50 (m, 4H). LCMS $t_R$=1.424 min in 2 min chromatography, 30-90AB_ELSD, MS ESI calcd. for $C_{30}H_{51}$ $[M+H-2H_2O]^+$ 411, found 411.

Step 5. Synthesis of Compounds 75-A and 75-B. To a solution of Compound 73 (70 mg, 0.157 mmol) in MeOH (30 mL) was added Pd/C (dry, 150 mg). The mixture was stirred at 50° C. for 72 hrs under H$_2$ (50 psi). The mixture was filtered, concentrated and purified by combi-flash (0-15% of EtOAc in PE) to give Compound 75-A (10 mg, 14%) as an off-white solid and Compound 75-B (12 mg, 17%) as a off-white solid.

Compound 75-A: $^1$H NMR (400 MHz, CDCl$_3$) δ 3.20-3.10 (m, 1H), 2.00-1.94 (m, 1H), 1.94-1.70 (m, 4H), 1.70-1.10 (m, 19H), 1.20-1.00 (m, 9H), 1.00-0.80 (m, 17H), 0.65 (s, 3H). LCMS $t_R$=1.424 min in 2 min chromatography, 30-90AB_ELSD, MS ESI calcd. for $C_{30}H_{51}$ $[M+H-2H_2O]^+$ 411, found 411.

Compound 75-B: $^1$H NMR (400 MHz, CDCl$_3$) δ 3.16-3.13 (m, 1H), 1.98-1.94 (m, 1H), 1.90-1.80 (m, 1H), 1.70-1.58 (m, 4H), 1.56-1.36 (m, 8H), 1.34-1.16 (m, 9H), 1.15-0.96 (m, 7H), 0.95-0.91 (m, 4H), 0.89 (s, 9H), 0.88-0.84 (m, 3H), 0.82 (s, 3H), 0.70-0.60 (m, 4H). LCMS $t_R$=1.416 min in 2 min chromatography, 30-90AB_ELSD, purity 98.0%, MS ESI calcd. for $C_{30}H_{51}$ $[M+H-2H_2O]^+$ 411, found 411.

Materials and Methods

The compounds provided herein can be prepared from readily available starting materials using the following general methods and procedures, for example, as described in WO 2013/036835 and WO 2014/160480. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

$^1$H-NMR reported herein (e.g., for the region between δ (ppm) of about 1 to about 4 ppm) will be understood to be an exemplary interpretation of the NMR spectrum (e.g., exemplary peak integratations) of a compound. Exemplary general method for preparative HPLC: Column: Waters RBridge prep 10 μm C18, 19*250 mm. Mobile phase: acetonitrile, water (NH$_4$HCO$_3$) (30 L water, 24 g NH$_4$HCO$_3$, 30 mL NH$_3$·H$_2$O). Flow rate: 25 mL/min Exemplary general method for analytical HPLC: Mobile phase: A: water (10 mM NH$_4$HCO$_3$), B: acetonitrile Gradient: 5%-95% B in 1.6 or 2 min Flow rate: 1.8 or 2 mL/min; Column: XBridge C18, 4.6*50 mm, 3.5 μm at 45 C.

NMDA Potentiation

NMDA potentiation was assessed using either whole cell patch clamp of mammalian cells which expressed NMDA receptors.

Whole-Cell Patch Clamp of Mammalian Cells (IONWORKS BARRACUDA® (IWB))

The whole-cell patch-clamp technique was used to investigate the effects of compounds GlunN1/GluN2A glutamate receptors expressed in mammalian cells. The results are shown on Table 1.

HEK293 cells were transformed with adenovirus 5 DNA and transfected with cDNA encoding the human GRIN1/GRIN2A genes. Stable transfectants were selected using G418 and ZEOCIN™ (phleomycins)-resistance genes incorporated into the expression plasmid and selection pressure maintained with G418 and ZEOCIN™ (phleomycins) in the medium. Cells were cultured in Dulbecco's Modified Eagle Medium/Nutrient Mixture (D-MEM/F-12) supplemented with 10% fetal bovine serum, 100 μg/ml penicillin G sodium, 100 μg/ml streptomycin sulphate, 100 μg/ml Zeocin, 5 μg/ml blasticidin and 500 μg/ml G418.

Test article effects were evaluated in 8-point concentration-response format (4 replicate wells/concentration). All test and control solutions contained 0.3% DMSO and 0.01% KOLLIPHOR® (polyethoxylated castor oil) EL (C5135, Sigma). The test article formulations were loaded in a 384-well compound plate using an automated liquid handling system (SCICLONE® ALH3000, Caliper Life Sciences). The measurements were performed using IWB platform following this procedure:

Electrophysiological Procedures:
- a) Intracellular solution (mM): 50 mM CsCl, 90 mM CsF, 2 mM $MgCl_2$, 5 mM EGTA, 10 mM HEPES. Adjust to pH 7.2 with CsOH.
- b) Extracellular solution, HB-PS (composition in mM): NaCl, 137; KCl, 1.0; $CaCl_2$), 5; HEPES, 10; Glucose, 10; pH adjusted to 7.4 with NaOH (refrigerated until use).
- c) Holding potential: −70 mV, potential during agonist/PAM application: −40 mV.

Recording Procedure:
- a) Extracellular buffer will be loaded into the PPC plate wells (11 µL per well). Cell suspension will be pipetted into the wells (9 µL per well) of the PPC planar electrode.
- b) Whole-cell recording configuration will be established via patch perforation with membrane currents recorded by on-board patch clamp amplifiers.
- c) Two recordings (scans) will be performed. First, during pre-application of test article alone (duration of pre-application ~5 min) and second, during test articles and agonist ($EC_{20}$ L-glutamate and 30 µM glycine) co-application to detect positive modulatory effects of the test article.

Test Article Administration: The first pre-application will consist of the addition of 20 µL of 2× concentrated test article solution and, second, of 20 µL of 1× concentrated test article and agonist at 10 µL/s (2 second total application time).

TABLE 1

| Structure | GluN2A PCA IWB Ephys % potentiation at 3 µM |
|---|---|
| 1 | B |
| 1-A | B |
| 1-B | C |
| 2 | A |
| 3 | C |
| 4 | C |
| 6 | C |
| 7 | C |
| 8 | A |
| 9 | B |
| 10 | C |
| 11 | C |
| 12 | A |
| 13 | C |
| 14 | A |
| 15 | C |
| 16 | C |
| 17 | B |
| 18 | C |
| 19 | C |
| 20 | C |
| 21 | C |
| 22 | C |
| 23 | C |
| 23 | C |
| 25 | C |
| 26 | C |
| 28 | C |
| 29 | B |
| 30 | C |
| 31 | C |
| 32 | C |
| 33 | A |
| 34 | C |
| 35 | B |
| 36 | C |
| 37 | C |
| 38 | C |
| 39 | A |
| 40 | C |
| 41 | C |
| 41-A | C |
| 41-B | C |
| 42 | B |
| 43 | B |
| 44 | C |
| 44-A | C |
| 44-B | B |
| 45 | C |
| 46 | C |
| 47 | C |
| 48 | C |
| 50 | C |
| 51 | C |
| 52 | C |
| 53 | C |
| 54 | C |
| 55 | C |
| 56 | C |
| 66 | B |
| 67 | A |
| 68 | C |
| 70 | C |

For Table 1, "A" indicates 10 to 75%, "B" indicates potentiation of >75% to 150%; "C" indicates potentiation of >150%; and "ND" indicates not determinable or not determined.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing"

are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

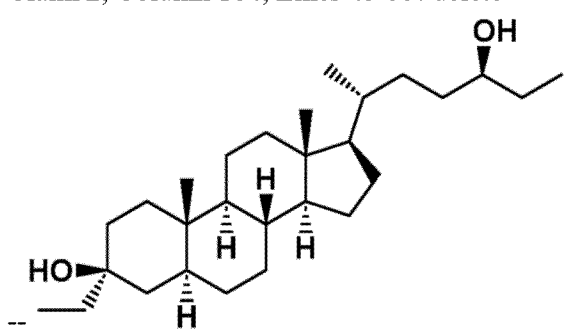

What is claimed is:

1. A compound selected from the group consisting of:

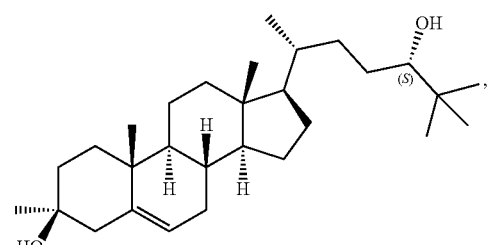

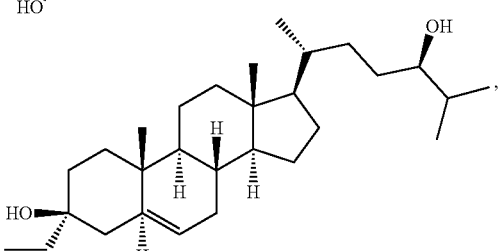

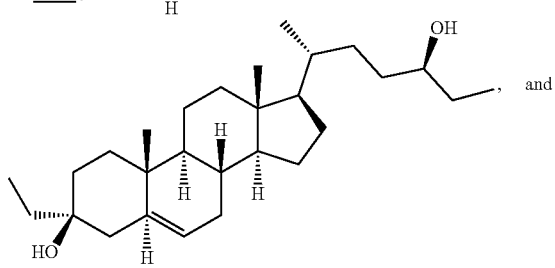

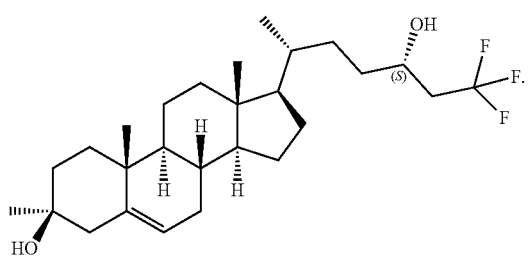

2. A pharmaceutically acceptable salt of a compound selected from the group consisting of:

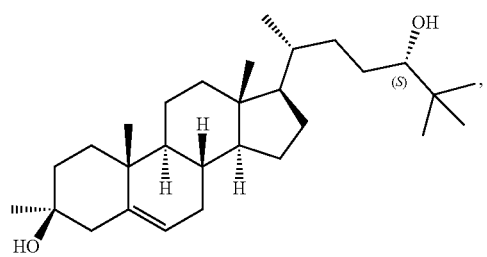

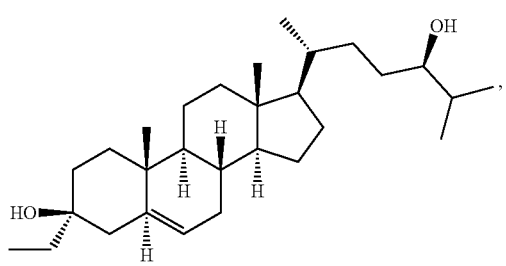

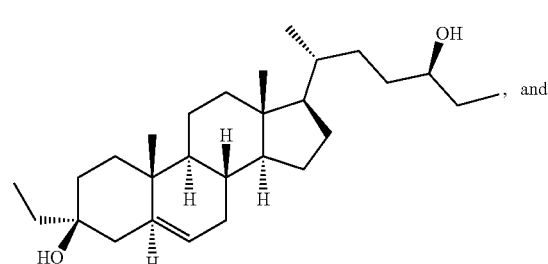

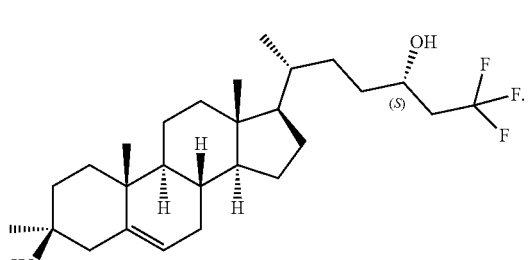

3. The compound of claim 1, wherein the compound is:

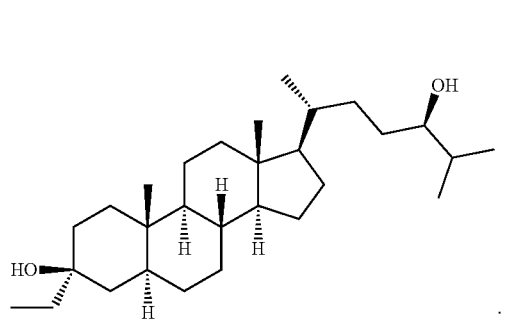

4. The pharmaceutically acceptable salt of a compound of claim 2, wherein the compound is:

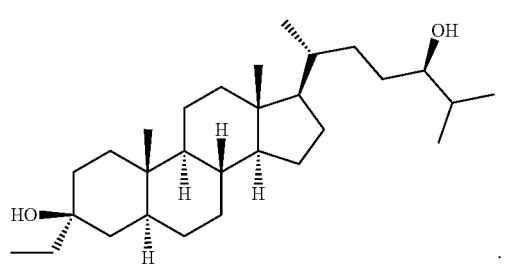

5. The compound of claim 1, wherein the compound is:

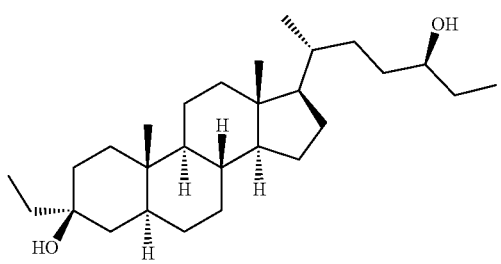

6. The pharmaceutically acceptable salt of a compound of claim 2, wherein the compound is:

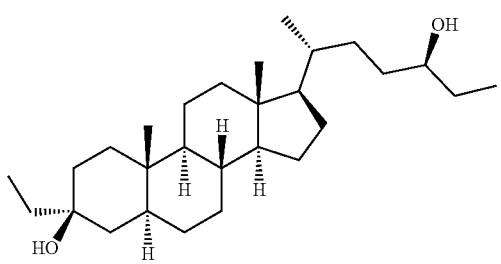

7. The compound of claim 1, wherein the compound is:

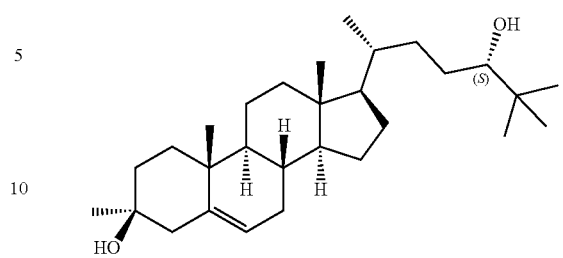

8. The pharmaceutically acceptable salt of a compound of claim 2, wherein the compound is:

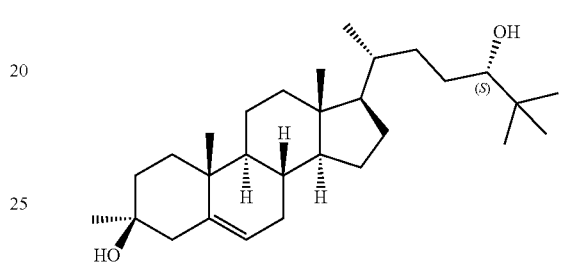

9. The compound of claim 1, wherein the compound is:

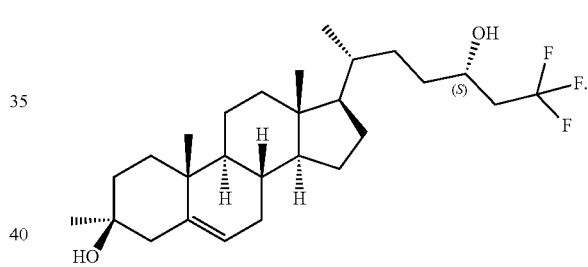

10. The pharmaceutically acceptable salt of a compound of claim 2, wherein the compound is:

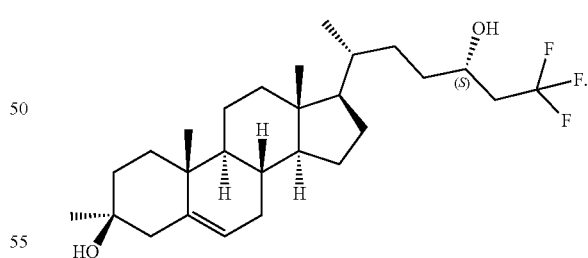

11. A pharmaceutical composition comprising a pharmaceutically acceptable salt of a compound of any one of claim 2, 4, 6, 8 or 10 and a pharmaceutically acceptable carrier.

12. A pharmaceutical composition comprising a compound of any one of claim 1, 3, 5, 7, or 9 and a pharmaceutically acceptable carrier.

* * * * *

UNITED STATES PATENT AND TRADEMARK OFFICE
CERTIFICATE OF CORRECTION

Page 1 of 2

PATENT NO. : 11,732,000 B2
APPLICATION NO. : 17/396034
DATED : August 22, 2023
INVENTOR(S) : Francesco G. Salituro et al.

It is certified that error appears in the above-identified patent and that said Letters Patent is hereby corrected as shown below:

In the Claims

Claim 1, Column 163, Lines 45-55: delete " 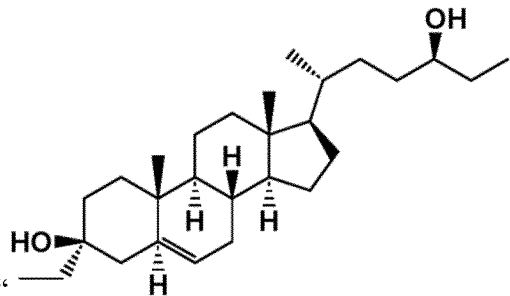 " and insert
-- 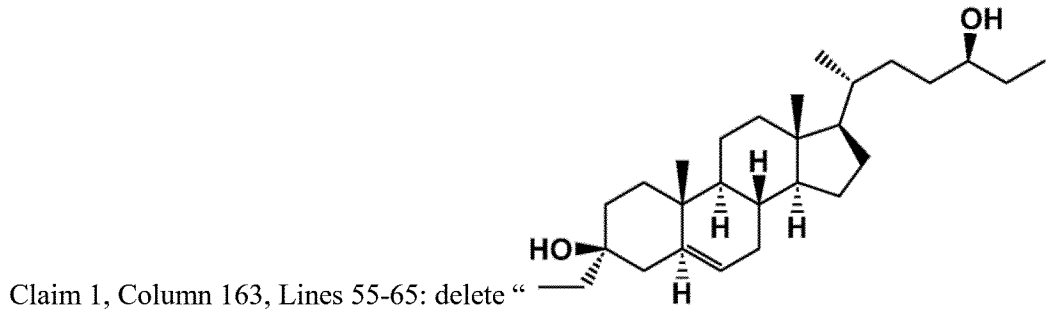 --.

Claim 1, Column 163, Lines 55-65: delete " 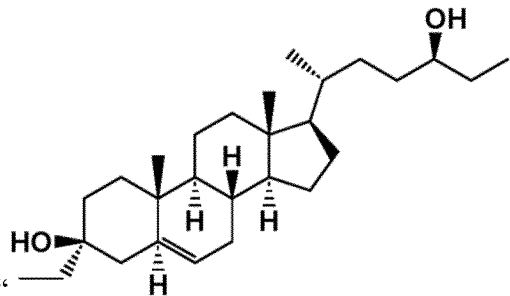 " and insert

Signed and Sealed this
Twenty-sixth Day of March, 2024

*Katherine Kelly Vidal*

Katherine Kelly Vidal
*Director of the United States Patent and Trademark Office*

CERTIFICATE OF CORRECTION (continued)
U.S. Pat. No. 11,732,000 B2

Claim 2, Column 164, Lines 30-40: delete " 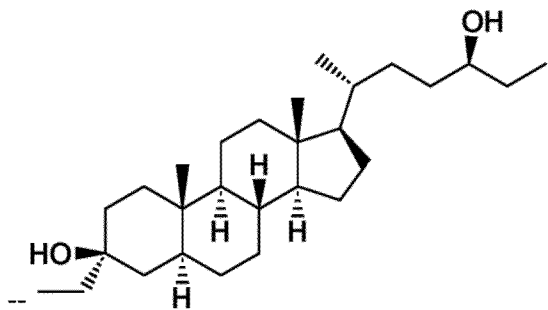 " and insert

" 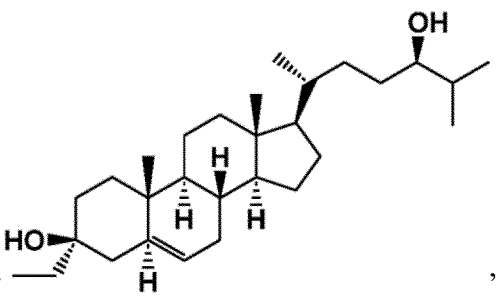 ".

Claim 2, Column 164, Lines 45-55: delete " 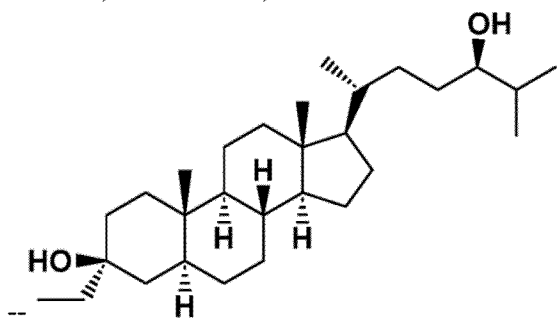 " and insert

" 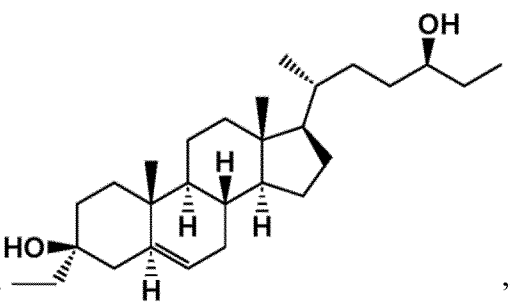 ".